US006632937B1

(12) United States Patent
Swanson et al.

(10) Patent No.: US 6,632,937 B1
(45) Date of Patent: Oct. 14, 2003

(54) NUCLEIC ACIDS AND PROTEINS FROM *CENARCHAEUM SYMBIOSUM*

(75) Inventors: Ronald V. Swanson, La Jolla, CA (US); Robert A. Feldman, Poway, CA (US); Christa Schleper, Darmstadt (DE)

(73) Assignee: Diversa Corporation, San Diego, CA (US)

( * ) Notice: Subject to any disclaimer, the term of this patent is extended or adjusted under 35 U.S.C. 154(b) by 0 days.

(21) Appl. No.: 09/408,020

(22) Filed: Sep. 29, 1999

Related U.S. Application Data

(60) Provisional application No. 60/102,294, filed on Sep. 29, 1998.

(51) Int. Cl.[7] ........................ C07H 2/04; C07K 14/195
(52) U.S. Cl. ....................................... 536/23.7; 530/350
(58) Field of Search .......................... 536/23.7; 530/350

(56) References Cited

PUBLICATIONS

X57760, A. Fainsod Jul. 8, 1992.*
AF016442, Wilson et al., Aug. 7, 1997.*
AF083071, Schleper et al., Oct. 6, 1998.*
Baker et al. Protein structure prediction and structural genomics. Science. (Oct. 5, 2001) vol. 294, pp. 93–96.*
Ainsworth et al., "T. aestivum AGP–S mRNA," *Database EMBL* Accession No. X66080 (May 13, 1992) XP002136936 (abstract).
DeLong et al., "Application of Gebomics for Understanding the Evolution of Hyperthermophilic and Nonthermophilic Crenarchaeota," *Biological Bulletin* 196(3):363–365 (Jun. 1999).
Krejci et al., "Rattus norvegicus acetylc holinesterase–associated collagen," *Database EMBL* Accession No. AF007583 (Nov. 1, 1997) XP002130622 (abstract).
Preston et al., "A psychrophilic crenarchaeon inhabits a marine sponge: *Cenarchaeum symbiosum* gen. nov., sp. nov.," *Proc. Natl. Acad. Sci. USA* 93:6241–6246 (Jun. 1996); & "Cenarchaeum symbiosum small subunit ribosomal RNA gene sequence," *Database Genbank* Accession No. U51469 (Aug. 13, 1996) XP002130621 (abstract).
Schleper et al., "Genomic analysis reveals chromosomal variation in natural populations of the uncultured psychrophilic archaeon Cenarchaeum symbiosum," *J. Bacteriol.* 180(19):5003–5009, *Database EMBL* XP–002136935; & "*Cenarchaeum symbiosum* strain B," *Database EMBL* Accession No. AF083072 (Sep. 23, 1998) XP002136935 (abstract).
Schleper et al., "Characterization of a DNA polymerase from the uncultivated psychrophilic archaeon *Cenarchaeum symbiosum*," *Journal of Bacteriology* 179(24):7803–7811 (Dec. 1997) XP00872756; & "*Cenarchaeum symbiosum* DNA polymerase gene," *Database Genbank* Accession No. AF028831 (Jan. 6, 1998) XP002130624 (abstract).
Stein et al., "Characterization of Uncultivated Prokaryotes: Isolation and Analysis of a 40–Kilobase–Pair Genome Fragment from a Planktonic Marine Archaeon," *Journal of Bacteriology* 178(3):591–599 (Feb. 1996) XP002050143.
Suzuki et al., "Pig gad65 mRNA forglutamic acid decarboxylase," *Database EMBL* Accession No. D31848 (Apr. 28, 1995) XP002130623 (abstract).

* cited by examiner

*Primary Examiner*—Ardin H. Marschel
*Assistant Examiner*—Marjorie A. Moran
(74) *Attorney, Agent, or Firm*—Fish & Richardson P.C.

(57) ABSTRACT

The present application relates to nucleic acids and polypeptides from *Cenarchaeum symbiosum.* Methods of making the polypeptides and antibodies against the polypeptides are also described.

2 Claims, 7 Drawing Sheets

| SEQ ID NO: | Gene | Strain | | TATA Box | | | Coding Start | | TATA to Start (bp) |
|---|---|---|---|---|---|---|---|---|---|
| 81 | Hypoth 03 | A | AAGCTAGACT | TTTAAT | TGGG | ATCCGGCGGG | GCGGCGCATG | ~~~~~~~~~~ ~~~~~~~~~~ | 25 |
| 82 | | B | AAGCTAAACT | TTTAAT | TGGG | ATCCGGCGAG | CCGGCGCGTG | ~~~~~~~~~~ ~~~~~~~~~~ | |
| 83 | Hypoth 02 | A | GGAAACTTTG | ATTATA | CGGG | CGTGCTGCCC | CGGGGCCCAT | G~~~~~~~~~ ~~~~~~~~~~ | 26 |
| 84 | | B | GGAAACTTTG | ATTATA | CGGG | CGTACATTCC | CGGGGCCCAT | G~~~~~~~~~ ~~~~~~~~~~ | |
| 85 | ORF 02 | A | AAGGCAAGGT | AATAAT | AGCC | TGCCGTCTGT | AACGGCCGTA | TG~~~~~~~~ ~~~~~~~~~~ | 27 |
| 86 | | B | ACGGCAAGGT | AATAAT | AGCC | TGCCGTCCGT | ACCTGCCGTA | TG~~~~~~~~ ~~~~~~~~~~ | |
| 87 | ORF 03 | A | CATGGAACTA | GATATT | AACC | GGTTCCGCGG | ATCCCATGCA | TG~~~~~~~~ ~~~~~~~~~~ | 27 |
| 88 | | B | CATGGAACTA | GATAAT | AACC | GGTCCCGCGG | GTACAATGCA | TG~~~~~~~~ ~~~~~~~~~~ | |
| 89 | PPI | A | ATACCGAGAA | GTTATA | GCAG | GGTATGGAAT | GTGCGCGCGC | ATG~~~~~~~ ~~~~~~~~~~ | 28 |
| 90 | | B | AGCACGACAA | GTTATA | GCAG | GGTACAAAGG | AGCAGCGCAC | ATG~~~~~~~ ~~~~~~~~~~ | |
| 91 | GSAT | A | ATCCGCCCTG | ATTAAA | TTAT | GGGGGGAGCG | GCCTGCTGCC | GTG~~~~~~~ ~~~~~~~~~~ | 28 |
| 92 | | B | ATCCGGCCTC | ATTAAA | TTAC | GGGGGGTACA | ACCTGCTGCC | GTG~~~~~~~ ~~~~~~~~~~ | |
| 93 | ORF 05 | A | CCTTCATACA | CATAAA | TCCC | GCTTGGATGT | GCGGCTGCGC | ATG~~~~~~~ ~~~~~~~~~~ | 28 |
| 94 | | B | ACTTCATACA | CATAAA | TCCC | GCCTGAACGG | TCGTCCGCGC | ATG~~~~~~~ ~~~~~~~~~~ | |
| 95 | deaminase | A | .GGCATATAC | CATAAT | ATGC | CGGGCGGTGG | CACCATGGCC | GTTG~~~~~~ ~~~~~~~~~~ | 29 |
| 96 | | B | CCGCATATAC | CATAAT | ATGC | CGGGCGGGGG | CAGGCTGCCC | .GTG~~~~~~ ~~~~~~~~~~ | |
| 97 | RNA helic | A | TGTACGAAAC | CATAAA | ACAA | CAGGCCGCGT | CAGGGCCGCG | CGTG~~~~~~ ~~~~~~~~~~ | 29 |
| 98 | | B | GGGTAGAAAC | CATAAA | ACAA | CAGGCCGCGG | CAGGGCG.CG | CGTG~~~~~~ ~~~~~~~~~~ | |
| 99 | ORF 06 | A | ..ACACGCAG | TATAAA | CGGG | GGCCCGGGCG | GCGCGTATCA | CATG~~~~~~ ~~~~~~~~~~ | 29 |
| 100 | | B | ATACACGTGG | TATAAA | CAGA | GG.CCGGACG | GCGCGGACCA | CATG~~~~~~ ~~~~~~~~~~ | |

FIG. 2A

| SEQ ID NO: | Gene | Strain | | TATA Box | | | Coding Start | | | TATA to Start (bp) |
|---|---|---|---|---|---|---|---|---|---|---|
| 101 | tRNA-tyr | A | GCGATAGTTA | TTTAAA | ACTA | GGATGCCGAT | CACGGATCGT | CCCA~~~~~~ | ~~~~~~~~~~ | 29 |
| 102 | | B | GCGATAGTTA | TTTAAA | ACTA | GGATGCCGGG | CACCCGTCGT | CCCA~~~~~~ | ~~~~~~~~~~ | |
| 103 | TBP | A | CCGGGCCCCG | GTTAAA | ATAG | CG.CACGGGC | GGATCCTGAC | CAATG~~~~~ | ~~~~~~~~~~ | 30 |
| 104 | | B | CCGGGCCCCG | GTTAAA | ATAG | AGTGCGGCCG | GGCACCGGAT | CAATG~~~~~ | ~~~~~~~~~~ | |
| 105 | TIM | A | GCGTCGATAG | AATAAA | TACG | CGCAGGGGGC | CCCGTGGCGC | GATCGCCCGT | G~~~~~~~~~ | 36 |
| 106 | | B | GCGTCGATAG | AATAAA | TACG | CGC.GGGGCC | GCGGTGC... | GATCGCCCGT | G~~~~~~~~~ | |
| 107 | Hypoth 01 | A | ATTTCAACTA | CATAAA | TGCC | TAGTTACGCA | GAAATAGCAA | ACGACGTACT | TCGACTAATG | 45 |
| 108 | | B | ACTTCAACTA | CATAAA | TGCC | TAGCTACGCA | GAAATATCAA | ACAAAGTACT | TCGACTAATG | |
| 109 | ORF 01 | A | ACGGCAGGCT | ATTATT | ACCT | TGCCTTGCGT | TGTA //..G | CGGGGTGCGG | CAGGGGATG | 52 |
| 110 | | B | ACGGCAGGCT | ATTATT | ACCT | TGCCGTGTG. | TACA //..G | AGGGGGCCTG | CCGGGAGTG | |
| 111 | Methylase | A | CTACAACGAT | TTTAAG | TCGG | CGCCGGGGCA | GCCG.//..G | ATGTGGGGCA | GGCAACATG | 140 |
| 112 | | B | CTACAAAGAT | TTTAAG | ACGG | CGCGGGTGCC | GCGG.//..T | GGCACGGGGG | CCTATCTTG | |
| 113 | 16S RNA | A | TCGGCGATGG | TTTATA | TGCC | CATGGACGGG | CCGATCCGAT | CGTACGTGAC | GC.//..AAT | 220 |
| 114 | | B | CCGGCGATGG | TTTATA | TGCC | CATGGACAAG | GCGATCCGAT | CGTACGTGAC | GC.//..AAT | |
| | Archael promoter consensus | | | YTTAWA | | | | | | |

FIG. 2B

NUCLEIC ACIDS AND PROTEINS FROM *CENARCHAEUM SYMBIOSUM*

RELATED APPLICATIONS

The present application claims benefit of U.S. Provisional Patent Application Serial No. 60/102,294, filed Sep. 29, 1998, the disclosure of which is incorporated herein by reference in its entirety.

BACKGROUND OF THE INVENTION

The identification and characterization of organisms which inhabit a diverse range of ecosystems leads to a greater understanding of the operation of such ecosystems. In addition, because the physiology of such organisms is adapted to function in the particular habitat which the organism inhabits, the enzymes which carry out the organism's physiological processes may possess characteristics which provide advantages when they are utilized in therapeutic procedures, industrial applications, or research applications. Furthermore, by determining the sequences of these organisms' genes, insight into their biochemical pathways and processes may be gained without the necessity of culturing the organisms in the laboratory, thereby enabling the physiological characterization of organisms which are recalcitrant to growth in the laboratory.

Molecular phylogenetic surveys have recently revealed an ecologically widespread Crenarchaeal group that inhabits cold and temperate terrestrial and marine environments. To date these organisms have resisted isolation in pure culture, so their phenotypic and genotypic characteristics remain largely unknown. In order to characterize the physiology of these archaea, to develop methodological approaches for characterizing uncultivated microorganisms and identifying their presence in a sample, and to identify enzymes produced by these archae which may be useful in therapeutic, industrial, or laboratory applications, genomic analyses of the non-thermophilic crenarchaeote *Cenarchaeum symbiosum* was undertaken.

Non-thermophilic Crenarchaeota are one of the more abundant, widespread and frequently recovered prokaryotic groups revealed by molecular phylogenetic approaches. These microorganisms were originally detected in high abundance in temperate ocean waters and polar seas. (DeLong, E. F. 1992. Archaea in coastal marine environments. *Proc. Natl. Acad. Sci.* 89, 5685–5689; DeLong, E. F et al. 1994. High abundance of Archaea in Antarctic marine picoplankton. *Nature* 371, 695–697; Fuhrman, J. A., et al. Davis. 1992. Novel major archaebacterial group from marine plankton. *Nature* 356, 148–149; Massana, R., et al. 1997. Vertical distribution and phylogenetic characterization of marine planktonic Archaea in the Santa Barbara Channel. *Appl. Env. Microb.* 63, 50–56; McInerney, J. O. et al. 1995. Recovery and phylogenetic analysis of novel archaeal rRNA sequences from a deep-sea deposit feeder. *Appl. Env. Microb.* 61, 1646–1648; Preston, C. M. et al. 1996. A psychrophilic crenarchaeon inhabits a marine sponge: *Cenarchaeum symbiosum* gen. *nov.,* sp. *nov. Proc. Natl. Acad. Sci.* USA 93, 6241–6246) Representatives have now been reported in terrestrial environments and freshwater lake sediments, indicating a widespread distribution. (Bintrim, S. B. et al. 1997. Molecular phylogeny of Archaea from soil. *Proc. Natl. Acad Sci.* USA 94, 277–282; Jurgens, G. et al. 1997. Novel group within the kingdom Crenarchaeota from boreal forest soil. *Appl. Env. Mircob.* 63, 803–80515, Kudo, Y. et al. 1997. Peculiar archaea found in Japanese paddy soils. *Biosc. Biotech. Biochem.* 61, 917–920; Ueda, et al. 1995. Molecular phylogenetic analysis of a soil microbial community. *Eur. J. Soil Sci.* 46, 415–421; Hershberger, K. L. et al. 1996. Wide diversity of Crenarchaeota. *Nature* 384, 420; MacGregor, B. J. 1997. Crenarchaeota in Lake Michigan sediment. *Appl. Env. Microb.* 63, 1178–1181 et al.; Schleper, C.et al. 1997. Recovery of crenarchaeotal ribosomal DNA sequences from freshwater-lake sediments. *Appl. Env. Microb.* 63, 321–323) The ecological distribution of these organisms was initially surprising, since their closest cultivated relatives are all thermophilic or hyperthermophilic. No representative of this new archaeal group has yet been obtained in pure culture, so the phenotypic and metabolic properties of these organisms, as well as their impact on the environment and global nutrient cycling, remain unknown. Since growth temperature and habitat characteristics vary so widely between non-thermophilic and the hyperthermophilic Creanarchaeota, these groups are likely to differ greatly with respect to their specific physiology and metabolism.

To gain a better perspective on the genetic and physiological characteristics of non-thermophilic crenarchaeotes, a genomic study of *Cenarchaeum symbiosum* was begun. This archaeon lives in specific association with the marine sponge *Axinella mexicana* off the coast of California, allowing access to relatively large amounts of biomass from this species. (Preston, C. M. et al. 1996. A psychrophilic crenarchaeon inhabits a marine sponge: *Cenarchaeum symbiosum* gen. *nov.,* sp. *nov. Proc. Natl. Acad. Sci.* USA 93, 6241–6246) The approach taken herein differs in several respects from now standard genomic characterization of cultivated organisms, and also from comparable studies of uncultivated obligate parasites or symbionts. *C. symbiosum* has not been completely physically separated from the tissues of its metazoan host. Therefore, its genetic material needs to be identified within the context of complex genomic libraries that contain significant amounts of eucaryotic DNA, as well as DNA derived from members of Bacteria.

Molecular phylogenetic surveys of mixed microbial populations have revealed the existence of many new lineages undetected by classical microbiological approaches. (DeLong, E. F. 1997. Marine microbial diversity: the tip of the iceberg. *Tibtech* 15, 2–9.; Pace, N. R. 1997. A molecular view of microbial diversity and the biosphere. *Science* 276, 734–740) Furthermore, quantitative rRNA hybridization experiments demonstrate that some of these novel prokaryotic groups represent major components of natural microbial communities. These molecular phylogenetic approaches have altered current views of microbial diversity and ecology, and have demonstrated that traditional cultivation techniques may recover only a small, skewed fraction of naturally occurring microbes. However, phylogenetic identification using single gene sequences provides a limited perspective on other biological properties, particularly for novel lineages only distantly related to cultivated and characterized organisms. Consequently, additional approaches are necessary to better characterize ecologically abundant and potentially biotechnologically useful microorganisms, many of which resist cultivation attempts.

SUMMARY OF THE INVENTION

One embodiment of the present invention is an isolated, purified, or enriched nucleic acid comprising a sequence selected from the group consisting of SEQ ID NO: 1 and SEQ ID NO: 2, the sequences complementary to SEQ ID NO: 1 and SEQ ID NO: 2, fragments comprising at least 10 consecutive nucleotides of SEQ ID NO: 1 and SEQ ID NO:

2, and fragments comprising at least 10 consecutive nucleotides of the sequences complementary to SEQ ID NO: 1 and SEQ ID NO: 2. One aspect of the present invention is an isolated, purified, or enriched nucleic acid capable of hybridizing to the nucleic acid of this embodiment under conditions of high stringency. Another aspect of the present invention is an isolated, purified, or enriched nucleic acid capable of hybridizing to the nucleic acid of this embodiment under conditions of moderate stringency. Another aspect of the present invention is an isolated, purified, or enriched nucleic acid capable of hybridizing to the nucleic acid of this embodiment under conditions of low stringency. Another aspect of the present invention is an isolated, purified, or enriched nucleic acid having at least 70% homology to the nucleic acid of this embodiment as determined by analysis with BLASTN version 2.0 with the default parameters. Another aspect of the present invention is an isolated, purified, or enriched nucleic acid having at least 99% homology to the nucleic acid of this embodiment as determined by analysis with BLASTN version 2.0 with the default parameters.

Another embodiment of the present invention is an isolated, purified, or enriched nucleic acid comprising a sequence selected from the group consisting of SEQ ID NOs: 5, 9, 13, 25, 27, 29, 31, 33, 37, 41, 45, 57, 59, 61, 63, 65, 67, 71, 75, 79 and the sequences complementary thereto. One aspect of the present invention is an isolated, purified, or enriched nucleic acid capable of hybridizing to the nucleic acid of this embodiment under conditions of high stringency. Another aspect of the present invention is an isolated, purified, or enriched nucleic acid capable of hybridizing to the nucleic acid of this embodiment under conditions of moderate stringency. Another aspect of the present invention is an isolated, purified, or enriched nucleic acid capable of hybridizing to the nucleic acid of this embodiment under conditions of low stringency. Another aspect of the present invention is an isolated, purified, or enriched nucleic acid having at least 70% homology to the nucleic acid of this embodiment as determined by analysis with BLASTN version 2.0 with the default parameters. Another aspect of the present invention is an isolated, purified, or enriched nucleic acid having at least 99% homology to the nucleic acid of this embodiment as determined by analysis with BLASTN version 2.0 with the default parameters.

Another embodiment of the present invention is an isolated, purified, or enriched nucleic acid comprising at least 10 consecutive bases of a sequence selected from the group consisting of SEQ ID NOs: 5, 9, 13, 25, 27, 29, 31, 33, 37, 41, 45, 57, 59, 61, 63, 65, 67, 71, 75, 79 and the sequences complementary thereto. One aspect of the present invention is an isolated, purified, or enriched nucleic acid having at least 70% homology to the nucleic acid of this embodiment as determined by analysis with BLASTN version 2.0 with the default parameters.

Another embodiment of the present invention is an isolated, purified, or enriched nucleic acid comprising a sequence selected from the group consisting of SEQ ID NOs: 3, 7, 11, 15, 17, 19, 21, 23, 35, 39, 43, 47, 49, 51, 53, 55, 69, 73, 77 and the sequences complementary thereto. One aspect of the present invention is an isolated, purified, or enriched nucleic acid capable of hybridizing to the nucleic acid of this embodiment under conditions of high stringency. Another aspect of the present invention is an isolated, purified, or enriched nucleic acid capable of hybridizing to the nucleic acid of this embodiment under conditions of moderate stringency. Another aspect of the present invention is an isolated, purified, or enriched nucleic acid capable of hybridizing to the nucleic acid of this embodiment under conditions of low stringency. Another aspect of the present invention is an isolated, purified, or enriched nucleic acid having at least 70% homology to the nucleic acid of this embodiment as determined by analysis with BLASTN version 2.0 with the default parameters. Another aspect of the present invention is an isolated, purified, or enriched nucleic acid having at least 99% homology to the nucleic acid of this embodiment as determined by analysis with BLASTN version 2.0 with the default parameters.

Another embodiment of the present invention is an isolated, purified, or enriched nucleic acid comprising at least 10 consecutive bases of a sequence selected from the group consisting of SEQ ID NOs: 3, 7, 11, 15, 17, 19, 21, 23, 35, 39, 43, 47, 49, 51, 53, 55, 69, 73, 77 and the sequences complementary thereto. One aspect of the present invention is an isolated, purified, or enriched nucleic acid having at least 70% homology to the nucleic acid of this embodiment as determined by analysis with BLASTN version 2.0 with the default parameters. Another aspect of the present invention is an isolated, purified, or enriched nucleic acid having at least 99% homology to the nucleic acid of this embodiment as determined by analysis with BLASTN version 2.0 with the default parameters.

Another embodiment of the present invention is an isolated, purified, or enriched nucleic acid encoding a polypeptide having a sequence selected from the group consisting of SEQ ID NOs: 6, 10, 14, 26, 28, 30, 32, 34, 38, 42, 46, 58, 60, 62, 64, 66, 68, 72, 76, and 80.

Another embodiment of the present invention is an isolated, purified, or enriched nucleic acid encoding a polypeptide comprising at least 10 consecutive amino acids of a polypeptide having a sequence selected from the group consisting of SEQ ID NOs: 6, 10, 14, 26, 28, 30, 32, 34, 38, 42, 46, 58, 60, 62, 64, 66, 68, 72, 76, and 80.

Another embodiment of the present invention is an isolated, purified, or enriched nucleic acid encoding a polypeptide having a sequence selected from the group consisting of SEQ ID NOs: 4, 8, 12, 16, 18, 20, 22, 24, 36, 40, 44, 48, 50, 52, 54, 56, 70, 74, and 78.

Another embodiment of the present invention is an isolated, purified, or enriched nucleic acid encoding a polypeptide comprising at least 10 consecutive amino acids of a polypeptide having a sequence selected from the group consisting of SEQ ID NOs: 4, 8, 12, 16, 18, 20, 22, 24, 36, 40, 44, 48, 50, 52, 54, 56, 70, 74, and 78.

Another embodiment of the present invention is an isolated or purified polypeptide comprising a sequence selected from the group consisting of SEQ ID NOs: 6, 10, 14, 26, 28, 30, 32, 34, 38, 42, 46, 58, 60, 62, 64, 66, 68, 72, 76, and 80. Another aspect of the present invention is an isolated or purified polypeptide comprising at least 10 consecutive amino acids of the polypeptides of this embodiment. Another aspect of the present invention is an isolated or purified polypeptide having at least 70% homology to the polypeptide of this embodiment as determined by analysis with FASTA version 3.0t78 with the default parameters. Another aspect of the present invention is an isolated or purified polypeptide having at least 99% homology to the polypeptide of this embodiment as determined by analysis with FASTA version 3.0t78 with the default parameters. Another aspect of the present invention is an isolated or purified polypeptide having at least 70% homology to an isolated or purified polypeptide comprising at least 10 consecutive amino acids of the polypeptides of this embodiment as determined by analysis with FASTA version 3.0t78 with the default parameters. Another aspect of the present invention is an isolated or purified polypeptide having at least 99% homology to the polypeptide of to an isolated or purified polypeptide comprising at least 10 consecutive amino acids of the polypeptides of this embodiment as determined by analysis with FASTA version 3.0t78 with the default parameters.

Another aspect of the present invention is an isolated or purified polypeptide comprising a sequence selected from the group consisting of SEQ ID NOs: 4, 8, 12, 16, 18, 20, 22, 24, 36, 40, 44, 48, 50, 52, 54, 56, 70, 74, and 78. One aspect of the present invention is an isolated or purified polypeptide comprising at least 10 consecutive amino acids of the polypeptides of this embodiment. Another aspect of the present invention is an isolated or purified polypeptide having at least 70% homology to the polypeptides of this embodiment as determined by analysis with FASTA version 3.0t78 with the default parameters. Another aspect of the present invention is an isolated or purified polypeptide having at least 99% homology to the polypeptides of this embodiment as determined by analysis with FASTA version 3.0t78 with the default parameters. Another aspect of the present invention is An isolated or purified polypeptide having at least 70% homology to an isolated or purified polypeptide comprising at least 10 consecutive amino acids of the polypeptides of this embodiment as determined by analysis with FASTA version 3.0t78 with the default parameters. Another aspect of the present invention is an isolated or purified polypeptide having at least 99% homology to an isolated or purified polypeptide comprising at least 10 consecutive amino acids of the polypeptides of this embodiment as determined by analysis with FASTA version 3.0t78 with the default parameters.

Another embodiment of the present invention is an isolated or purified antibody capable of specifically binding to a polypeptide comprising a sequence selected from the group consisting of SEQ ID NOs: 6, 10, 14, 26, 28, 30, 32, 34, 38, 42, 46, 58, 60, 62, 64, 66, 68, 72, 76, and 80.

Another embodiment of the present invention is an isolated or purified antibody capable of specifically binding to a polypeptide comprising at least 10 consecutive amino acids of one of the polypeptides of SEQ ID NOs: 6, 10, 14, 26, 28, 30, 32, 34, 38, 42, 46, 58, 60, 62, 64, 66, 68, 72, 76, and 80.

Another embodiment of the present invention is an isolated or purified antibody capable of specifically binding to a polypeptide having a sequence selected from the group consisting of SEQ ID NOs: 4, 8, 12, 16, 18, 20, 22, 24, 36, 40, 44, 48, 50, 52, 54, 56, 70, 74, and 78.

Another embodiment of the present invention is an isolated or purified antibody capable of specifically binding to a polypeptide comprising at least 10 consecutive amino acids of one of the polypeptides of SEQ ID NOs: 4, 8, 12, 16, 18, 20, 22, 24, 36, 40, 44, 48, 50, 52, 54, 56, 70, 74, and 78.

Another embodiment of the present invention is a method of making a polypeptide having a sequence selected from the group consisting of SEQ ID NOs: 6, 10, 14, 26, 28, 30, 32, 34, 38, 42, 46, 58, 60, 62, 64, 66, 68, 72, 76, and 80 comprising introducing a nucleic acid encoding said polypeptide, said nucleic acid being operably linked to a promoter, into a host cell.

Another embodiment of the present invention is a method of making a polypeptide comprising at least 10 amino acids of a sequence selected from the group consisting of the sequences of SEQ ID NOs: 6, 10, 14, 26, 28, 30, 32, 34, 38, 42, 46, 58, 60, 62, 64, 66, 68, 72, 76, and 80 comprising introducing a nucleic acid encoding said polypeptide, said nucleic acid being operably linked to a promoter, into a host cell.

Another embodiment of the present invention is a method of making a polypeptide having a sequence selected from the group consisting of SEQ ID NOs: 4, 8, 12, 16, 18, 20, 22, 24, 36, 40, 44, 48, 50, 52, 54, 56, 70, 74, and 78 comprising introducing a nucleic acid encoding said polypeptide, said nucleic acid being operably linked to a promoter, into a host cell.

Another embodiment of the present invention is a method of making a polypeptide comprising at least 10 amino acids of a sequence selected from the group consisting of the sequences of SEQ ID NOs: 4, 8, 12, 16, 18, 20, 22, 24, 36, 40, 44, 48, 50, 52, 54, 56, 70, 74, and 78 comprising introducing a nucleic acid encoding said polypeptide, said nucleic acid being operably linked to a promoter, into a host cell.

Another embodiment of the present i method of generating a variant comprising obtaining a nucleic acid comprising a sequence selected from the group consisting of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77, the sequences complementary to the sequences of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77, fragments comprising at least 30 consecutive nucleotides of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77, and fragments comprising at least 30 consecutive nucleotides of the sequences complementary to SEQ ID NOS. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 and changing one or more nucleotides in said sequence to another nucleotide, deleting one or more nucleotides in said sequence, or adding one or more nucleotides to said sequence. In one aspect of the present invention, the method further comprises the step of testing the enzymatic properties of a translation product of said variant.

Another embodiment of the present invention is a computer readable medium having stored thereon a sequence selected from the group consisting of a nucleic acid code of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 and a polypeptide code of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78.

Another embodiment of the present invention is a computer system comprising a processor and a data storage device wherein said data storage device has stored thereon a sequence selected from the group consisting of a nucleic acid code of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 and a polypeptide code of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78. In one aspect of the present invention, the computer system further comprises a sequence comparer and a data storage device having reference sequences stored thereon. For example, the sequence comparer may comprise a computer program which indicates polymorphisms. In another aspect of the present invention is the computer system of this embodiment further comprises an identifier which identifies features in said sequence.

Another embodiment of the present invention is a method for comparing a first sequence to a reference sequence wherein said first sequence is selected from the group consisting of a nucleic acid code of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 and a polypeptide code of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78 comprising the steps of reading said first sequence and said reference sequence through use of a computer program which compares sequences; and determining differences between said first sequence and said reference sequence with said computer program. In one aspect of the present invention, the step of determining differences between the first sequence and the reference sequence comprises identifying polymorphisms.

Another embodiment of the present invention is a method for identifying a feature in a sequence selected from the group consisting of a nucleic acid code of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 and a polypeptide code of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78 comprising the steps of reading said sequence through the use of a computer program which identifies features in sequences and identifying features in said sequence with said computer program.

BRIEF DESCRIPTION OF THE DRAWINGS

FIGS. 2A and 2B show(s) the sequences surrounding the TATA boxes of several promoters from *Cenarchaeum symbiosum* and the distances from the TATA boxes to the initiation codons in these sequences.

DEFINITIONS

Figure 1:
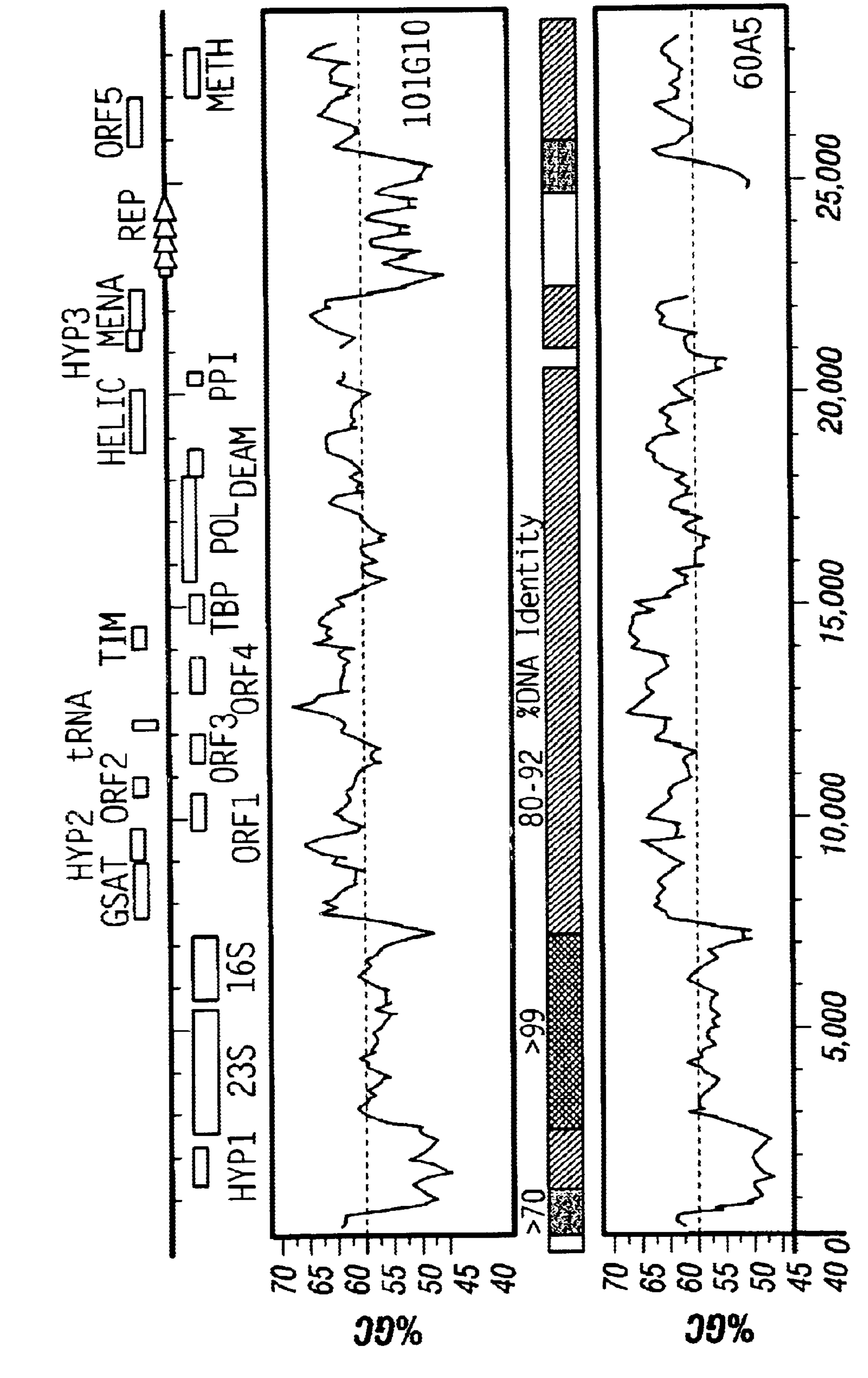
FIG. 1 shows the locations of coding regions, the %G-C. and the %DNA identity between the approximately 28 Kb of common sequence in fosmids 101G10 and 60A5.

The term "gene" means the segment of DNA involved in producing a polypeptide chain; it includes regions preceding and following the coding region (leader and trailer) as well as, where applicable, intervening sequences (introns) between individual coding segments (exons).

As used herein, the term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, the term "purified" does not require absolute purity; rather, it is intended as a relative definition. Individual nucleic acids obtained from a library have been conventionally purified to electrophoretic homogeneity. The sequences obtained from these clones could not be obtained directly either from the library or from total human DNA. The purified nucleic acids of the present invention have been purified from the remainder of the genomic DNA in the organism by at least $10^4$–$10^6$ fold. However, the term "purified" also includes nucleic acids which have been purified from the remainder of the genomic DNA or from other sequences in a library or other environment by at least one order of magnitude, preferably two or three orders, and more preferably four or five orders of magnitude.

As used herein, the term "recombinant" means that the nucleic acid is adjacent to "backbone" nucleic acid to which it is not adjacent in its natural environment. Additionally, to be "enriched" the nucleic acids will represent 5% or more of the number of nucleic acid inserts in a population of nucleic acid backbone molecules. Backbone molecules according to the present invention include nucleic acids such as expression vectors, self-replicating nucleic acids, viruses, integrating nucleic acids, and other vectors or nucleic acids used to maintain or manipulate a nucleic acid insert of interest. Preferably, the enriched nucleic acids represent 15% or more of the number of nucleic acid inserts in the population of recombinant backbone molecules. More preferably, the enriched nucleic acids represent 50% or more of the number of nucleic acid inserts in the population of recombinant backbone molecules. In a highly preferred embodiment, the enriched nucleic acids represent 90% or more of the number of nucleic acid inserts in the population of recombinant backbone molecules.

A promoter sequence is "operably linked to" a coding sequence when RNA polymerase which initiates transcription at the promoter will transcribe the coding sequence into mRNA.

"Recombinant" polypeptides or proteins refer to polypeptides or proteins produced by recombinant DNA techniques; i.e., produced from cells transformed by an exogenous DNA construct encoding the desired polypeptide or protein. "Synthetic" polypeptides or protein are those prepared by chemical synthesis.

A DNA "coding sequence" or a "nucleotide sequence encoding" a particular polypeptide or protein, is a DNA sequence which is transcribed and translated into a polypeptide or protein when placed under the control of appropriate regulatory sequences.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described herein are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the gel electrophoresis may be performed to isolate the desired fragment.

"Oligonucleotide" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

DETAILED DESCRIPTION OF THE PREFERRED EMBODIMENT

In order to begin the characterization of *Cenarchaeum symbiosum,* a large region of the *C. symbiosum* genome was sequenced. In particular, two overlapping *C. symbiosum*-derived fosmid inserts of approximately 42 kb and 33 kb were sequenced. The sequences of the two fosmid inserts revealed that there are at least two major variants or strains of *C. symbiosum* that coexist inside the sponge tissues of a single sponge. This complexity of the *C. symbiosum* population was not detected in initial studies based solely on direct sequencing of PCR amplified SSU genes. (Preston, C. M. et al. 1996. A psychrophilic crenarchaeon inhabits a marine sponge: *Cenarchaeum symbiosum* gen. *nov.,* sp. *nov. Proc. Natl. Acad. Sci.* USA 93, 6241–6246) This natural variation would also have been lost upon isolation of a pure culture.

The *Cenarchaeum symbiosum* sequences obtained from the two fosmids containing overlapping genomic inserts are provided in the accompanying sequence listing and are identified as SEQ ID NO: 1 and SEQ ID NO: 2. The two fosmid sequences were not entirely identical in their overlapping portions but instead contained differences. Upon further investigation, it was discovered that the two fosmid sequences were derived from two different, but closely related, strains of *Cenarchaeum symbiosum* (called variant A and variant B) which may simultaneously inhabit a single sponge.

Within the sequences of the fosmid inserts, numerous open reading frames encoding polypeptides having homology to known proteins, as well as open reading frames encoding proteins which do not exhibit homology to known proteins, were identified. Homology was determined using the program FASTA with the default parameters. The polypeptides encoded by these sequences are identified in the accompanying sequence listing as SEQ ID NOs: 6, 10, 14, 26, 28, 30, 32, 34, 38, 42, 46, 58, 60, 62, 64, 66, 68, 72, 76 and 80 (polypeptides with homology to known proteins) and SEQ ID NOs: 4, 8, 12, 16, 18, 20, 22, 24, 36, 40, 44, 48, 50, 52, 54, 56, 70, 74 and 78 (polypeptides without homology to known proteins). In addition, sequences encoding the 16S rRNA, the 23S rRNA and a tyrosine tRNAs were also identified.

One aspect of the present invention is an isolated, purified, or enriched nucleic acid comprising one of the sequences of SEQ ID NOs: 1, 2, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79 the sequences complementary thereto, or a fragment comprising at least 10, 15, 20, 25, 30, 35, 40, 50, 75, 100, 150, 200, 300, 400, or 500 consecutive bases of one of the sequences of SEQ ID NOs: 1, 2, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79 or the sequences complementary thereto. The isolated, purified or enriched nucleic acids may comprise DNA, including cDNA, genomic DNA, and synthetic DNA. The DNA may be double-stranded or single-stranded, and if single stranded may be the coding strand or non-coding (anti-sense) strand. Alternatively, the isolated, purified or enriched nucleic acids may comprise RNA.

As discussed in more detail below, the isolated, purified, or enriched nucleic acids of one of SEQ ID NOs: 1, 2, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79 may be used to prepare one of the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or fragments comprising at least 5, 10, 15, 20, 25, 30, 35, 40, 50, 75, 100, or 150 consecutive amino acids of one of the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80.

Accordingly, another aspect of the present invention is an isolated, purified, or enriched nucleic acid which encodes one of the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or fragments comprising at least 5, 10, 15, 20, 25, 30, 35, 40, 50, 75, 100, or 150 consecutive amino acids of one of the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80. The coding sequences of these nucleic acids may be identical to one of the coding sequences of one of the nucleic acids of SEQ ID NOs: 1, 2, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79 or a fragment thereof or may be different coding sequences which encode one of the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or fragments comprising at least 5, 10, 15, 20, 25, 30, 35, 40, 50, 75, 100, or 150 consecutive amino acids of one of the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 as a result of the redundancy or degeneracy of the genetic code. The genetic code is well known to those of skill in the art and can be obtained, for example, on page 214 of B. Lewin, Genes VI, Oxford University Press, 1997, the disclosure of which is incorporated herein by reference.

The isolated, purified, or enriched nucleic acid which encodes one of the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 may include, but is not limited to: only the coding sequence of one of SEQ ID NOs: 1, 2, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79; the coding sequences of SEQ ID NOs: 1, 2, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79 and additional coding sequences, such as leader sequences or proprotein sequences; or the coding sequences of SEQ ID NOs: 1, 2, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79 and non-coding sequences, such as introns or non-coding sequences 5' and/or 3' of the coding sequence. Thus, as used herein, the term "polynucleotide encoding a polypeptide" encompasses a polynucleotide which includes only coding sequence for the polypeptide as well as a polynucleotide which includes additional coding and/or non-coding sequence.

Alternatively, the nucleic acid sequences of SEQ ID NOs: 1, 2, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79 may be mutagenized using conventional techniques, such as site directed mutagenesis, or other techniques familiar to those skilled in the art, to introduce silent changes into the polynucleotides of SEQ ID NOs: 1, 2, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79. As used herein, "silent changes" include, for example, changes which do not alter the amino acid sequence encoded by the polynucleotide. Such changes may be desirable in order to increase the level of the polypeptide produced by host cells containing a vector encoding the polypeptide by introducing codons or codon pairs which occur frequently in the host organism.

The present invention also relates to polynucleotides which have nucleotide changes which result in amino acid substitutions, additions, deletions, fusions and truncations in the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80. Such nucleotide changes may be introduced using techniques such as site directed mutagenesis, random chemical mutagenesis, exonuclease III deletion, and other recombinant DNA techniques. Alternatively, such nucleotide changes may be naturally occurring allelic variants which are isolated by identifying nucleic acids which specifically hybridize to probes comprising at least 10, 15, 20, 25, 30, 35, 40, 50, 75, 100, 150, 200, 300, 400, or 500 consecutive bases of one of the sequences of SEQ ID NOs: 1, 2, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79 or the sequences complementary thereto to nucleic acids from *Cenarchaeum symbiosum* or related organisms under conditions of high, moderate, or low strigency as provided herein.

The isolated, purified, or enriched nucleic acids of SEQ ID NOs: 1, 2, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79, the sequences complementary thereto, or a fragment comprising at least 10, 15, 20, 25, 30, 35, 40, 50, 75, 100, 150, 200, 300, 400, or 500 consecutive bases of one of the sequences of SEQ ID NOs: 1, 2, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79 or the sequences complementary thereto may also be used as probes to identify the presence of *Cenarchaeum symbiosum* in a biological sample. In such procedures, a biological sample potentially harboring *Cenarchaeum symbiosum* is obtained and nucleic acids are obtained from the sample. The nucleic acids are contacted with the probe under conditions which permit the probe to specifically hybridize to any complementary sequences from *Cenarchaeum symbiosum* which are present therein.

Where necessary, conditions which permit the probe to specifically hybridize to complementary sequences from *Cenarchaeum symbiosum* may be determined by placing the probe in contact with complementary sequences from *Cenarchaeum symbiosum* as well as control sequences which are not from *Cenarchaeum symbiosum*. In some analyses, the control sequences may be from organisms related to *Cenarchaeum symbiosum*. Alternatively, the control sequences may be from organisms which are not related to *Cenarchaeum symbiosum*. Hybridization conditions, such as the salt concentration of the hybridization buffer, the formamide concentration of the hybridization buffer, or the hybridization temperature, may be varied to identify conditions which allow the probe to hybridize specifically to nucleic acids from *Cenarchaeum symbiosum*.

If the sample contains nucleic acids from *Cenarchaeum symbiosum*, specific hybridization of the probe to the nucleic acids from *Cenarchaeum symbiosum* is then detected. Hybridization may be detected by labeling the probe with a detectable agent such as a radioactive isotope, a fluorescent dye or an enzyme capable of catalyzing the formation of a detectable product.

Many methods for using the labeled probes to detect the presence of nucleic acids from *Cenarchaeum symbiosum* in a sample are familiar to those skilled in the art. These include Southern Blots, Northern Blots, colony hybridization procedures, and dot blots. Protocols for each of these procedures are provided in Ausubel et al. Current Protocols in Molecular Biology, John Wiley 503 Sons, Inc. 1997 and Sambrook et al., Molecular Cloning: A Laboratory Manual 2d Ed., Cold Spring Harbor Laboratory Press, 1989, the entire disclosures of which are incorporated herein by reference.

Alternatively, more than one probe (at least one of which is capable of specifically hybridizing to any complementary sequences from *Cenarchaeum symbiosum* which are present in the nucleic acid sample), may be used in an amplification reaction to determine whether the nucleic acid sample contains nucleic acids from *Cenarchaeum symbiosum*. Preferably, the probes comprise oligonucleotides. In one embodiment, the amplification reaction may comprise a PCR reaction. PCR protocols are described in Ausubel and Sambrook, supra. Alternatively, the amplification may comprise a ligase chain reaction, 3SR, or strand displacement reaction. (See Barany, F., "The Ligase Chain Reaction in a PCR World", *PCR Methods and Applications* 1:5–16 (1991); E. Fahy et al., "Self-sustained Sequence Replication (3SR): An Isothermal Transcription-based Amplification System Alternative to PCR", *PCR Methods and Applications* 1:25–33 (1991); and Walker G. T. et al., "Strand Displacement Amplification-an Isothermal in vitro DNA Amplification Technique, *Nucleic Acid Research* 20:1691–1696 (1992) the disclosures of which are incorporated herein by reference in their entireties). In such procedures, the nucleic acids in the sample are contacted with the probes, the amplification reaction is performed, and any resulting amplification product is detected. The amplification product may be detected by performing gel electrophoresis on the reaction products and staining the gel with an interculator such as ethidium bromide. Alternatively, one or more of the probes may be labeled with a radioactive isotope and the presence of a radioactive amplification product may be detected by autoradiography after gel electrophoresis.

Probes derived from sequences near the ends of the sequences of SEQ ID Nos: 1 and 2 may also be used in chromosome walking procedures to identify clones containing genomic sequences located adjacent to the sequences of SEQ ID Nos: 1 and 2. Such methods allow the isolation of genes which encode additional proteins expressed in *Cenarchaeum symbiosum* and facilitate the further physiological characterization of the organism.

Another aspect of the present invention is a method for determining whether a sample contains variant A and/or variant B of *Cenarchaeum symbiosum.* In such procedures, a sample potentially harboring variant A and/or variant B *Cenarchaeum symbiosum* is obtained and nucleic acids are obtained from the sample. The nucleic acids are contacted with the probe under conditions which permit the probe to specifically hybridize to any complementary sequences from variant A or variant B of *Cenarchaeum symbiosum* which are present therein. Preferably, the probe comprises a sequence having one or more nucleotides which differ between variant A and variant B. Conditions in which the probe specifically hybridizes to nucleic acids from one of the variants but not to nucleic acids from the other variant may be determined by contacting the probe with its corresponding sequence from variant A and variant B and varying the hybridization conditions, such as the salt concentration of the hybridization buffer, the formamide concentration of the buffer, or the hybridization temperature, to identify conditions in which the probe hybridizes to the corresponding sequence from one variant but not to the corresponding sequence from the other variant. Hybridization of the probe to nucleic acids from the *Cenarchaeum symbiosum* variant is then detected using any of the procedures described above.

The isolated, purified, or enriched nucleic acids of SEQ ID NOs: 1, 2, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79, the sequences complementary thereto, or a fragment comprising at least 10, 15, 20, 25, 30, 35, 40, 50, 75, 100, 150, 200, 300, 400, or 500 consecutive bases of one of the sequences of SEQ ID NOs: 1, 2, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79 or the sequences complementary thereto may be used as probes to identify and isolate cDNAs encoding the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80. In such procedures, a cDNA library is constructed from a sample containing *Cenarchaeum symbiosum.* The cDNA library is then contacted with a probe comprising a coding sequence, or a fragment of a coding sequence, encoding one of the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or a fragment thereof under conditions which permit the probe to specifically hybridize to sequences complementary thereto. cDNAs which hybridize to the probe are then detected and isolated. Procedures for preparing and identifying cDNAs are disclosed in Ausubel et al. Current Protocols in Molecular Biology, John Wiley 503 Sons, Inc. 1997 and Sambrook et al., Molecular Cloning: A Laboratory Manual 2d Ed., Cold Spring Harbor Laboratory Press, 1989, the disclosures of which are incorporated herein by reference.

The isolated, purified, or enriched nucleic acids of SEQ ID NOs: 1, 2, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79, the sequences complementary thereto, or a fragment comprising at least 10, 15, 20, 25, 30, 35, 40, 50, 75, 100, 150, 200, 300, 400, or 500 consecutive bases of one of the sequences of SEQ ID NOs: 1, 2, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79 or the sequences complementary thereto may be used as probes to identify and isolate related nucleic acids. In some embodiments, the related nucleic acids may be cDNAs or genomic DNAs from organisms other than *Cenarchaeum symbiosum.* For example, the other organisms may be organisms which are related to *Cenarchaeum symbiosum.* In such procedures, a nucleic acid sample containing nucleic acids from the related organism, such as a cDNA or genomic DNA library from the related organism, is contacted with the probe under conditions which permit the probe to specifically hybridize to related sequences. Hybridization of the probe to nucleic acids from the related organism is then detected using any of the methods described above.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's, and 0.5 mg/ml polyriboadenylic acid. Approximately $2\times10^7$ cpm (specific activity 4–$9\times10^8$ cpM/ug) of $^{32}P$ end-labeled oligonucleotide probe are then added to the solution. After 12–16 hours of incubation, the membrane is washed for 30 minutes at room temperature in 1×SET (150 mM NaCl, 20 mM Tris hydrochloride, pH 7.8, 1 mM $Na_2EDTA$) containing 0.5% SDS, followed by a 30 minute wash in fresh 1×SET at Tm-10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature of the probe may be calculated using the following formulas:

For probes between 14 and 70 nucleotides in length the melting temperature (Tm) is calculated using the formula: Tm=81.5+16.6(log [Na+])+0.41(fraction G+C)−(600/N) where N is the length of the probe.

If the hybridization is carried out in a solution containing formamide, the melting temperature may be calculated using the equation Tm=81.5+16.6(log [Na+])+0.41(fraction G+C)−(0.63% formamide)−(600/N) where N is the length of the probe.

Prehybridizationmay be carried out in 6×SSC, 5×Denhardt's reagent, 0.5% SDS, 100 μg denatured fragmented salmon sperm DNA or 6×SSC, 5×Denhardt's reagent, 0.5% SDS, 100 μg denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15–25° C. below the Tm. For shorter probes, such as oligonucleotide probes, the hybridization may be conducted at 5–10° C. below the Tm. Preferably, for hybridizations in 6×SSC, the hybridization is conducted at approximately 68° C. Preferably, for hybridizations in 50% formamide containing solutions, the hybridization is conducted at approximately 42° C.

All of the foregoing hybridizations would be considered to be under conditions of high stringency.

Following hybridization, the filter is washed in 2×SSC, 0.1% SDS at room temperature for 15 minutes. The filter is then washed with 0.1×SSC, 0.5% SDS at room temperature for 30 minutes to 1 hour. Thereafter, the solution is washed at the hybridization temperature in 0.1×SSC, 0.5% SDS. A final wash is conducted in 0.1×SSC at room temperature.

Nucleic acids which have hybridized to the probe are identified by autoradiography or other conventional techniques.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

Nucleic acids which have hybridized to the probe are identified by autoradiography.

For example, the preceding methods may be used to isolate nucleic acids having a sequence with at least 97%, at least 95%, at least 90%, at least 85%, at least 80%, or at least 70% homology to a nucleic acid sequence selected from the group consisting of one of the sequences of SEQ ID NOS. 1, 2, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79, fragments comprising at least 10, 15, 20, 25, 30, 35, 40, 50, 75, 100, 150, 200, 300, 400, or 500 consecutive bases thereof, and the sequences complementary thereto. Homology may be measured using BLASTN version 2.0 with the default parameters. For example, the homologous polynucleotides may have a coding sequence which is a naturally occurring allelic variant of one of the coding sequences described herein. Such allelic variants may have a substitution, deletion or addition of one or more nucleotides when compared to the nucleic acids of SEQ ID NOs: 1, 2, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 and 79 or the sequences complementary thereto.

Additionally, the above procedures may be used to isolate nucleic acids which encode polypeptides having at least 99%, 95%, at least 90%, at least 85%, at least 80%, or at least 70% homology to a polypeptide having the sequence of one of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or fragments comprising at least 5, 10, 15, 20, 25, 30, 35, 40, 50, 75, 100, or 150 consecutive amino acids thereof as determined using the FASTA version 3.0t78 algorithm with the default parameters.

Another aspect of the present invention is an isolated or purified polypeptide comprising the sequence of one of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or fragments comprising at least 5, 10, 15, 20, 25, 30, 35, 40, 50, 75, 100, or 150 consecutive amino acids thereof. As discussed above, such polypeptides may be obtained by inserting a nucleic acid encoding the polypeptide into a vector such that the coding sequence is operably linked to a sequence capable of driving the expression of the encoded polypeptide in a suitable host cell. For example, the expression vector may comprise a promoter, a ribosome binding site for translation initiation and a transcription terminator. The vector may also include appropriate sequences for amplifying expression.

Promoters suitable for expressing the polypeptide or fragment thereof in bacteria include the *E. coli.* lac or trp promoters, the lacI promoter, the lacZ promoter, the T3 promoter, the trp promoter, the gpt promoter, the lambda $P_R$ promoter, the lambda $P_L$ promoter the trp promoter, promoters from operons encoding glycolytic enzymes such as 3-phosphoglycerate kinase (PGK), and the acid phosphatase promoter. Fungal promoters include the α factor promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Mammalian expression vectors may also comprise an origin of replication, any necessary ribosome binding sites, a polyadenylation site, splice donor and acceptor sites, transcriptional termination sequences, and 5' flanking nontranscribed sequences. In some embodiments, DNA sequences derived from the SV40 splice and polyadenylation sites may be used to provide the required nontranscribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

In addition, the expression vectors preferably contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in E. coli, and the S. cerevisiae TRP1 gene.

In some embodiments, the nucleic acid encoding one of the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or fragments comprising at least 5, 10, 15, 20, 25, 30, 35, 40, 50, 75, 100, or 150 consecutive amino acids thereof is assembled in appropriate phase with a leader sequence capable of directing secretion of the translated polypeptide or fragment thereof. Optionally, the nucleic acid can encode a fusion polypeptide in which one of the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or fragments comprising at least 5, 10, 15, 20, 25, 30, 35, 40, 50, 75, 100, or 150 consecutive amino acids thereof is fused to heterologous peptides or polypeptides, such as N-terminal identification peptides which impart desired characteristics, such as increased stability or simplified purification.

The appropriate DNA sequence may be inserted into the vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are disclosed in Ausubel et al. Current Protocols in Molecular Biology, John Wiley 503 Sons, Inc. 1997 and Sambrook et al., Molecular Cloning: A Laboratory Manual 2d Ed., Cold Spring Harbor Laboratory Press, 1989, the entire disclosures of which are incorporated herein by reference. Such procedures and others are deemed to be within the scope of those skilled in the art.

The vector may be, for example, in the form of a plasmid, a viral particle, or a phage. Other vectors include chromosomal, nonchromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

The host cell may be any of the host cells familiar to those skilled in the art, including prokaryotic cells, eukaryotic cells, mammalian cells, insect cells, or plant cells. As representative examples of appropriate hosts, there may be mentioned: bacterial cells, such as E. coli, Streptomyces, Bacillus subtilis, Salmonella typhimurium and various species within the genera Pseudomonas, Streptomyces, and Staphylococcus, fungal cells, such as yeast, insect cells such as Drosophila S2 and Spodoptera Sf9, animal cells such as CHO, COS or Bowes melanoma, and adenoviruses. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transfornants or amplifying the genes of the present invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described by Gluzman, Cell, 23:175 (1981), and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Alternatively, the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or fragments comprising at least 5, 10, 15, 20, 25, 30, 35, 40, 50, 75, 100, or 150 consecutive amino acids thereof can be synthetically produced by conventional peptide synthesizers. In other embodiments, fragments or portions of the polypeptides may be employed for producing the corresponding full-length polypeptide by peptide synthesis; therefore, the fragments may be employed as intermediates for producing the full-length polypeptides.

Cell-free translation systems can also be employed to produce one of the polypeptides of SEQ ID Nos: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or fragments comprising at least 5, 10, 15, 20, 25, 30, 35, 40, 50, 75, 100, or 150 consecutive amino acids thereof using mRNAs transcribed from a DNA construct comprising a promoter operably linked to a nucleic acid encoding the polypeptide or fragment thereof. In some embodiments, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The present invention also relates to variants of the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or fragments comprising at least 5, 10, 15, 20, 25, 30, 35, 40, 50, 75, 100, or 150 consecutive amino acids thereof. The term "variant" includes derivatives or analogs of these polypeptides. In particular, the variants may differ in amino acid sequence from the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 by one or more substitutions, additions, deletions, fusions and truncations, which may be present in any combination.

The variants may be naturally occurring or created in vitro. In particular, such variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures.

Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. Preferably, these nucleotide differences result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described in Leung, D. W., et al., Technique, 1:11–15 (1989) and Caldwell, R. C. & Joyce G. F., PCR Methods Applic., 2:28–33 (1992), the disclosure of which is incorporated herein by reference in its entirety. Briefly, in such procedures, nucleic acids to be mutagenized are mixed with PCR primers, reaction buffer, $MgCl_2$, $MnCl_2$, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA segment of interest. Oligonucleotide mutagenesis is described in Reidhaar-Olson, J. F. & Sauer, R. T., et al., Science, 241:53–57 (1988), the disclosure of which is incorporated herein by reference in its entirety. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in U.S. patent application Ser. No. 08/677,112, filed Jul. 9, 1997 and U.S. patent application Ser. No. 08/942,504, filed Oct. 31, 1997, the disclosures of which are incorporated herein by reference in their entireties.

Still another method of genrating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described in Stemmer, W. P., PNAS, USA, 91:10747–10751 (1994), the disclosure of which is incorporated herein by reference. Briefly, in such procedures a plurality of nucleic acids to be recombined are digested with DNAse to generate fragments having an average size of 50–200 nucleotides. Fragments of the desired average size are purifed and resuspended in a PCR mixture. PCR is conducted under conditions which facilitate recombination between the nucleic acid fragments. For example, PCR may be performed by resuspending the purified fragments at a concentration of 10–30 ng/$\mu$l in a solution of 0.2 mM of each dNTP, 2.2 mM MgCl2, 50 mM KCL, 10 mM Tris HCl, pH 9.0, and 0.1% Triton X-100. 2.5 units of Taq polymerase per 100 $\mu$l of reaction mixture is added and PCR is performed using the following regime: 94° C. for 60 seconds, 94° C. for 30 seconds, 50–55° C. for 30 seconds, 72° C. for 30 seconds (30–45 times) and 72° C. for 5 minutes. However, it will be appreciated that these parameters may be varied as appropriate. In some embodiments, oligonucleotides may be included in the PCR reactions. In other embodiments, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some embodiments, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described in PCT Published Application WO 91/16427, the disclosure of which is incorporated herein by reference in its entirety.

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in Arkin, A. P. and Youvan, D. C., PNAS, USA, 89:7811–7815 (1992), the disclosure of which is incorporated herein by reference in its entirety.

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in Delegrave, S. and Youvan, D. C., Biotechnology Research, 11:1548–1552 (1993), the disclosure of which incorporated herein by reference in its entirety. Random and site-directed mutagenesis are described in Arnold, F. H., Current Opinion in Biotechnology, 4:450–455 (1993), the disclosure of which is incorporated herein by reference in its entirety.

In some embodiments, the variants are created using shuffling procedures wherein portions of a plurality of nucleic acids which encode distinct polypeptides are fused together to create chimeric nucleic acid sequences which encode chimeric polypeptides. Shuffling procedures are described in U.S. patent application Ser. No. 08/677,112, filed Jul. 9, 1996, U.S. patent application Ser. No. 08/942, 504, filed Oct. 31, 1997, U.S. Pat. No. 5,939,250, issued Aug. 17, 1999, and U.S. patent application Ser. No. 09/375, 605, filed Aug. 17, 1999, the disclosures of which are incorporated herein by reference in their entireties.

The variants of the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 may be (i) variants in which one or more of the amino acid residues of the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 are substituted with a conserved or non-conserved amino acid residue (preferably a conserved amino acid residue) and such substituted amino acid residue may or may not be one encoded by the genetic code.

Conservative substitutions are those that substitute a given amino acid in a polypeptide by another amino acid of like characteristics. Typically seen as conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp and Glu with another acidic residue; replacement of a residue bearing an amide group, such as Asn and Gln, with another residue bearing an amide group; exchange of a basic residue such as Lys and Arg with another basic residue; and replacement of an aromatic residue such as Phe, Tyr with another aromatic residue.

Other variants are those in which one or more of the amino acid residues of the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 includes a substituent group.

Still other variants are those in which the polypeptide is associated with another compound, such as a compound to increase the half-life of the polypeptide (for example, polyethylene glycol).

Additional variants are those in which additional amino acids are fused to the polypeptide, such as a leader sequence, a secretory sequence, a proprotein sequence or a sequence which facilitates purification, enrichment, or stabilization of the polypeptide.

In some embodiments, the fragments, derivatives and analogs retain the same biological function or activity as the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80. In other embodiments, the fragment, derivative, or analog includes a proprotein, such that the fragment, derivative, or analog can be activated by cleavage of the proprotein portion to produce an active polypeptide.

Another aspect of the present invention are polypeptides or fragments thereof which have at least 70%, at least 80%, at least 85%, at least 90%, at least 95%, or more than 95% homology to one of the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or a fragment comprising at least 5, 10, 15, 20, 25, 30, 35, 40, 50, 75, 100, or 150 consecutive amino acids thereof. Homology may be determined using a program, such as FASTA version 3.0t78 with the default parameters, which aligns the polypeptides or fragments being compared and determines the extent of amino acid identity or similarity between them. It will be appreciated that amino acid "homology" includes conservative amino acid substitutions such as those described above.

The polypeptides or fragments having homology to one of the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or a fragment comprising at least 5, 10, 15, 20, 25, 30, 35, 40, 50, 75, 100, or 150 consecutive amino acids thereof may be obtained by isolating the nucleic acids encoding them using the techniques described above.

Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to one of the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or a fragment comprising at least 5, 10, 15, 20, 25, 30, 35, 40, 50, 75, 100, or 150 consecutive amino acids thereof using a program such as FASTA version 3.0t78 with the default parameters.

The polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or fragments comprising at least 5, 10, 15, 20, 25, 30, 35, 40, 50, 75, 100, or 150 consecutive amino acids thereof invention may be used in a variety of applications. For example, the polypeptides or fragments thereof may be used to catalyze biochemical reactions. In particular, the polypeptides of SEQ ID NOs: 14 and 46, which have homology to glutamate semialdehyde amino transferase, or fragments thereof, may be used to catalyze the synthesis of 5-aminolevulinate from S-4-amino-5-oxopentanoate. The polypeptides of SEQ ID NOs: 26 and 58, which have homology to triose phosphate isomerase, or fragments thereof, may be used to catalyze the synthesis of glycerone phosphate from D-glyceraldehyde 3-phosphate. The polypeptides of SEQ ID NOs: 32 and 64, which have homology to dCMP deaminase, or fragments thereof, may be used to catalyze the reaction of deoxyctidine and water to produce deoxyuridine and ammonia. The polypeptides of SEQ ID NOs: 38 and 72, which have homology to the MenA protein, or fragments thereof, may be used to catalyze the synthesis of menaquinone. The polypeptide of SEQ ID NO: 80, which has homology to glucose-1-dehydrogenase, may be used to catalyze the synthesis of D-glucono-1,5-lacctone from D-glucose.

The polypeptide of SEQ ID NO: 10, which has homology to lysyl tRNA synthetase, or fragments thereof, may be used to identify compounds capable of specifically inhibiting the growth of *Cenarchaeum symbiosis,* since tRNA synthetases are attractive targets for agents which inhibit growth.

Agents which specifically inhibit the activity of the lysyl tRNA synthetase from *Cenarchaeum symbiosum* may be identified using a variety of methods known to those skilled in the art. For example, a plurality of agents may be generated using combinatorial chemistry or recombinant DNA libraries encoding a large number of short peptides. The lysyl tRNA synthetases from *Cenarchaeum symbiosum* and control organisms are contacted with the agents and those agents which bind to the lysyl tRNA synthetase from *Cenarchaeum symbiosum* but not to the enzyme from the control organisms are identified. *Cenarchaeum symbiosum* is then contacted with the identified agents to determine which agents inhibit the organism's growth.

The polypeptides of SEQ ID NOs: 28 and 60, which have homology to the TATA box binding protein, or fragments thereof, may be used to identify promoters in nucleic acids from *Cenarchaeum symbiosis.* In such procedures, the polypeptide or fragment thereof is allowed to contact the nucleic acid and binding of the polypeptide or fragment thereof to the nucleic acid is detected. Binding may be detected by performing a gel shift analysis, a nuclease protection analysis, or by detecting the retention of the nucleic acid on a column matrix having the TATA box binding protein, or a fragment thereof, affixed thereto.

Compounds which specifically inhibit the binding of the TATA box binding protein of *Cenarchaeum symbiosis* to promoters may also be used to inhibit growth of the organism. Such compounds may be identified as described above.

Similarly, agents which specifically inhibit the activity of the polypeptides of SEQ ID NOs: 34 and 66, which have homology to RNA helicase, may be used to inhibit the growth of *Cenarchaeum symbiosis.* Such agents may be identified as described above.

The polypeptides of SEQ ID NOs: 30 and 62, which have homology to DNA polymerase I, or fragments thereof, may be used to insert a detectable label into a nucleic acid or to generate blunt ends on nucleic acids which have been digested with a restriction endonuclease.

The polypeptides of SEQ ID NOs: 42 and 76, which have homology to site specific DNA methyltranseferases, or fragments thereof, may be used in procedures in which it is desirable to protect nucleic acid sequences from digestion with restriction endonucleases. For example, a nucleic acid sequence having one or more restriction sites therein may be treated with the polypeptides of SEQ ID NOs: 42 or 76 prior to the addition of linkers to the nucleic acid. Thereafter, the linkers may be digested with the restriction enzyme, while the sites in the remainder of the nucleic acid are protected from digestion.

The polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80, or fragments comprising at least 5, 10, 15, 20, 25, 30, 35, 40, 50, 75, 100, or 150 consecutive amino acids thereof, may also be used to generate antibodies which bind specifically to the polypeptides or fragments. The resulting antibodies may be used to determine whether a biological sample contains *Cenarchaeum symbiosum.* In such procedures, a biological sample is contacted with an antibody capable of specifically binding to one of the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or fragments comprising at least 5, 10, 15, 20, 25, 30, 35,40,50, 75, 100, or 150 consecutive amino acids thereof. The ability of the biological sample to bind to the antibody is then determined. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. A variety of assay protocols which may be used to detect the presence of *Cenarchaeum symbiosum* in a sample are familiar to those skilled in the art. Particular assays include ELISA assays, sandwich assays, radioimmunoassays, and Western Blots.

Polyclonal antibodies generated against the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or fragments comprising at least 5, 10, 15, 20, 25, 30, 35, 40, 50, 75, 100, or 150 consecutive amino acids thereof can be obtained by direct injection of the polypeptides into an animal or by administering the polypeptides to an animal, preferably a nonhuman. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique (Kohler and Milstein, 1975, Nature, 256:495–497, the disclosure of which is incorporated herein by reference), the trioma technique, the human B-cell hybridoma technique (Kozbor et al., 1983, Immunology Today 4:72, the disclosure of which is incorporated herein by reference), and the EBV-hybridoma technique (Cole, et al., 1985, in Monoclonal Antibodies and Cancer Therapy, Alan R. Liss, Inc., pp. 77–96, the disclosure of which is incorporated herein by reference).

Techniques described for the production of single chain antibodies (U.S. Pat. No. 4,946,778, the disclosure of which is incorporated herein by reference) can be adapted to produce single chain antibodies to the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or fragments comprising at least 5, 10, 15, 20, 25, 30, 35, 40, 50, 75, 100, or 150 consecutive amino acids thereof. Alternatively, transgenic mice may be used to express humanized antibodies to these polypeptides or fragments thereof.

Antibodies generated against the polypeptides of SEQ ID NOs: 4, 6, 8, 10, 12, 14, 16, 18, 20, 22, 24, 26, 28, 30, 32, 34, 36, 38, 40, 42, 44, 48, 50, 52, 54, 56, 58, 60, 62, 64, 66, 68, 70, 72, 74 76, 78, and 80 or fragments comprising at least 5, 10, 15, 20, 25, 30, 35, 40, 50, 75, 100, or 150 consecutive amino acids thereof may be used in screening for similar polypeptides from other organisms and samples. In such techniques, polypeptides from the organism are contacted with the antibody and those polypeptides which specifically bind the antibody are detected. Any of the procedures described above may be used to detect antibody binding. One such screening assay is described in "Methods for Measuring Cellulase Activities", *Methods in Enzymology,* Vol 160, pp. 87–116, which is hereby incorporated by reference in its entirety.

As used herein the term "nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77" encompasses the nucleotide sequences of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77, fragments of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77, nucleotide sequences homologous to SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 or homologous to fragments of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77, and sequences complementary to all of the preceding sequences. The fragments include portions of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 comprising at least 10, 15, 20, 25, 30, 35, 40, 50, 75, 100, 150, 200, 300, 400, or 500 consecutive nucleotides of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77. Preferably, the fragments are novel fragments. Homologous sequences and fragments of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 refer to a sequence having at least 99%, 98%, 97%, 96%, 95%, 90%, 85%, 80%, 75% or 70% homology to these sequences. Homology may be determined using any of the computer programs and parameters described herein, including BLASTN version 2.0 with the default parameters. Homologous sequences also include RNA sequences in which uridines replace the thymines in the nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77. The homologous sequences may be obtained using any of the procedures described herein or may result from the correction of a sequencing error. It will be appreciated that the nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 can be represented in the traditional single character format (See the inside back cover of Stryer, Lubert. *Biochemistry,* 3rd edition. W. H Freeman & Co., New York.) or in any other format which records the identity of the nucleotides in a sequence.

As used herein the term "polypeptide codes of SEQ ID NOS. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78"encompasses the polypeptide sequence of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78 which are encoded by the extended cDNAs of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77, polypeptide sequences homologous to the polypeptides of SEQ ID NOS. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78, or fragments of any of the preceding sequences. Homologous polypeptide sequences refer to a polypeptide sequence having at least 99%, 98%, 97%, 96%, 95%, 90%, 85%, 80%, 75% or 70% homology to one of the polypeptide sequences of SEQ ID NOS. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78. Homology may be determined using any of the computer programs and parameters described herein, including FASTA version 3.0t78 with the default parameters or with any modified parameters. The homologous sequences may be obtained using any of the procedures described herein or may result from the correction of a sequencing error. The polypeptide fragments comprise at least 5, 10, 15, 20, 25, 30, 35, 40, 50, 75, 100, or 150 consecutive amino acids of the polypeptides of SEQ ID NOS. 6, 10, 14, 26,28, 30, 32, 34, 38, 42, 46, 58, 60, 62, 64, 66, 68, 72, 76, 80,4, 8, 12, 16, 18, 20, 22, 24, 36, 40, 44, 48, 50, 52, 54, 56, 70, 74, and 78. Preferably, the fragments are novel fragments. It will be appreciated that the polypeptide codes of the SEQ ID NOS. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78 can be represented in the traditional single character format or three letter format (See the inside back cover of Starrier, Lubert. *Biochemistry,* 3rd edition. W. H Freeman & Co., New York.) or in any other format which relates the identity of the polypeptides in a sequence.

It will be appreciated by those skilled in the art that the nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 and polypeptide codes of SEQ ID NOS. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78 can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77, one or more of the polypeptide codes of SEQ ID NOS. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78. Another aspect of the present invention is a computer readable medium having recorded thereon at least 2, 5, 10, 15, or 20 nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77.

Another aspect of the invention is a computer readable medium having recorded thereon one or more of the nucleic acid codes of SEQ ID NOs. 1, 2, 5, 9, 13, 25, 27, 29, 31, 33, 37, 41, 45, 57, 59, 61, 63, 65, 67, 71, 75, and 79. Another aspect of the present invention is a computer readable medium having recorded thereon at least 2, 5, 10, or 15 of SEQ ID NOs. 1, 2, 5, 9, 13, 25, 27, 29, 31, 33, 37, 41, 45, 57, 59, 61, 63, 65, 67, 71, 75, and 79.

Another aspect of the present invention is a computer readable medium having recorded thereon one or more of the nucleic acid codes of SEQ ID NOs. 3, 7, 11, 15, 17, 19, 21, 23, 35, 39, 43, 47, 49, 51, 53, 55, 69, 73 and 77. Another aspect of the present invention is a computer readable medium having recorded thereon at least 2, 5, 10, or 15 of SEQ ID NOs. 3, 7, 11, 15, 17, 19, 21, 23, 35, 39, 43, 47, 49, 51, 53, 55, 69, 73 and 77.

Another aspect of the present invention is a computer readable medium having recorded thereon one or more of the polypeptide codes of SEQ ID NOS. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78. Another aspect of the present invention is a computer readable medium having recorded thereon one or more of the the polypeptide codes of SEQ ID NOS. 6, 10, 14, 26, 28, 30, 32, 34, 38, 42, 46, 58, 60, 62, 64, 66, 68, 72, 76, and 80. Another aspect of the present invention is a computer readable medium having recorded thereon one or more of the the polypeptide codes of SEQ ID NOS. 4, 8, 12, 16, 18, 20, 22, 24, 36, 40, 44, 48, 50, 52, 54, 56, 70, 74, and 78.

Another aspect of the present invention is a computer readable medium having recorded thereon at least 2, 5, 10, 15, or 20 polypeptide codes of SEQ ID NOS. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78. Another aspect of the present invention is a computer readable medium having recorded thereon at least 2, 5, 10, or 15 polypeptide codes of SEQ ID NOS. 6, 10, 14, 26, 28, 30, 32, 34, 38, 42, 46, 58, 60, 62, 64, 66, 68, 72, 76, and 80. Another aspect of the present invention is a computer readable medium having recorded thereon at least 2, 5, 10, or 15 polypeptide codes of SEQ ID NOS. 4, 8, 12, 16, 18, 20, 22, 24, 36, 40, 44, 48, 50, 52, 54, 56, 70, 74, and 78.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Figure 3:
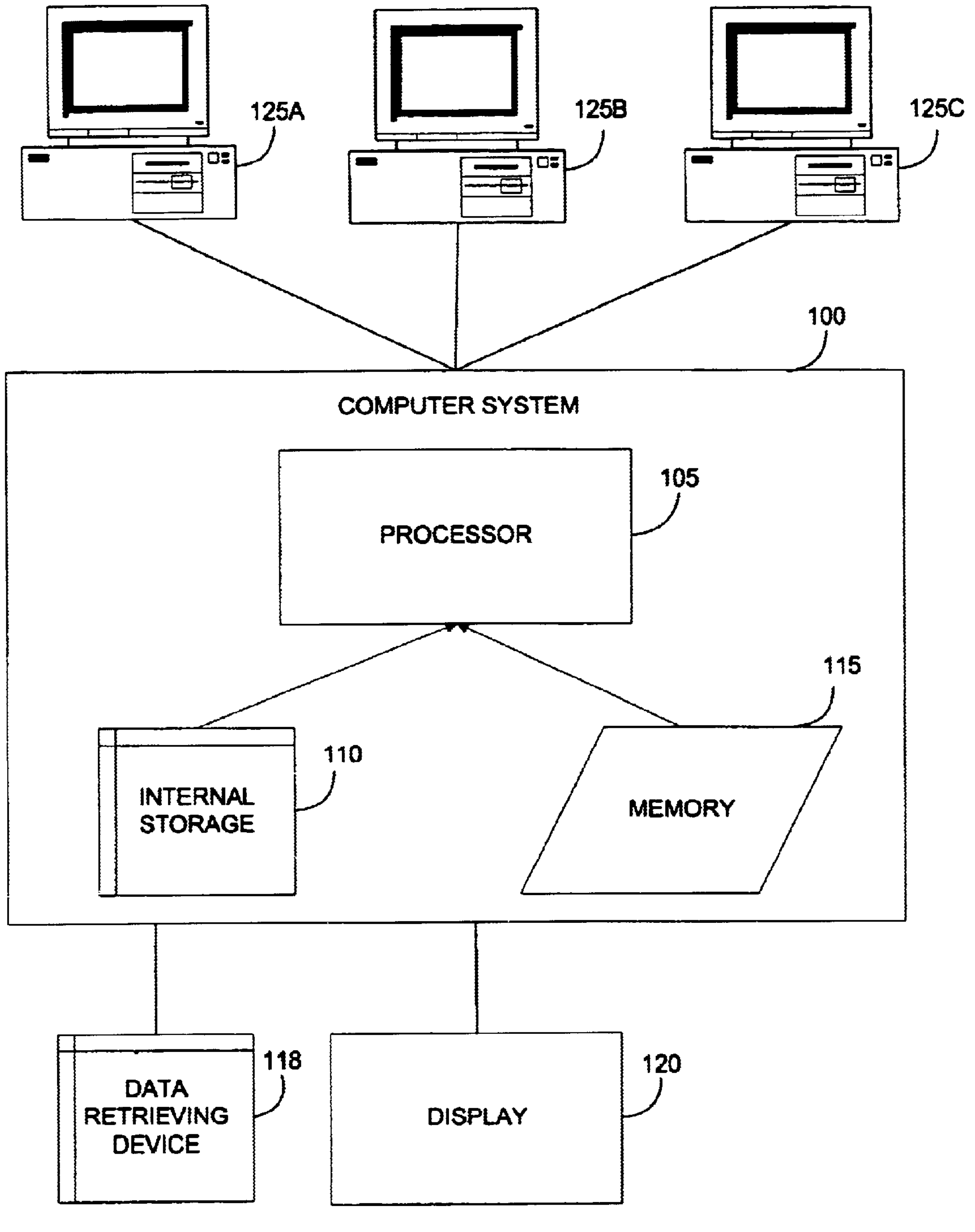
FIG. 3 is a block diagram of an exemplary computer system.

Embodiments of the present invention include systems, particularly computer systems which store and manipulate the sequence information described herein. One example of a computer system 100 is illustrated in block diagram form in FIG. 3. As used herein, "a computer system" refers to the hardware components, software components, and data storage components used to analyze the nucleotide sequences of the nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 or the sequences of the polypeptide codes of 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78. The computer system 100 preferably includes a processor for processing, accessing and manipulating the sequence data. The processor 105 can be any well-known type of central processing unit, such as the Pentium III from Intel Corporation, or similar processor from Sun, Motorola, Compaq or International Business Machines.

Preferably, the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer system s are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer system s 125*a–c* in a network or wide area network to provide centralized access to the computer system 100.

Software for accessing and processing the nucleotide sequences of the nucleic acid codes of SEQ ID Nos.1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 or the polypeptide codes of SEQ ID NOs. 6, 10, 14, 26, 28, 30, 32, 34, 38, 42, 46, 58, 60, 62, 64,66, 68, 72, 76, 80, 4, 8, 12, 16, 18, 20, 22, 24, 36, 40, 44, 48, 50, 52, 54, 56, 70, 74, and 78 (such as search tools, compare tools, and modeling tools etc.) may reside in main memory 115 during execution.

In some embodiments, the computer system 100 may further comprise a sequence comparer for comparing the above-described nucleic acid codes of SEQ ID Nos. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 or the polypeptide codes of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78 stored on a computer readable medium to reference nucleotide or polypeptide sequences stored on a computer readable medium. A "sequence comparer" refers to one or more programs which are implemented on the computer system 100 to compare a nucleotide sequence with other nucleotide sequences and/or compounds stored within the data storage means. For example, the sequence comparer may compare the nucleotide sequences of the nucleic acid codes of SEQ ID Nos. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 or the polypeptide codes of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78 stored on a computer readable medium to reference sequences stored on a computer readable medium to identify homologies or structural motifs. Various sequence comparer programs identified elsewhere in this patent specification are particularly contemplated for use in this aspect of the invention. Protein and/or nucleic acid sequence homologies may be evaluated using any of the variety of sequence comparison algorithms and programs known in the art. Such algorithms and programs include, but are by no means limited to, TBLASTN, BLASTN, BLASTP, FASTA, TFASTA, and CLUSTALW (Pearson and Lipman, 1988, *Proc. Natl. Acad. Sci. USA* 85(8):2444–2448; Altschul et al., 1990, *J. Mol. Biol.* 215(3):403–410; Thompson et al., 1994, *Nucleic Acids Res.* 22(2):4673–4680; Higgins et al., 1996, *Methods Enzymol.* 266:383–402; Altschul et al., 1990, *J. Mol. Biol.* 215(3):403–410; Altschul et al., 1993, *Nature Genetics* 3:266–272).

In one embodiment, protein and nucleic acid sequence homologies are evaluated using the Basic Local Alignment Search Tool ("BLAST") which is well known in the art (see, e.g., Karlin and Altschul, 1990, *Proc. Natl. Acad. Sci. USA* 87:2267–2268; Altschul et al., 1990, *J. Mol. Biol.* 215:403–410; Altschul et al., 1993, *Nature Genetics* 3:266–272; Altschul et al., 1997, *Nuc. Acids Res.* 25:3389–3402). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992, *Science* 256:1443–1445; Henikoff and Henikoff, 1993, *Proteins* 17:49–61). Less preferably, the PAM or PAM250 matrices may also be used (see, e.g., Schwartz and Dayhoff, eds., 1978, *Matrices for Detecting Distance Relationships: Atlas of Protein Sequence and Structure,* Washington: National Biomedical Research Foundation). BLAST programs are accessible through the U.S. National Library of Medicine, e.g., at www.ncbi.nlm.nih.gov.

The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990, *Proc. Natl. Acad. Sci. USA* 87:2267–2268).

The parameters used with the above algorithms may be adapted depending on the sequence length and degree of homology studied. In some embodiments, the parameters may be the default parameters used by the algorithms in the absence of instructions from the user.

Figure 4:
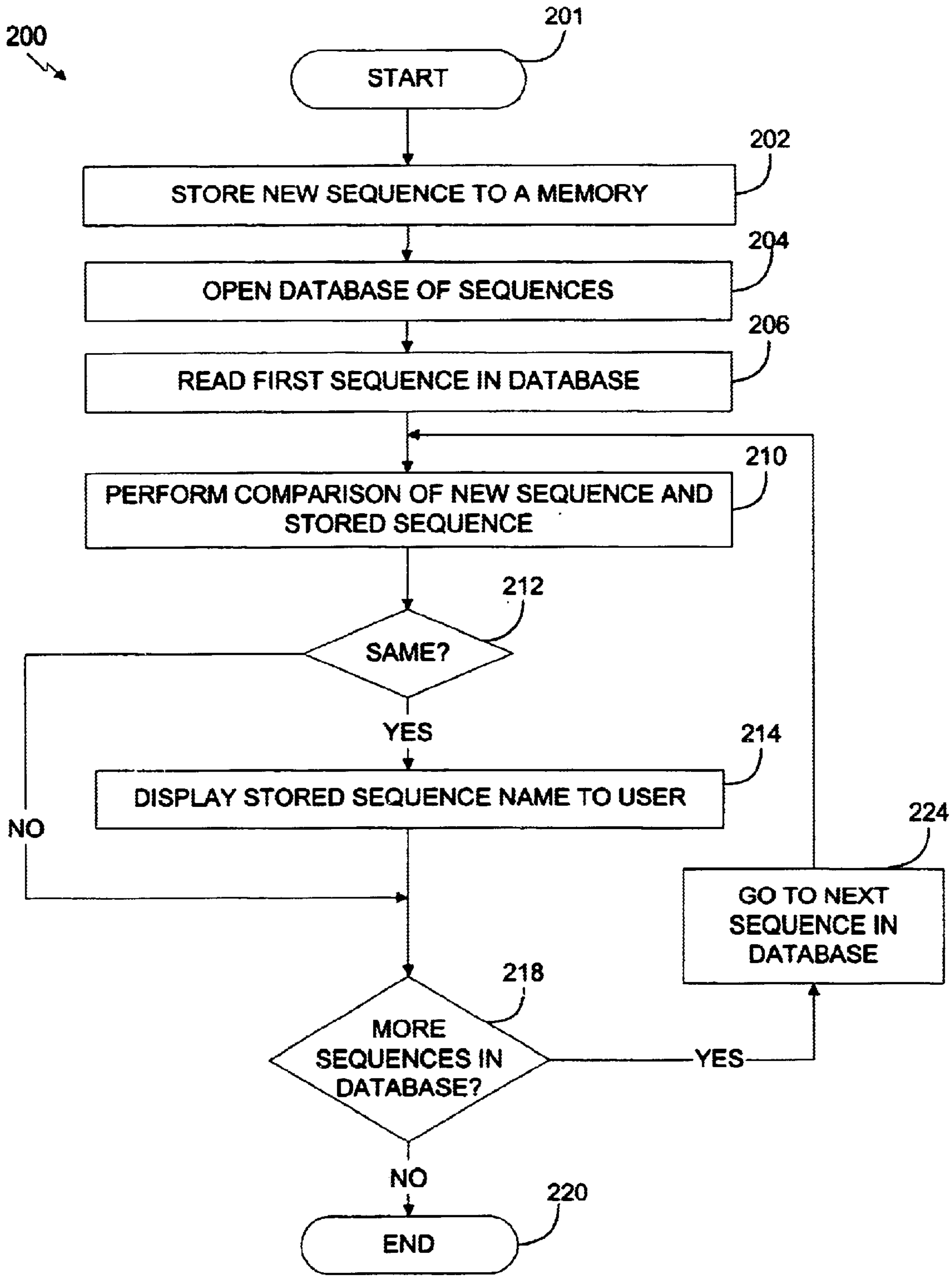
FIG. 4 is a flow diagram illustrating one embodiment of a process 200 for comparing a new nucleotide or protein sequence with a database of sequences in order to determine the homology levels between the new sequence and the sequences in the database.

FIG. 4 is a flow diagram illustrating one embodiment of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220.

However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the present invention is a computer system comprising a processor, a data storage device having stored thereon a nucleic acid code of SEQ ID Nos. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 or the polypeptide codes of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78, a data storage device having retrievably stored thereon reference nucleotide sequences or polypeptide sequences to be compared to the nucleic acid code of SEQ ID Nos.1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 or the polypeptide codes of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78 and a sequence comparer for conducting the comparison. The sequence comparer may indicate a homology level between the sequences compared or identify structural motifs in the above described nucleic acid code of SEQ ID Nos. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 or the polypeptide codes of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78 or it may identify structural motifs in sequences which are compared to these nucleic acid codes and polypeptide codes. In some embodiments, the data storage device may have stored thereon the sequences of at least 2, 5, 10, 15, 20, 25, 30 or 40 or more of the nucleic acid codes of SEQ ID Nos. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 or the polypeptide codes of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78.

Another aspect of the present invention is a method for determining the level of homology between a nucleic acid code of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 or the polypeptide codes of SEQ ID NOs. 6, 10, 14, 26, 28, 30, 32, 34, 38,42, 46, 58, 60, 62, 64, 66, 68, 72, 76, 80, 4, 8, 12, 16, 18, 20, 22, 24, 36, 40, 44, 48, 50, 52, 54, 56, 70, 74, and 78 and a reference nucleotide sequence or polypeptide sequence, comprising the steps of reading the nucleic acid code or the polypeptide code and the reference nucleotide or polypeptide sequence through the use of a computer program which determines homology levels and determining homology between the nucleic acid code or polypeptide code and the reference nucleotide or polypeptide sequence with the computer program. The computer program may be any of a number of computer programs for determining homology levels, including those specifically enumerated herein, including BLAST2N or BLASTN with the default parameters or with any modified parameters. The method may be implemented using the computer system s described above. The method may also be performed by reading at least 2, 5, 10, 15, 20, 25, 30 or 40 or more of the above described nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 orthepolypeptide codes of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78 through use of the computer program and determining homology between the nucleic acid codes or polypeptide codes and reference nucleotide sequences or polypeptide sequences.

Figure 5:
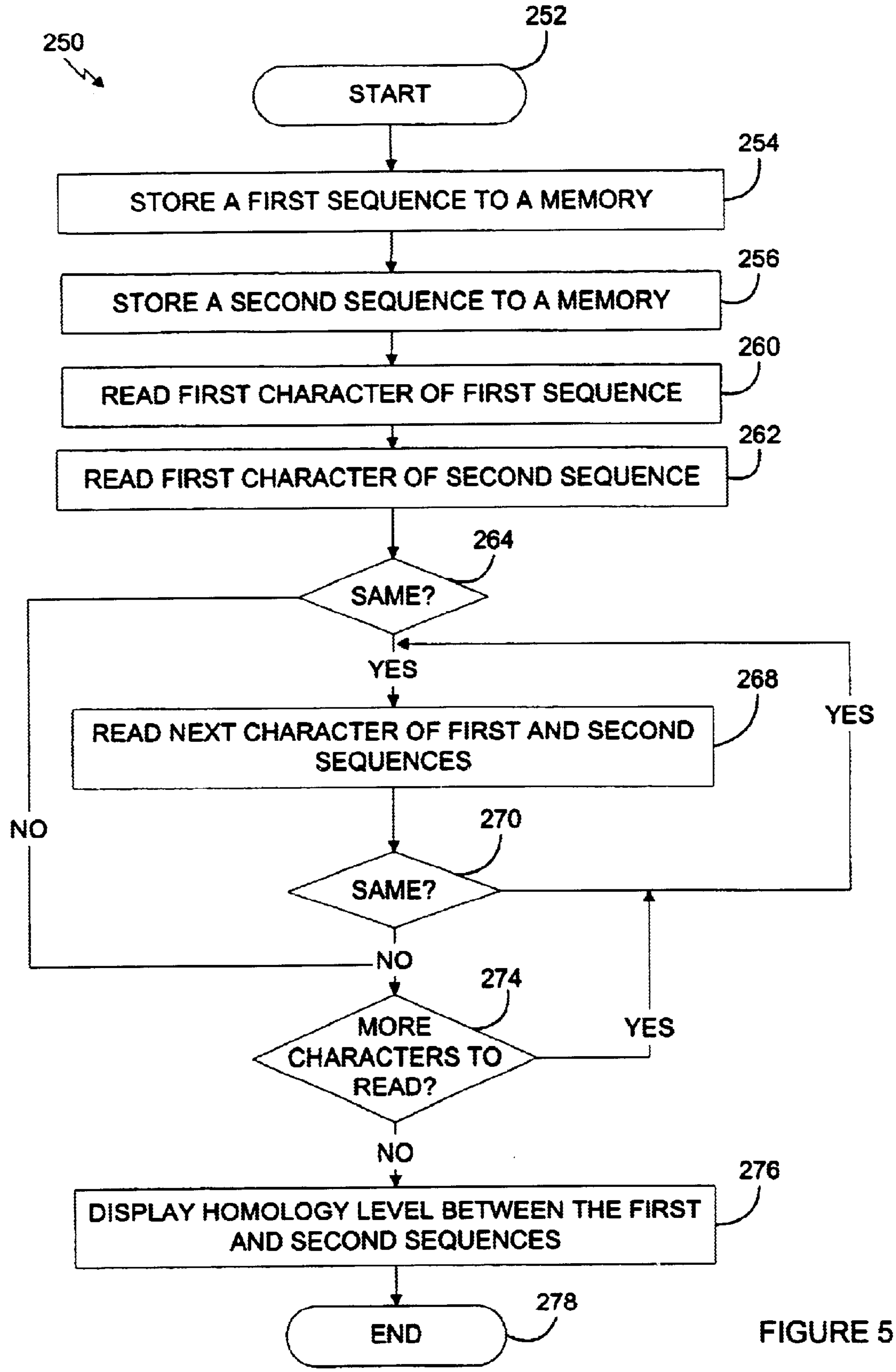
FIG. 5 is a flow diagram illustrating one embodiment of a process 250 in a computer for determining whether two sequences are homologous.

FIG. 5 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it is preferably in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there aren't any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of the nucleic acid codes of the present invention, to reference nucleotide sequences in order to determine whether the nucleic acid code of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 differs from a reference nucleic acid sequence at one or more positions. Optionally such a program records the length and identity of inserted, deleted or substituted nucleotides with respect to the sequence of either the reference polynucleotide or the nucleic acid code of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77. In one embodiment, the computer program may be a program which determines whether the nucleotide sequences of the nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 contain a single nucleotide polymorphism (SNP) with respect to a reference nucleotide sequence.

Figure 6:
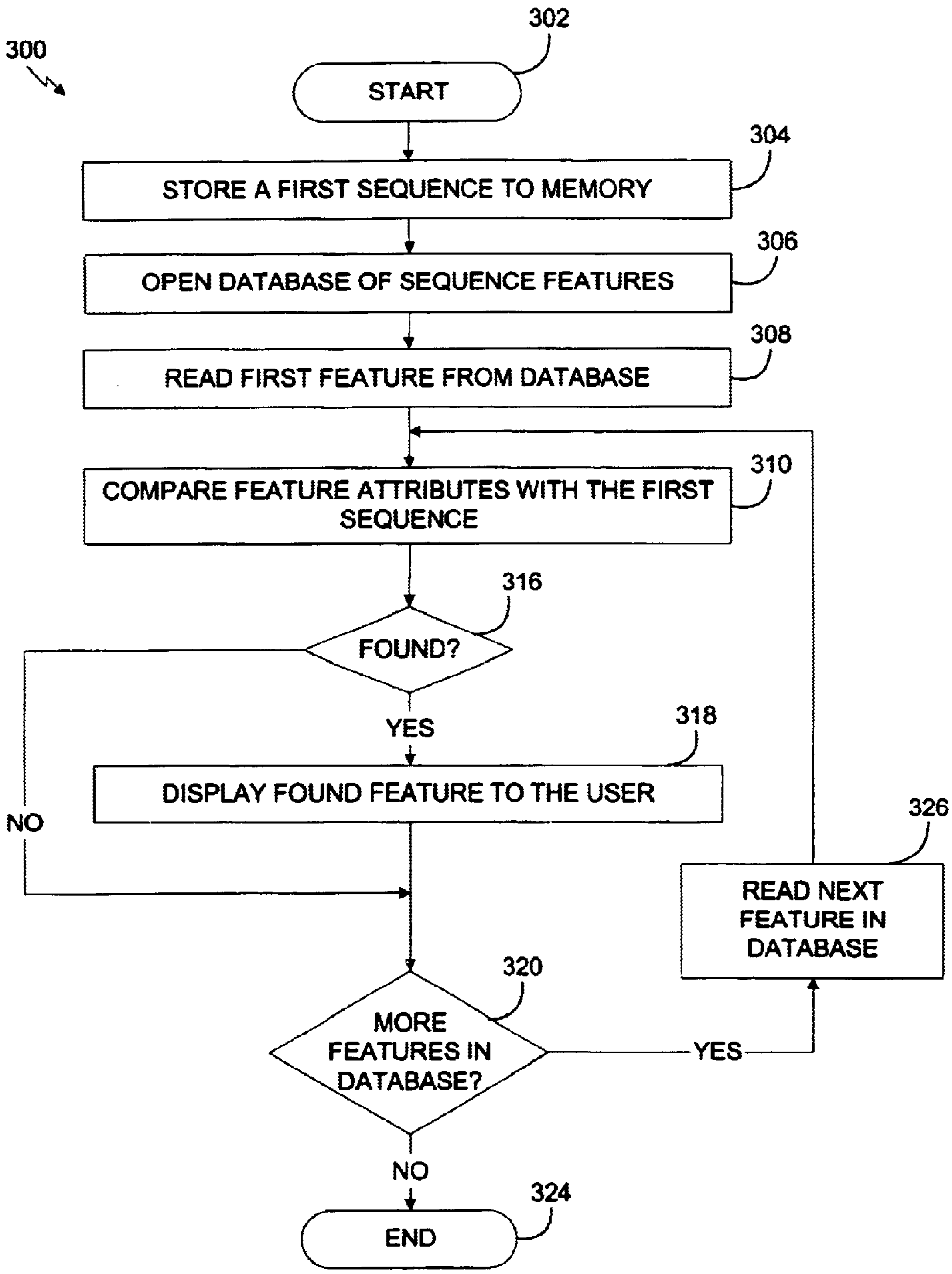
FIG. 6 is a flow diagram illustrating one embodiment of an identifier process for detecting the presence of a feature in a sequence.

Accordingly, another aspect of the present invention is a method for determining whether a nucleic acid code of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms. The method may be implemented by the computer system s described above and the method illustrated in FIG. 6. The method may also be performed by reading at least 2, 5, 10, 15, 20, 25, 30, or 40 of the nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 and the reference nucleotide sequences through the use of the computer program and identifying differences between the nucleic acid codes and the reference nucleotide sequences with the computer program.

In other embodiments the computer based system may further comprise an identifier for identifying features within the nucleotide sequences of the nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 or the polypeptide codes of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78.

An "identifier" refers to one or more programs which identifies certain features within the above-described nucleotide sequences of the nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 or the polypeptide codes of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78. In one embodiment, the identifier may comprise a program which identifies an open reading frame in the nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77.

FIG. 7 is a flow diagram illustrating one embodiment of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group and can be accessed on the worldwide web at the address gcg.com. Alternatively, the features may be structural polypeptide motifs such as alphas helices, beta sheets, or functional polypeptide motifs such as enzymatic active sites, helix-turn-helix motifs or other motifs known to those skilled in the art.

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence.

It should be noted, that if the feature attribute is not found in the first sequence at the decision state 316, the process 300 moves directly to the decision state 320 in order to determine if any more features exist in the database.

Accordingly, another aspect of the present invention is a method of identifying a feature within the nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35,39, 43, 47, 49, 51, 53, 55, 69, 73 and 77 or the polypeptide codes of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78 comprising reading the nucleic acid code(s) or polypeptide code(s) through the use of a computer program which identifies features therein and identifying features within the nucleic acid code(s) with the computer program. In one embodiment, computer program comprises a computer program which identifies open reading frames. The method may be performed by reading a single sequence or at least 2, 5, 10, 15, 20, 25, 30, or 40 of the nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 or the polypeptide codes of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78 through the use of the computer program and identifying features within the nucleic acid codes or polypeptide codes with the computer program.

The nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 or the polypeptide codes of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78 may be stored and manipulated in a variety of data processor programs in a variety of formats. For example, the nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 or the polypeptide codes of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78 may be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparers, identifiers, or sources of reference nucleotide sequences or polypeptide sequences to be compared to the nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 or the polypeptide codes of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78. The following list is intended not to limit the invention but to provide guidance to programs and databases which are useful with the nucleic acid codes of SEQ ID NOs. 1, 2, 5, 9, 13, 25, 27, 29, 31, 33, 37, 41, 45, 57, 59, 61, 63, 65, 67, 71, 75, 79, 3, 7, 11, 15, 17, 19, 21, 23, 35, 39, 43, 47, 49, 51, 53, 55, 69, 73 and 77 or the polypeptide codes of SEQ ID NOs. 6, 10, 14, 26, 28, 30, 32, 34, 38, 42, 46, 58, 60, 62, 64, 66, 68, 72, 76, 80, 4, 8, 12, 16, 18, 20, 22, 24, 36, 40, 44, 48, 50, 52, 54, 56, 70, 74, and 78.

The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, *J. Mol. Biol.* 215: 403 (1990)), FASTA (Pearson and Lipman, *Proc. Natl. Acad. Sci. USA,* 85: 2444 (1988)), FASTDB (Brutlag et al. Comp. App. Biosci. 6:237–245, 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwents's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

The present invention will be further described with reference to the following examples; however, it is to be understood that the present invention is not limited to such examples.

In order to begin the physiological characterization of *Cenarchaeum symbiosum,* it was necessary to obtain enriched preparations of *Cenarchaeum symbiosum* for use in the construction of genomic DNA libraries in fosmid based vectors. Genomic DNA libraries were constructed from two enriched preparations using the methods described in Example 1 below.

EXAMPLE 1

Enrichment of *Cenarchaeum symbiosum* Cells in Samples Obtained from *Axinella Mexicana*

Enriched preparations of *Cenarchaeum symbiosum* for use in the preparation of the first fosmid genomic DNA library were obtained essentially as described in Preston, C. M. et al. 1996. A psychrophilic crenarchaeon inhabits a marine sponge: *Cenarchaeum symbiosum* gen. *nov.,* sp. *nov. Proc. Natl. Acad. Sci.* USA 93, 6241–6246, the disclosure of which is incorporated herein by reference. Briefly, a small individual of *A. mexicana* was incubated in calcium- and magnesium-free artificial seawater (ASW) containing 0.25 mg/ml Pronase. The tissue was then homogenized and enriched for archaeal cells by differential centrifugation.

Enriched preparations of *Cenarchaeum symbiosum* for use in preparing the second fosmid genomic DNA library were obtained from a different sponge individual using the following improved enrichment procedure. A small individual of *A. mexicana* was incubated in calcium- and magnesium-free artificial seawater (460 mm NaCl, 11 mM KCl, 7 mM $Na_2SO_4$, 2 mM $NaHCO_3$) containing 0.25 mg/ml Pronase at room temperature for one hour. The sponge tissue was rinsed in artificial seawater and homogenized in a blender. Large particles and spicules were removed by low-speed centrifugation (4000 rpm, Sorvall GSA rotor at 4° C.). The supernatant was next centrifuged at 5000 rpm for 5 min. at 4° C. to remove large sponge cells, and the resulting supernatant was centrifuged at 10,000 rpm in a GSA rotor at 4° C. for 20 min. to collect the *Cenarchaeum symbiosum* cells. Following centrifugation, the recovered cell fraction containing *Cenarchaeum symbiosum* was further incubated for 1 hr at 4° C. in 10 mM Tris/HCl pH 8 and 200 mM EDTA. The cells were then pelleted and subsequently purified on a 15% Percoll (Sigma) cushion in artificial sea water centrifuged at 2500 rpm in a Beckman SS34 rotor. Archaeal cells banded in the light, upper fraction after centrifugation. This cell fraction was washed in ASW and resuspended in TE buffer (10 mM TrisHCl pH 8, 0.1 mM EDTA). The additional incubation step was found to increase the lysis of sponge cells, which resulted in an enhanced separation of archaeal and eukaryotic cells in the percoll gradient.

Quantitative hybridization experiments were performed as described in DeLong, E. F. 1992. Archaea in coastal marine environments. *Proc. Natl. Acad Sci.* 89, 5685–5689, the disclosure of which is incorporated herein by reference, using an oligonucleotide specific for archaea having the sequence GTGCTCCCCCGCCAATTCCT (SEQ ID NO: 115). These hybridization experiments indicated that 25% to 30% of the total rRNA from this fraction was derived from archaea.

The enriched cell preparations were then utilized to construct fosmid libraries as described in Example 2 below.

EXAMPLE 2

Construction of Fosmid Libraries

DNA was extracted from the enriched preparations of Example 1 and inserted into fosmids as described in Preston, C. M. et al. 1996. A psychrophilic crenarchaeon inhabits a marine sponge: *Cenarchaeum symbiosum* gen. *nov.,* sp. *nov. Proc. Natl. Acad. Sci.* USA 93, 6241–6246 and Stein, J. L. et al. 1996. Characterization of uncultivated prokaryotes: isolation and analysis of a 40-kilobase-pair genome fragment from a planktonic marine archaeon. *J. Bacteriol.* 178, 591–599, the disclosures of which are incorporated herein by reference. A vertical cross section of sponge (0.5 g) was mechanically dissociated in 0.22 μm filtered, autoclaved seawater using a tissue homogenizer. Cell lysis was accomplished by incubating the dissociated cells in 1 mg of lysozyme per ml for 30 min. at 37° C. followed by an incubation for 30 min. at 55° C. with 0.5 mg of proteinase K per ml and 1% SDS. The tubes were finally placed in a boiling water bath for 60 sec to complete lysis. The protein fraction was removed with two extractions with phenol:chloroform:isoamyl alcohol (50:49:1), pH 8.0, followed by a chloroform: isoamyl alcohol (24:1) extraction. Nucleic acids were ethanol-precipitated and resuspended in TE buffer (10 mM Tris.HCl/1 mM $Na_2$-EDTA, pH 8.0). Approximately 5 μg of DNA was purified by CsCl equilibrium density gradiant ultracentriguation on a Beckman Optima tabletop ultracentrifuge using a TLA100 rotor.

The genomic DNA obtained above was inserted into fosmids as follows. The genomic DNA was partially digested with Sau3AI (Promega) and treated with heat-labile phosphatase (HK phosphatase; Epicentre). The partially digested genomic DNA was ligated with pFOS (See U. J. Kim et al., Nucleic Acids Res. 20:1083–1085 (1992), the disclosure of which is incorporated herein by reference) which had previously been digested with AatII, phosphatase treated (HK phosphatase), and subsequently digested with BamHI. The ligation mixture was used for in vitro packaging with the Gigapack XL packaging system (Stratagene) selecting for DNA inserts of 35 to 45 kb. The phage particles were transfected into *E. coli* DH10B (Bethesda Research LaboratoriesP and the cells were spread onto LB plates supplemented with 12.5 μg/ml chloramphenicol.

EXAMPLE 3

Identification of Fosmids Containing the *Cenarchaeum symbiosum* rRNA Operon The fosmid libraries constructed above were screened to identify clones containing the rRNA operon. PCR reactions were conducted on the library using primers known to amplify the rRNA operon.

The first fosmid library yielded seven unique clones, out of a total of 10,236 recombinant fosmids, which contained the *Cenarchaeum symbiosum* rRNA operon. The second fosmid library yielded eight unique clones, out of a total of 2100 recombinant fosmids, which contained the *Cenarchaeum symbiosum* rRNA operon.

The sequences of the 16S rRNA genes in each of the 15 fosmids containing the *Cenarchaeum symbiosum* rRNA operon were determined. The sequences of the small subunit rRNA genes of these 15 fosmids exhibited variations with respect to one another. Ten of the fosmids contained a small subunit rRNA gene having the sequence of the 16S rRNA gene in the insert of SEQ ID NO: 1, while the remaining fosmids contained a small subunit rRNA gene having the sequence of the 16S rRNA gene in the insert of SEQ ID NO: 2. As discussed in more detail below, the differences in the sequences of the rRNA genes may be used to determine whether a sample contains *Cenarchaeum symbiosum* variant A or *Cenarchaeum symbiosum* variant B.

In addition to determining the sequences of the rRNA genes, the sequences adjacent to the rRNA genes were also determined.

EXAMPLE 4

Fosmid Sequencing

Partial restriction enzyme digests were conducted on two purified fosmids, fosmid 101G10 (which contains the variant A sequence) and fosmid 60A5 (which contains the variant B sequence). The partially digested DNA was used to construct plasmid libraries containing inserts of 1–2 kb. The resulting plasmids were sequenced using Applied Biosystems (ABI, Foster City, Calif.) Prism Dye-terminator FS reaction mix. Direct sequencing from fosmids was used for gap filling and resequencing to ensure accuracy. Fosmid sequencing was performed by using DNA from a single 3 ml overnight culture purified on an Autogen 740 automated plasmid isolation system. Each reaction consisted of one preparation of DNA directly resuspended by the addition of 16 μl $H_2O$, 8 μl oligonucleotide primer (1.4 pmol/μl) and 16 μl ABI Prism Dye-terminator FS reaction mix. Cycle sequencing was performed with a 96° C. 3 min. preincubation followed by 25 cycles of the sequence 96° C. 20 sec./50° C. 20 sec./60° C. 4 min. and a 5 min. post-cycling incubation at 60° C. Sequencing reaction products were analyzed on ABI 377 Prism Sequencers.

The complete sequences of the *Cenarchaeum symbiosum* derived inserts in the two fosmids are provided in the accompanying sequence listing as SEQ ID NO: 1 (fosmid 101G10) and SEQ ID NO: 2 (fosmid 60A5). The insert of fosmid 101G10 (SEQ ID NO: 1, designated variant A) was 32,998 bp and was syntenic over ca. 28 kbp with the 42,432 bp insert of fosmid 60A5 (SEQ ID NO:2, designated variant B). Analysis of the common 28 kbp region is shown in FIG. 1.

Although the sequences of both fosmids could be aligned unambiguously over most of the overlapping region, four large insertion/deletions ranging in size from 142 bp to 1994 bp were identified between positions 20,500 and 25,800. The longest insertion contained a repetitive element of 1784 bp, that was found in the sequence of SEQ ID NO: 1 between menA and ORF05. It was composed of a 3-fold direct repeat of 575 bp (rep1 through 3 in FIG. 1), with repeats exhibiting only minor sequence variation (95.8% to 98.7% identity).

A segment of 56 bp at the start of this repeat was also found adjacent to the 3' terminus of the third direct repeat. No obvious structural or sequence similarities to known repeats or mobile genetic elements from other organisms were identified within the repeat sequence. Its occurrence in only one variant and its relatively low G+C content relative to the rest of the fragment suggest that it may have been acquired by horizontal transfer from a different genetic context.

The sequenced regions contained several open reading frames or RNA encoding sequences. Some of the identified open reading frames encode proteins having homology to previously identified proteins. In particular, some of the open reading frames encode proteins involved in several metabolic pathways, providing insight into the physiology of *Cenarchaeum symbiosum.*

An open reading frame which encodes a protein having homology to glutamate semialdehyde aminotransferase (a protein involved in heme biosynthesis) was identified between nucleotides 7604–8908 of the insert from fosmid 101G10 (SEQ ID NO: 1) and between nucleotides 23558–24682 of the insert from fosmid 60A5 (SEQ ID NO: 2). These open reading frames have been assigned SEQ ID NOs: 45 and 13 respectively in the accompanying sequence listing, while the polypeptides they encode have been assigned SEQ ID NOs: 46 and 14 respectively in the accompanying sequence listing. A gene encoding glutamate semialdehyde aminotransferase has also been detected in a rRNA operon containing genomic fragment of a planktonic marine crenarchaeote. (Stein, J. L. et al. 1996. Characterization of uncultivated prokaryotes: isolation and analysis of a 40-kilobase-pair genome fragment from a planktonic marine archaeon. *J. Bacteriol.* 178, 591–599)

An open reading frame encoding a protein having homology to triose-phosphate isomerase was identified between 13944–14612 of the insert from fosmid 101G10 (SEQ ID NO: 1) and between nucleotides 29655–30491 of the insert from fosmid 60A5 (SEQ ID NO: 2). These open reading frames have been assigned SEQ ID NOs: 57 and 25 respectively in the accompanying sequence listing, while the polypeptides they encode have been assigned SEQ ID NOs: 58 and 26 respectively in the accompanying sequence listing. This triosephosphate isomerase represents the first such protein sequence reported in a crenarchaeote, and shares known archaeal signature sequences and deletions which distinguish archaeal triosephosphate isomerase genes from their eucaryal and eubacterial homologues.

An open reading frame encoding a protein having homology to the TATA binding protein was identified between 14616–15164 of the insert from fosmid 101G10 (SEQ ID NO: 1) and between nucleotides 30501–31049 of the insert from fosmid 60A5 (SEQ ID NO: 2) on the strands complementary to the insert strands provided in SEQ ID NOs: 1 and 2. These open reading frames have been assigned SEQ ID NOs: 59 and 27 respectively in the accompanying sequence listing, while the polypeptides they encode have been assigned SEQ ID NOs: 60 and 28 respectively in the companying sequence listing. This TATA box-binding protein (TBP) is similar to other known archaeal TBP's and is N-terminally truncated with respect to the eukaryal homologs. It shares 49% amino acid similarity with TBP from *Pyrococcus woesii.*

An open reading frame encoding a protein having homology to DNA polymerase (a protein involved in DNA replication and repair) was identified between nucleotides 15488–18025 of the insert from fosmid 101G10 (SEQ ID NO: 1) and between nucleotides 31371–33905 of the insert from fosmid 60A5 (SEQ ID NO: 2) on the strands complementary to the insert strands provided in SEQ ID NOs: 1 and 2. These open reading frames have been assigned SEQ ID NOs: 61 and 29 respectively in the accompanying sequence listing, while the polypeptides they encode have been assigned SEQ ID NOs: 62 and 30 respectively in the accompanying sequence listing.

The DNA polymerase of *Cenarchaeum symbiosum* has a high degree of similarity to the crenarchaeal homologs from the extreme thermophiles *Sulfolobus acidocaldarius* and *Pyrodictium occultum* (54% and 53% resp.) and exhibits all conserved motifs of B-(a-)type DNA polymerases and 3'-5'-exonuclease motifs, both indicative of archaeal polymerases. A more detailed phylogenetic analysis and biochemical characterization of the *C. symbiosum* polymerase has been published elsewhere. (Schleper, C., et al. 1997. Characterization of a DNA polymerase from the uncultivated psychrophilic archaeon *Cenarchaeum symbiosum.* J. Bact. 179, 7803–7811)

An open reading frame which encodes a protein having homology to dCMP deaminase (a protein involved in pyrimidine synthesis) was identified between nucleotides 18022–18663 of the insert from fosmid 101G10 (SEQ ID NO: 1) and between nucleotides 33902–34456 of the insert from fosmid 60A5 (SEQ ID NO: 2) on the strands complementary to the insert strands provided in SEQ ID NOs: 1 and 2. These open reading frames have been assigned SEQ ID NOs: 63 and 31 respectively in the accompanying sequence listing, while the polypeptides they encode have been assigned SEQ ID NOs: 64 and 32 respectively in the accompanying sequence listing.

An open reading frame encoding a protein having homology to the ATP dependent RNA helicase (a protein involved in translation) was identified between nucleotides 18638–20149 of the insert from fosmid 101G10 (SEQ ID NO: 1) and between nucleotides 34559–36067 of the insert from fosmid 60A5 (SEQ ID NO: 2). These open reading frames have been assigned SEQ ID NOs: 65 and 33 respectively in the accompanying sequence listing, while the polypeptides they encode have been assigned SEQ ID NOs: 66 and 34 respectively in the accompanying sequence listing. The identified ATP RNA helicase is highly similar in sequence to homologues found in the genomic sequences of three euryarchaeota (Bult, C., et al. Complete genome sequence of the methanogenic archaeon, *Methanococcus jannaschii. Science* 273, 1058–1073; Klenk, H. P. et al. 1997. The complete genome sequence of the hyperthermophilic, sulphate-reducing archaeon *Archaeoglobus fulgidus. Nature* 390, 364–370; Smith, D. R.et al. 1997. Complete genome sequence of *Methanobacterium thermoautotrophicum* delta H: functional analysis and comparative genomics. *J. Bacteriol.* 179, 7135–7155).

An open reading frame encoding a protein having homology to MenA (a protein involved in menaquinone biosynthesis) was identified between nucleotides 20956–21834 of the insert from fosmid 101G10 (SEQ ID NO: 1) and between nucleotides 37404–38282 of the insert from fosmid 60A5 (SEQ ID NO: 2). These open reading frames have been assigned SEQ ID NOs: 71 and 37 respectively in the accompanying sequence listing, while the polypeptides they encode have been assigned SEQ ID NOs: 72 and 38 respectively in the accompanying sequence listing.

An open reading frame encoding a protein having homology to the site specific DNA methyltransefrase proteins involved in restriction/modification was identified between nucleotides 2637–27454 of the insert from fosmid 101G10 (SEQ ID NO: 1) and between nucleotides 40563–41669 of the insert from fosmid 60A5 (SEQ ID NO: 2) on the strands complementary to the insert strands provided in SEQ ID NOs: 1 and 2. These open reading frames have been assigned SEQ ID NOs: 75 and 41 respectively in the accompanying sequence listing, while the polypeptides they encode have been assigned SEQ ID NOs: 76 and 42 respectively in the accompanying sequence listing.

An open reading frame encoding a protein having homology to the histone H1 DNA binding protein was identified between nucleotides 10625–1134 of the insert from fosmid 60A5 (SEQ ID NO: 2). This open reading frame has been assigned SEQ ID No: 5 in the accompanying sequence listing, while the polypeptide it encodes has been assigned SEQ ID No: 6 in the accompanying sequence listing.

An open reading frame encoding a protein having homology to lysyl tRNA synthetase was identified between nucleotides 13046–14620 of the insert from fosmid 60A5 (SEQ ID NO: 2). This open reading frame has been assigned SEQ ID No: 9 in the accompanying sequence listing, while the polypeptide it encodes has been assigned SEQ ID No: 10 in the accompanying sequence listing.

A hypothetical open reading frame was identified between nucleotides 11478–13046 of the insert from fosmid 60A5 (SEQ ID NO: 2). This open reading frame has been assigned SEQ ID No: 7 in the accompanying sequence listing, while the polypeptide it encodes has been assigned SEQ ID No: 8 in the accompanying sequence listing.

An open reading frame encoding a protein having homology to peptidylprolyl cis/trans isomerase (a chaperone) was identified between nucleotides 20156–20434 of the insert from fosmid 101G10 (SEQ ID NO: 1) on the strand complementary to that provided in the sequence listing. This open reading frame has been assigned SEQ ID No: 67 in the accompanying sequence listing, while the polypeptide it encodes has been assigned SEQ ID No: 68 in the accompanying sequence listing.

An open reading frame encoding a protein having homology to glucose-1-dehydrogenase was identified between nucleotides 28065–29843 of the insert from fosmid 101G10 (SEQ ID NO: 1). This open reading frame has been assigned SEQ ID No: 79 in the accompanying sequence listing, while the polypeptide it encodes has been assigned SEQ ID No: 80 in the accompanying sequence listing.

A hypothetical open reading frame designated Hypothetical 01 was identified between nucleotides 1358–2290 of the insert from fosmid 101G10 (SEQ ID NO: 1) and between nucleotides 17329–18213 of the insert from fosmid 60A5 (SEQ ID NO: 2) on the strands complementary to the insert strands provided in SEQ ID NOs: 1 and 2. These open reading frames have been assigned SEQ ID NOs: 43 and 11 respectively in the accompanying sequence listing, while the polypeptides they encode have been assigned SEQ ID NOs: 44 and 12 respectively in the accompanying sequence listing.

A hypothetical open reading frame designated Hypothetical 02 was identified between nucleotides 8961–9767 of the insert from fosmid 101G10 (SEQ ID NO: 1) between nucleotides 24913–25728 of the insert from fosmid 60A5 (SEQ ID NO: 2). These open reading frames have been assigned SEQ ID NOs: 47 and 15 respectively in the accompanying sequence listing, while the polypeptides they encode have been assigned SEQ ID NOs: 48 and 16 respectively in the accompanying sequence listing.

An open reading frame designated ORF 01 was identified between nucleotides 9772–10479 of the insert from fosmid 101G10 (SEQ ID NO: 1) and between nucleotides 25732–26427 of the insert from fosmid 60A5 (SEQ ID NO: 2) on the strands complementary to the insert strands provided in SEQ ID NOs: 1 and 2. These open reading frames have been assigned SEQ ID NOs: 49 and 17 respectively in the accompanying sequence listing, while the polypeptides they encode have been assigned SEQ ID NOs: 50 and 18 respectively in the accompanying sequence listing.

An open reading frame designated ORF 02 was identified between nucleotides 10545–10922 of the insert from fosmid 101G10 (SEQ ID NO: 1) and between nucleotides 26504–26881 of the insert from fosmid 60A5 (SEQ ID NO: 2). These open reading frames have been assigned SEQ ID NOs: 51 and 19 respectively in the accompanying sequence listing, while the polypeptides they encode have been assigned SEQ ID NOs: 52 and 20 respectively in the accompanying sequence listing.

An open reading frame designated ORF 03 was identified between nucleotides 11382–11987 of the insert from fosmid 101G10 (SEQ ID NO: 1) and between nucleotides 27337–27936 of the insert from fosmid 60A5 (SEQ ID NO: 2) on the strands complementary to the insert strands provided in SEQ ID NOs: 1 and 2. These open reading frames have been assigned SEQ ID NOs: 53 and 21 respectively in the accompanying sequence listing, while the polypeptides they encode have been assigned SEQ ID NOs: 54 and 22 respectively in the accompanying sequence listing.

An open reading frame designated ORF 04 was identified between nucleotides 12916–13737 of the insert from fosmid 101G10 (SEQ ID NO: 1) and between nucleotides 28822–29631 of the insert from fosmid 60A5 (SEQ ID NO: 2) on the strands complementary to the insert strands provided in SEQ ID NOs: 1 and 2. These open reading frames have been assigned SEQ ID NOs: 55 and 23 respectively in the accompanying sequence listing, while the polypeptides they encode have been assigned SEQ ID NOs: 56 and 24 respectively in the accompanying sequence listing.

An open reading frame designated Hypothetical 03 was identified between nucleotides 20554–20955 of the insert from fosmid 101G10 (SEQ ID NO: 1) and between nucleotides 37002–37403 of the insert from fosmid 60A5 (SEQ ID NO: 2). These open reading frames have been assigned SEQ ID NOs: 69 and 35 respectively in the accompanying sequence listing, while the polypeptides they encode have been assigned SEQ ID NOs: 70 and 36 respectively in the accompanying sequence listing.

An open reading frame designated ORF 05 was identified between nucleotides 25151–26377 of the insert from fosmid 101G10 (SEQ ID NO: 1) and between nucleotides 39454–40572 of the insert from fosmid 60A5 (SEQ ID NO: 2). These open reading frames have been assigned SEQ ID NOs: 73 and 39 respectively in the accompanying sequence listing, while the polypeptides they encode have been assigned SEQ ID NOs: 74 and 40 respectively in the accompanying sequence listing.

An open reading frame encoding a protein with no homology to known proteins was identified between nucleotides 3–10421 of the insert from fosmid 60A5 (SEQ ID NO: 2). This open reading frame has been assigned SEQ ID No: 3 in the accompanying sequence listing, while the polypeptide it encodes has been assigned SEQ ID No: 4 in the accompanying sequence listing.

An open reading frame designated ORF06 was identified between nucleotides 27535–28002 of the insert from fosmid 101G10 (SEQ ID NO: 1). This open reading frame has been assigned SEQ ID No: 77 in the accompanying sequence listing, while the polypeptide it encodes has been assigned SEQ ID No: 78 in the accompanying sequence listing.

A gene coding for $tRNA^{Tyr}$ was identified between nucleotides 12129–12251 of the insert from fosmid 101G10 (SEQ ID NO: 1) and between nucleotides 28058–28180 of the insert from fosmid 60A5 (SEQ ID NO:2). This tRNA contains a 45 bp intron in the vicinity of the anticodon loop.

Table 1 shows the level of homology between the open reading frames in the inserts from fosmid 101G10 and fosmid 60A5 at the nucleic acid level. Table 1 also shows the level of homology at the amino acid level between the polypeptides encoded by the insert from fosmid 101G10 and fosmid 60A5. Nucleic acid homology was calculated using BLASTN with the default parameters. Amino acid homology was calculated using FASTA with the parameters. As shown in Table 1 and FIG. 1, the protein coding regions were highly similar in both nucleic acid and deduced amino acid sequences.

Over the 28 kb common region in the 101G10 and 60A5 inserts, the inserts shared >99.2% identity in their ribosomal RNA genes, approximately 87.8% overall DNA identity, an average of 91.6% similarity in ORF amino acid sequence, and complete colinearity of protein encoding regions. As shown in Table 1, in protein coding regions the DNA identity of the two contigs ranged from 80.9% (triose phosphate isomerase) to 91.5% (Hypothetical 03). Within intergenic regions the identity dropped to 70–86%, and small insertions or deletions were found frequently. The high similarity in coding regions and upstream sequences aided in the identification of genes, start codons, and putative transcriptional promoter motifs (see below). Genes appear as densely packed in *C. symbiosum* as they are in other sequenced archaeal genomes (Bult, C., et al. 1996. Complete genome sequence of the methanogenic archaeon, *Methanococcus jannaschii. Science* 273, 1058–1073, Klenk, H. P. et al. 1997. The complete genome sequence of the hyperthermophilic, sulphate-reducing archaeon *Archaeoglobus fulgidus*. *Nature* 390, 364–370; Smith, D. R., et al. 1997. Complete genome sequence of *Methanobacterium thermoautotrophicum* delta H: functional analysis and comparative genomics. *J. Bacteriol.* 179, 7135–7155).

The ribosomal RNA operon of *Cenarchaeum symbiosum* is composed of the genes for the 16S and 23S rRNAs separated by a spacer of 131 bp. This organization is typical of crenarchaeotes, and differs from rRNA operons of euryarchaeotes, which usually contain 5S RNA and tRNA genes. (Garrett, R. A. et al. 1991. Archaeal rRNA operons. *TIBS* 16, 22–26). The large subunit rRNA genes are located between nucleotides 2680–5674 of SEQ ID NO: 1 (fosmid 101G10) and between nucleotides 18645–21639 of SEQ ID NO: 2 (fosmid 60A5). The small subunit rRNA genes are located between nucleotides 5806–7278 of SEQ ID NO: 1 (on the opposite strand from that shown in the Sequence Listing, as indicated in FIG. 1) and between nucleotides 21771–23243 of SEQ ID NO: 2. The large and small subunit rRNA genes in the two fosmids were 99.2% and 99.3% identical, respectively.

As mentioned above, the sequences of the *Cenarchaeum symbiosum* derived inserts in fosmids 101G10 and 60A5 had a high degree of homology but were not completely identical. The sequence of the insert in fosmid 101G10 was designated variant A, while the sequence of the insert in fosmid 60A5 was designated variant B. Such sequence differences could arise if the fosmid inserts were derived from two closely related but distinct strains of *Cenarchaeum symbiosum* or, alternatively, the sequence differences could be due to cloning or sequencing artifacts. To confirm that the fosmid inserts were in fact derived from two closely related strains, portions of the inserts in a plurality of different fosmids were sequenced to determine whether they were identical to either of the inserts in fosmids 101G10 and 60A5, as would be the case if there were in fact two closely related strains of *Cenarchaeum symbiosum.*

In particular, the ribosomal RNA spacer regions of variant A and variant B contained 10 distinguishing signature nucleotides and the 16S rRNA genes of variant A and variant B contained two distinguishing nucleotides. Example 5 provides the results of a PCR based analysis of the 16S rRNA gene and the 16S-23S spacer region in 13 different fosmid inserts.

EXAMPLE 5

PCR Based Analysis of Fosmid Inserts to Determine whether they Contain the Variant A or Variant B Sequences Primers 21F and 459R-LSU (CTTTCCCTCACGGTA, SEQ ID NO: 116) were used to amplify the 16S-23S spacer region from the fosmids. The amplification products were sequenced using primer SP23rev (CTA TTG CCG TCT TTA CACC, SEQ ID NO: 117).

PCR reactions with two archaea-specific 16S rDNA primers (21F and 958R (DeLong, E. F. 1992. Archaea in coastal marine environments. *Proc. Natl. Acad. Sci.* 89, 5685–5689, the disclosure of which is incorporated herein by reference), one of which was biotinylated, were used to amplify a 950 base pair (bp) fragment from the fosmids. The PCR products were purified and sequenced as described in Preston, C. M. et al. 1996. A psychrophilic crenarchaeon inhabits a marine sponge: *Cenarchaeum symbiosum* gen. *nov.,* sp. *nov. Proc. Natl. Acad. Sci.* USA 93, 6241–6246 with primer 519R 16S rDNA.

The results of this analysis are shown in Table 2. As shown in Table 2, in samples obtained from several unique rRNA operon-containing fosmids, a sequence identical to either variant A (101G10) or variant B (60A5) was present.

The above methods may also be used to determine whether a biological sample contains variant A and/or variant B. In such procedures, nucleic acids are obtained from the biological sample, amplified using the above primers, and sequenced using the above oligonucleotide to determine whether the sample contains the variant A and/or the variant B sequence.

Similarly, the amplification reaction may be conducted using any primers which generate amplification products having sequences which differ between variant A and variant B. The amplification products may then be sequenced to determine whether they have the sequence of variant A and/or variant B. In some embodiment, the amplification reaction may be conducted under conditions in which the amplification primers specifically hybridize to one of the variants.

RFLP analyses were also be used to assess whether the fosmids contained the sequence of variant A or variant B as described in Example 6 below.

EXAMPLE 6

RFLP Based Analysis of Fosmids to Determine Whether They Contain the Variant A or Variant B Sequences Primer set 21F (DeLong, E. F. 1992. Archaea in coastal marine environments. *Proc. Natl. Acad. Sci.* 89, 5685–5689) and 459R-LSU for the amplification of 2.2 kbp of the ribosomal operon, primer set GSAT810F (GAATCCGCC CCCGACTATCTT, SEQ ID NO: 118) and 16S37REV (CATGGCTTAGTATCAATC SEQ ID NO: 119) for the amplification of the 16S RNA-GSAT region (2.2 kbp) and primer set Cenpol357F (ACITACAACGGI GACGAY-TTTGA SEQ ID NO: 120) and Cenpol735R (CACCCCGAARTAGTTYTTYTT SEQ ID NO: 121) for an internal DNA polymerase fragment (of 1134 bp) were used in PCR reactions with 5 ng of purified fosmids. The PCR products were cut with TaqI and HpaII (16S-23S RNA), HaeIII and RsaI (GSAT-16S RNA) or HaeIII and AvaII (polymerase) and analyzed on 2% agarose gels.

The results are shown in Table 2. If the pattern did not exactly match but closely resembled the RFLP of either type A or B, it was assigned as a lower case letter (a or b, Table 2), meaning that at least 3 out of 4 or 3 out of 5 bands created by restriction digest appear identical in size to the ones from either type A or B. As shown in Table 2, RFLP patterns of the 1150 bp fragment covering the 5'-end of the GSAT gene and 16S gene and the internal fragment of 1134 bp from the DNA polymerase gene revealed that all fosmids analyzed could again be assigned to either the A or B type, although slight variations were also detected (lower case letters in Table 2), suggesting that both variants exhibit further microheterogeneity which is detectable in protein coding and intergenic regions.

The above methods may also be used to determine whether a biological sample contains variant A and/or variant B. In such procedures, nucleic acids are obtained from the biological sample, amplified using the above primers, and digested as described above to determine whether the sample contains the variant A and/or the variant B sequence. Similar analyses may also be performed using other portions of the sequences of SEQ ID NOs: 1 and 2 which are different from one another.

To further confirm the existence of two closely related strains of *Cenarchaeum symbiosum,* biological samples were obtained from several individual sponges and analyzed to determine whether the samples contained variant A and/or variant B. Example 7 below provides the results of a PCR analysis of the *Cenarchaeum symbiosum* 16S rRNA genes in samples obtained from several individual sponges in different locations and at different times.

EXAMPLE 7

Analysis of Samples from Individual Sponges

The 16S rRNA genes of variant A and variant B differ at positions 175 and 183.7 (*E. coli* numbering). PCR reactions with two archaea-specific 16S rDNA primers (21F and 958R (DeLong, E. F. 1992. Archaea in coastal marine environments. *Proc. Natl. Acad Sci.* 89, 5685–5689, the disclosure of which is incorporated herein by reference), one of which was biotinylated, were used to amplify a 950 base pair (bp) fragment from total nucleic acids derived from several different sponge individuals. The PCR products were purified and sequenced as described in Preston, C. M. et al. 1996. A psychrophilic crenarchaeon inhabits a marine sponge: *Cenarchaeum symbiosum* gen. *nov.,* sp. *nov. Proc. Natl. Acad. Sci.* USA 93, 6241–6246 with primer 519R, the disclosure of which is incorporated herein by reference.

The amplification products were sequenced to determine whether they corresponded to variant A and/or variant B. The results are shown in Table 3. As shown in Table 3, in 15 out of 16 cases U/C ambiguities were found at the signature positions, indicating the presence of both variants in samples obtained from a single sponge (Table 3). Only one sponge (S4) yielded an unambiguous sequence identical to variant A, but variant B was detected in this individual by another criterion (see below).

Hybridization analyses were also used to determine whether individual sponges harbored variant A and/or variant B. The results of these analyses are provided in Example 8 below.

EXAMPLE 8

Hybridization Based Analysis of Samples Obtained from *Axinella Mexicana* to Determine Whether the Samples Contain Variant A and/or Variant B Two oligonucleotides specific for each variant type were designed from the 23S rDNA gene sequences of fosmids 101G10 and 60A5. The probes differed in 3 positions and have the sequences ACACTTCAACTATTTCCTG (SEQ ID NO: 122 variant A) and ACACTTTGACTATTTCGTG (SEQ ID NO: 123, variant B). Nucleic acid samples from individual sponges (300 ng) and controls (fosmids 101G10 and 60A5, 50 ng each) were denatured, bound to nylon membranes (Hybond-N, Amersham), hybridized with the labeled probes (Massana, R. et al. 1997. Vertical distribution and phylogenetic characterization of marine planktonic Archaea in the Santa Barbara Channel. *Appl. Env. Microb.* 63, 50–56, the disclosure of which is incorporated herein by reference in its entirety) and washed at 41.5° C. Hybridization was analyzed by autoradiography.

The results are provided in Table 3. In the samples from the majority of host sponges examined, the presence of both 23S rRNA variants was observed, confirming that the specific association of *C. symbiosum* with its host typically involves the presence of both variants.

The data provide strong evidence that these genomic clones are derived from two very closely related, but distinct strains, as opposed to representing two ribosomal RNA operon regions originating from the same organism. This conclusion is consistent with the observation that all crenarchaeota characterized to date contain only one ribosomal RNA operon (Garrett, R. A. et al. 1991. Archaeal rRNA operons. *TIBS* 16, 22–26).

The high conservation between the inserts in fosmid 101G10 and fosmid 60A5 was not entirely confined to coding regions but also extended into adjacent upstream sequences. Due to this upstream similarity, and also because the average G+C content of the sequences was relatively high, it was possible to readily identify prospective transcriptional (A+T rich) promoter elements. A motif corresponding to the consensus of the archaeal TATA-box-like element (C/T-T-T-A-T/A-A) (Hain, J. et al. 1992. Elements of an archaeal promoter defined by mutational analysis. *Nucl. Acids. Res.* 20, 5423–5428) was identified upstream of nearly all genes (FIG. 2). The exceptions were the genes encoding MenA and DNA polymerase which are located immediately downstream of other ORFs and may therefore be transcribed as polycistronic mRNAs. In vivo and in vitro studies in other archaea have shown that initiation of transcription occurs consistently 24 to 28 bp downstream from the central T of this motif (Hain, J et al. 1992. Elements of an archaeal promoter defined by mutational analysis. *Nucl. Acids. Res.* 20, 5423–5428; Palmer, J. R. and Daniels, C. J. 1995. In vivo definition of an archaeal promoter. *J. Bacteriol.* 177 1844–1849). For twelve of the protein encoding genes, the promoter element was found 25 to 30 bp upstream of the ORF (FIG. 2), suggesting that transcriptional initiation occurs in close proximity to, or directly at, the translational start codon.

A similar observation has been made for 30 of the predicted 100 strong and medium promoters from 156 kbp sequence of *Sulfolobus solfataricus* (Sensen, C. W. et al. 1996. Organizational characteristics and information content of an archaeal genome: 156 kb of sequence from *Sulfolobus solfataricus* P2. *Molec. Microb.* 22, 175–191). Transcription initiation at, or in close proximity to, the translational start codons has been mapped for some genes in *Halobacterium salinarium* (Brown, J. W. et al. 1989. Gene structure, organization, and expression in archaebacteria. *CRC Crit. Rev. Microb.* 16, 287–337) and *S. solfataricus* (Klenk, H. P., et al. 1993. Nucleotide sequence, transcription and phylogeny of the gene encoding the superoxide dismutase of Sulfolobus acidocaldarius. *Biochim. Biophys. Acta* 1174 95–98), and alternative mechanisms for initial mRNA-ribosome contact in Archaea have been hypothesized (Brown, J. W. et al. 1989. Gene structure, organization, and expression in archaebacteria. *CRC Crit. Rev. Microb.* 16, 287–337).

The promoters listed in FIG. 2, or fragments thereof, may be used in expression vectors or expression systems. In one embodiment, the promoters listed in FIG. 2 may be operably linked to coding regions and introduced into archaebacteria, and in particular *Cenarchaeum symbiosum,* to express the encoded gene product in the archaebacterial cells.

Alternatively, the promoters listed in FIG. 2 may be operably linked to coding regions and introduced into host cells which are not normally capable of directing transcription from archaebacterial promoters. In addition, genes encoding the proteins required for transcription from these promoters are also introduced into the host cells. The genes encoding these transcription factors may be on the same vector as the promoter from *Cenarchaeum symbiosum* or on a different vector. In some embodiments, the genes encoding these transcription factors are linked to an inducible promoter. Expression of the transcription factors is induced when it is desired to express the proteins which are operably linked to the promoter from *Cenarchaeum symbiosum.*

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims. All documents cited herein are incorporated herein by reference in their entirety.

TABLE 1

Comparison of Overlapping Coding Sequences from Fosmid 101G10 and Fosmid 60A5

| Gene | Functional | % Identity | |
|---|---|---|---|
| Name[1] | Category | Nucleotide | Amino Acid |
| Hypothetical 01 | unknown | 81.4 | 76.6 |
| 23S | translation | 99.16 | |
| 16S | translation | 99.3 | |
| GSAT | heme biosynthesis | 83.2 | 83.8 |
| Hypothetical 02 | unknown | 83.4 | 81.4 |
| ORF 01 | unknown | 83.3 | 85.7 |
| ORF 02 | unknown | 89.9 | 95.2 |
| ORF 03 | unknown | 87.9 | 86.7 |
| $tRNA^{tyr}$ | translation | 99.2 | |
| ORF 04 | unknown | 87.8 | 88.1 |
| TIM | glycolysis | 80.9 | 83.3 |
| TBP | transcription | 83.4 | 86.3 |
| DNA polymerase | replication/repair | 89.0 | 93.9 |
| dCMP deaminase | pyrimidine synthesis | 85.7 | 89.8 |
| RNA helicase (ATP dependent) | translation | 86.1 | 92.2 |
| PPI | chaperone | 88.4 | 92.5 |
| Hypothetical 03 | unknown | 91.5 | 92.4 |
| MenA | menaquinone biosynthesis | 86 | 89.4 |
| ORF 05 | unknown | 87.5 | 90.6 |
| Methylase | restriction/modification | 86.4 | 87.5 |

[1]Hypothetical: open reading frame (ORF) with similarity to proteins of unknown function from the databases.
ORF = open reading frame identified by similarity between both fosmids, including upstream promoter sequence; GSAT = glutamate semialdehyde aminotransferase; TIM = triose-phosphate isomerase; TBP = TATA box-binding protein; PPI = peptidylprolyl cis/trans isomerase.

TABLE 2

Analysis of Polymorphism at Four Distinct Loci in Different Fosmids

| Fosmid | 16S RNA*[1] | 16S–23S spacer*[2] | 16S-GSAT*[3] HaeIII | RsaI | DNA Pol*[3] HaeIII | AvaII |
|---|---|---|---|---|---|---|
| 101G10 | A | A | A | A | A | A |
| 60A5 | B | B | B | B | B | B |
| 15A5 | B | B | — | — | b | b |
| 43H4 | A | — | — | — | A | A |
| 60H6 | A | A | — | — | a/b | B |
| 69H2 | A | — | — | — | A | A |
| 87F4 | B | — | — | — | b | a/b |
| C1H5 | A | A | A | A | | |
| C4H1 | A | A | A | A | | |
| C4H9 | A | A | A | A | A | B |
| C7D4 | A | A | A | A | A | A |
| C8B8 | B | B | B | B | B | b |
| C15A3 | A | A | A | A | | |
| C17D2 | B | — | b | B | B | b |
| C20B5 | A | A | a | a/b | | |

*[1]: partial sequence (101G10 through 87F4) or RFLP analysis (C1H5 through C20B5).
*[2]: partial sequence.
*[3]: RFLP analysis of PCR products; A/B: identical pattern to either 101G10 (=A) or 60A5 (=B); a, b: similar pattern to either A or B (see materials and methods). Fosmids C1H5, C4H1, C15A3 and C20B5 did not yield PCR products with polymerase-specific primers. The first seven fosmids were isolated from a first library, the last 8 fosmids (prefix C) are from a second library.
—= not determined.

TABLE 3

Detection of *C. symbiosium* Variants in Natural Populations of *A. mexicana*

| *A. mexicana* Individual or Isolated DNA Source* | Variation in 16S rDNA Positions** 175 | 183.7 | Variations in 23S rRNA Hybridization Variant Type A | Variant Type B |
|---|---|---|---|---|
| fosmid 101G10 from s12 | U | U | + | – |
| fosmid 60A5 from s12 | C | C | – | + |
| s12 | Y | Y | + | + |
| s1 | — | — | + | + |
| s2 | — | — | + | + |
| s3 | Y | Y | + | + |
| s4 | U | U | + | w |
| s5 | Y | Y | — | — |
| s6 | Y | Y | + | + |
| s7 | — | — | + | w |
| s8 | Y | Y | + | + |
| s9 | Y | Y | + | w |
| s10 | — | — | + | + |
| s11 | Y | Y | + | + |
| s13 | — | — | + | + |
| s14 | — | — | + | w |
| s16 | — | — | + | + |
| s17 | — | — | – | w |
| s18 | Y | Y | – | w |
| s19 | — | — | + | + |
| s20 | — | — | + | + |
| s21 | — | — | + | + |
| s22 | — | — | + | + |
| s23 | — | — | + | + |
| s24 | — | — | + | + |
| s25 | — | — | + | + |
| s26 | — | — | + | + |
| s27 | — | — | + | + |
| s28 | — | — | + | + |
| s29 | — | — | + | + |
| s30 | — | — | + | + |
| hs1 | — | — | + | + |
| hs2 | — | — | + | + |
| hs3 | Y | Y | + | w |
| hs4 | Y | Y | + | w |
| hs5 | Y | Y | + | + |
| hh1 | — | — | w | w |
| hh2 | Y | Y | + | + |
| hh3 | Y | Y | + | + |
| Aq1 | Y | Y | — | — |
| Aq2 | Y | Y | — | — |
| Aq3 | — | — | + | + |

*s = Naples Reef; hs = Haskle; hh = Hermit Hole; Aq = captive sponge.
**Y = direct sequence of PCR product yields C and U at the same position.
— = not determined; w = weakly positive.

What is claimed is:

1. An isolated, purified, or enriched nucleic acid comprising a sequence as set forth in SEQ ID NO:1, or a sequence complementary to SEQ ID NO:1.

2. An isolated fragment of the nucleic acid of claim 1, wherein the nucleic acid fragment encodes a polypeptide having DNA polymerase activity.

* * * * *

SEQUENCE LISTING

<160> NUMBER OF SEQ ID NOS: 123

<210> SEQ ID NO 1
<211> LENGTH: 32998
<212> TYPE: DNA
<213> ORGANISM: Cenarchaeum symbiosum
<220> FEATURE:
<221> NAME/KEY: CDS
<222> LOCATION: (7604)...(8908)
<221> NAME/KEY: CDS
<222> LOCATION: (8961)...(9767)
<221> NAME/KEY: CDS
<222> LOCATION: (10545)...(10922)
<221> NAME/KEY: CDS
<222> LOCATION: (13944)...(14612)
<221> NAME/KEY: CDS
<222> LOCATION: (18638)...(20149)
<221> NAME/KEY: CDS
<222> LOCATION: (20554)...(20955)
<221> NAME/KEY: CDS
<222> LOCATION: (20956)...(21834)
<221> NAME/KEY: CDS
<222> LOCATION: (25151)...(26377)
<221> NAME/KEY: CDS
<222> LOCATION: (27535)...(28002)
<221> NAME/KEY: CDS
<222> LOCATION: (28065)...(29483)

<400> SEQUENCE: 1
gatccttgac ctctgcgctt attgcagcca tggactgacc ggccgtgcgg ggctaaataa 60
agctgaggcg ccgcctgcag gctctgctca gccgttgatt atacagtact cgcactcgca 120
ggtcttgctt tcgtcatctt ttgccctgca cttggcgtgc tggcccgact ggcactggac 180
gcagatctcg tctatgttgt ctatcgaggt gtactttttg gactggtcaa agccgaagcc 240
gccgtccttt ggtccaacca tgaagcggtc agggccgtta tgccttaatt atctttgccg 300
tcggggcggg gccgcttctg ccggcgggag cccccttga ggccgctccc cggctcgttg 360
tcccacaggt gcatgctgcc cctgatcata aacgagccga ctatgattgc tacaagcccg 420
cccactatca gtataaacag cctagccacg ccccccattc tgcccatgcg tgtaatatgc 480
tgcacctgta aacaaacatt gcgcggggca tgggccgtcc ggacagacag aactgcccat 540
gagacaggtg cctgcgggcc ggtaagctac attaatttat caccccccac gggcgggccc 600
catgagcagg accaagagaa taatcatctg ggcatcccata ctgggcgggg ggataatcta 660
ctttctcgtc cagggcgaga ttgccagaaa tgtattgtcc tgagaacaga agccatgcag 720
caactgcccg atcgtttttc aggtacctac tgggcttttt ggagttcgtt gatcaaaagc 780
ggtacaggta ttctatacat gccagtcttg gctggaaaaa taaattgaag atcggcggat 840
cctatctacg agcgcctgcc tgcttttcac ttgactagcc ggagtacttc gtctgcaatt 900
tctgtatagc taggcattta tgtagttgag atacatgtcc gcgggatccg tttcatagtc 960
tgaatcaaac accggatcat tccttctctt taattcctta aatgcctgat gcagttcaag 1020
caggacggtt acatcatcgc gtttgattat ccgttctgtt gtttcagctt tttgctcatt 1080
ctcatccatg attataggct acggtatttg actaaaaagg tttccatctt catgagtcgt 1140
gtgtttgccg tggaattacc taccggggga acataaaaaa atgagtcata aacagcgcac 1200
tgcatccacc gtggacccat gagacaacga gccggcagcg gtgcacagca ccgagtacaa 1260
ccccgcaatc gtcttatcca acgacctgcc ctatgaaaac tccagacgga tctcttccgg 1320
gcatccagta cccatgtatg tgagaattct gactatctta ccgtggtgtt ggcagtgtct 1380

-continued

```
caacgacggt attaccgagg tgattcatga taattttgtt gactggagta tactgaaaca   1440
tggtatttgc cgcatgaaat actgacagca ccagatcttg aaattcttgt tcatcttcca   1500
gatcagttac ttttaagcca atccttttac attcttctct cgatatgcgc cttccatgac   1560
tgtgatattt tttagaggaa gacattattt ctgatatttt ttttgacttt tttaccgctg   1620
cagactcgtt ctcaaacatg tatctagcca gccatttttg tacaagttcc acacttagct   1680
tctggctgct aatgcatttt tgaattagcc cgggaggata ttgccctaac agtggaagcc   1740
atgcgccgag cctccccggg tgtttttctg acaccgactg tgcttcttga aactcgctaa   1800
ttagaaactg tgcagacatt atgtgcatgc cggtcctggt tggaataata aattgggggt   1860
cggtgggacc tatcgatgag tgtttaccca ttaccaggca attcgatgag catgcaagca   1920
tcgcagctgc cgacatcgcg gcatatggga taatgatccg gacattttta aattttgcac   1980
gtatgtatga gacgattgct tcggtggact cgacggagcc ccccggactg tggagtatta   2040
aatctaattt cttagtcttt aaatcacgca tcatcctcat aaatccatac aggtcaccat   2100
ttgttatgag agcttcatta gacgtatgcg cttcgtccgt tatccagttg gtcgcataca   2160
gtattgtatc cctccccgaa tactgttgca attttgaaag atagtcgtga agtactacac   2220
caggtgcctg ctcaccgact gactccatta gtcgaagtac gtcgtttgct atttctgcgt   2280
aactaggcat ttatgtagtt gaaatgacta cccgcgggaa tcataccata gtctgtgtcg   2340
tatgacttgc ctttttttctt catcaatttc tcatattcct catgcagttc gagcaggatg   2400
gccatgtcac tacgtttgtt cgtctgtttt gttgtctcgg gcttttggtc catattatta   2460
tccatgctag taaaggacta tgttccttta aaaaggttcg tgattttaat ttccaagtgt   2520
ttgcctcgca atttcctcca aggcacatga aaaacgggcc acaggcagag cacagcatcc   2580
gctggggacc catgaaataa gcccccggcg gtgcacagca tccgctgggg gctcaataaa   2640
aaaatgagtc atcatgcata gtctctatgt aaatggctga accggtgttt tggtcgatta   2700
gtaaaggctg gctcaccact cgccgaagct tgtgggatac accaccttcc tatcaacgca   2760
gtcttcttct gcgaaccttc atccgaagaa ggaatatctt gtctcgggat aggattcgtg   2820
cttagatgct ttcagcactt agcctagatg gcttagctgc ccggcctgcc ctgtcggaca   2880
accggtagac cagtggccac gcctctctgt tcctctcgta ctaagagcga cttcccctca   2940
gatattcgcg cttccatcag gcagaggccg acctgtctca cgacggtcta aacccagctc   3000
atgttccctt ttaataggcg agcagcctca cccttggccc ctgctgcagg accaggatag   3060
gaaaagccga catcgaggta ccaaaccgcg gggtcgatag gagctctcgc ccgcgacgag   3120
cctgttatcc ctggggtaat ttttctgtca cctccgggcc ccaatagtgg gcacacgaag   3180
gatcgctaag ccagactttc gtctatgaat tccgtgcgtt tggaaatcca ttcagtctag   3240
tttttggctt tgccctcttc agcggatttc tgacccgctt gaactaaact ttgggcccct   3300
ttgatatctt ttcaaagggg tgccgcccca gccgaactgc ccacctgcac atgtccccgg   3360
tcttcaccgg gtaagtggca ctgcaggaaa tgtctggtgt tacatcggcg tcccctgacg   3420
tcccaaagaa cgccaggaaa tgactcccag atacgctatg cactccctgc tataccacaa   3480
gcacaagctg cagtaaaact ccacggggtc ttctctcccc gatggaagat gatggactgt   3540
tcgtccacct tatgtggctt caccgggttg taggcgggga cagtggggct ctcgttgttc   3600
cattcatgca cgtcggaact tacccgacaa ggcatttggc taccttaaga gagtcagagt   3660
tactcccggc gttaaccggt ccttagctcg gttgaaccca agttttagat accggcaccg   3720
gccaggattc agcgactata catacccttt cgggctagca gtcgcctgtg tttttattaa   3780
```

-continued

```
acagtcgaaa cccccttgtc actgcaacct gctgccgcca ttcctcatga cagctgcagg   3840
catcccttat acctaagcta caggactaat ttgccgaatt ccctcgccat acggtatacc   3900
cgtagcacct tagtttacta aaccagcgca cctgtgtcgg atctgggtac gaacttgcag   3960
tttgctagcc gcacggtctt tcatggtctc ctggaatcgg gaaaactctg ctaacgcaaa   4020
gccactcccg cctcgggcct gttctcgtca ttacgacact cccaggccct cgaacggttc   4080
gacacgacga cggtcatgtt ccccctatcc ggaagcgaac catgcggttc aaacgctccc   4140
tgcaaggtac cagaatatta actggtttcc cattcggact actctgttga ggcagtcctt   4200
aggatcgact aactccaggc tgacgacgca ttgcctggaa acccttgcgc ttacggtggt   4260
gcggattctc accgcactat gctgttactg ccaccaggat ctgcaataga aatcggtcca   4320
caggacgtca ccgccctgct tcgtcccaat cactacgcca acctaccacg gtgcacctat   4380
cacggtgcac gtctggagta tcggtactct gctttagccc cgtccgtttt tgtggcgccc   4440
tcgctcggca ggtaagttgt tacacacttt ttgaaggata gctacttctg agcttacctc   4500
cctgctgtct tggcgatgac acgcactttg gcttgacact tagcagaaat ttggggacct   4560
taactccagt ctgggttaaa cccctctcgg tcgtgaacct tacgtcacac gaacccgtgt   4620
ccatgcttct gcgatgtgta tccgttcgga gtttgaatgg atggtgagga atctcttccc   4680
cgcgccaccc tatcagtgct ctaccggaaa caccatctcc acatagcacg ccctgcgaga   4740
cgcttcggtt ggaactagca agcgccagtc tagattggtt tttgacccct attcccaagt   4800
cacacaaacg agttgcacgt cagaactgct gcagacctcc agtgggcttt cgcccacctt   4860
catcttgctc aggaatagat cgactggctt ctagccttac cgccatgact taacgcactt   4920
tcacacgctt ctcctcacaa tgctgcgaga attcggtttc ccttcggcta cgcctttcta   4980
ggcttaacct cgccatgaca gcaagctccc tggcccgtgt ttcgagacgg aacgcatgac   5040
actgacgaca tgagctccgg actttcagct ccattgctgg aacctccggt ccgaaaaaat   5100
cgtctttcat gccatgcacg tctgtaagca ataggtttca tgcacttttc accccccttc   5160
cggggtactt ttcagctttc cctcacggta ctagtacact atcggtcttg agagatattt   5220
agcctttgat gctactttca ccaatcttcg ctgcccactg ccaaggacaa ctactcgggt   5280
gctggccctg ccccattcca cttcgtctag gggggtatca ccctctaagc cggaacattt   5340
cagaacactt caactatttc ctggggccat tgcgccgcac caaaacacca catctcggcc   5400
gcgttaccgc ggcagattca gtttgggctc tttccttttc gatcgcctct acttgggaaa   5460
tctctattga tttctcttcc tcgtggtact aagatgcttc aattcccacg gttcgacctc   5520
cgcttgcgcg gagtatacag gattcctatt cggaaatctc gggatcaacg ggtgcgtgca   5580
cctaccccga gcttatcgca gcttgccacg tccttcttct ctcctcaagc ctagcaatcc   5640
tcctattgcc gtctttacac cggcatattc agccacatat tacacgacta tgcatgatga   5700
tcatcgcagt ccccagggga gggggccgct acatccttca tacaccactt gcgtggtgca   5760
ttgcaccatg caaagatcat gtgcattctg ttcaaaccag tttctaagga ggtgatccga   5820
ccgcaggttc ccctacggtc accttgttac gacttttccc ttgtcgctta cctcaagttc   5880
gataacgcca attagacgtc acctcactaa aagcaaactt caatgaaacg acgggcggtg   5940
tgtgcaagga gcagggacgt attcactgcg cggtaatgac gcgcggttac tagggattcc   6000
agattcgtga gggcgagttg cagccctcag tcataactgt ggtagcgttt ggggattacc   6060
tcctcctttc ggatatggaa cccattgtca ctaccattgc agcccgcgtg tggccccaga   6120
```

-continued

```
gtttcggggc atactgacct gccgtggccc tttccttcct ccgcattaac tgcggcggtc   6180
ccgctaattc gccccactgc tccggagagc aatggtggca actagaggca aggatctcgc   6240
tcgttacctg acttaacagg acatctcacg gcacgagctg gcgacggcca tgcaccacct   6300
ctcagcttgt ctggtagagt cttcagcttg accttcacac tgctgtctct ccgggtaaga   6360
tttctggcgt tgactccaat tgaaccgcag gcttcacccc ttgtggtgct cccccgccaa   6420
ttcctttaag tatcatactt gcgtacgtac ttcccaggcg gcaaacttaa cggcttccct   6480
gcggcactgc actggctctt acgccaatgc atcactgagt ttgcattgtt tacagctggg   6540
actacccggg tatctaatcc ggtttgctcc cccagctttc atccctcacc gtcggacgtg   6600
ttctagtaga ccgccttcgc cacagggggt catcgataga tcagaggatt ttaccccttc   6660
ctaccgagta ccgtctacct ctcccactcc ctagccgtgc agtatttccg gcagcctatg   6720
cgttgagcgc atagatttaa ccgaaaactt acacggcagg ctacggatgc tttaggccca   6780
ataatcctcc tgaccacttg aggtgctggt tttaccgcgg cggctgacac cagaacttgc   6840
ccacccctta ttcgccggtg gttttaagac cggtaaaaga tttctttagc agaaaacact   6900
cggattaacc ttgtcgtgct ttcgcacatt gcaaagtttt ctcgcctgct gcgccccata   6960
gggcctgggt ccgtgtctca gtacccatct ccgggcctct cctctcagag cccgtatctg   7020
ttatagcctt ggtgggccat tacctcacca acaagctgat agaccgcagt cccatcctac   7080
ggcgataaat catttgggcc acaaaccatt ccaggcatag tggcctatcg gatattattc   7140
tcagtttccc gaggttatcc ccgtccatag gttagattga ctacgtgtta ctgagccgtc   7200
tgccttgtat tgctacaatg actcgcatgg cttagtatca atccgatagc agtcaggtcc   7260
ggcaggatca accggattca taattggatt attttttttt tgttaagtac gcttgtactt   7320
ttggaattga acagaatgca cataatcttc acatctcaga tatgaccctt cgatcatacc   7380
ctcattctgt gtgcgtaact ggaggccagc gaatcacaat atggtacaat accatgcatt   7440
catcgcaagc gccgctcttg cgtcacgtac gatcggatcg gcccgtccat gggcatataa   7500
accatcgccg atttccgccc ccggcagccc cgatcagggg ccggatctgc ctgtatgatg   7560
gcgatccgcc ctgattaaat tatgggggga gcggcctgct gccgtggatc tggaacgcga   7620
gtacagggca aagaccggcg gctcggcccg gatctttgcc aggtcgaaaa agtaccacgt   7680
cggcggggtc agccacaaca taaggttcta cgagccgtat ccgtttgtga caaggtccgc   7740
gagcggcaag cacctcgtcg acgtggacgg gaacaagtat gtagactact ggatggggca   7800
ctggagcctg atactggggc acgcgccggc gccagtcagg tcggcagtag aggggcagct   7860
tcgccgcggc tggatccacg ggaccgtcaa cgagcagacg atgaatctct cggagataat   7920
acgcggcgcg gtaagcgtgg cagaaaagac aaggtacgtc acgtcgggga cggaggccgt   7980
catgtatgcg gcaaggctgg cgcgcgcgca tacgggcaga aaaataatag caaaggcgga   8040
cggcggctgg cacgggtacg cgtcggggct gctcaagtcg gtcaactggc cgtatgatgt   8100
gcccgagagc gggggggctcg tcgacgaaga gcactctata tccattccgt acaacgatct   8160
tgaaggttcc ctggatgttc ttgggcgcgc aggcgacgac ttggcatgcg tgataatcga   8220
gccgctgctg ggcggcggcg gctgcatacc ggcggatgag gactatctgc gcggcataca   8280
ggagtttgtg cattcaaggg gcgcgctgct tgtcctcgac gagatagtga cagggttccg   8340
gtttaggttt ggctgcgcgt atgctgcagc agggctggac cccgatatag tggcgctcgg   8400
caagatagtc gggggcggat tccccatagg ggtgatatgc ggcaaggacg aggtgatgga   8460
aatctccaac actatatcgc atgcaaagtc cgacagggcg tacatcggcg gcggcacatt   8520
```

-continued

```
ctctgcaaac cccgccacga tgacagcggg cgcggcagcg ctcggggagc tcaaaaagag   8580
aaagggcaca atatacccga ggataaactc catgggggac gacgcaaggg acaagctctc   8640
aaagatattt gggaacaggg tatccgtgac cggaaggggc tcgctgttca tgactcactt   8700
tgttcaagat ggcgccggca gggtctcaaa tgctgcagat gcggcagcct gcgatgttga   8760
gctgctgcac aggtaccacc tggacatgat cacccgggac ggcatattct ttctgccggg   8820
caagctgggg gccatatcgg cggcgcactc aaaggccgac ctcaagacca tgtattccgc   8880
atcagagcgc tttgcagaag gcctatgagg tatagcgccg gaggaaactt tgattatacg   8940
ggcgtgctgc cccggggccc atgatactct tcggcaagag cgaccccgcc gagctggtgc   9000
gccaggcgga cctcctgtgc agcaagaacc agttcagggc ggcaataggc ctgtacggga   9060
aaatcctcaa ggacgacccg cagaacaggg gcgtcctgca caaaaagggg ctggcccaga   9120
acagggcaaa aaagtactct gatgcgatca cgtgctttga ccggctgctc gagcttgaca   9180
acaaggacgc gcccgcgtac aacaacaagg ccatagccca ggccgagctc ggagacacgg   9240
catccgcgct ggaaaactac ggcagggcca tcgaggccga cccgcggtac gcgccggcgc   9300
gcttcaacag ggccgtgctg ctcgacaggc tgggcgagca tgaggaggcg ctgccggacc   9360
tcgacagggc agccgagctg gaccgacgca agccgaaccc gaggttctac aaggggatag   9420
tgctcggcaa gatgggcagg cacgaagagg cgctggcctg cttcaagggc gtgtgcaaga   9480
ggcatcccgg ccacgccgac tcacagttcc acgtggggat agagcttacc gagcttggca   9540
ggcacgccga ggccctcggg gagcttgcat cactgcccgc ggagcaccgc gagaacgcca   9600
atgtattgta tgccagggcg cgcagcctct cgggccttgg cagggaggac gaatccatag   9660
cgcacctgca aaaggcggcc aaaaaagatt ccaagacgat aaaaaagtgg gcccgcgcag   9720
aaaaggcctt tgacggaata cgggacgatc ccggttcaaa aagatagccg gctagaggat   9780
ctttttttctt gccgcgtcaa tccgcatcat gcggaccttt tttttgggcc ccacaagtcg   9840
cgattcatag actggtacat agaccacctc caccgccttt gcggcaaact cctcccgcag   9900
gtcgcgcatg ccgtcaggcg gggcccgcg cagcttctct tttagttttg agagcgcctc   9960
ttctgtctcc acctcggggc tccgcacatt ctctgacgca tcgagtatcc tccgcgggta  10020
cggctccacc gcgccgggcc ccgtcttgta gggaaagtcc gtctcgccgc cgtgccggtc  10080
aaggcacatc atcccttctg attccgcaaa gacatgctct tctagctcga ggtcgaccct  10140
gttcttgccg agccctgccg agagcgtctt gtgtatgcgc gacttggacc ttatgggaaa  10200
gacgccgtcg cctagcacca cctcgatcac gttctggtcc accttgatcg ggtgaaccgc  10260
ctttctgaaa aaatccgcag agtacctggc ggagacccgg atcagcgcct cgtggaccag  10320
ctttacagaa tgcacatgga cgtcttcttt ccgcggggcc ctcataaggg ccctaaaggc  10380
acccgtcttc tttgcctcta tcatggcccg agccgactcc tcagtcatgg cgttccgcag  10440
gaccgccgtc ctggtctttc cagtcatccc ctgccgcacc ccgcataagg catactatac  10500
aacgcaaggc aaggtaataa tagcctgccg tctgtaacgg ccgtatgagg tcggagggca  10560
ggcccggata catcgaaaag ttcctaaaga gggcggacaa ggcgatagac aatgcagtcg  10620
agcagggcgt caagagggca gacgagatac tagatgacgc agtcgagctc ggcaagatca  10680
ccgtgggcga ggcgcaaaaa agaagcgatg tgctgctcaa gcaggccgag cgggagagca  10740
agcggctcaa gtcaaggggc gccaaaaagc tcgaaaaggg catagggggcg gcaaaaaaga  10800
tggcagccgg caagggcgac gcgctagaga ccctggcaaa gctcggcgag ctgagaaagg  10860
```

-continued

```
cggggatcat aacggagaag gagtttcgcg ccaagaaaaa gaagcttctc gcggagatct  10920
gacttgaagc cgctagacta tacccgggac ggctcgataa aggaggtcac aaagaggtgg  10980
tttataggca cgccgtccct tgtcgacctt gcaggcgagc tcggcatatc tgagagcaac  11040
atattccacg tgacatttcc cgacggcgca aagaccaccc tgcatacgca cgagggcggg  11100
cagctgctca tagtgacctc gggcaccggc agcatgtcaa tatttgaaaa gaccggcgga  11160
ggcgaggcgg aatttgcaat aaaagagaca gacaggatac cgctaaagca gggcagcatc  11220
cagtacatac ctgccggcgt gctcacgtgc acggcgcaac agacggcacc accctgtccc  11280
atatagcggt aaactacccg tcgccatcgg gaaaggagcc gtatacatta tggtatgaat  11340
ccgactttgc cagccgggtc accggcgtgc tgtaaattat attatttgag cctctccagt  11400
atcgacaggc ttacaaggtt ggtcatcgtt atccccttgc ggatcacttc ccttctagtc  11460
ttttcgcagt acttgttgac gctctggtgg ctcttttcgc tggatacctc gagcaccaca  11520
atgttcccgc tgtacgggaa ggcaaacttt ggcggaatcc tcgagcatac atccatgcgc  11580
cctattcccg ccctgcctat cttctccttt cttgccacta ccgacgccac ctcgcgtatg  11640
tcctcctcgg aatctccgta ttccagatag tacatggata catagctcat cccgggggat  11700
tccctttcga atatctcctc gtccatgctg aataaatagg aagggccgcc cccgcggccc  11760
tccaccgcct ttatcatttt ggggccgttt ttgaaccttg ccagcaggta gtggctggcc  11820
tgctgctcaa agtacggctt gcttttggac gagaaagtgg cggtcacaaa gtacatctcg  11880
cctacgttcc tcgacgagga ccattcctcc ttgagctcta tcgaggcatg gtcgtgcgtg  11940
tatggcgtgc aggcatatcc ccccggggag gcctccgtct tggacatgca tgggatccgc  12000
ggaaccggtt aatatctagt tccatgccgc cttgggggc gggggccccg cctgtggccg  12060
gccccggggc aggcgtgcgt ggatccatgc gatagttatt taaaactagg atgccgatca  12120
cggatcgtcc caagctagct cagcctggta gagcttccgg ctgtagatgt cggccttggc  12180
tgaccgtata acagcatatc aggcatacag agaccgggtt gtcgaaggtt caattccttc  12240
gcttgggacc acataaaact gccgcgggta caccgcgcat gccgctgcgc agtgcatgca  12300
atgtgcccag tttgcccgcg ccgtgaaaga tggaattctg tccgtgcact gccgcatata  12360
tgccgcggcg cgcctgcatg ttgtgccctg ctcgtacgcg caaatgtcag gagctgccgc  12420
gccaaaagac ggcgcgttca ctgccgcgca tatgccgcgg ctgcatgctg tgccctgcct  12480
atacacggaa agatcaggag ctgccgcgcc agaacactgc gcggcgcgtg cgccgcgcgg  12540
cagggccgcg cccgtccgcc gcatcgcgcg accgggacct ctgccgctcc agcaatgtat  12600
cgagcgccga gtcgtcgact agagtgcgcg ccggcaggcc gcctggcgtc ggcacgccct  12660
gcatccccat ggcccggcgc atctcatcgt tctccctccg gagccggctc tccttctcat  12720
caagcctgct gctcatcctg tcgagaaaca tcacatccga gttgtataga tccctgcgct  12780
gctccatcat gcacagtatg tggcgcaatc gggactggtc gcatattccg gatgccatga  12840
gctccatgac cccgtctttt gtgtgcccat tctgattccc cccgggccgc cttgcggccc  12900
cgcgcatccc ggacctcatc gccgcttcct caggtattcc cggactatcc tgttggcaag  12960
ccgggtctcg tctgtcccct cgcgctcggc cagcctggag agctttcttg cgccgttctt  13020
gcccagctct attggtatct ttttcttgat gcccaccttg cgcatcctct ttagtattat  13080
cttgtggccg gagcgggggc tctgggcaag caacctcagg tagatccgcc tcgacggcct  13140
gtcgagcttt gctatctttg ataccacctt gagcgcctgg gatatggtcg gcaccgcctg  13200
gtagagcctt gtcgcctcgt cccgggatat ggtgcccggt accatcgcct tgatcttgtc  13260
```

-continued

```
cggtacgccc gcaaagccgt ggtatttctt gaacgtgggc atcgacatgc cgagcttttt  13320
tgcggcctcg gattttgtcg tctgctcggc caggaacttg catgcgtctg caagctcccg  13380
cgggctcatc tggagacggt gcaggttctc tacaaccgat gcggcctttg catcatccag  13440
gccgtactct gtatccttgg ttatcaccag aaacttggac ttttttgcgc ccaggtactt  13500
gagggccgca agccggtggt gccccgatat gaggaggtac agcccctgc cgcccctctg  13560
tatgacgggc gggttctgca gcccctctga tctgatcgac tttgcgatat cccgcacccg  13620
ggacctgtcc agcctccttg cctgcgcctc cttccacaca tgcacatttt tgaggggcac  13680
ctcgcggagg gtctgcttta tcttgggctt gtagcgccga accaacgtac ttttcaagat  13740
gcggatcctt gttaactgtg tttggtaagt ttatcacaac aattaggtta gatagagctg  13800
ttcccacgcg gcaatcccct gtatacgcac gcaaatccgc gcatactccc ccgggaggcg  13860
ttctggggcc ccggggctca cgagcccgga acctggggtg ccccgcgggg gcgtcgatag  13920
aataaatacg cgcagggggc cccgtggcgc gatcgcccgt gctgataata aactgcaaaa  13980
actacaagga ggcggccggc ggcagaattg acagcctagc ggcggcagcc gccggggcgg  14040
ccgcaaaata cggcgtcagg atagctcttg ccccgccgca gcacctgctg ggcgcagtaa  14100
agggggaaga tcttacagtt ctggcgcagc atatagacga caagggggtt ggaagcacca  14160
caggatatgt cgtgccggag ctgctgggag aatccggcgt ctctggcgcg ctcatcaacc  14220
acagcgagca ccgcgtatca gctgaccagg tggcaagcct tgtgcccagg ctcaggggtc  14280
tggatatgat ctccgtggtc tgtgtaaagg attccgccga ggcggcaaat ctctcccggc  14340
accggcccga ctacatagct atcgagcctc ccgagctgat aggctcgggc aggtccgtct  14400
catcggagag gcccgagctg atagggagg cagcagaggc catcaggggg gcggatggaa  14460
caaagctgct ctgcggggcg ggcataacat caggcgctga tgtgcgcaag gccctcgagc  14520
tcggctccaa ggggatcctc gtggcaagcg gggtggtaaa atcatcagac cccgctgcgg  14580
ccatagccga gctggcacag gccatgtcct gagtactagg cccccgcgtt attgaggcgc  14640
gtcagcaggt caaacgacga cctgcgcagc tcatccggcg acttggcgcc cgctatcacc  14700
atctttcccg acgcaaagac tagaaagctg cagctgtcca gcccttgag tatcatcccg  14760
ggaaacgacc cgggatcata tacagcgcca ggcatgcgcg acgatatcct gtctatggga  14820
acattcctac cggcatccac cgtggctaca atattgcgca cgacgggcct tatcttgcag  14880
tcgccggcag ccccgttgcg caccaggtgg agccgcgcct cgtgcagctg cccaaacgag  14940
gccctcacgg atctggcgcc gacggatatc atcttgccag aaatgaatac agtcaccctc  15000
ccctgcatgc cgggcgtctt tatgtagccg cacctgccgc cgtatacggc ctcatcatac  15060
atgcagcacg gcatggcggc catctttttt gcgctcaccc tttgtacaag gtctgatgtg  15120
ctgacgacat tgacgacccg gggccgcgtc cggggatcca gcattggtca ggatccgccc  15180
gtgcgctatt ttaaccgggg cccgggcggc cgcctcgcca tcttgtcata cttgcgcttc  15240
atcaaaatta cagtgaccat cagggttatg ccggccacgt tggtccctat tatgtagacg  15300
tcccatatgt gcaccccgta tgttatccag agcacagagc cagcccctat gaacatggtt  15360
agataccacg agacgtccct gaggctcttt gtcttgtacg ccttgattat ctggtgcacc  15420
catccggaga gtatcagtac gccgccggcc acggccacga catccagcag tgctatatcc  15480
acggtggtca tttgaaaaag aactgctcca ttccagtctg ctttggcttg cccagcatct  15540
cgtcaaagtc aaggcccatg gacgaggtga gctggtccag agtagactcc atgaactcta  15600
```

-continued

```
gatactttga cgtgtccacc tctcctgcct gggccatctc gacaggcttg acgcctgtct  15660
tgttcatcac ctttacgtac gatattatgt cgccttttt gacctccctt gcgttctcga  15720
gcagtctggc cgcccgtatg tgctgcggga cggtctttac gtattcagag ggcgccttgc  15780
ttatcatcac attgaacgcc agatccgcca gcgggacccc cctctcctcc agcctcttcc  15840
cggatgccgc tatggccttt gagatcttta gctttgccga ttcaaactcg tcctcggtct  15900
gtacagccga cagtatgtcg agcagcgaat agaacagctc ctttatgaac gggggcgtgt  15960
gcgacttttt ccccgtcagg cccttgacgt cgaccttgcc ggactttgtc accccgaaat  16020
agtttttctt cctgttagat agcacgacat acctgtactc tttgtccacc tcgagctcga  16080
cgccgtgctc ctttttggcg tgctcgacta tatcatggat ctgccgctcc tctggattct  16140
ttatgaacag cgaatcggtg tccccgtaca gcacctttac gcccatctgc tcgcagtgcg  16200
atatggtctg catgatgata tagcgcccga ccgccgtggt ggcctcggcg gcaggcagaa  16260
agtacagcgg gaatatctcg gcgcccatca ccccgtagct tgcgtttagc accaccttga  16320
gggcctggct gatcacagta tactgctgcc gctgctcctc cgttatagac tggctctttg  16380
agaggctctt gtaatagttg acgcgcaggt cgcggagcga tcctattatc atcgatgtaa  16440
gcccgttgtt tttcgtgcat acccagtggt tggtatcggg gatggtgttc tttctgcatt  16500
cgggatgaac gcacctgacg gtctcgtacg agaggtttcg cacctttatt atgctaggat  16560
acaggcttgc aaaatccata actgtaacat caaagtgtat gccctcttca ggctcgacta  16620
cgagaccacc gcggaacttt ttgtccttga ttacggcgtc gttgcttacc tgttgagacc  16680
tcttttccag ctcgtccctg cggggtatca gcgcgttgcg ctgcctgtgc tcatagtaca  16740
gcaggctcct tatccactgc gagacgccca tgcgggacat atcatcgatg ggcatccggg  16800
caatcctgct ggtcaccacc aggaggtcca tcagtatctc gttcccaaag gtgctaagct  16860
ccagcgtcag gcgcgcgtca tgatagcaat agtttgcagt ctggtataga gtgagatccc  16920
cgagagacac gccataatcg accttgccct cgccgagcat cgccttggac acgctgttca  16980
gggagtaatc tgtatacttt gccgcaaatg catacagctg gaacgacctg ttcgagaagg  17040
tcctgtacag gtccagatgg acgccgtgcc ggagcgtggc cgaatcccgc atcatgtaca  17100
ggggtatgtc ggaatccgcc acgccgaggc gccgggcccg attgtacatg tacggcatgt  17160
caaagtcgtc cccgttgtat gtaagcacaa acgggtacga gcctattatt gctagcgcgt  17220
cgcggatcat gtccgcctcc ttgtcctcgt cgtagaacac cacctcgacc ccgggggtca  17280
catcgtttgc gccctcgtcc gcgccgctct tcaggacaag gacctttctg aggccgtcgg  17340
tggcggcaaa ccccactgct gtgaccctcc tgtccgagat cttggcatcg gggatcctgc  17400
cctcctctga atccacctcg atgtcaaagc tgaggcgcct tatccggggt atgggctggt  17460
tgagcaggtc cgcccacccc gctatgaact cgcggaactc tttcctgtcg gccatgccct  17520
cgtctatgag cttgtcccag agaaggctct tgagggccag ttttacctcg tcggatattg  17580
gcatgtcatg cggaatcacc tccccgcctg ataccgaata gtacctgccc actaccaggc  17640
ccgcgtcata cagatagttc tcgtaatact ttatgtcgga ttcccacgtg tctatcacgt  17700
ttctgatgct cttctccgag tgggtcccgc ctatcgcaag aggatcagag acggttatct  17760
tggagacggg cacctccttg tcggctatca ggtcgtgccg catgacctgc tctatcccga  17820
gcacgtcctc cctgccccca agaaagccga gctcggaggg cggcagcctc gtataacagt  17880
agggcttgtg ccccgtgttg tccgtccagt ggatgatctt ttgcgattcc gactcgtaga  17940
acttgaggac cacggccctt gcctggccat cataggttgc agatacaagc agtgacgggg  18000
```

-continued gaatctcttc atcctgtgca gtcagcgcac cggcacctcc tttgttcccc cgggcatcct 18060
tgacgcccag tatgtgatct tctccttgtc catcatggtt atgctggccg atgcatcttt 18120
taccagcttg gaggcgttct ccggatatgt atccaggcag acaaaccgcc tgattcctat 18180
ggtcaccgcc atctttgtgc actctaaaca cggagagaac gtcgtataca tggtggcgtt 18240
gcctccccct gcgcctattc ccagtatcgc acagtgcatt atcgcgttgg cctctgcatg 18300
gttgcacagg caccggtcca ggccctcgcc tgagcggatc ttgccctcca tgcgctctat 18360
gcacctttcg cacccgccct cgaagcagtt ctttacgccg gggggcgtcc cgttgtatcc 18420
tgtggccagc tgcctgtgat ccctgactat gacggccccc acctttctga ccatgcagtt 18480
ggatcggagc tttgccagct ccgcctgcag catgaaatat tcgtcccagg acgggcgctc 18540
aaaaccgctc aacggccatg gtgccaccgc ccggcatatt atggtatatg ccccggtgta 18600
cgaaaccata aaacaacagg ccgcgtcagg gccgcgcgtg gagaccgcac acataacggg 18660
caaatacgta gagcccggcg ccgtcgagag gcgcgactac caggtgggcc ttgccgagca 18720
ggccatacgg gaaaactgca tagtggtgct gcctaccggc ctcggcaaga cggccgtggc 18780
cctgcaggtg atctcccact atttggacga aggcaggggg gctctcttcc ttgcgccgac 18840
aagggtgctg gtaaaccagc accgccagtt cctgggcagg gcccttacca tatccgatat 18900
taccctggtc acaggcgagg acaccgtccc gaggcgcaaa aaagcttggg gcggcagcgt 18960
gatctgcgcc acccccgaga taacaagaaa cgacatagcg cgcggaatgg tcccgctcga 19020
acagttcggc ctggttgtgt tcgacgaggc ccacagggcg gtgggcgact atgcctattc 19080
cgcaatagcg cgtgcagtgg gggagaactc tagaatgatc ggcatgactg cgacccttcc 19140
aagcgagagg gagaaagccg acgagataat gggcactctt ctctcaaaga gcatagcaca 19200
aaggaccgaa gacgacccgg atgtaaagcc ctacgtgcag gagaccgaaa ctgaatggat 19260
aaaggtggag ctgcccccgg agatgaagga gatccaaaag ctcctgaaga tggccctcga 19320
cgaaagatat gcggccctca agaggtgcgg ctatgatctc ggctcgaaca ggtcgctctc 19380
ggctctgctc cgccttcgca tggtcgttct aagcggcaac aggcgggcgg caaagccttt 19440
gtttactgcg atacgcatca catacgcgct caacatattc gaggcccacg ggtcacgcc 19500
gtttctaaag ttctgcgaga ggaccgtcaa gaaaaagggc gccggtgttg cagagctgtt 19560
cgaggaggac agaaacttta caggggccat ggcgcgcgca aaggcggcgc aggcagccgg 19620
catggagcat ccaaagatac caaagttgga agaggctgtg cgcggggcca aagggaaggc 19680
gctggtcttt acaagctaca gggactctgt cgatttaata cactcaaagc tgcaggctgc 19740
cgggataaac tcggggatcc tcataggaaa ggcgggagaa aagggcctca agcagaaaaa 19800
acaggtagag actgtcgcca agttccgcga cgggggatac gacgtgctcg tatctacaag 19860
agtgggcgag gagggcctcg acatatcgga ggtaaacctt gtggtattct atgacaatgt 19920
cccaagctcg ataaggtatg tgcagagaag gggcaggacc ggcaggaagg acgcgggcaa 19980
gctggtggta ctgatggcaa aggggactat agacgaggca tactactgga taggccggcg 20040
caagattact gccgccaggg gcatggggga caggatgaac aagtcgcttg cagcgggggg 20100
ccctgcgcca aaggcagccc caaaaaaggg gctcgagggc tatttctagg cgggcttatc 20160
ccaggcgctt tatcacgtgg tagccaaact cggattttac cggctcggat acctcgccta 20220
cctgcaggcg gaacgcggca tcctcaaacg gctttaccat cttgcccctg ccaaagtagc 20280
ccaagctgcc gtccctcttt gcgctgcccc cgtctatcga gagctccttt gccagctttc 20340

-continued

```
caaacttttc gcccgccttg aggcgctctt gcactgcgag cgcctcgccc tgcttttta  20400
ccagtatgtg cgagcacttt atcttgtccg ccatgcgcgc gcacattcca taccctgcta  20460
taacttctcg gtatgcaggg ccctgccggc cggcagatct tccgggcggg cccgccaagc  20520
tagactttta attgggatcc ggcggggcgg cgcatgtctt tgtattttac gataaagacg  20580
gccaacctgg ccctgcccga cgtggtaaag aggtacaacc acgtcctggc gtgcaagagc  20640
gaggtgatga gggccgagaa gcagatccag gtgtccatct cgtcgtcggg cggtctggac  20700
aagtacgcgg agctcaagca gcagttcaac tcgaggataa ccgagttcta ccgctcgata  20760
gaggagctgg agaagacggg cgtggtggtc aagagcatag acgaggggct cctggacttt  20820
cccgcaaagc gctttgggga cgacatctgg ctgtgctgga aggtgggcga gcgcgagatc  20880
aagttctggc atgaaaagga ctcggggttt gacggaagaa agcccataga ggtaagtgac  20940
gagtcactag tgtagatgct ctcctcctgg ctgcgcgtaa tacgcgtccg gttcctgctc  21000
gcgtcggtga tagccgtatc agcgggcctt gccctctcct ggtggcacgg ccacggaata  21060
gacgcgctca cagcggcact caccatggcc ggagtggccg ctcttcatgc aagcgtggac  21120
atgctcaacg actactggga ctacaagcgc ggcatagata cgagaaccaa gaggaccccg  21180
atgagcgggg ggacaggggt gctgccagag ggcctgctga gcccccgcca ggtgtaccgc  21240
gccggcatca tatcactggt gctcgggact gccgccggcg catactttgt gatcacaacg  21300
gggcccgtca tagctgcgat actcggcttt gcggtggtct cgatttactt ttactcgaca  21360
aggattgtgg actcgggcct ctccgaggtg ctcgtcgggg tcaagggggc gatgatcgtc  21420
cttggcgcct actacataca ggcgcccgag atcacgccgg ccgccctcct cgtcggcgcg  21480
gcagtggggg cgctgtcatc tgcggtcctc tttgtggcgt cgtttccgga ccacgacgca  21540
gacaaggagc gcggcagaaa aacgctggtg ataatactgg gcaaaaagag ggcctcgcgc  21600
atactctggg tctttccagc tgtggcgtat tcatccgtga tagcgggggt gattatccag  21660
gtgctgccag tgtactccct cgccatgctg cttgccgccc cccttgcggc aatatcggca  21720
aggggccttg ccaaagagta tgacggggac aggatcatac gggtcatgcg cggcacgctg  21780
cggttcagca ggactgcagg cgcgctgctg gtgctgggaa tactgcttgg ttgagtggaa  21840
ctagactcga gactgtgtaa gcataagatg ggcatgcgat caagtaccag aaccgataga  21900
attattctcc ataaaatcat ggaattccca caccccctga taaagatctg aagatctctg  21960
cccctctgac ggaccagtcc agacgaaagc gccatctcat caaaagggtc ggtatttgaa  22020
ttagtcacgt atgttgggga cgaacgtagt gaagtaccag cacaatctgt ccatcttcac  22080
ccagatcatg cgattctaac tgcaccatga gagtcaatcg ggtgtaaata aattgggatc  22140
acttattcta ctatcacgtt atcatctgtc atgtcaacga agatggtttg tataatctgc  22200
gggttcctaa tatctccaat gtcatcagaa gttacttctt tcgtttctcc atcccgcaga  22260
gtaacattgt gctgtcccat aggctgatag agcttctatg tatatgaaaa cttaccaact  22320
ttacagggaa ttggaagata aatcaagggt tgttgaataa gtcgactagg aggcagcata  22380
gtataatctc ctttgtacat tatgcgtaca tagccaccaa ccggttgtaa agcgacaccc  22440
tgatcaggat ttcccgcatg atgctccctg ccttcctggc ctgcacggac tcgccgaata  22500
tctttttgga cccctcaaac accatctcca cggatgtcca gcagtcgtat ccaatatcct  22560
tgttccactc gtcgtaccgg cccacctagg ccttgaccac gagctgcccg gcacggcagc  22620
ccgtgcccaa cctcgagttt atcctgatcg tggagatgaa catgtgtaac tgcagtcacg  22680
gaaaccttca gtttctggac agctatcttg ggtctagctt aaacatacgc aacgtattgg  22740
```

-continued

```
cagaattact agatttctat ggtcatgctt tcttctgtca ctctatcgaa cacggcacgt  22800
ataatgtgtg tgcgcttttc atctacaaga cttgagcagg ttattacttt tgattccccg  22860
caccgcatag taacgtcttg tatgtccatt atgaattaag acatctacgc gtataaaaac  22920
atagtattgt taccggggcg gggctacccc agggtagcat catccccctt gtacatcatg  22980
tgagcatggc cacaaaccgg ctgcaggcca acacctcgat caagatctac cgaatgatgt  23040
cccctccctt cctggcctgc acggcatcgc cgaatatctt tttgaacccc gcaaacacca  23100
tctccacgga tgtcctgcgg ccgtatccaa tatccttgtt ccactcgtcg taccggccca  23160
cctaggcctt gaccacgagc tgcccggcac ggcagcccgt gcccaacctc gagtttatcc  23220
tgatcgtgga gatgaacatg tgtaactgca gtcacggaaa ccttcagttt ctggacagct  23280
atcttgggtc tagcttaaac atacgcaacg tattggcaga attactagat ttctatggtc  23340
atgctttctt ctgtcactct atcgaacacg gcacgtataa tgtgtgtgcg cttttcatct  23400
acaagacttg agcaggttat tacttttgat tccccgcacc gcatagtaac gtcttgtatg  23460
tccattatga attaagacat ctacgcgtat aaaaacatag tattgttacc ggggcggggc  23520
taccccaggg tagcatcatc cccccttgtac atcatgtgag catggccaca aaccggctgc  23580
aggccaacac ctcgatcaag atctaccgaa tgatgtcccc tcccttcctg gcctgcacgg  23640
catcgccgaa tatctttttg aaccccgcaa acaccatctc cacggatgtc ctgcggccgt  23700
atccaatatc cttgtcccac tcgtcgtact ggcccacttg ggccttgacc acgaactgcc  23760
cggcacggca gcccgtgccc aacctcgagt ttatcctgat cgtggagatg aacatgtgga  23820
actgcaggca cggaaacctt cagtttctgg acagctatct tgggtctagc ttaaacatac  23880
gcaacgtatt ggcagaatta ctagatttct atggtcatgc tttcttctgt cactctatcg  23940
aacataaaac gtataatatg tgaacgcttt tcatctacaa gacttgtgga ggttattact  24000
tttgattccc cgcaccgtag agtaacgtct tgcatgtcca taagggatta agacatctac  24060
gcgtataaaa acatagtatt gttaccgggg cggggttacc ccagggtagc atcatccccc  24120
ttgtacatca tgtgagcatg gccacaaacc ggctgcaggc caacacctcg atcaagatct  24180
cccgaatgat gtcccctccc ttcctggcct gcacggcctc gccgaatatc tttttgaacc  24240
ccgcaaacac cgtccggttc cccgtaccag ttcggcatgc agacgtcttt aatcaggccg  24300
acaactctgc cgtagttgta ccctccaggt ttctccatta caaggccgga atcttttgat  24360
ccaaatattt ttcggcgcac gatggcgcct aattaggcag ggttagtcag caggctcaat  24420
caatatgcct attttactct tttacccacg gcttctacca ctttttttaca cccattacaa  24480
atgaacctct gtggcccggt gtccatttta atggatgaat ccgtgctgtc ctcatgtgaa  24540
cacaacggac acttgaaagt gtacctgtat ggaaatgtcg ggggggcgtc cttttcaccc  24600
aagacttttt ctatgtatat tgtgcaacat ttggcatgat acaccattcc ccctttcttg  24660
gtataatgtt gagtgcccgc aacatccttc ttgcacagag cacataatcc gggattcgat  24720
tcgtgccact ccacacagga agtatggcat ttaaaatcag aataaggcat gatggagcct  24780
tctagattct tcatgcatat ccctcaaagc tttttcatgt ccatgttctc ccccaaatgc  24840
catattactt aactattctg ttgtgcactg ctgacaaggc cctgaagttt ccgagtactc  24900
aaacacctgt acttcacaac acagtgtaaa acctcggggg atcacaagga aaggagctcg  24960
gtccaaaacc aagaccgata tggatagaga aagagaatac acgccgcggc ttttggggat  25020
ttatccgcgg cgggttgggt gatatcaagt gccagctcag gggcacgac atgccgcagg  25080
```

-continued atgtgatgga gatcaaggga cggcaatata catggcactg catgccgcag gtgtggccat 25140
aacctgataa ttgaggcccg cggctgtgcc tacagcacgg gatattggcg cagaacgggg 25200
caatctcaca ctttgtaccc ttcatacaca taaatcccgc ttggatgtgc ggctgcgcat 25260
gatcagcggg catgccacgg ccgagggtac acagaggata gccgagatgt ccggcgcaca 25320
ccatgacaac tacaaggtgg tagacgggct gcacctctcc aacgtgggga tgggcaccta 25380
ccttggcgac gcggatgacg ccaccgacag ggccgtcaca gacgcggtca agaggtcaat 25440
caagtcgggg ataaacgtca tagataccgc gataaactac cgcctccaga gggccgagcg 25500
ttccgtgggc agggccgtta cagagctctc agaggagggg ctggtatcca gggaccagat 25560
attcatatcc acaaaggcgg gatacgtgac caacgattca gaggtctccc tcgacttttg 25620
ggagtatgta aaaaaggaat acgtcggtgg cggcgtcata cagtccgggg acatatcctc 25680
gggataccac tgcatgaagc ccgcgtatct agaggaccag ctaaagagaa gccttgcaaa 25740
catgaacgtc gactgcatag atcttgtcta cgtgcacaac ccggtggagg ggcagatcaa 25800
ggaccgcccc gtgccggaga tcctcgaggg gataggcgag gcctttgcca tgtacgagaa 25860
aatgcgggag gctggccgca taaggtatta cgggctcgcc acgtgggagt gcttccgggt 25920
cgcagagggc gacccgcaga gcatgcagct cgaagcagtg gtaaaaaagg ccaaggatgc 25980
cggcggggag aaccacggct ttaggttcat acagctgcca ttcaaccagt actttgacca 26040
ggcctacatg gtaaagaacc aggggacggg cggcggcaag tcatccatac tggaggcggc 26100
agccgcgctg gacattggcg tgttcacaag cgtcccgttc atgcagggca agctgctcga 26160
gcctggcctg ctgccggagt ttggcgggct ctcgcccgcc ctgcggtccc tgcagttcat 26220
caggtctaca ccgggagtgc ttgccccct gccggggcac aagtccagcc tgcatacaga 26280
cgagaaccta aagatcatgg gcgtgccccc cattcctcct gacaagttcg gggagcttgt 26340
ggccagcctt acctcatggt cgcccggcca gaaatagtca gcgtgttccc tcgggcatta 26400
tctggtctag cacctttttt ggcagcttcg agtccgcaga atctttcaca ttgcgccggg 26460
tcctgtccac gttggcagga tacaggtcta ttcccgtaaa gcccctcttg aggcacgccg 26520
agactatccc cgttgtgccc cttcccgcaa acggatccag cacatagtcg ccctctcttg 26580
tggcaaactt tactatccgg gatacgaggt cttctgggaa caccgcaaag tgctcgttgc 26640
cgtggtgcgc ctttgtggat atctcccaga cgttcccagg gttcttgccc cgggggttgc 26700
atgctgcaaa tatcggatag tgctcgtggc cccctatccg cttgcgcgtc gcatgccttt 26760
tgaacttgcg gtagcatgtc gggcagtgct tttcggggtc atacccgtgg gcccgcgata 26820
tctcctcggt ggttggcagc tcgtcaaacg gcgtctcggg ggacgagccg tgtatcactg 26880
ctgcaatcct ccctatggct tcagggtccc tcctcccggg ggagaactgc agccggtcgc 26940
gctccggctt cctgttgacc ccgctcaggg cctcgttgcc ctggacgcgt atcgggtcta 27000
tgtcaaaggc gggggattcc gactttgata gcaccagcac aaactcgtac gcctgcgtaa 27060
ggttctgctt cgagctctgt gatagcgcgt ttttcttgta ccagactata tcctcttgaa 27120
agtggtaccc aaggtctaca agtctgagcg cgagccggtg cgggaccatc agcttccggc 27180
gccgcctccg ggtgtcgcct atcactatga agaggctgcc gtcgtcggta agcaggtcca 27240
tgcagctctt gaacacccct gccagctcct cgacgaactc atcaggcgtc ccctcctggc 27300
ccagctcgga gggatccgac ccgtactttc tgtgcccgta atacgggggg gaagtgacgg 27360
ccagcctgta cctgccgcgc tcgccattct tttttgcaag cctgggcagc accgcccggg 27420
catccccccg gataacctgg aaccggttgt tcatgttgcc tgccccacat caggctggac 27480

-continued

```
ggacagatct gcgcagcagg cgggccgcgc gatcctacgg gtcatacaca ttctatgcgg  27540
ctgccccggc gccgacttaa aatcgttgta ggatgcggcg ccgcagatgc attgcccgcc  27600
ttatacaccg cccgggatcg gccgccttgc agcacacgca gtataaacgg gggcccgggc  27660
ggcgcgtatc acatgtggat aaaggacgaa ttcctcggcc cgggcaacaa gatgaggctg  27720
ctctacctga tactgcccat ctatgggtat atctttctgg agtactatcc gttctttccc  27780
tggatggcca cctactggtg gtcagtagct ctcagccccc cgatagtgcc cacgcattat  27840
gccggggagg ccctggggcg gctgatcggg gatcacgtat tgtttggcat caccacaaag  27900
tacgtctatg cggcaatatg gctcggcatg gcccatggga taatcctgct ggcagggcgc  27960
ctccggggac ctaggcaggc gccacggacg ggcatcccat aggctctggg gcatccgcgg  28020
gtccccgcgg tccaattaaa tacagcaagg aacgggtagt ttcgttgaag ctgcaaggca  28080
agactgccgt gatcaccggc agtggtaccg ggatcgggct ggcggtggca aggaaatttg  28140
ccgagaacgg ggccagcgtg gtaatactcg gaaggagaaa ggagcccctc gatgaggcag  28200
cagcagagct caaaaagata gcggaatctg caggctgcgg ggcctcgatc aggatattcg  28260
ccggggtgga cgtggccgac gaatccgcga taacgaaaat gttcgacgag ctgtccagct  28320
caggtgtaac cgtggacata ctggtgaaca atgccggcgt gtcggggccc gtcacgtgct  28380
ttgccaacaa tgatctagaa gagttccgcg gggcagtcga catacacctg accggctcct  28440
tctggacatc gagggaggcc ctcaaggtca tgaaaaaggg ctccaagatt gtcaccatga  28500
ctacgttttt tgcagaagag aggccactcg agcagaggcc gtacaggttc cgcgacccgt  28560
atacaaccgc acagggcgca aagaacaggc tcgccgaggc gatgtcgtgg gatcttttag  28620
accgcgggat aacatcgata gcgaccaacc ccggccccgt ccattctgac aggatataca  28680
agacggtata cccgagggcg gcactcgagt ttgtcagggt ttcagggttt gaggacctgc  28740
agccagaaga agtcgaggtg gcaggcggca ggctaatcca cctgctcggc gcggacgacg  28800
atgcaagaaa aaaaggcata gcagaggccg cagagcactt tgccaagcta aagcccgtgg  28860
atcccgcaaa gctagaggcc acccttgatg ccctgctcgc aaagatcaag gggatagccg  28920
aaaagataca ggccaacact gcaaggatga taccagacgg ggagtttctc tcccaggacc  28980
aggtggccga gacggtactc gccctctgcg atgacaagat ggccaagacg gtaaacggcc  29040
gcgtaatccc cgccgacagg gtattctacc cggtaagggc gcatgtggcc aatgccgctc  29100
cgcgcgtgcc cccgcacgac tattccgggg gatgcgtcct attcatgata gatgcagcag  29160
acgacaggga tgtagaaagg gcgaccgccc tggcatccca tgtggaaagc cacgggggca  29220
cggcagtctg catagtctca gaagactcgc cccgcgcggc aaaggagatg atagcgtcaa  29280
agttccactc gcatgcgagc cacatagaca aggtagacga gataaacagg tggctgagcg  29340
ctgcatcaac aaagataggc cccatatctg cagtggtcca cctgtccggc aggatgccaa  29400
aatccggcag cctaatggat ctctccagaa aagaatggga cgcgctggtt gacaggttca  29460
tagggacgcc ggctgccgtc ctgcacaggt cgcttgagca ctttgcaccc ggcgggcgca  29520
aggacccccg tttgttcaag ggcaagagcg gcgtcatcgt gataataggc cccgacctgc  29580
ccgcggggaa aaaggcctcc ggcgccgaga gggcaagggc ggagatcttc cggggtgcgc  29640
tcaggccgct gacgactaca gtcaaccagg agctcagcga tgtgctaaag tcaaacgtgc  29700
gcctgtttac catccttccc ggcagggcgg acgggggcga gaccgatgat tcccgcatat  29760
ctgctgcaat cgactacttt ctgacccccg aggctgtctc gtccggcgag gtcatattct  29820
```

-continued

```
gcgtagacga gaacaggggc tagcccgcca cagcgtccca gaagagtttt gctgccacta  29880

caagtatgac cactgccgcc agtatgcgca ggcccctctc cctcaggttc agcgagagct  29940

tggcgcccag caggcccccc gcaaacgcgc cagacgagag cagcagtgca tggtaaaagt  30000

cagtgtgccc cagcagcgta tgggtgacca tgccggtaaa tgccacaaac atcaggacca  30060

gctgcgcggt gggcgcggcc ctccacatgc tcatgcccat tatcgccacc atgagcggga  30120

caaatacaag gcccccgcct atcccaaaga agctcgatat tatccccgcg aaaaagctgg  30180

ccgctatgga tagcagcagg acggtcaggt gggagcgccg ctgcccctcc ccaatcctgc  30240

tgctgagcag caggtatgca gcagatccca ccaggacgat cccaaagaac aatctgaaga  30300

tatcaggcgt tgctgcggcg gagaatagcg cccctagaac ggtaccgggc agcgccagca  30360

ggcccagcgt cagccccgtc cggtagtcta tcctcttctg cctggcatat gacgcggtgg  30420

ccgccgacgc gctgctaaat gccgcaaaga ggctgctgct ggctgcagcc gtcggtgaaa  30480

agcccataaa ggtcagcacg ggaaccacca cgaacccgcc gccaagcccc accatcgagc  30540

cgattacccc ggctgccagg ccaagcagcg gcagccatac ctcctccatg acaacctgcg  30600

gcactgctgt tatgtataat accgtttttg gggcgagga aacggatatc atgcctagaa  30660

gccgtctgtg ctatccctgc cgacccccaa gccccaccca cttcacactc atctagtaag  30720

caaatcttgc accaagccgg atattttcca tggttttggc aataaattca ataaacagta  30780

cgttcggtca tactgcatgg caaaagagac catagggaac cgcccagtcg atatcatgaa  30840

ggagggcaac gaggtcaaga tagtattcca ccccattcta aaaggggcaa aacaccccga  30900

cgcggccgta ttctcgataa aactgtcgaa aaaagattta gagatcatca ggaatgcttt  30960

ctaacatact gtaaaatctc aaaaacatac tgcaacgtgc gatttatata cgggaaatgc  31020

gatcgcgata tagtgacaaa atataaccga tccgctagtg aaagcatggg atcggagacc  31080

tatgggtttg atgccatacg aggcatgcaa gctaaccacg aatattacgt taccatatgt  31140

cctctaaaga ttattcccaa gctcttcata ttcaacgagt atgagctccc ggcaaagctc  31200

agagctcaaa ggacactccg aaaatctaga attccaaccc tcaaggacta catactaagc  31260

aatcctgacg agtacatatt ctcgtccctc gctgcatcgg tggatgggcg catgaagttt  31320

atcccagccc cgcatctggg gccagatggt aaaatgggca gactccacat agacatgtcc  31380

tccaagctaa taatcaacga cggacaacac cgccgcaagg caatagaggc agccttgctc  31440

gagaagccgg atctgggcaa tgagtcaatt tcagttgtat tttttgagga tcgagggctt  31500

aaacgctgtc agcaaatgtt ttccgatctg aacaaaaatg ctgtcaaacc atccaagtca  31560

ctcaatatac tgtatgacaa caggaatcca ttttctcgtt ttatagtgga catggtagat  31620

gagatagatg ttttccggga cagggtagag ctggaaaaga ccaccatagg gaaaaatgcc  31680

aaggaagcat ttactcttgg gggattgtct gatgcaacaa tgagactgtt cggcaaaaaa  31740

tccttgtcgc gacccagcaa ggaacaaaag ggactcataa aggagttctg gaaatgcgtc  31800

tcagccaaca tgcaagaatg gggacggtta gtagacggcg aaatgtcggc agacgagctg  31860

cgtgcaaact atgtcaatgg ccataccaac tgccttaatt cactagggga ggtaggccga  31920

acagtaatca agcagcatcc agaatcgtgg aaaagaaagc tttcctctct gtctcggatt  31980

gactggtcca gggaaaacga ggtgtgggag ggcaatctta tacagggtaa gaagatggtg  32040

aggaccacca tcggaataat gctcggggct ggcgtcatac ttcgggaatg cagcatacga  32100

gttcctgaag agattgagag gtatgagaaa tgacatctgt gtttgacaag cggacgactg  32160

acagcatata cgacgaggta cgctcagtat acctcaacga tgcacgccct tggatccttg  32220
```

-continued

```
ggtttagtgg cggaaaagac tcgacatgca tggtacagat tgtatggaaa gccctctcgg  32280

aactacctgc agacaagctg gacaaaaaga tctacatagt gtcgtcggac accttggtag  32340

agtccccaca gatagtggag cggctgacca agtcacttga cagcatagag aaggcggcaa  32400

aagaggccca tattccaata tcgaccaacc tactgcggcc tccgattact gacacattct  32460

gggtccggat actgggcatg gggtaccctg cccccacctc catgttcaga tggtgcactg  32520

atatgctcaa aatagcaaac gctgacaggt tcatcaaaga gagagtctcc gagtatgggg  32580

aggtcatagt tttgctgggc acccgcaaga gcgagagcgc cacccggcag caggtaatga  32640

atctgctgga gatagagaat agcgttctaa gccaccataa aaaattcgca cagacctacg  32700

tgtatacccc cctggtggac tttgaggcgg aggacgtatg gaactacctg ctccagaata  32760

agaatccatg ggcgataac aaccgagacc tacttgccct gtatcaggat gccaatgcgg  32820

cagagtgccc tcttgtggtg gacaccagca cgccatcctg cggaggtggc aggttcggct  32880

gctggacgtg cacggtggta gacaagcaaa agtctctgga cagcatgatt gaaaacggtc  32940

atgaatggat ggaaccgctg gcagaattgc gccacattct aaagcagaca caggatcc    32998


<210> SEQ ID NO 2
<211> LENGTH: 42432
<212> TYPE: DNA
<213> ORGANISM: Cenarchaeum symbiosum
<220> FEATURE:
<221> NAME/KEY: CDS
<222> LOCATION: (3)...(10421)
<221> NAME/KEY: CDS
<222> LOCATION: (10625)...(11434)
<221> NAME/KEY: CDS
<222> LOCATION: (11478)...(13046)
<221> NAME/KEY: CDS
<222> LOCATION: (13046)...(14620)
<221> NAME/KEY: CDS
<222> LOCATION: (23558)...(24862)
<221> NAME/KEY: CDS
<222> LOCATION: (24913)...(25728)
<221> NAME/KEY: CDS
<222> LOCATION: (26504)...(26881)
<221> NAME/KEY: CDS
<222> LOCATION: (29655)...(30491)
<221> NAME/KEY: CDS
<222> LOCATION: (34559)...(36067)
<221> NAME/KEY: CDS
<222> LOCATION: (37002)...(37403)
<221> NAME/KEY: CDS
<222> LOCATION: (37404)...(38282)
<221> NAME/KEY: CDS
<222> LOCATION: (39454)...(40572)

<400> SEQUENCE: 2

ggatccccgc gccgccagga gagggcagcc ttggcggggt ggcaatatcc gacgacggga     60

ggtacatgta cgcaatcggc agggatctgc tcacagtata ccggtataca atgaacccgc    120

cccatgacat agcctcggcc gcgctcggtg cgcagtcatt ttctctgcct ggcggcatca    180

gccccgcccc cggcgcgccg accggccttg acatctcgga tgacggccgc cacctgtacg    240

tcccggacga aaacggcgtc gtgtacaggt ttgatctgga aagcccgtac aggctagacg    300

gcggcacgtt tggctcttct gtttatgtgg gatccgacgt tgccgcgccc cgcggcgtat    360

acgtggcgcc gggcggcagc ctcatgctgg tctcggatag tgcagacggc accatccaca    420

ggtacgagct ggcaagcccg tacgagccgg cgggcgcggc aaacagggga tcattcgacg    480

tgtcggatat ggacggctcg cctgtcgggg cggggtttgc gggcggcctg cacatgtatg    540

tcgcgggaaa cgacaccgga agggtctacc agtatccggc gggcacgcac cagatacagg    600
```

-continued

```
aggcagccgc agggccgcgg ctgctctcgg ccgtcctgga caaagacgga accctgaggg    660
cggcctttga cggcacggta gacgcgggat ccgtgcagcc cgggatgatc accatcaggg    720
acggccatgg ctccaacacg ggaataccc  ttttgcttgc cgggggtgcc gcggactctg    780
atgtcatgac atttgtggtc cccgagaaag acagggcaga ggctgccgca tacggggacc    840
agtcgctgca tgttcccgcc gcggcgctgg cggggactgg cggcgggccg tttgtgcccg    900
acttttccgg gggctcgctg ctggcgtccc tgtaccggca cgagcggccg ttccagggcg    960
aggagatggc acggacggag agatccgaca ggtacgcgct tactgtaact gcaggcggga   1020
gtcagatgca tgtgggcggc gccggcggaa acatcacctg gtacgatctt ggcacgcccc   1080
atgacataac gaccggcgtc cgcgcgggat ccgacatcct gccggcgtat ccatccgcgg   1140
gcagaaacgt ggtgccgtca ataacgggca ttgccttctc ggatgacggc atgcggttgt   1200
ttgcagcaaa ccggggcgac cgcattccaa tgtaccagct ggacagcccg tacgacatag   1260
ggagcgccag cctcgaggga accctgttta cggggttcca gtcgggcatt gcattctcgg   1320
atgacggcac gcgcatgttt gccgccctgc tcaccgagaa tgccatacgg cagtacgacc   1380
tggagggccc ctatgacata cgcggggcgg gcaatgcggg ccagtacgac ctggacatcc   1440
cgctgcaccc aggactgctg ttcctgctga cctcgggggt gcacttttcg cccgacggga   1500
cgaggatgtt cgtcggcgag gggatatcag atgcggagga tgccaacgcg aacagggatg   1560
tcaacgtcaa cctgtggcac aggtttgatc tctccacgcc gtttgatgtg ctcacggcgg   1620
agcgcgtgga cacgtacgag tacagcacgg ggccggcagg cgatctcgag gacctctccc   1680
tgtcccctga cggccgcaga ttgtacaccc tgtcgagcga gagggtaagc tcaagcgagt   1740
atacaatcac ccgggcccag tactggctgc cagaaccgta cgacgtgacg ccgccgtacc   1800
atgtgccgtc attcaacgca agccaggggg gcaacctggc agacccctac gggatggcct   1860
tctcgcccga cgggaccagg ctgctggtca cggggcacgg gcagacgaat gcaaagctgt   1920
tccacctgaa tccgcccttt gatgtgggca cggccgtgtt ccacgaccac ggcaggttcc   1980
gccccggggg gcccgcaagc gagatcgagg cgtcggggat atccctgtct gccgacggct   2040
ccaggatgtt tctctccgac cgcggccgcg gggccatcag ccagtacacg ctggttgcgc   2100
cctttgatgt ggagtttgcg tcggatgtgt ccgcggatgg gcagctcgac gttggcgccc   2160
aggatgcgct tcccggcggg cttgccttct cgcccggggg gacgaggcta ttcatggtgg   2220
gaggcatgga caggtcagtt cacatgtatt ccctgaatac gccgtttgac ctgggcgggg   2280
cagagcatgc ggcgtcgttt ggcgtggggg acagggtctc ggatcccctc ggcatcgcct   2340
ttgggaacgg ggggactaaa atgctaatag ccgatacgac aggctttgtg cacgggtacg   2400
accttggcgc cccgtacgat atctcgggcc ccgcgtacag cggcatattt gacgccggcg   2460
gcagcatccg ggacgtggcc gtcggcgggg ggtccatgtt catactcgag gggggagacgg  2520
accgggtgta tgagcaccgc cccggcatat acccggtggt ctcagcactg gacgggccgg   2580
cgctggtctc tgctgcagca gatgcaaggg tgggtgcggc cgaggtgctc tttgatcgcg   2640
cggtggatgt tggcgggata gaccccgggg gggtccgcat agtggatgca gcaggccccc   2700
tgcccggcgt ggtgatctcg gatgccgtca taccaggcga ggatcccggc gtggccaggt   2760
tcagcctgtc ggacgcggag gtccttgccg tgtccgggta tgccgagccg agtctggtct   2820
ttggaaggca tgcggtgccg ggcgcggcag gcggcacatt tccctcccag ataggcaacg   2880
ccacggagct tgtgggatcg attccgaatc cgaccctgga ttttgggacg accctgacgg   2940
```

-continued

```
gggcggcatt ctcggcggac gggacggtgg tatttctctc agacggcccc accggcaggg   3000

tgtacccgta ttcactgaat atcccctttg acatatcgtc tgcggcgcct gggggctttg   3060

taatcgtgcc cgtcggagtc tcggacattg cgttttctgc cgacgggcgg aacatgctag   3120

tcgcggacga aaccggggga atacacaggt acctggcccg cagcccgtac gagataggca   3180

cggatttcat caaatcatcc ctgggtgagt ttgtcgagac attctcggcg gcgccccgcg   3240

tgcaggatct tgccggcatc gccttttcgc acgacggcat gatcatgctt gcggccggcg   3300

gctcggggtc tgtgcaccgg tactcgctgc catccccgta tgcagtatcg gggccaaat    3360

acgaggagac ggcgatgatt ggcgggagcc cgtcggggct ggagttctcg tccgacggcc   3420

tgaggatgtt tgttcccgat gcgggctcgg agacggcggc agtctacggc cttgccgccc   3480

cctacgggat tggcgaggcg gagccgctgc cgccgctgtt cctgggggta ggggcagaag   3540

aggccacgct ctcgcctgac ggcaggcaca tcctagttcc cggcaggccc ggcctgtccc   3600

agtactcgct gttctcgacg aatcttgagc tgtgcgcgga gccccggggc attgacgggg   3660

gatcgtgcga agatgggata tacgcctttg agagtccggg caggggcgag ggcgtatcgc   3720

ttgccgcctc gataacggcg gcagacgggc caggaattgg cgagctgcac gggtttgcag   3780

gcccgccgat gccggcgcct gtcatggagc aggtcacact ggattcgcgg gagggcacac   3840

tcagggtcag gctggacagg acagtggacg tcgacacggt gcgcccctat aagatgtggg   3900

tggaggattc agacggcagc cagacaaccc tggcaaattc aacactgttg aatgccgaaa   3960

actcgaacat tctgctcttc aggctggatg atgcggccgc aggcaaaata tccgggtata   4020

catcccccgt gtttcgcacg tggtcgtcgc cgttcctggg cacagacgga gccaccaggc   4080

cccatacgct gggctttgga gacgtgcgcc ttgcggatat atacgatgca tccggggatg   4140

tcccgtcgcc gtcgggcatt gagttttcag atgacggcat gaggatgttc gttacgggga   4200

tcggcacgcc aggcatcaac atattcacac tgtccgcccc ctttgacata acattgccga   4260

agcattccgg ctcaaccaac ataggcggcc tgtccgtgtc tgatctggca tttgcaaaca   4320

atgggaacag cctcacggtg ctcgatgtgg acggggtgtt gcgcgtctac gcccttgggg   4380

acgattacaa tgtggtcacc ggaaccaccc agaagtttag gattacgctc gataccacac   4440

agggcatacc caattccatt tacacatctc cggacggcct gtcacagttt gtggcatatg   4500

atgacaggat tgacttgtac gtgcttggca gcccaaacga catatcgtcg acaaccgaga   4560

taatcccgta ttcgctgcca aggccggacc cgccaaccgg catggacttt acgccagacg   4620

ggcgcaggat gttcctgtcc accgagaacg ggatagacca gtacctgctt tcagaaccgt   4680

ttgcagtcac cacgtcggta tttttgcgca cgatccccat tgacggaggg gcggagggaa   4740

tacggtttgt agacaacgga aggggcctgt ttgtgccggg cgccgacggc atcatccaga   4800

ggcacgagct catctacccg tacggggcca gcacgtcgtt gttggagacc gtcagggacg   4860

gcgtgacgga cggcggtccg ggcgagaacc cggccgccgg agagatccgc cttgcgggca   4920

cattcaatgc atccgataat gtacagtcgc cgtcgggcat tgagttttca ggcgacggca   4980

cggggatgtt tgttaccggg tttggggccg cgggcgtgaa tgaattctcc ctgtccgccc   5040

cctttgatac aaccctcccg gtgcatgtgg aattgcacga tataggcggc cagccggcag   5100

ttgatctggc gtttgcagaa gatggcagga ccctcctgtt gctggccgcg gatggaacac   5160

tggatttcta cagccttgcc ggtgatgcct atgatatagg ggaagcatcc cgtacttttc   5220

aagtgccgtt tgaggatgcc gcgggtgctg tgcccggcgc cttttaccag cctccggatg   5280

gctcgtctat tattgccgca tttgacggca ggattgacca gtatgtggtg atccccttcg   5340
```

-continued

```
agttcgtgtc atatccactg acaaggcccg gcacgcccac agggattgac tttgcgccag   5400
acgggcgctg gatgttcctg tccaccgaga acgggataga ccagtacctg ctgtcgatcc   5460
cctttgacgt gcgcagcctg acgtatacgg gaaccattcc agtagacggg gtggagggaa   5520
tgcagtttgc ggacaacggc agggcactgt ttttggcgga cagtgaaggc ttgatttaca   5580
attatgacct ggaggacccg tatgctctgg atggcaacac aatttccgtg gaattctcgt   5640
ttgacggtag cgtgatgtat gtgctggagt acgacacaaa aagggtggtc tcgtacgagt   5700
tggagtttcc ctttgacgta tcgagcagaa cacgtgcaga cacgctggac ataccacaaa   5760
ttgactcacc aagacacgtt gcagtctcga tgcccggcaa ccacctgtac ataacaaact   5820
cggtgtttgg ggaagatgac accatacact cctatggaat atctaacaat gacatatcgt   5880
cggcatcata catcggcgag gaaggcatcc cggaacccgt gataaacggg attgactttt   5940
ccaacaacgg ccgccgcatg tttctgattg ggggcaacgg gttcgactac caggtgatac   6000
atgactacat gctaggcaca agatacgaca tatccagcag gagcctgctt gatacatatg   6060
ccattccagg gccggttgtt tttcccgcgg gccttgattt ctcgtttgac aggctgtcca   6120
tgtttataat aagcaccgcc ggttcggtat acaggtacgg cctggacgat ccgttcatag   6180
ttgaaacaat ggactatcag gagtctttcc ggctgcccgt accatcagcg gctgataatt   6240
caatatcgga tctggcattc ggcagcagcg gcctgaatgc cgtaatatcg cacgaggggc   6300
tcgacaccct gtacagcttt gtactggaca tcccgtatgg ggccgaattg gatattgaca   6360
ggcttgagct tccgctggtg ggggttccga cgggattcga gttctcggac aacgggcgcc   6420
agttgtacat tggcgcgttt cgtgactctc aatcctcgcc aggcaccctg cctgcgggcc   6480
tgcagcgcta tgagcttggc ataccatatg acctggcttc ggctgtattt gcgcagtccc   6540
tgggaatatt cgattttcct cccttcaacg gcatgcgggc caatggcagc ttggcaggat   6600
tacatgtgcc gcccgatgga agcatcctgt tcagggccgg aaatgccgaa agaaccgtaa   6660
tcagctatga catggacagc catgatttgg atacattatc attcagggaa tcattcaaac   6720
cagatgtcgg acagtcgaca cccaacataa gggacatgga catatccccg gacggcatgt   6780
tcctctacct gcttcaaggc gatgttctgg acatgtacaa ccttacagat agttattcgc   6840
ttgatgcccc ggcatatgcg ggtaccctgg atttggaacc ggaggatgta atacccaggg   6900
ggatttcatt ctcacgggat ggcacgagtc tgtttatgac aggcgaagac gtggaccaca   6960
ttcacgaata tgcattgaat gaaccatggg acatacgcaa tgccatactt gcaggctccc   7020
tgtccataag cgcagtgaat ggtgcaccgc gggggctgga tatatcggag gatggcacaa   7080
ctgcacatac tatgcgcggg cgtgactttg acacggggcc cgcatccctg gtaaaccaca   7140
tattgccagg ccaatattcc ctgctgacgg atgcgccggc gtttgcatac cccgtggagg   7200
aggagggtgc accgggggat cttgcattct ccgatgacgg catgcgcatg ttcgtggcgg   7260
gcgtaaacaa ccatttaaga cagtacaacc tgctgtcgcc gtatgacact gaaaatgcag   7320
aacatttcat ctcgacggat ctgctgactg cggacagggg ccccacgggt cttgtatttt   7380
cagatgagaa cgactttttc agcacaggcg ccagggccca atttgtgcgc cagtttacga   7440
caaaccgccc gtacgacgca tccacaataa cactgagtga caacggactg tacaaggtga   7500
gcgtggacgg cctgccgtcc ggcatacggt ttacccccga cggcatgaag atgttcatat   7560
cgggccagga gacggccatg atataccagt attccctgcc gtccccgtat gacacatccg   7620
gggcggtcag ggacagggtt gagatagtcg cagggctctt tagaaatgca ggtttgtccg   7680
```

-continued

```
tcgggttgaa cgagcccagt ccttccggct ttgacttttc ggaggacgga atggagctgt   7740
acgtgacggg gtcgggcctt gttcacaggt atttcctgcc atcgccatac ggcctcgaag   7800
atgcagcgta cgggggcagc ttccacacgt tcagggagag cacgccgctg ggagtggtgg   7860
tgcgggggga tgccatgttt gtggccgggg acagtactga ttccatattg aaatattccc   7920
tgaacgcaca acctgtcggc aacataaccc atgccgatac gcgcgccggg attgccgaca   7980
gggcggagat cgtgtttggg gcaatggcag atacgcgcgc cgagattctc gacggcgccg   8040
atgtagttca taagagtgtg aaaattgacg tattcccaat atcggagggc ataacagtgg   8100
gcagggcact ttatccagag gacgccgcca tacttgatga cggcgcgaat gccacgcata   8160
atagggttgt aatcattgtt cacgacataa cagaaggcga tgcgccgtcc atacatgatg   8220
agccgattgc cgtggggatt tacgccctcg gccctatgga tacaatcgcc gtggttgatc   8280
tccaccgcct ggccgtatcc gcatccttgt ccgggggtga ttccccgtcg gcctcagatg   8340
catccggagt agtggccgag agccgcagaa acgcggtgga caggcctggc gtggaagagc   8400
gcataggaca tggtgtatcc ctggaggcgg ccgacaggcc tgccgtcgac aacatgatgg   8460
atacggatag tgccggcgtg tacgaccgca gtccggacga cgggcccgcc gtatccgaca   8520
ggtccgcgct ggggcttgcc cggatggcag ccgacaggcc tgcagtcgat gacatgatgg   8580
atacggatag tgccggcgtg tacgaccgca gcccggacga cgggcccgcc atatccgaca   8640
ggtccgcgct ggggcttgcc cggatggcag ccgacaggcc tgcagtcgac gacatgatgg   8700
atacgggcag tgccggcgtg tacgaccgca gcccggacga cgggcccgcc atatccgaca   8760
ggtccgcgct ggggcttgcc cggatggcag ccgacaggcc tgcagtcgat gacatgatgg   8820
atacgggcag tgagagcacg agcaggcttg gaccggttga caggccagaa atagtcgagc   8880
gccacagcct ggccgcgtct gtatacctgt ccgggggcga ttccccgtcg gtcgcagacg   8940
gtcatgatgt ggagtccgag ggccgcagag acggggggga caggcctggc atcgacgagc   9000
gtatagtcat caagatctcg tacagccgcg gcgcagccga tgcgcccaga gtggaggatg   9060
caatggagac ttccggcgtg accgcgtaca gccgcggcgc agccgatgcg cccagagtgg   9120
aggatgcaat ggagacttcc ggcgtgaccg tccccaggcg cagtaccatg gacgcgccca   9180
cagtggccga tgaccacagc ctggcccgga ccgcatccat atccgaaggc gattccccga   9240
catttgcaga ggcgcgccgc gcggataccg ttggggatat agacgaggtg gacgcgccca   9300
cagtggccga tgaccacagt ctggcccggg ccgcatccat atccgaaggc gattccccga   9360
catttgcaga ggtgcgccgc gcggataccg ttggggatat agacgaggtg gacgcgcccg   9420
ccgtggccga gaggctcctg gcagtcctcg gcctgcaggc ccctgattcg ccgggagtgt   9480
gggatactgt aggaatagat cactcggaga tttcaggcga tcctgtgccg gagccaagag   9540
tagtgcccag gggcggtggc ggtgggggag gcggttcttc gaaccgcggc cttgaaccgc   9600
atggcggcgg gtatgagatt gactttgagt tccgcataga cggcaggctg gtgctcttca   9660
atgggacaga cgtgctagcc gaatccggca aggacctgct catccgtccg gtgttccggc   9720
cggaggggag tttcaacata tttgatatgg aggtgttgtt taccgccccc ggcggggaga   9780
tatcgactgc ctactacaac agggctggaa tcctcatggg gattgactgc ggcgagctga   9840
ttatgaccga tacgacgtat tcatgcgaca tgctggacat attcggagat gagatatacc   9900
atgtggagag gcttgacgca ttcaacggca tggtcatctc cttggacggc cccctcgacg   9960
ggacggtcag tgtatcgctt cgtgacaacc acggcatccc gctggcgcag catcggctgc  10020
ataaatacga gattttgatt ttggacgccg ctgaaaacag acccctgtca gtctcgacgg  10080
```

-continued

```
accccaagcc cgtggaggat ccatcgcccg tgcagcatat agagtccctc cagatggatc  10140
cggagcccgt ggagtccgag cccctcccga tggactccga gcccgtggag gatctggaac  10200
ctgtgcagca tctagagtcc ctcccgatgg accccgagcc cgtggaggat ctggaacctg  10260
tgcagcatct cgagcccgtg cagggatccc cgcccgtgca gggagggccg gagtccgtgg  10320
agtcaggcat agcatacacg ctatggcagt tcctttcagg actgctggat gccctgggtc  10380
ttgccgaccc ggatgtcgga tctgtccaaa aaacgtcctg atgcgttcaa aaagccggcc  10440
ctgcccccgt gtgcgcggcc atgcttcaac atgatgggtt tgaagggacc agcccgcggt  10500
cctgccggca tccaattccc gagatcctgt tacgtgcatc ggccatccct gtacgctgcc  10560
acatggttac tttgtgtgat catttccggg cagagatcaa gtcattgatt ggaaaactta  10620
aatcatgcat gggatcgagg gcggccgggg agatatgtcg gagaattttg tggcgttttg  10680
cgtggcgtgc gccaggggag tcacaaagga cgagatgaag tatgtagacg ggagggtctt  10740
ccacaaagag tgccatgcaa ggcacggcgg gcagatccgc ttccccaacc cagaggtcga  10800
gcagcgcgtg gccgagctga aggtggacct gatacagatg agaaaccagc tggccgagat  10860
gaacagggcg tcgggggacg gaggggtgca ttccagcgcc acctctgcgg ccgaggccga  10920
gcagcacagg gccgagctaa aggtacagct ggtgcagatg agaaaccagc tggccgagat  10980
gaacaggaag gcccccggaa agccggcacg gaaaaaggcc gcaggcaaga ctgcacggag  11040
aaagagcggc aagaagacgg tgcgcaggaa gaccggcaag aggactgccg gtaagaaggc  11100
cggggcgcgg aggaagacta cggtcaagag gacggcgcgg aggaagacca cggcaaagaa  11160
ggcagccggc agaaaggccg gggcgcgcag aaaggccaca gtcaagagga cggtgcacaa  11220
aaagattgga gtgcggagga agactacggc aaggaggacg gccggtaaga gtacggtgcg  11280
caggaagagc acagtcaaga ggacggtgca caggaagacc ggcaagaagg cagtagtacg  11340
caggaagagc acagtcaaga ggacggcacg gaggccggcc ggcagaaaga cccccggaag  11400
ggccgcgcgc agggccggcg caaagaggcg ctagcctgct gattaggaat ttaaggcggg  11460
cgccgggcag caggtaaatg cagtcgcttg gacggctaga cgaggcgtgc gcggagatat  11520
cgcgcagcct gcttgaatac gagtccccca ccgccggtga tgtccggacg gagatcagaa  11580
gggcatgcac aaagtactcg ctccggagga tcccaaagaa ccgcgagata ctggccaccg  11640
ccaggggtca ggactttgac aggctgcgcc ccctgctgct caaaaagccc gtaaagaccg  11700
catccggggt ggccgtgata gcagtcatgc ccatgccgta cgcgtgcccc cacggcagat  11760
gcacatactg ccccggcggg gaggcgtcga acacacccaa cagctatacc ggcggcgagc  11820
ccatagcggc gggcgccatg aacagcgggt acgacccgga agagcaggtc cgcgcgggtc  11880
tggcccggct gcgcgcgcac ggccacgatg tagccaagct ggagatagta atagtgggcg  11940
gcacattcct gttcatgccg caggagtacc aggagtggtt cgtcaagtcc tgttatgacg  12000
cgctcaacgg gtccgcttcc gcggggatgg aggaggccaa gcaccgaaat gaaactgccg  12060
tgcacagaaa cgtgggcctc accatagaga ccaagccgga ctattgcagg acagagcatg  12120
tggacgcgat gctcggcttt ggggccacgc gcgtggagat aggcgtgcag agcctccggg  12180
aggaggtcta cttgagggtc aaccgggggc acggctacca ggatgtgaca gagtcgtttg  12240
ccgccgccag ggatgcaggc tacaaggtgg ctgcccacat gatgccagga ctcccggggg  12300
ccaccccgga aggcgacatc gaggatctgc gcatgctgtt tgaggatccc gcgctcaggc  12360
cggacatgct caaggtgtac cccgcgctag tagtaagggg cacccccatg tatgaggagt  12420
```

-continued

```
attcgagggg cgagtattcc ccgtatacgg aagaggaggt catccgggtg ctctccgagg  12480
ccaaggcgcg cgtgcccagg tgggcgagga taatgcgcgt gcagcgcgag atacaccccg  12540
acgagatagt ggccgggccg aggagcggca acctccgcca gctggtgcac aagaggctcc  12600
aagagcaggg ccgccgatgc cgctgcatac ggtgcaggga ggcggggctc gcggggagga  12660
ccgtgccgca gaagctccgt attgacaggg cggactattc ggcctcgggg gggagagaat  12720
cgtttatctc gcttgtagac ggggatgatg ccatctatgg ctttgtgcgc ctgcgcaagc  12780
cctccggagc agcacacagg ccggaggtca caccggaatc ctgcataata cgcgagctgc  12840
acgtatacgg caggtcgctt ggcctcggcg agaggggcgg catacagcac tcgggtctag  12900
gcagaaggct cgtctcagaa gcagagtctg ccgcccgtga gcttggcgcg ggcaggctcc  12960
ttgtgataag cgccgtcggg acaaggggtt actatcgcag gctcggatat tcacgcacgg  13020
gcccctacat ggggaaggtg ctctgatgga gacgataggc cgcggcacct ggatagacaa  13080
gctggcgcat gaactggtag agcgcgaaga ggccctcggc cgggatacag agatgataaa  13140
cgtcgagagc ggccttggcg cgtccgggat accccacatg gggagcctcg gggatgcagt  13200
cagggcgtac ggcgtggggc tcgccgtcgg cgacatgggg cacagcttcc ggctcatagc  13260
gtactttgac gacctcgacg ggctccgcaa ggtccccgag ggcatgccat cctcgctaga  13320
agagcacata gcccgtcccg tctcggcgat acccgacccc tacgggtgcc acgattccta  13380
cggcatgcac atgagcggcc tgctgctaga ggggctcgac gcactgggca tagagtatga  13440
ctttaggcgg gcaagggaca cgtaccgcga cggcctgctc gcagaacaga tccacaggat  13500
actatcgaac agctcggtaa taggggagaa gatagccgag atggtgggcc aggaaaagtt  13560
tcgcagcagc ctgccgtact ttgcagtctg tgaacagtgc gggaagatgt acacggccga  13620
gtccgttgaa tacctggcag acagccgcaa ggtgcggtac aggtgcggcg acgccgaggt  13680
aggcggaaga aagatcgccg gctgcgggca cgagggcgag gcggacacgg gcggagccgg  13740
cggcaagctc gcctggaagg tggagtttgc cgcaaggtgg caggcgtttg atgtacgctt  13800
tgaggcatac ggcaaggaca tcatggactc tgtaaggata aacgactggg tctccgacga  13860
gatactatcc agcccgcacc cccaccatac aaggtacgag atgttcctcg acaagggcgg  13920
caaaaagata tcaaagtcgt caggaaacgt ggtcacgccg cagaaatggc tcaggtacgg  13980
cacccccag tcgatactgc tcctcatgta caagcgcatc acgggggcgc gggagcttgg  14040
cctcgaggat gtgccatccc tgatggacga gtacggcgat cttcagcgcg agtactttgc  14100
gggagggggc aggggcggga aagcccgcga ggccaagaac aggggggctat tcgagtatac  14160
gaacctgctg gaggcacagg aggggccgcg gccgcatgcg ggctaccggc tgctagtcga  14220
gctctccagg ctgttcaggg agaataggac cgagcgcgtc acaaaaaaagc tcgtcgagta  14280
cggggtaatt gacgggccct cgcccgggat cgagcggctc atagcactgg ccggaaacta  14340
tgcagacgac atgtattctg ccgagagaac agaggtggag cttgacgggg ccacaagggg  14400
ggccctctcg gagctggcag aaatgctcgg ttccgccccg gagggcggac tgcaggatgt  14460
catatacggc gtggccaagt cccacggggt gcccccgcgc gactttttca aggcgctgta  14520
caggataata ctggatgcat ccagcgggcc gaggataggc cccttcatag aggacatagg  14580
cagggagaag gtggcaggta tgatacgggg gcgcctctga tggtccacga cgtacacaac  14640
cggcggcgga gcggcggctt tttcctgata atactgggcg ccctcatctt catcacggcc  14700
ccgctgtacc tctcagattc gccggagctt ggggcggcag ccatagcctt tggctttgtc  14760
gtgggcgggg cggggttcta tctcaacttt atcaaaaaga aatcctaggg ggcccggccc  14820
```

-continued

```
aagcatttta tggcaagccc ctgtgggagc acccatggga ttgttcagga aaaagagccc  14880
cgaagaatcc gagccggggc cggacgagcc cgggcccgag gcggagatgg aaaaggtgag  14940
ggcggacctt gccggcgtgc agagagacgt ggtcaaaaag tattccgagc tgacggccct  15000
ctcagagaag ctcgagaggg taaagacaga gtatgattcc accgtgggct cgctgatgtc  15060
cgagagaaag gggctcgccg aggcgaaaaa agagtccgca tcgctcgagg aggcgcgcgc  15120
aggcctcgcc gaagaagtcg agcagaagag ggcaaaactc gaccaggcgg agattgacct  15180
tggggataga aagggcagga tagaggagct cgaccgcgcc cacgcggctc tcgccgggat  15240
aaaggaggag tcagacaggg gccgcgccga gctgcacgag atcaagcgga agatcctcga  15300
gtcacagggc gcgctcgaca gggccaggga cgcgcaggcc aaggcggaag cggagctgca  15360
caattccgcc gaggggctca agtccgcccg ggacgaggcc ggaaagctct cccaggagcg  15420
cgacaatata cgggccgaga tagatcttgc aaaaaaggag ctaaaggtgg tccggggcca  15480
gatggagtcg tcccccgagg ggggcgccga aaagcacgtg gtcgaggccg caagcgcgat  15540
ggtctcgtcg ctcacccaga ggctggctgc cgccgagagg gagcttggcg tggtaaagaa  15600
ggtattggag agggagagaa gggggcgcgg tcaggattcc gaatagatct tttccactt   15660
gctcttcatt tcttcctcgc tcattcccag atcgtacagg ggtgatgtga tatcgcggat  15720
ttcatccacc gttatcttta ccacggaaga tatcccgctc tttatgccgg tctttttaaa  15780
atgggacgcc atcgtatcga actcttcgcc tgaatcgagc acggcggcag tgccggtaaa  15840
gcggtagccc tttctgagca gcgggtctat aacgttgatc tctatggcgg ggttggcgcg  15900
caggttctcg acggtattgg gtgaccttat gttggcaaac gccaggtgcc cctcgtccca  15960
tacgatcaca gagcccttgg gcgagaggtt cggcttgttg tccggggtta cagtggccac  16020
aaagcccatc ttgatgcggt tgacgtgatc ccttacctct gttccgatgg tcgccatggg  16080
ctatccggtc atgcggggtt aaataaagct ggggtgcagc cgcagacact cagccgttga  16140
ttatacagta ctcgcactcg caggtcttgc tctcgtcatc ttttgccctg cattttgcgt  16200
gctggcccga ctggcactgg acgcagatct cgtctatgtt gtctatcgag gtgtatttct  16260
tggactggtc aaagccgaag ccaccgtcct ttggtccaac catacagcgg ttatgccgcc  16320
gtaccttaat tatctttgcc gtcggggcgg ggccgcttct gccggcggga gccccccttg  16380
aggccgcccc ccggctcgtt gtcccacaga tgcatgctgc cccggatcat aaacgagccg  16440
actatgatcg ccacaagccc gcccaccacc agtatgaaca gccttgccag gcccgccaac  16500
ccgcccatgc gtgtaatatg cggcacccgt aaacaaacat tgcgcgaaga aacaggggta  16560
ttccaggggc caaggcccgc aagctacatt aatttatcag tccggagggg cgggccccat  16620
gagcagagtc aaggcgatag ccatctgggt ggccatgata ggcggaggca tagccttctt  16680
tttcgcctcg gactatgttg tagaagtaat gaggtaaacg gggaaaacag gatccaatac  16740
ggtttcttat cctccctgtc catggcggcc ccgttcatat aaagtcccaa cgttcaatgt  16800
gccagatacg atggtccctc acaggggaat ttggactgtc ccgtgatgtt ggtggtttag  16860
gaaacgcatt acctaggcat ttatgtagtt gaggtgcacg tccgagggat ctgtttcatt  16920
atctggatca aataatggaa cttttctctt cattaatttc ctacattccg cctgcagttc  16980
aagcatgatg gttacatcat cacgttcgat tatccgttct gttgtttcgg ttttttgctc  17040
actcccatcc atgccaatat acgacggcat ttgtctaaaa aggtttccat cttcaagagt  17100
cgtgtgtttg ccgtgcaatt acctcccagg ggagcataaa aaataagcca taaacgatgc  17160
```

-continued

```
acagcatccg ccatggacct atgaaaaaac aagtcgtcag tggcgcacag tatccgatac  17220
aacctctcaa tcgtgtcatc cggcaactct gcaccatgga aactccggac gatcgctatt  17280
ctatacatgc tggttatcgt acctgtgaga atcctaatca tcctacggct atgttgatgg  17340
tttgctgata actgaattac cgaggtgatt cgcgatgatt ttgttgattg gagtaaattg  17400
agacaggata tccgctgcat gagataccga caatgtcaga tcctgaaatt cttggtcggc  17460
ttctagatca gttattttca aaccgatgcc cctacactcc tctcgcgata tgtatctccc  17520
atgactgtaa tattttccag gagaagctaa cattccagat attttttttg atttttctgc  17580
cgcatcagac tcgccagcaa acatgtggtc ttccagccat ttttgtacaa gcacttcagc  17640
tagtttctgg ctgctaatgc atttttgaac cagtccagga ggatattgtc ctaacaatgg  17700
aagccatgcg ccaagcctgc ccggatgttt ttcagatacc acctgcactt cttgcaactc  17760
gtcaattaga agctgtgcag acattatttg catgccaatc ttggttggga aaataaattg  17820
gggatcagcg ggtcctatag acgagtgttt gcccattacc agggaatttg atgcgcaagc  17880
aagcatcgag gctgctgaca ttgcggcata cggtatgatg acccgaatat catcatattt  17940
cgcatgaagg tatgtgacaa tcgattctgc agactcggca gaacctccag gactgtggag  18000
tatcagatcc aattttttag tctttaaatc acgcatcatc ctcataaatc catacaggtc  18060
accatttgtt atgagagctt cattaggcgt atgcggttcg tccgtcatcc agttggtcgc  18120
atatagaatt gtgtccctcc ccgaatactg ttgcaatttt gaaagatagt cgtgaagtac  18180
cacaccaggt gcctgctcac cggctgactc cattagtcga agtactttgt ttgatatttc  18240
tgcgtagcta ggcatttatg tagttgaagt ggctgccggc gggaattaac ccatagtctg  18300
aatcgtatga cttgcctttt ttcttcatca atttctcata tacctcatgc aggtctagca  18360
ggatggccat gtcactgcgc ttgcttggta attttgttgt ctcgggcttt tggtcgatat  18420
tcttctccat gccgataaaa gtcggtgttt ctttaaaaac gttcatgatt ttaattttcg  18480
agtctttgcc gtgcaatttc ctccagagat cataaaaaat gagtcataaa cggtgcacag  18540
catccgctgt ggacccatga aatgggcccc cggcggtgca cagcatccgc tgggggctca  18600
ataaaaaaaa tgagtcatca tgcatagtct ctatgtaaat ggctgaaccg gtgttttggt  18660
cgattagtaa aggctggctc tccactcgcc gaagcttgtg ggttacacca ccttcctatc  18720
aacgcagtct tcttctgcga accttcatcc gaagaaggaa tatcttgtct cgggatagga  18780
ttcgtgctta gatgctttca gcacttagcc tagatggctt agctgcccgg cctgccctgt  18840
cggacaaccg gtagaccagt ggccacgcct ctctgttcct ctcgtactag gagcgacttc  18900
ccctcagata ttcgcgcttc catcaggcag aggccgacct gtctcacgac ggtctaaacc  18960
cagctcatgt tccctttttaa taggcgagca gcctcaccct tggcccctgc tgcaggacca  19020
ggataggaaa agccgacatc gaggtaccaa accgcggggt cgataggagc tctcgcccgc  19080
gacgagcctg ttatccctgg ggtaattttt ctgtcacctc cgggccccaa tagtgggcac  19140
acgaaggatc gctaagccag actttcgtct atgaattccg tgcgtttgga aatccattca  19200
gtctagtttt tggctttgcc ctcttcagcg gatttctgac ccgcttgaac taaactttgg  19260
gcccctttga tatcttttca aaggggtgcc gccccagccg aactgcccac ctgcacgtgt  19320
ccccggtctt caccgggtaa gtggcactgc aggaaatgtc tggtgttaca tcggcgtccc  19380
ctgacgtccc aaagaacgcc aggaaaagac tcccagatac gctatgcact ccctgctata  19440
ccacaagcac aagctgcagt aaaactccac ggggtcttct ctccccgatg gaagatgatg  19500
gactgttcgt ccaccttatg tggcttcacc gggttgtagg cggggacagt ggggctctcg  19560
```

-continued

```
ttgttccatt catgcacgtc ggaacttacc cgacaaggca tttggctacc ttaagagagt  19620
cagagttact cccggcgtta accggtcctt agctcggttg aacccaagtt ttagataccg  19680
gcaccggcca ggattcagcg actatacata ccctttcggg ctagcagtcg cctgtgtttt  19740
tattaaacag tcgaaacccc cttgtcactg caacctgctg ccgccattcc tcatgacagc  19800
tgcaggcatc ccttatacct aagctacagg actaatttgc cgaattccct cgccatacgg  19860
tatacccgta gcaccttagt ttactaaacc agcgcacctg tgtcggatct gggtacgaac  19920
ttgcagtttg ctagccgcac ggtctttcat ggtctcctgg agtcgggga actctgctaa  19980
cgcaaagcca ctcccgcctc gggcctgttc tcgtcattac gacactccca ggccctcgaa  20040
cggttcgaca cgacgacggt catgctcccc ctatccggaa gcgaaccatg cggttcaaat  20100
gctccctgca aggtaccaga atattaactg gtttcccatt cggactactc tgttgaggca  20160
gcccttagga tcgactaact ccaggctgac gacgcattgc ctggaaaccc ttgcgctttc  20220
ggtggtgcgg attctcaccg cactatgctg ttactgccgc caggatctgc aatagaaatc  20280
ggtccacagg acgtcaccgc cctgcttcgt cccaatcact acgccaacct accacggtgc  20340
acctgccacg gtgcacgtcc ggagtatcgg tactctgctt tagccccgtc cgtttttgtg  20400
gcgccctcgc tcggcaggta agttgttaca cactttttga aggatagcta cttctgagct  20460
tacctccctg ctgtcttggc gacgacacgc actttggctt gacacttagc agaaatttgg  20520
ggaccttaac tccagtctgg gttaaacccc tctcggtcgt gaaccttacg tcacacgaac  20580
ccgtgtccat gcttctgcga tgtgtatccg ttcggagttt gaatggatgg tgaggaatct  20640
cttccccgcg ccaccctatc agtgctctac cggaaacacc atctccacat agcacgccct  20700
gcgagacgct tcggttggaa ctagcaagcg ccagtctaga ttggtttttg accccctattc  20760
ccaagtcaca caaacgagtt gcacgtcaga actgctgcag acctccagtg ggctttcgcc  20820
caccttcatc ttgctcagga atagatcgac tggcttctag ccttaccgcc atgactcaac  20880
gcactttcac acgcttctcc tcacaatgct gcgagaattc ggtttccctt cggctacgcc  20940
tttctaggct taacctcgcc atgacagcaa gctccctggc ccgtgtttcg agacggaacg  21000
cacgacactg acgacatgag ctccggactt ttagctccat tgctggaacc tccggtccga  21060
aaaaatcgtc tttcatgccg tgcacgtctg taagcaatag gtttcatgca cttttcaccc  21120
cccttccggg gtacttttca gctttccctc acggtactag tacactatcg gtcttgagag  21180
atatttagcc tttgatgcta ctttcaccaa tcttcgctgc ccactgccaa ggacaactac  21240
tcgggtgctg gccctgcccc attccacttc gtctaggggg gtatcaccct ctaagccgga  21300
acatttcaga acactttgac tatttcgtgg ggccattgcg ccgcaccaaa acaccacatc  21360
tcggccgcgt taccgcggca gattcagttt gggctctttc cttttcgatc gcctctactt  21420
gggaaatctc tattgatttc tcttcctcgt ggtactaaga tgcttcaatt cccacggttc  21480
gacctccgct tgcgcggagt atacaggatt cctattcgga aatctcggga tcaacgggtg  21540
cgtgcaccta ccccgagctt atcgcagctt gccacgtcct tcctctctcc tcaagcctag  21600
caatcctcct attgccgtct ttacaccggc atattcagcc acatattaca cgactatgca  21660
tgatgatcat cgcggtcccc aggggagggg cccgctacat ccttcatacg ccactttcgt  21720
gacgcattgc accatgtgaa gatatgtgca ccccgttcaa accagtttct aaggaggtga  21780
tccgaccgca ggttccccta cggtcacctt gttacgactt ttcccttgtc gcttacctca  21840
agttcgataa cgccaattag acgtcacctc actaaaagca aacttcaatg aaacgacggg  21900
```

-continued

```
cggtgtgtgc aaggagcagg gacgtattca ctgcgcggta atgacgcgcg gttactaggg  21960
attccagatt cgtgagggcg agttgcagcc ctcagtcata actgtggtag cgtttgggga  22020
ttacctcctc ctttcggata tggaacccat tgtcactacc attgcagccc gcgtgtggcc  22080
ccagagtttc ggggcatact gacctgccgt ggccctttcc ttcctccgca ttaactgcgg  22140
cggtcccgct aattcgcccc actgctcctg agagcaatgg tggcaactag aggcaaggat  22200
ctcgctcgtt acctgactta acaggacatc tcacggcacg agctggcgac ggccatgcac  22260
cacctctcag cttgtctggt aaagtcttca gcttgacctt cacactgctg tctctccggg  22320
taagatttca ggcgttgact ccaattgaac cgcaggcttc accccttgtg gtgctccccc  22380
gccaattcct ttaagtttca tacttgcgta cgtacttccc aggcggcaaa cttaacggct  22440
tccctgcggc actgcactgg ctcttacgcc aatgcatcac cgagtttgca ttgtttacag  22500
ctgggactac ccgggtatct aatccggttt gctcccccag ctttcatccc tcaccgtcgg  22560
acgtgttcta gtagaccgcc ttcgccacag gggtcatca atagatcaaa ggattttacc  22620
ccttcctact gagtaccgtc tacctctccc actccctagc cgtgcagtat ttccggcagc  22680
ctatgcgttg agcgcataga tttaaccgaa aacttacacg gcaggctacg gatgctttag  22740
gcccaataat cctcctgacc acttgaggtg ctggttttac cgcggcggct gacaccagaa  22800
cttgcccacc ccttattcgc cggtggtttt aagaccggta aaagatttct ttagcagaaa  22860
acactcggat taaccttgtc gtgctttcgc acattgcaaa gttttctcgc ctgctgcgcc  22920
ccatagggcc tgggtccgtg tctcagtacc catctccggg cctctcctct cagagcccgt  22980
atctgttata gccttggtgg gccattacct caccaacaag ctgatagacc gcagtcccat  23040
cctacggcga taaatcattt gggccacaaa ccattccagg catggtggcc tatcgggtat  23100
tattctcagt ttcccgaggt tatccccgtc cataggttag attgactacg tgttactgag  23160
ccgtctgcct tgtattgcta caatgactcg catggcttag tatcaatccg atagcagtca  23220
ggtccggcag gatcaaccgg attcttattt ggattatttt ttttttcaaa gtacgcctgt  23280
acttttggaa ttgaacggaa tgcacataat cttcacatct cagatatgac ccttcgatca  23340
gatcctcatt ctgtgtgcgt aactggaggc ctgcgaatca caaaatggta caataccatg  23400
gcttcatcgc aagcgccgct cttgcgtcac gtacgatcgg atcgccttgt ccatgggcat  23460
ataaaccatc gccggtttcc gggcccgatc ggacccttga tcggcccgcg gggggcgatc  23520
cggcctcatt aaattacggg gggtacaacc tgctgccgtg gatctagagc gcgagtacag  23580
ggcaaagacc aggggctcgg cggggatatt tgcccggtcg agaaggtacc atgtaggggg  23640
ggtcagccac aacataaggt actatgagcc gtacccgttt gttacaaggt cggcgcgcgg  23700
caagcacctt gtggacgtcg acgggaacaa gtataccgac tattggatgg ggcactggag  23760
cctgatactc ggccacgcgc cggcgcaagt aaggtcggca gtggaggggc agctgcgccg  23820
cggctggata cacgggaccg caaacgagcc caccatgcgg ctctcggaga tcatacgcgg  23880
ggcggtaaag gcggcagaga agataaggta tgttacatcc ggcacggagg ccgtcatgta  23940
tgcggcaagg atggcgcgcg cacgcacggg aaaaaaagtg atagcaaagg tcgacggcgg  24000
ctggcacgga tacgcgtcgg ggctgctaaa gtcggtcaac tggccgtacg atgtgcccga  24060
gagcgggggg ctcgtcgacg aggagcacac cgtgtccatc ccgtacaaca atctggaggg  24120
atccctggag gcgctaaggc gcgcaggggg cgaccttgca tgtgtcatag tcgagccgat  24180
gcttggcggc ggcggctgca taccggcaga accggactat ctccgcggca tacaggagtt  24240
tgtgcattcg aagggtgcac tgttcattct cgacgagata gtcacggggt tccggttcga  24300
```

-continued

```
ctttggctgc gcgtacaaga aaatggggct ggaccccgac gtggtggcgc tgggaaagat  24360
agtcgggggc ggattcccca taggtgtggt gtgcggcaag gacgaggtga tgtgcatctc  24420
cgataccggc gcgcatgcaa gaaccgagag ggcgtacatt ggcggcggca ccttttctgc  24480
aaaccccgcg acgatgactg cgggtgccgc ggcactcggt gcactcaggg agagaagggg  24540
cacactatac cccagaataa actccatggg ggacgacgca agggcgcggc tctcgaggat  24600
attcgacggc agggttgcag tgaccggcag gggctcgctg ttcatgacgc actttacacc  24660
ggatggggcc cgcaggatat ccagcgcggc agatgctgcc gcctgcgatg tgcatctgct  24720
gcacaggtac cacctggaca tgattacaag ggacggcata ttctttctgc caggcaagct  24780
gggggccata tctgccgccc actcaagggc ggaccttggg gccatgtatt cggcgtctga  24840
gcgctttgcg gggggactgt gagttatacc catgggaaac tttgattata cgggcgtaca  24900
ttcccggggc ccatgatact cttcggcaag agcgacccct ccgacctgct ccgccaggcc  24960
gatcttttgt gcagtgggaa caagtacaag gcggcagtgg gcctgtacag caggatactc  25020
aaggacgacc cgcagaacag gatggtcctg cagagaaagg gcctcgccct caacaggata  25080
agaaggtact ctgatgccat aacgtgcttt gatctgctgc tcgagctgga tgatggcgac  25140
gcgcctgcat acaacaacaa ggccatagcc caggccgagc tgggcgatac ggcatccgcc  25200
ctggagaact atggcagggc catcgaagcc agccccaggt acgcgccggc gtactttaac  25260
agggccgtcc tgctcgacag gctcggcgag cacgaagacg cgctgccgga cctcgacaag  25320
gcgacaaggc tggacaggga caaggccaac ccgaggttct acaaggggat agtcctggga  25380
aagatgggcc ggcatgcaga ggcgctgtcc tgcttcaagg aggtgtgcag ggcggaccac  25440
ggccacgccg actcacagtt ccacgtggcg atagaggtag ccgagctcgg caaacacgcc  25500
gaagccctcg gtgagcttgc ggcactgccc gcagagtacc gcgagaacgc aaacgttctc  25560
tacgcccggg cgcgcagcct cgccggcctg gacaggtacg acgagtccat tgcacacctg  25620
caaaaggccg ccagaaagga ctccaagaca ataaaaaagt gggcccgcgc cgagaaggcc  25680
tttgatcata tacgggatga tcccaggttc aaaaagatag ccgggtaaac cctacagcat  25740
ctttttttctt gccgcgtcta tccgcattat ccggaccttt tttttgggcc ccacaagccg  25800
cgactcgtag acaggggcat acacttcttc gaccgatctg actgcaaact cctcccggag  25860
gtcgcgcatg ccgtcaggcg ggggcccgcg gagctttacc cggagttttt ccagcgccac  25920
cccggtgtct atctccgggc gccgcacatt ctccgacgaa tcaagcatgc gccgcgggta  25980
cggctcgacc gcgccggtcc ccgtcttgta gggaaagccg gtctccccgc cgtgccggtc  26040
aaggcacatc acgccctctg attccgcgta tacgtgctcc tcgagttcca gatcgaccct  26100
gttcttgccg cgcccggcgg acagggtctt gcgtatgcgc gactttgacc ttatcgggaa  26160
gacgccgtcg cccagcacca cctcgatcac gttctgatcc accttgatcg ggtgcacggc  26220
ccttctgaaa aagtcggccg agtaccgggc ggagacgcgg atgagcgcct cgtggacgag  26280
ccttacggaa tgtacatgga cgtcctcctt tgggggcgcc ctcatcatgg ccctgaatgg  26340
ccccgtcttt tttgcctcga tcatggcccg ggcggactgt tcagtcatgg cgttgcgcag  26400
gacgatgatc cttgtcttgt cagtcactcc cggcaggccc cctcatccgg catgccctgt  26460
acacacggca aggtaataat agcctgccgt ccgtacctgc cgtatgaggt cagaagagag  26520
gccgggtcac attgaaaagt tcctaaagag ggcggacaag gcgatcgaca gcgcggtcga  26580
gcagggcgtc aagagggccg acgagatact agacgatgca gtcgagctcg gcaagattac  26640
```

-continued

```
ggtgggcgag gcgcagagga ggagcgatgt gctgctcaaa caggccgagc gggagagcag  26700
gcggctcaag tccaagggcg ccaaaaagct cgaaaagggc ataggcgccg caaaaaagat  26760
ggcagcaggc aagggcgacg cgctcgagac gctcgcaaag ctcggcgagc tcagaaaggc  26820
ggggatcata acggagaaag agtttcgcgc caaaaagaaa aagctcctcg cagagatctg  26880
acatgaaggc cataatctac tcccgggacg gctccgcaaa ggaggtcaca aagaggtggt  26940
ttgtcggtac tccttcactg atgaaccttg caggcgacct tggcatgacc gagagtgaca  27000
tattccatgt gacatttccc gacggcgcca agacgaccct gcacacacac gaaggcgggc  27060
agctgctgat agtcacctcc ggaacgggca gcatgtcggt ctttgaaaag accggcggcg  27120
gggataccga ctttgcgata aaagagaccg accgcatacc gctaaaggag ggcagcatac  27180
agtacatacc ggcgggtaca ttgcacgtgc acggcgccat cgagggcacc accctctccc  27240
acatagcggt aaactatccc tccccgtcgg gaaaggagcc gtataccatc tggtacgaat  27300
ccgactttgc gaacagggtc accggcgtgc tataagctac tttagccgct ccagtatgga  27360
caggctcaca aggttggtca tcgttatccc cttgcggatg acctcgcgcc gcgtcttctc  27420
gcagtacttg ttgacgctct ggtagctctt ctcgctggag acctcgagga ctattatgtt  27480
cccgctgtac ggaaaggcaa actttggcgg caccctcgag cagacgtcca tgcgccctat  27540
tcccgccctg cctatcttct cctttctccc caccacggac gccacctcgc atatgtcctc  27600
ctcggaatcg ccgtactcca gatagtacac cgatacatag ctcaccccgg gggactccct  27660
ctcgaatatg tcctcgtcca tgctaaacac ataggatgcg ccctcccccc ggcccaccgc  27720
cttgatcatt ctgggggcgt ccttgaacct tgccagcagg tagtggttgg cctgcggtgc  27780
aaagtacggc tggctctcgg acgagaacgt ggcggtcaca aagtacatct cgcggacgtt  27840
cctcgacgag gcccacgcgt ccttgagctc gatcgaggcg tgatcgtgcg tgtatggcgt  27900
gcaggcatgc ccgcccgggg cccccgtctg ggacatgcat tgtacccgcg ggaccggtta  27960
ttatctagtt ccatgggggc gcagggcgcc gcccccgtgt ggcatgcgtg gatccatgcg  28020
atagttattt aaaactagga tgccgggcac ccgtcgtccc aagctagctc agcctggtag  28080
agcttccggc tgtagatgtc ggccttggct gaccgtataa cagcatatca ggcatacaga  28140
gaccgggttg tcgaaggttc aactccttcg cttgggacca cattataacg gctgccgcct  28200
catgcggctg tgcacggcat ccgtacacgt tccatgcacg ggtgccgcgg cgtgccatat  28260
gcatggatgg tgcatgtaca atgcacgggt gccgcgacgc actatacgca tggatggtgc  28320
actatagatg cggctaaatg tgcacggcag agccgcaggg cccgggccgc gtgcacctat  28380
attctgccct gtcccagggt caggagccgc gtcgccagaa cgatgtgcgg cgcccgcgcc  28440
gcacggcggg gccgccgggg gcgcacgaca ccgcatcgcc ggacctggcg ccatttctct  28500
ccagcagtgc gtcgagcgca gaatcgtcga ctagcgtgcg ggatggcagc ccgcccgggg  28560
taggcacgcc ctgcagctcc attgcccggc gcatctcctc gttctccatg cggaggcggc  28620
gctccttctc ctcgagcctg ctgctcatcc tgtcgaggaa cattacatct gaattgtaca  28680
gctccctttg ctgccccatc atgcagagga tatggcgcag ccttgacgta tcgcatatac  28740
cggatgccat gagctccctg accccgtcct ccgtgtggcc gatgtgccgg ccccccgccg  28800
atgccctgcg cacgccggac ctcatcgctg cttcctcagg tactcccgga ctatcctgtt  28860
ggcaagccgg gtctcgtcgg tgccctcgcg ctcggccacc cgggcaagct ttcttgcgcc  28920
gttcttgccg agctctatgg ggatcttctt cctgacgccc gtcttgcgca ccctctttag  28980
caggatcctg tggcccgagc gggggctctg ggctagcagc ctcaggtaga tccgcctcga  29040
```

-continued cggccgatca agccttgata tgttcagcgc caccttgagc gcctgggaga cggtcgggac 29100
ggcctggtac agctttgtcg cctcgtcccg ggatatggtc ccggggacta gcgccttgat 29160
cttctccggc acgcccgcaa agccgtggta ctttttgaac gtgggcatcg acatgccgag 29220
cttccttgcg gcctcggcgc gggtcatctg ctcggcgaga aacctgcacg cgtcggcgag 29280
ctcccggggg ctcatctgca tccggtgcag gttctccacg accgatgccg cctttgcgtc 29340
ctccaggccg tactccgtat ccttggttat cacaagaaac ttggactttt ttgcgcccag 29400
atgctttagg gccgcaagcc tgtggttccc cgatatgagc aggtacagcc ccctgccgcc 29460
cctctgtatt acgggcgggt tctgcaggcc ctcggacctg atcgactttg caatctccct 29520
caccctggac ctgtccagcc tccttgcctg cgcgtccttc cacacgtgca cgttcttgag 29580
gggcacctcg cgtaggacct gctttatccg gggcttgtag cgccgagcca acgtactcta 29640
caagatacaa atccttgtta actgtgtttg gtaagtttat cacaacaatt aggttagata 29700
gagctgttcc cccgcaggcc cccgtgcacg tactctatcg cgcagccccc cgggggacag 29760
ccggaaccgg gggctgccgg ggcgggatcc cgggcgtcga tagaataaat acgcgcgggg 29820
ccgcggtgcg atcgcccgtg ctgataataa actgcaaaaa ctatgaggag gccgccggcg 29880
gcaggatccg cgggctggca gatgccgcgg ccggggctgc cgccaggtac ggcgtcagga 29940
tagcgatagc cccgccgcag cacctgctgg gcattatagc aggccgggat cttggcgtgc 30000
tggcccagca tgtcgacgac aaggggacgg ggagcaccac agggtatgtc gtcccggagc 30060
tgctaaaaca gtcgggggtc tccgggggcca taatcaacca cagcgagcac cgcgtacccg 30120
cggaccaggt ggcgggcctg gtaccaaggc tcaggggcct tggcatggtc tcggtggtct 30180
gcgtcaggga tcccgccgag gccgccgatc tctcccggta ttgccccgac tacatagcga 30240
tagagcctcc cgagctgata ggttccggca ggtccgtctc gacagagagg ccccaggtca 30300
tacaagaggc cgcagaggcc atcagggggg ctggcggcgt aaagctgctc tgcggggcgg 30360
gcataacctc cggggcggac gtgcgcaggg ccctcgagct tggctccgag ggcattcttg 30420
tggcaagcgg ggtcgtaaag tcggcagacc ccgcaggggc catcggggag cttgcccggg 30480
ccatgtcctg acgcaccatt ctaggcgccc gcgccgttga ggcgcgccag caggtcaaac 30540
gacgacctgt atagctcgcc tggcgaccgg gcgcccgcta tcaccacctt tcccgacgca 30600
aacacaagga agctgcagct gcccagcccc tttagtatca tgccgggaaa cgaccccggg 30660
tcgtacaccg cgccgggtat ccgcgacgat atcctgtcta tgggaacagt ccgtcctgca 30720
tccactgtcg ccaccatatt gcgtacgacg ggccttgtac acccgccggc cgccgccccg 30780
ttccggaaca ggtgcagccg ggcctcgtgc agctgcgcaa acgatgccct cacggagctg 30840
gcgccgacgg atatcatctt gcccgagaga aacaccgtca cgcgcccccg catgccgggt 30900
gttttgatat agccgcacct gccgccgtat accgcctcgt cgtacatgca gcatggcatg 30960
gcggccatct tttttgcgcc caccctccgg cccaggtcgg cggtactcac aacgttgacc 31020
accctgggcc gtttccttgg atccagcatt gatccggtgc ccggccgcac tctattttaa 31080
ccggggcccg ggcggcagcc ccgcggccct gtcgtacctg cgctttagca gcattacggc 31140
ggccatcagc gccaccccgg ccacgttggt ccctattatg tagacgtccc atatgtgcac 31200
gccgtaggct atccagagca tggcccccgc gcctatcagc atggtcagat accacgatac 31260
atccctgagg ctctttgtcc tgtacgcctt gactatctgg tgcacccatc ccgacagtat 31320
cagcacgccg ccggcagccg ccacgatatc cagcagggcg atatccacgt tcatttgaaa 31380

-continued

```
aagaactgct ccatgccggt ctgctttggc ttgccgagta tctcgtcaaa gtcaaggccc  31440
atggacgagg tgagctggtc gagcgtcgac tccatgaact cgaggtactt tgacgtgtcc  31500
acctcgcctg cccgggccat ctccaccggc ttgacgccgg tcttgttcat cacctttacg  31560
tacgatatta tgtcgccctt tttgacctcc cttgcgttct ccagcagcct tgccgcccgt  31620
atgtgctgcg ggacggtctt gacatattcg gagggcgcct tgcttatcat cacattgaac  31680
gccaggtcca cgagggggat ctgcctctcc tcgagcctct tgccgcacgc ggcgatcgcc  31740
tttgagatcc tcatcttggc tgactcgaac tcgtcctcgc tctcgactcc tgagagtatg  31800
tcgagcagcg agtagaagag ctcctttatg aacgggggcg tgtgcgactt tttgcccgtc  31860
agccccttga cgtcgacctt gcctgcccgg gtcaccccga aatagttttt tttcctgttg  31920
gatagcacga catacctgta ctctttgtcc acttcgagct ccacaccgtg ctccttcttt  31980
gcatgctcga ctatctcgtg gatctgcctc tcttcgggat cctttatgaa cagagaatcg  32040
gtgtccccgt acagcaccct cactcccatc tgctcgcagt gcgatatcgt ctgcatgatg  32100
atatagcgcc cgacagcagt ggtggcctct gccgcgggta aaaagtacag cgggaatatc  32160
tcggcgccca tcacgccgta gcttgcgttg agcacgacct tgagggcctg gctgattacg  32220
gtatactgct gccgctgctc ctccgtaatg gatgtgctct ttgagaggct cttgtaatag  32280
ttgacgcgca ggtcccgcag cgagccgatt atcatcgatg tcaggccgtt gtttttgta  32340
catacccagt ggttggtatc ggggatggtg ttctttttgc attctgcatg cacgcaccgg  32400
acggtctcgt acgagaggtt cctcaccttt atgatactgg gatacaggct cgcaaagtcc  32460
atcaccgtaa catcaaagtg tatgccctct tcaggctcga cgacaaggcc cccgcggaac  32520
tttttatcct ttattaccgc gtcgttgctc acctcgcgcg acctgccctc cagctcgtcc  32580
ctccgcggta tgagcgcgtt tcgctgtctg tgctcatagt acagcaggct gcgtatccac  32640
tgcgagacgc ccatgcggga catgtcatcg atgggcatcc gggctattct gctggtcacc  32700
accagcaggt ccatgagtat ctcgttgcca aaggtgctaa gctcgagcgt caggcgcgcg  32760
tcgtgatagc aatagtttgc agtctggtat aaggtgagat cccccagttt gaccccatag  32820
tcgaccttgc cctcgccgag catcgccttt gtgacgctgt taagggaata gtccgtgtac  32880
tttgccgcaa aggcgtacag ctggaatgac ctgttcgaga aggtcctgta caggtccagg  32940
tggactccgt gccggagcgt ggcagaatcc cgcatcatgt acaaaggaat gtcagagtca  33000
gatactccga ggcgccgtgc cctgttgagc atgtacggca tgtcaaagtc gtcgccgttg  33060
tacgtcagaa caaacgggta cgagcctatt accgatagcg cgtcgcggat catgtcagct  33120
tccttgtcgt agaataccac ctcgacaccg gggtcacgc cgttctcgcc ctcttctgcg  33180
ccgctcctca ggacgaatac ctgttttagg ccgtcggtgg cggcaaaccc caccgccgta  33240
accctcctgt cggatatctt ggggtcgggg atcctgccct cctctgaatc cacctcgata  33300
tcaaagctga ggcgccgtat cctgggtatg ggctggttga gcaggtccgc ccaccccgct  33360
atgaactcgc ggaactcttt tctgtccgcc atgccctcgt ctacaacctt gtcccagagg  33420
aggctcttga gggccagctt tacctcgtcg gatatgggca tgtcatgcgg gattaccttg  33480
ccgccggata ccgaatagta cctgcccacg accaggctct tgtcgtacag atagttctca  33540
tagtacttta tgtcggattc ccacgtgtcc atgatgttgc ggatgctctt ctccgagttg  33600
gtcccgccta tggcaagggg gtcggccaca gttatcttgg tgacgggcac atccttgtcg  33660
gctatcaggt cgtgccgcat gacctgctcc gttcctagca catcctccct gccttcaagc  33720
tccccaagct cggagggggg ctgcctcgta tagcagtagg gcttgtgccc cgtattgtcc  33780
```

-continued

```
gtccagtgta cgatcttttg tgattccggc tcgtaaaact tgaggacgac cgcccctgcc 33840
tggctgtcgt atgttgcaga taccagcagc gacgggggta tctctacggc atcttgcacc 33900
gtcaccgcac cggcacctcc ttgctgcctc cgggcatcct tgacgcccag tacgagatct 33960
tttccttgtc catcatggtt atctcggagg atgtctcttt taccagccgg gaggtgttct 34020
cggggtaggt atcaaggcag acaaaccgcc tgatccctat cgttacggcc atcttggtac 34080
actccagaca cggcgagaac gtggtgtaca tggtggcccc cccgcccccc gcgcctatcc 34140
cgagtatcgc acagtgcatt atagcgttgg cctctgcatg gttgcacagg caccggtcca 34200
gggcctcgcc tgacttgatc ctgccctcga tgcgctcggc acacctctcg cagccgccct 34260
cgtagcagtt cttgacgcca ggaggcgtcc cgttataccc tgtggcgagc tgccggtggt 34320
ccctcactat tacggccccc accttgcgga ctatacagtt ggatcggagc tttgcaagct 34380
ccgcctgcag catgaaatat tcatcccagg tagggcgctc aaagccgctc acgggcagcc 34440
tgcccccgcc cggcatatta tggtatatgc gggacggggc cgtccacccg cacccccgta 34500
tatggatctg cgatcagggg gtagaaacca taaaacaaca ggccgcggca gggcgcgcgt 34560
ggagactggg cacataacgg gcaggtacat cgagcccggt gccgtcgaga ggcgcgacta 34620
ccaggtgggc ctggcggaac aggccatacg ggagaactgt atcgtggtgc tcccgacggg 34680
cctcggcaag actgccgtcg ccctccaggt gatcgcccac tatctcgacg agggccgcgg 34740
ggcgctcttc cttgccccta caagggtcct ggtaaaccag caccgccagt tcctgggcag 34800
ggcccttacc atatccgata ttacactggt cacgggagag gacaccattc cccggcgcaa 34860
aaaggcgtgg ggaggcagcg tgatctgcgc cacgcccgag atagcaagaa atgatataga 34920
gcgcggcctg gtcccgctcg aacagttcgg cctggtcata ttcgacgagg cccacagggc 34980
ggtgggcgac tatgcctatt cttccatagc gcgggcggta ggggataact ccaggatggt 35040
gggcatgact gcgacgcttc ccagcgagag ggagaaggca gacgagataa tgggcaccct 35100
gctctccagg agcatagccc agaggacaga agacgacccg gacgtaaagc cctatgtaca 35160
ggagactgcc accgagtgga taaaggtgga tcttcccccc gagatgaagg agatacagag 35220
gctcctcaag ctggccctcg acgagaggta ttcctccctc aagaggtgcg ggtacgatct 35280
tggctcgaac aggtcgctct cggcgctgct ccggctgcgc atggtggtgc ttggcggcaa 35340
caggcgcgcg gccaagccgc tgttcactgc gatacgcata acgtacgcgc taaacatatt 35400
cgaggcgcac ggggtcacgc cctttctaaa gttctgcgag aggacctcca agaaaaaggg 35460
cgtcggcgtg gcggagctgt tcgaacagga ccggaacttt acaggggcca tcgcgcgcgc 35520
aaaggccgcg caggcggcag gcatggagca tcccaagata ccaaagctcg aggatgccgt 35580
ccgcggggcc cggggaaagg cgctggtctt tacgagctat cgtgattctg tcgacctcat 35640
acactcaaga ctcaaggcgg ccgggataaa ctcgggcatc ctgataggaa aggcgggaga 35700
aaagggccta aagcagagaa aacaggtgga gactgtggca aagttccgtg acggcgggta 35760
cgacgtgctg gtatcgacga gggtcggcga ggaggggctc gacatatcgg aggtcaacct 35820
ggtgatattc tatgacaatg tgccaagctc gatcaggtac gtgcagagga gggggagaac 35880
aggcagaaag gacgccggca ggctgatagt attgatggca aaggggacga tagacgaggc 35940
atactattgg attggtcggc gcaagatgag cgccgccaag ggcatgggtg agaggatgaa 36000
ccggtcgctg gcggcaggcg gggctgctgc caaggccgct ccaaagggac tcgaggggta 36060
cttttagccg aggcgcttta tcacgtgata gccaaactct gactttatgg gttccgagat 36120
```

-continued

```
ctcgcctatc tgcagccgga acgcggcctc ttcaaacggc tttaccatct ttcccctgcc  36180
aaagtagccg agactgccgt ccctctttgc actgcccccg tccatggaga gctcctttgc  36240
gagcctgcca aacttttccc cggccttgag gcgctctttt actgctagcg cctcgccctg  36300
tttttttacc agtatgtgcg agcactttat cttgtctgcc atgtgcgctg ctcctttgta  36360
ccctgctata acttgtcgtg ctgccggggc gcggtcatcc cgcagggcct gtattctgcc  36420
aggaactgtt aatccgcagg gactggtttc cccgtattat cctgtcatat acagggggga  36480
ttcggcggtc cacgtgtatt aacacctaaa gcagggataa acgtgtgaga acaagtgggc  36540
acccggaacg aatgttacgg catactggag gataaccaga taaaggaact agaacaaggc  36600
agcggcatcg acgtaccgtt gctggaccac gagggcagtc agttccattc caacagaata  36660
catcttacac tgggcaatat cgtatctccg cttgagcttg gtgacggcag tatgacaaac  36720
cccgggacgg acctgacacc atacgacgta aagtcaatag gcatggggcg caccataaag  36780
cgatatgcaa agtaccgttc tgaaggatcg caggccgtcc gcatggatgt catattcatg  36840
tcccgtgccg cctgggatga gatggataaa ggcaaggcat gaccggccgg ttttggggca  36900
tactgccggt atacagcggg aacaggcatt cagagacttt ggcggattcc gtgtgacccg  36960
ccccaagcta aacttttaat tgggatccgg cgagccggcg cgtgtcatcg tactttacca  37020
taaagaccgc caacctggcc ctgcccgacg tggtcaaaaa gtacaaccac gtcctggcat  37080
gcaagagcga ggtgatgagg gccgagaagc agatccagac gtccatctcc tcgtctagcg  37140
ggctcgacaa gtactcggag ctcaagcaac agttcaactc ccggataacc gagttctacc  37200
gctcgataga agagctggaa aagaccggtg cggtggtcaa gagcatagac gagggcctgc  37260
tggactttcc cgcaaagcgc tttggggacg acatctggct gtgctggaag acaggcgagc  37320
gcgagatcaa gttctggcat gaaaaggact ctggttttgg cggaagaaag cccatagagg  37380
taagtgacga gtcactagtg tagatgctct ccgcctggtt gcgcgtaata cgcgtccgct  37440
tcctgctcgc gtcggtgata gccgtctcgg cgggcctcgc cctctcctgg tggcacggcc  37500
acgaaataga cgcattctcc gccgcgctca ccatggccgg cgtggccgcg ctccacgcaa  37560
gcgtggacat gctcaacgat tattcggact acaagcgcgg catagatacc ataaccaaga  37620
ggaccccgat gagcggcgga acaggggtgc tgccagaagg cctgcttacc cccggccagg  37680
tgcaccgcgc cggcatcata tcgctggtcc tgggctctgc tgtcggcgcg tactttgtgg  37740
tcacaacggg gcccgtcata gccatgatac tcggctttgc cgtagtctcg atatactttt  37800
actcgacgag gattgtagac tcgggcctct ccgaggtctt tgtggccgtc aaggggggcga  37860
tgatcgtcct tggcgcctac tacatacagg cgcccgagat aacgcctgcc gccgttctgg  37920
tgggggcggc cgtgggcgcc ctctcgtcgg cggtcctctt tgtggcgtcg tttccagacc  37980
acgatgcgga caagtcccgc ggcagaaaga cgcttgttat aatcctgggc aaggagaggg  38040
cctcgcggat cctctgggtg ttccccgcag tggcatactc gtccgttata acgggggtca  38100
tcctgcagtt cctgccggtg catgcactaa ccatgctgct tgcagccccc cttgcagtaa  38160
ttgcggcaaa aggccttgcc agggagtacg gcggggacgg gatcatacgg gtcatgcgcg  38220
gcacgctgcg gtttagcagg gttgcaggcg ccctgctggt gttgggcatt ctgttgggct  38280
gagtggagct aggttcgaga cgatgtaagc ttaaactagg tatgcaattg gatcacttag  38340
attctactaa cacgccatcg tcttttacat caacgaatat agttcgtata acctgcgagt  38400
tatcatcatc cctgacgttc tcgggagtta tttcttttga ttccccgtct tgtagaacaa  38460
cgctgtactt atccataatt aggtaaaact tctacatgta taaaaacgta ctatcttcac  38520
```

-continued

```
ggggccccgg caggcctttg ggatttttcg ctgcgtcaag tccgagtgtt ttcagggtgt  38580
gtgggtactc tgaaaaatcc cgggggcttt ccggcagggt acacaagaat agttaagtaa  38640
tgcagcattc aaagtaaaac atggacatga acaagctctg cgggatatgc atgaggagtc  38700
tggtgggtga gatcatgcct tatttccatt acaagtgcca taccgcctgt gtaaaatggc  38760
atgaatccaa tcccgggttg tgtgccctgt gcaaaaagga tgtcacgggg attaaacatt  38820
ttacaaagat agggggaatg gtataccatg aagactgttg tacaatattt gtggaaaaag  38880
tcctgggtca aaagaacaac cccccaaaat tcccgtatac gtacagtttt acatgtccgt  38940
cgtgctcaca cgaggacagc gtggatacgg ccgtcaagat ggacaccggg ccgcagagat  39000
tcatctgcaa cgggtgcaga aaaaaggtaa aagccacggg taaaaggata agataggcat  39060
cttgattggc cccgccgtat acaagatgaa atcatgcatt ctaaatacca gggcttgaga  39120
acgcaataaa accccggatg cctgccggaa gagtccggtc ataaaatccg gcccccgtac  39180
cggaggatct gtcggttgtg ggatggatat catccacttg ccattacatc acgccaattc  39240
gcgtgcagtc ctgcccgtgc ggcagggata caaagccatg atgcagaact ggaggcaccc  39300
atccggggaa actgcaggct gccccggaat ctaaaggtgc aaatggctgc agaacccccg  39360
gaccggcggg tcgcaccccg ggcgggatac caacgaacgg acccgcaccg tacacttcat  39420
acacataaat cccgcctgaa cggtcgtccg cgcatgatca gcgggcacgc cacggccgag  39480
ggtacacgca ggatagccga gatgtcgggc gcccatatcg acaactacaa gatggtcgac  39540
gggctgcacc tctccaacgt ggggatgggc acctaccttg gcgacgcgga tgacgccacc  39600
gacagggccg tcacggacgc agtcaagagg tccgtcaaaa caggcataaa cgtcatagat  39660
acggcgataa actaccgcct ccagagggcc gagcgctctg tcggcagggc cgtcacggag  39720
ctctcagaag aggggctcgt atcaagggac caaatattca tatcgacaaa ggcgggctat  39780
gtaacaaacg actccgaggt ctcgcttgac ttttgggagt atgtgaaaaa agagtacgtc  39840
gggggcggcg tgatccaggc aggcgacata tcctccggat accactgcat gaagcccgcc  39900
tatctagagg accagctgaa gaggagcctt gcaaacatgg gcctcgactg tatcgacctt  39960
gtctacgtgc acaaccccgt cgaggggcag atcaaggacc gccccatacc ggagatcctc  40020
gactgtatag gagaggcctt tgccatgtac gagaaggcaa gggaggatgg ccgcatcaga  40080
tactatgggc tcgccacgtg ggagtgcttt cgtgttgcag gggacaaccc gcagaatgtc  40140
cagctcgaag acgttgtaaa gaaggccaaa gacgcaggcg gggacaacca cggattcaag  40200
ttcatacagc tgcccttcaa ccagtacttt gaccaggctt acatgctaaa gaaccagacg  40260
gtggacggca gaaagctgtc catactggat gcggcagtat cccttggcgt cggtgtgttc  40320
acgagtgtcc cgttcatgca aggcaagctg ctcgagcctg gcctgctgcc ggagtttggc  40380
gggctctccc ccgccctgcg atccctgcag tttatcaggt ctacaccagg cgtgcttgcc  40440
cccctgccgg ggcacaactc agctgcgcat acagacgaga acctcaagat catgggcgtg  40500
ccccccatcc cgcctgacaa gttcggggag cttgtggcca gcctcacctc gtggtcgccc  40560
ggtcagaaat agccggtcag ctgcctctcg ggcattatct ggtcgagcac ctttttttgag  40620
agccgtgaat cggcggaatc ctgcacgttg cgccgggccc ttgccacgtt ggcaggatac  40680
aggtctatcc cggtaaagcc cctcttgagg catgcagaga ctattcccgt ggtccccctg  40740
cctgcaaacg ggtccagcac gtaatcgccc tcttttgtgg caaactttac tatcctggat  40800
acaaggtctt ctgggaatac cgcaaagtgc tcgtttccat ggtgcgcctt tgtggatatc  40860
```

-continued

```
tcccagacgt tccccgggtt cttgccccgc gggttgcatg cggcaaatat cggatagtgc  40920

tcgtggcccc ctatcctctt gcgcgtcgca tgcctccgga acttgcgata gcacgtgggg  40980

cagtactttt cggggtcata gccgtgggcc catgatattt ccccggtggt tggcagctcg  41040

tcaaacggcg taccaggcgt tgagccgtgt atcacggctg caatcctccc tattgcctcg  41100

ggatccctct tcccgggggc gaactgcagc cggtcatttg cgggtttgct gtttatcccg  41160

ctcagggcct cgttgccctg gacgcgtatc gggtttatgt cataggcggg ggtatccgac  41220

tttgagagga ccagaacaaa ctcgtacgcc tgcgtcaggt tttgccgcga gctttgcgag  41280

atggcgtttc gcttgtacca gattatatcc tcctggaaat ggtacccaag atccaccagc  41340

cttagcgcga gccggtgcgg gaccatcagc ttgtggcgcc gcctcctggt atcacctatc  41400

actatgaaga ggctcccgtc gtctgttagc aggtccatgc agctcttgaa tactcctgcc  41460

agctcctcga tgaactcgtc tggcgtcttt tcctggccca gctcggaggg ctccgacccg  41520

tactttctgt gcccgtaata gggaggggat gttaccgcca gtctgtacct gccgcgctcg  41580

gctgtattct ttgccagccg cggcagcacc tcccgggcgt cgccctgcag tatctggaac  41640

ttttcactca agataggccc ccgtgccatc catctgcccc tgcgcgatcc gacaagtcgt  41700

attcatcttg taccgcggca cccgcgccgt cttaaaatct ttgtagctta taccggcgcg  41760

ccgcagatgc ggtacaatcc ctccggtgct cccgcgatcc ggcgcggtgc catcagccgc  41820

cccgtttccc cttccggggg ccccgccacc atacacgtgg tataaacaga ggccggacgg  41880

cgcggaccac atgtggataa aggacgagtt tcttggcaaa ggcaacaaga tgaggctgct  41940

ctacatcata ctgcccatct acgggtacct cttcctggag tactggccgt tcctgccctg  42000

gatggctaca ttctggtggt cggtggcgct cagcccccct attctcctga tgccttatgc  42060

cggggaggcc ataggtcagc tgatcggcgg gcatgtattg tttggagttg tcacaaagta  42120

tgtctatgcg gcagtatggc tgggcatggc acacgggata atcctcctga cagggcgcct  42180

cagggccagg gctggtaccc tgcgcgaatc ccccgcatag ccccggcagg gcccgttgtt  42240

ccggatggcc aaggccggcg catacatccc atgatgcata gaccgggggg acatgatcgc  42300

agcagatcgt tccatgccgc ccccgtacgc tctggggcgc acctagtcag ggcggggccc  42360

cccgcggtcc aattaaatac ggcaaggaac ggggggtctc gttgaaactg cagggcagga  42420

ctgccgtgat cc                                                      42432


<210> SEQ ID NO 3
<211> LENGTH: 10419
<212> TYPE: DNA
<213> ORGANISM: Cenarchaeum symbiosum
<220> FEATURE:
<221> NAME/KEY: CDS
<222> LOCATION: (1)...(10419)

<400> SEQUENCE: 3

atc ccc gcg ccg cca gga gag ggc agc ctt ggc ggg gtg gca ata tcc       48
Met Pro Ala Pro Pro Gly Glu Gly Ser Leu Gly Gly Val Ala Ile Ser
 1               5                  10                  15

gac gac ggg agg tac atg tac gca atc ggc agg gat ctg ctc aca gta       96
Asp Asp Gly Arg Tyr Met Tyr Ala Ile Gly Arg Asp Leu Leu Thr Val
            20                  25                  30

tac cgg tat aca atg aac ccg ccc cat gac ata gcc tcg gcc gcg ctc      144
Tyr Arg Tyr Thr Met Asn Pro Pro His Asp Ile Ala Ser Ala Ala Leu
        35                  40                  45

ggt gcg cag tca ttt tct ctg cct ggc ggc atc agc ccc gcc ccc ggc      192
Gly Ala Gln Ser Phe Ser Leu Pro Gly Gly Ile Ser Pro Ala Pro Gly
```

-continued

```
    50                  55                  60

gcg ccg acc ggc ctt gac atc tcg gat gac ggc cgc cac ctg tac gtc      240
Ala Pro Thr Gly Leu Asp Ile Ser Asp Asp Gly Arg His Leu Tyr Val
 65                  70                  75                  80

ccg gac gaa aac ggc gtc gtg tac agg ttt gat ctg gaa agc ccg tac      288
Pro Asp Glu Asn Gly Val Val Tyr Arg Phe Asp Leu Glu Ser Pro Tyr
                 85                  90                  95

agg cta gac ggc ggc acg ttt ggc tct tct gtt tat gtg gga tcc gac      336
Arg Leu Asp Gly Gly Thr Phe Gly Ser Ser Val Tyr Val Gly Ser Asp
            100                 105                 110

gtt gcc gcg ccc cgc ggc gta tac gtg gcg ccg ggc ggc agc ctc atg      384
Val Ala Ala Pro Arg Gly Val Tyr Val Ala Pro Gly Gly Ser Leu Met
        115                 120                 125

ctg gtc tcg gat agt gca gac ggc acc atc cac agg tac gag ctg gca      432
Leu Val Ser Asp Ser Ala Asp Gly Thr Ile His Arg Tyr Glu Leu Ala
    130                 135                 140

agc ccg tac gag ccg gcg ggc gcg gca aac agg gga tca ttc gac gtg      480
Ser Pro Tyr Glu Pro Ala Gly Ala Ala Asn Arg Gly Ser Phe Asp Val
145                 150                 155                 160

tcg gat atg gac ggc tcg cct gtc ggg gcg ggg ttt gcg ggc ggc ctg      528
Ser Asp Met Asp Gly Ser Pro Val Gly Ala Gly Phe Ala Gly Gly Leu
                165                 170                 175

cac atg tat gtc gcg gga aac gac acc gga agg gtc tac cag tat ccg      576
His Met Tyr Val Ala Gly Asn Asp Thr Gly Arg Val Tyr Gln Tyr Pro
            180                 185                 190

gcg ggc acg cac cag ata cag gag gca gcc gca ggg ccg cgg ctg ctc      624
Ala Gly Thr His Gln Ile Gln Glu Ala Ala Ala Gly Pro Arg Leu Leu
        195                 200                 205

tcg gcc gtc ctg gac aaa gac gga acc ctg agg gcg gcc ttt gac ggc      672
Ser Ala Val Leu Asp Lys Asp Gly Thr Leu Arg Ala Ala Phe Asp Gly
    210                 215                 220

acg gta gac gcg gga tcc gtg cag ccc ggg atg atc acc atc agg gac      720
Thr Val Asp Ala Gly Ser Val Gln Pro Gly Met Ile Thr Ile Arg Asp
225                 230                 235                 240

ggc cat ggc tcc aac acg gga ata ccc ctt ttg ctt gcc ggg ggt gcc      768
Gly His Gly Ser Asn Thr Gly Ile Pro Leu Leu Leu Ala Gly Gly Ala
                245                 250                 255

gcg gac tct gat gtc atg aca ttt gtg gtc ccc gag aaa gac agg gca      816
Ala Asp Ser Asp Val Met Thr Phe Val Val Pro Glu Lys Asp Arg Ala
            260                 265                 270

gag gct gcc gca tac ggg gac cag tcg ctg cat gtt ccc gcc gcg gcg      864
Glu Ala Ala Ala Tyr Gly Asp Gln Ser Leu His Val Pro Ala Ala Ala
        275                 280                 285

ctg gcg ggg act ggc ggc ggg ccg ttt gtg ccc gac ttt tcc ggg ggc      912
Leu Ala Gly Thr Gly Gly Gly Pro Phe Val Pro Asp Phe Ser Gly Gly
    290                 295                 300

tcg ctg ctg gcg tcc ctg tac cgg cac gag cgg ccg ttc cag ggc gag      960
Ser Leu Leu Ala Ser Leu Tyr Arg His Glu Arg Pro Phe Gln Gly Glu
305                 310                 315                 320

gag atg gca cgg acg gag aga tcc gac agg tac gcg ctt act gta act     1008
Glu Met Ala Arg Thr Glu Arg Ser Asp Arg Tyr Ala Leu Thr Val Thr
                325                 330                 335

gca ggc ggg agt cag atg cat gtg ggc ggc gcc ggc gga aac atc acc     1056
Ala Gly Gly Ser Gln Met His Val Gly Gly Ala Gly Gly Asn Ile Thr
            340                 345                 350

tgg tac gat ctt ggc acg ccc cat gac ata acg acc ggc gtc cgc gcg     1104
Trp Tyr Asp Leu Gly Thr Pro His Asp Ile Thr Thr Gly Val Arg Ala
        355                 360                 365

gga tcc gac atc ctg ccg gcg tat cca tcc gcg ggc aga aac gtg gtg     1152
```

-continued

```
Gly Ser Asp Ile Leu Pro Ala Tyr Pro Ser Ala Gly Arg Asn Val Val
    370                 375                 380

ccg tca ata acg ggc att gcc ttc tcg gat gac ggc atg cgg ttg ttt     1200
Pro Ser Ile Thr Gly Ile Ala Phe Ser Asp Asp Gly Met Arg Leu Phe
385                 390                 395                 400

gca gca aac cgg ggc gac cgc att cca atg tac cag ctg gac agc ccg     1248
Ala Ala Asn Arg Gly Asp Arg Ile Pro Met Tyr Gln Leu Asp Ser Pro
                405                 410                 415

tac gac ata ggg agc gcc agc ctc gag gga acc ctg ttt acg ggg ttc     1296
Tyr Asp Ile Gly Ser Ala Ser Leu Glu Gly Thr Leu Phe Thr Gly Phe
            420                 425                 430

cag tcg ggc att gca ttc tcg gat gac ggc acg cgc atg ttt gcc gcc     1344
Gln Ser Gly Ile Ala Phe Ser Asp Asp Gly Thr Arg Met Phe Ala Ala
        435                 440                 445

ctg ctc acc gag aat gcc ata cgg cag tac gac ctg gag ggc ccc tat     1392
Leu Leu Thr Glu Asn Ala Ile Arg Gln Tyr Asp Leu Glu Gly Pro Tyr
    450                 455                 460

gac ata cgc ggg gcg ggc aat gcg ggc cag tac gac ctg gac atc ccg     1440
Asp Ile Arg Gly Ala Gly Asn Ala Gly Gln Tyr Asp Leu Asp Ile Pro
465                 470                 475                 480

ctg cac cca gga ctg ctg ttc ctg ctg acc tcg ggg gtg cac ttt tcg     1488
Leu His Pro Gly Leu Leu Phe Leu Leu Thr Ser Gly Val His Phe Ser
                485                 490                 495

ccc gac ggg acg agg atg ttc gtc ggc gag ggg ata tca gat gcg gag     1536
Pro Asp Gly Thr Arg Met Phe Val Gly Glu Gly Ile Ser Asp Ala Glu
            500                 505                 510

gat gcc aac gcg aac agg gat gtc aac gtc aac ctg tgg cac agg ttt     1584
Asp Ala Asn Ala Asn Arg Asp Val Asn Val Asn Leu Trp His Arg Phe
        515                 520                 525

gat ctc tcc acg ccg ttt gat gtg ctc acg gcg gag cgc gtg gac acg     1632
Asp Leu Ser Thr Pro Phe Asp Val Leu Thr Ala Glu Arg Val Asp Thr
    530                 535                 540

tac gag tac agc acg ggg ccg gca ggc gat ctc gag gac ctc tcc ctg     1680
Tyr Glu Tyr Ser Thr Gly Pro Ala Gly Asp Leu Glu Asp Leu Ser Leu
545                 550                 555                 560

tcc cct gac ggc cgc aga ttg tac acc ctg tcg agc gag agg gta agc     1728
Ser Pro Asp Gly Arg Arg Leu Tyr Thr Leu Ser Ser Glu Arg Val Ser
                565                 570                 575

tca agc gag tat aca atc acc cgg gcc cag tac tgg ctg cca gaa ccg     1776
Ser Ser Glu Tyr Thr Ile Thr Arg Ala Gln Tyr Trp Leu Pro Glu Pro
            580                 585                 590

tac gac gtg acg ccg ccg tac cat gtg ccg tca ttc aac gca agc cag     1824
Tyr Asp Val Thr Pro Pro Tyr His Val Pro Ser Phe Asn Ala Ser Gln
        595                 600                 605

ggg ggc aac ctg gca gac ccc tac ggg atg gcc ttc tcg ccc gac ggg     1872
Gly Gly Asn Leu Ala Asp Pro Tyr Gly Met Ala Phe Ser Pro Asp Gly
    610                 615                 620

acc agg ctg ctg gtc acg ggg cac ggg cag acg aat gca aag ctg ttc     1920
Thr Arg Leu Leu Val Thr Gly His Gly Gln Thr Asn Ala Lys Leu Phe
625                 630                 635                 640

cac ctg aat ccg ccc ttt gat gtg ggc acg gcc gtg ttc cac gac cac     1968
His Leu Asn Pro Pro Phe Asp Val Gly Thr Ala Val Phe His Asp His
                645                 650                 655

ggc agg ttc cgc ccc ggg ggg ccc gca agc gag atc gag gcg tcg ggg     2016
Gly Arg Phe Arg Pro Gly Gly Pro Ala Ser Glu Ile Glu Ala Ser Gly
            660                 665                 670

ata tcc ctg tct gcc gac ggc tcc agg atg ttt ctc tcc gac cgc ggc     2064
Ile Ser Leu Ser Ala Asp Gly Ser Arg Met Phe Leu Ser Asp Arg Gly
        675                 680                 685
```

-continued

```
cgc ggg gcc atc agc cag tac acg ctg gtt gcg ccc ttt gat gtg gag     2112
Arg Gly Ala Ile Ser Gln Tyr Thr Leu Val Ala Pro Phe Asp Val Glu
    690                 695                 700

ttt gcg tcg gat gtg tcc gcg gat ggg cag ctc gac gtt ggc gcc cag     2160
Phe Ala Ser Asp Val Ser Ala Asp Gly Gln Leu Asp Val Gly Ala Gln
705                 710                 715                 720

gat gcg ctt ccc ggc ggg ctt gcc ttc tcg ccc ggg ggg acg agg cta     2208
Asp Ala Leu Pro Gly Gly Leu Ala Phe Ser Pro Gly Gly Thr Arg Leu
                725                 730                 735

ttc atg gtg gga ggc atg gac agg tca gtt cac atg tat tcc ctg aat     2256
Phe Met Val Gly Gly Met Asp Arg Ser Val His Met Tyr Ser Leu Asn
            740                 745                 750

acg ccg ttt gac ctg ggc ggg gca gag cat gcg gcg tcg ttt ggc gtg     2304
Thr Pro Phe Asp Leu Gly Gly Ala Glu His Ala Ala Ser Phe Gly Val
        755                 760                 765

ggg gac agg gtc tcg gat ccc ctc ggc atc gcc ttt ggg aac ggg ggg     2352
Gly Asp Arg Val Ser Asp Pro Leu Gly Ile Ala Phe Gly Asn Gly Gly
    770                 775                 780

act aaa atg cta ata gcc gat acg aca ggc ttt gtg cac ggg tac gac     2400
Thr Lys Met Leu Ile Ala Asp Thr Thr Gly Phe Val His Gly Tyr Asp
785                 790                 795                 800

ctt ggc gcc ccg tac gat atc tcg ggc ccc gcg tac agc ggc ata ttt     2448
Leu Gly Ala Pro Tyr Asp Ile Ser Gly Pro Ala Tyr Ser Gly Ile Phe
                805                 810                 815

gac gcc ggc ggc agc atc cgg gac gtg gcc gtc ggc ggg ggg tcc atg     2496
Asp Ala Gly Gly Ser Ile Arg Asp Val Ala Val Gly Gly Gly Ser Met
            820                 825                 830

ttc ata ctc gag ggg gag acg gac cgg gtg tat gag cac cgc ccc ggc     2544
Phe Ile Leu Glu Gly Glu Thr Asp Arg Val Tyr Glu His Arg Pro Gly
        835                 840                 845

ata tac ccg gtg gtc tca gca ctg gac ggg ccg gcg ctg gtc tct gct     2592
Ile Tyr Pro Val Val Ser Ala Leu Asp Gly Pro Ala Leu Val Ser Ala
    850                 855                 860

gca gca gat gca agg gtg ggt gcg gcc gag gtg ctc ttt gat cgc gcg     2640
Ala Ala Asp Ala Arg Val Gly Ala Ala Glu Val Leu Phe Asp Arg Ala
865                 870                 875                 880

gtg gat gtt ggc ggg ata gac ccc ggg ggg gtc cgc ata gtg gat gca     2688
Val Asp Val Gly Gly Ile Asp Pro Gly Gly Val Arg Ile Val Asp Ala
                885                 890                 895

gca ggc ccc ctg ccc ggc gtg gtg atc tcg gat gcc gtc ata cca ggc     2736
Ala Gly Pro Leu Pro Gly Val Val Ile Ser Asp Ala Val Ile Pro Gly
            900                 905                 910

gag gat ccc ggc gtg gcc agg ttc agc ctg tcg gac gcg gag gtc ctt     2784
Glu Asp Pro Gly Val Ala Arg Phe Ser Leu Ser Asp Ala Glu Val Leu
        915                 920                 925

gcc gtg tcc ggg tat gcc gag ccg agt ctg gtc ttt gga agg cat gcg     2832
Ala Val Ser Gly Tyr Ala Glu Pro Ser Leu Val Phe Gly Arg His Ala
    930                 935                 940

gtg ccg ggc gcg gca ggc ggc aca ttt ccc tcc cag ata ggc aac gcc     2880
Val Pro Gly Ala Ala Gly Gly Thr Phe Pro Ser Gln Ile Gly Asn Ala
945                 950                 955                 960

acg gag ctt gtg gga tcg att ccg aat ccg acc ctg gat ttt ggg acg     2928
Thr Glu Leu Val Gly Ser Ile Pro Asn Pro Thr Leu Asp Phe Gly Thr
                965                 970                 975

acc ctg acg ggg gcg gca ttc tcg gcg gac ggg acg gtg gta ttt ctc     2976
Thr Leu Thr Gly Ala Ala Phe Ser Ala Asp Gly Thr Val Val Phe Leu
            980                 985                 990

tca gac ggc ccc acc ggc agg gtg tac ccg tat tca ctg aat atc ccc     3024
Ser Asp Gly Pro Thr Gly Arg Val Tyr Pro Tyr Ser Leu Asn Ile Pro
        995                 1000                1005
```

-continued

```
tttgacatatcgtctgcggcgcctgggggctttgtaatcgtgcccgtc     3072
Phe Asp Ile Ser Ser Ala Ala Pro Gly Gly Phe Val Ile Val Pro Val
    1010                1015                1020

gga gtc tcg gac att gcg ttt tct gcc gac ggg cgg aac atg cta gtc     3120
Gly Val Ser Asp Ile Ala Phe Ser Ala Asp Gly Arg Asn Met Leu Val
1025                1030                1035                1040

gcg gac gaa acc ggg gga ata cac agg tac ctg gcc cgc agc ccg tac     3168
Ala Asp Glu Thr Gly Gly Ile His Arg Tyr Leu Ala Arg Ser Pro Tyr
                1045                1050                1055

gag ata ggc acg gat ttc atc aaa tca tcc ctg ggt gag ttt gtc gag     3216
Glu Ile Gly Thr Asp Phe Ile Lys Ser Ser Leu Gly Glu Phe Val Glu
            1060                1065                1070

aca ttc tcg gcg gcg ccc cgc gtg cag gat ctt gcc ggc atc gcc ttt     3264
Thr Phe Ser Ala Ala Pro Arg Val Gln Asp Leu Ala Gly Ile Ala Phe
        1075                1080                1085

tcg cac gac ggc atg atc atg ctt gcg gcc ggc ggc tcg ggg tct gtg     3312
Ser His Asp Gly Met Ile Met Leu Ala Ala Gly Gly Ser Gly Ser Val
    1090                1095                1100

cac cgg tac tcg ctg cca tcc ccg tat gca gta tcg ggg gcc aaa tac     3360
His Arg Tyr Ser Leu Pro Ser Pro Tyr Ala Val Ser Gly Ala Lys Tyr
1105                1110                1115                1120

gag gag acg gcg atg att ggc ggg agc ccg tcg ggg ctg gag ttc tcg     3408
Glu Glu Thr Ala Met Ile Gly Gly Ser Pro Ser Gly Leu Glu Phe Ser
                1125                1130                1135

tcc gac ggc ctg agg atg ttt gtt ccc gat gcg ggc tcg gag acg gcg     3456
Ser Asp Gly Leu Arg Met Phe Val Pro Asp Ala Gly Ser Glu Thr Ala
            1140                1145                1150

gca gtc tac ggc ctt gcc gcc ccc tac ggg att ggc gag gcg gag ccg     3504
Ala Val Tyr Gly Leu Ala Ala Pro Tyr Gly Ile Gly Glu Ala Glu Pro
        1155                1160                1165

ctg ccg ccg ctg ttc ctg ggg gta ggg gca gaa gag gcc acg ctc tcg     3552
Leu Pro Pro Leu Phe Leu Gly Val Gly Ala Glu Glu Ala Thr Leu Ser
    1170                1175                1180

cct gac ggc agg cac atc cta gtt ccc ggc agg ccc ggc ctg tcc cag     3600
Pro Asp Gly Arg His Ile Leu Val Pro Gly Arg Pro Gly Leu Ser Gln
1185                1190                1195                1200

tac tcg ctg ttc tcg acg aat ctt gag ctg tgc gcg gag ccc cgg ggc     3648
Tyr Ser Leu Phe Ser Thr Asn Leu Glu Leu Cys Ala Glu Pro Arg Gly
                1205                1210                1215

att gac ggg gga tcg tgc gaa gat ggg ata tac gcc ttt gag agt ccg     3696
Ile Asp Gly Gly Ser Cys Glu Asp Gly Ile Tyr Ala Phe Glu Ser Pro
            1220                1225                1230

ggc agg ggc gag ggc gta tcg ctt gcc gcc tcg ata acg gcg gca gac     3744
Gly Arg Gly Glu Gly Val Ser Leu Ala Ala Ser Ile Thr Ala Ala Asp
        1235                1240                1245

ggg cca gga att ggc gag ctg cac ggg ttt gca ggc ccg ccg atg ccg     3792
Gly Pro Gly Ile Gly Glu Leu His Gly Phe Ala Gly Pro Pro Met Pro
    1250                1255                1260

gcg cct gtc atg gag cag gtc aca ctg gat tcg cgg gag ggc aca ctc     3840
Ala Pro Val Met Glu Gln Val Thr Leu Asp Ser Arg Glu Gly Thr Leu
1265                1270                1275                1280

agg gtc agg ctg gac agg aca gtg gac gtc gac acg gtg cgc ccc tat     3888
Arg Val Arg Leu Asp Arg Thr Val Asp Val Asp Thr Val Arg Pro Tyr
                1285                1290                1295

aag atg tgg gtg gag gat tca gac ggc agc cag aca acc ctg gca aat     3936
Lys Met Trp Val Glu Asp Ser Asp Gly Ser Gln Thr Thr Leu Ala Asn
            1300                1305                1310

tca aca ctg ttg aat gcc gaa aac tcg aac att ctg ctc ttc agg ctg     3984
Ser Thr Leu Leu Asn Ala Glu Asn Ser Asn Ile Leu Leu Phe Arg Leu
```

-continued

```
        1315                1320                1325

gat gat gcg gcc gca ggc aaa ata tcc ggg tat aca tcc ccc gtg ttt     4032
Asp Asp Ala Ala Ala Gly Lys Ile Ser Gly Tyr Thr Ser Pro Val Phe
    1330                1335                1340

cgc acg tgg tcg tcg ccg ttc ctg ggc aca gac gga gcc acc agg ccc     4080
Arg Thr Trp Ser Ser Pro Phe Leu Gly Thr Asp Gly Ala Thr Arg Pro
1345                1350                1355                1360

cat acg ctg ggc ttt gga gac gtg cgc ctt gcg gat ata tac gat gca     4128
His Thr Leu Gly Phe Gly Asp Val Arg Leu Ala Asp Ile Tyr Asp Ala
                1365                1370                1375

tcc ggg gat gtc ccg tcg ccg tcg ggc att gag ttt tca gat gac ggc     4176
Ser Gly Asp Val Pro Ser Pro Ser Gly Ile Glu Phe Ser Asp Asp Gly
            1380                1385                1390

atg agg atg ttc gtt acg ggg atc ggc acg cca ggc atc aac ata ttc     4224
Met Arg Met Phe Val Thr Gly Ile Gly Thr Pro Gly Ile Asn Ile Phe
        1395                1400                1405

aca ctg tcc gcc ccc ttt gac ata aca ttg ccg aag cat tcc ggc tca     4272
Thr Leu Ser Ala Pro Phe Asp Ile Thr Leu Pro Lys His Ser Gly Ser
    1410                1415                1420

acc aac ata ggc ggc ctg tcc gtg tct gat ctg gca ttt gca aac aat     4320
Thr Asn Ile Gly Gly Leu Ser Val Ser Asp Leu Ala Phe Ala Asn Asn
1425                1430                1435                1440

ggg aac agc ctc acg gtg ctc gat gtg gac ggg gtg ttg cgc gtc tac     4368
Gly Asn Ser Leu Thr Val Leu Asp Val Asp Gly Val Leu Arg Val Tyr
                1445                1450                1455

gcc ctt ggg gac gat tac aat gtg gtc acc gga acc acc cag aag ttt     4416
Ala Leu Gly Asp Asp Tyr Asn Val Val Thr Gly Thr Thr Gln Lys Phe
            1460                1465                1470

agg att acg ctc gat acc aca cag ggc ata ccc aat tcc att tac aca     4464
Arg Ile Thr Leu Asp Thr Thr Gln Gly Ile Pro Asn Ser Ile Tyr Thr
        1475                1480                1485

tct ccg gac ggc ctg tca cag ttt gtg gca tat gat gac agg att gac     4512
Ser Pro Asp Gly Leu Ser Gln Phe Val Ala Tyr Asp Asp Arg Ile Asp
    1490                1495                1500

ttg tac gtg ctt ggc agc cca aac gac ata tcg tcg aca acc gag ata     4560
Leu Tyr Val Leu Gly Ser Pro Asn Asp Ile Ser Ser Thr Thr Glu Ile
1505                1510                1515                1520

atc ccg tat tcg ctg cca agg ccg gac ccg cca acc ggc atg gac ttt     4608
Ile Pro Tyr Ser Leu Pro Arg Pro Asp Pro Pro Thr Gly Met Asp Phe
                1525                1530                1535

acg cca gac ggg cgc agg atg ttc ctg tcc acc gag aac ggg ata gac     4656
Thr Pro Asp Gly Arg Arg Met Phe Leu Ser Thr Glu Asn Gly Ile Asp
            1540                1545                1550

cag tac ctg ctt tca gaa ccg ttt gca gtc acc acg tcg gta ttt ttg     4704
Gln Tyr Leu Leu Ser Glu Pro Phe Ala Val Thr Thr Ser Val Phe Leu
        1555                1560                1565

cgc acg atc ccc att gac gga ggg gcg gag gga ata cgg ttt gta gac     4752
Arg Thr Ile Pro Ile Asp Gly Gly Ala Glu Gly Ile Arg Phe Val Asp
    1570                1575                1580

aac gga agg ggc ctg ttt gtg ccg ggc gcc gac ggc atc atc cag agg     4800
Asn Gly Arg Gly Leu Phe Val Pro Gly Ala Asp Gly Ile Ile Gln Arg
1585                1590                1595                1600

cac gag ctc atc tac ccg tac ggg gcc agc acg tcg ttg ttg gag acc     4848
His Glu Leu Ile Tyr Pro Tyr Gly Ala Ser Thr Ser Leu Leu Glu Thr
                1605                1610                1615

gtc agg gac ggc gtg acg gac ggc ggt ccg ggc gag aac ccg gcc gcc     4896
Val Arg Asp Gly Val Thr Asp Gly Gly Pro Gly Glu Asn Pro Ala Ala
            1620                1625                1630

gga gag atc cgc ctt gcg ggc aca ttc aat gca tcc gat aat gta cag     4944
```

-continued

```
Gly Glu Ile Arg Leu Ala Gly Thr Phe Asn Ala Ser Asp Asn Val Gln
        1635                1640                1645

tcg ccg tcg ggc att gag ttt tca ggc gac ggc acg ggg atg ttt gtt     4992
Ser Pro Ser Gly Ile Glu Phe Ser Gly Asp Gly Thr Gly Met Phe Val
    1650                1655                1660

acc ggg ttt ggg gcc gcg ggc gtg aat gaa ttc tcc ctg tcc gcc ccc     5040
Thr Gly Phe Gly Ala Ala Gly Val Asn Glu Phe Ser Leu Ser Ala Pro
1665                1670                1675                1680

ttt gat aca acc ctc ccg gtg cat gtg gaa ttg cac gat ata ggc ggc     5088
Phe Asp Thr Thr Leu Pro Val His Val Glu Leu His Asp Ile Gly Gly
                1685                1690                1695

cag ccg gca gtt gat ctg gcg ttt gca gaa gat ggc agg acc ctc ctg     5136
Gln Pro Ala Val Asp Leu Ala Phe Ala Glu Asp Gly Arg Thr Leu Leu
            1700                1705                1710

ttg ctg gcc gcg gat gga aca ctg gat ttc tac agc ctt gcc ggt gat     5184
Leu Leu Ala Ala Asp Gly Thr Leu Asp Phe Tyr Ser Leu Ala Gly Asp
        1715                1720                1725

gcc tat gat ata ggg gaa gca tcc cgt act ttt caa gtg ccg ttt gag     5232
Ala Tyr Asp Ile Gly Glu Ala Ser Arg Thr Phe Gln Val Pro Phe Glu
    1730                1735                1740

gat gcc gcg ggt gct gtg ccc ggc gcc ttt tac cag cct ccg gat ggc     5280
Asp Ala Ala Gly Ala Val Pro Gly Ala Phe Tyr Gln Pro Pro Asp Gly
1745                1750                1755                1760

tcg tct att att gcc gca ttt gac ggc agg att gac cag tat gtg gtg     5328
Ser Ser Ile Ile Ala Ala Phe Asp Gly Arg Ile Asp Gln Tyr Val Val
                1765                1770                1775

atc ccc ttc gag ttc gtg tca tat cca ctg aca agg ccc ggc acg ccc     5376
Ile Pro Phe Glu Phe Val Ser Tyr Pro Leu Thr Arg Pro Gly Thr Pro
            1780                1785                1790

aca ggg att gac ttt gcg cca gac ggg cgc tgg atg ttc ctg tcc acc     5424
Thr Gly Ile Asp Phe Ala Pro Asp Gly Arg Trp Met Phe Leu Ser Thr
        1795                1800                1805

gag aac ggg ata gac cag tac ctg ctg tcg atc ccc ttt gac gtg cgc     5472
Glu Asn Gly Ile Asp Gln Tyr Leu Leu Ser Ile Pro Phe Asp Val Arg
    1810                1815                1820

agc ctg acg tat acg gga acc att cca gta gac ggg gtg gag gga atg     5520
Ser Leu Thr Tyr Thr Gly Thr Ile Pro Val Asp Gly Val Glu Gly Met
1825                1830                1835                1840

cag ttt gcg gac aac ggc agg gca ctg ttt ttg gcg gac agt gaa ggc     5568
Gln Phe Ala Asp Asn Gly Arg Ala Leu Phe Leu Ala Asp Ser Glu Gly
                1845                1850                1855

ttg att tac aat tat gac ctg gag gac ccg tat gct ctg gat ggc aac     5616
Leu Ile Tyr Asn Tyr Asp Leu Glu Asp Pro Tyr Ala Leu Asp Gly Asn
            1860                1865                1870

aca att tcc gtg gaa ttc tcg ttt gac ggt agc gtg atg tat gtg ctg     5664
Thr Ile Ser Val Glu Phe Ser Phe Asp Gly Ser Val Met Tyr Val Leu
        1875                1880                1885

gag tac gac aca aaa agg gtg gtc tcg tac gag ttg gag ttt ccc ttt     5712
Glu Tyr Asp Thr Lys Arg Val Val Ser Tyr Glu Leu Glu Phe Pro Phe
    1890                1895                1900

gac gta tcg agc aga aca cgt gca gac acg ctg gac ata cca caa att     5760
Asp Val Ser Ser Arg Thr Arg Ala Asp Thr Leu Asp Ile Pro Gln Ile
1905                1910                1915                1920

gac tca cca aga cac gtt gca gtc tcg atg ccc ggc aac cac ctg tac     5808
Asp Ser Pro Arg His Val Ala Val Ser Met Pro Gly Asn His Leu Tyr
                1925                1930                1935

ata aca aac tcg gtg ttt ggg gaa gat gac acc ata cac tcc tat gga     5856
Ile Thr Asn Ser Val Phe Gly Glu Asp Asp Thr Ile His Ser Tyr Gly
            1940                1945                1950
```

-continued

```
ata tct aac aat gac ata tcg tcg gca tca tac atc ggc gag gaa ggc     5904
Ile Ser Asn Asn Asp Ile Ser Ser Ala Ser Tyr Ile Gly Glu Glu Gly
        1955                1960                1965

atc ccg gaa ccc gtg ata aac ggg att gac ttt tcc aac aac ggc cgc     5952
Ile Pro Glu Pro Val Ile Asn Gly Ile Asp Phe Ser Asn Asn Gly Arg
    1970                1975                1980

cgc atg ttt ctg att ggg ggc aac ggg ttc gac tac cag gtg ata cat     6000
Arg Met Phe Leu Ile Gly Gly Asn Gly Phe Asp Tyr Gln Val Ile His
1985                1990                1995                2000

gac tac atg cta ggc aca aga tac gac ata tcc agc agg agc ctg ctt     6048
Asp Tyr Met Leu Gly Thr Arg Tyr Asp Ile Ser Ser Arg Ser Leu Leu
                2005                2010                2015

gat aca tat gcc att cca ggg ccg gtt gtt ttt ccc gcg ggc ctt gat     6096
Asp Thr Tyr Ala Ile Pro Gly Pro Val Val Phe Pro Ala Gly Leu Asp
            2020                2025                2030

ttc tcg ttt gac agg ctg tcc atg ttt ata ata agc acc gcc ggt tcg     6144
Phe Ser Phe Asp Arg Leu Ser Met Phe Ile Ile Ser Thr Ala Gly Ser
        2035                2040                2045

gta tac agg tac ggc ctg gac gat ccg ttc ata gtt gaa aca atg gac     6192
Val Tyr Arg Tyr Gly Leu Asp Asp Pro Phe Ile Val Glu Thr Met Asp
    2050                2055                2060

tat cag gag tct ttc cgg ctg ccc gta cca tca gcg gct gat aat tca     6240
Tyr Gln Glu Ser Phe Arg Leu Pro Val Pro Ser Ala Ala Asp Asn Ser
2065                2070                2075                2080

ata tcg gat ctg gca ttc ggc agc agc ggc ctg aat gcc gta ata tcg     6288
Ile Ser Asp Leu Ala Phe Gly Ser Ser Gly Leu Asn Ala Val Ile Ser
                2085                2090                2095

cac gag ggg ctc gac acc ctg tac agc ttt gta ctg gac atc ccg tat     6336
His Glu Gly Leu Asp Thr Leu Tyr Ser Phe Val Leu Asp Ile Pro Tyr
            2100                2105                2110

ggg gcc gaa ttg gat att gac agg ctt gag ctt ccg ctg gtg ggg gtt     6384
Gly Ala Glu Leu Asp Ile Asp Arg Leu Glu Leu Pro Leu Val Gly Val
        2115                2120                2125

ccg acg gga ttc gag ttc tcg gac aac ggg cgc cag ttg tac att ggc     6432
Pro Thr Gly Phe Glu Phe Ser Asp Asn Gly Arg Gln Leu Tyr Ile Gly
    2130                2135                2140

gcg ttt cgt gac tct caa tcc tcg cca ggc acc ctg cct gcg ggc ctg     6480
Ala Phe Arg Asp Ser Gln Ser Ser Pro Gly Thr Leu Pro Ala Gly Leu
2145                2150                2155                2160

cag cgc tat gag ctt ggc ata cca tat gac ctg gct tcg gct gta ttt     6528
Gln Arg Tyr Glu Leu Gly Ile Pro Tyr Asp Leu Ala Ser Ala Val Phe
                2165                2170                2175

gcg cag tcc ctg gga ata ttc gat ttt cct ccc ttc aac ggc atg cgg     6576
Ala Gln Ser Leu Gly Ile Phe Asp Phe Pro Pro Phe Asn Gly Met Arg
            2180                2185                2190

gcc aat ggc agc ttg gca gga tta cat gtg ccg ccc gat gga agc atc     6624
Ala Asn Gly Ser Leu Ala Gly Leu His Val Pro Pro Asp Gly Ser Ile
        2195                2200                2205

ctg ttc agg gcc gga aat gcc gaa aga acc gta atc agc tat gac atg     6672
Leu Phe Arg Ala Gly Asn Ala Glu Arg Thr Val Ile Ser Tyr Asp Met
    2210                2215                2220

gac agc cat gat ttg gat aca tta tca ttc agg gaa tca ttc aaa cca     6720
Asp Ser His Asp Leu Asp Thr Leu Ser Phe Arg Glu Ser Phe Lys Pro
2225                2230                2235                2240

gat gtc gga cag tcg aca ccc aac ata agg gac atg gac ata tcc ccg     6768
Asp Val Gly Gln Ser Thr Pro Asn Ile Arg Asp Met Asp Ile Ser Pro
                2245                2250                2255

gac ggc atg ttc ctc tac ctg ctt caa ggc gat gtt ctg gac atg tac     6816
Asp Gly Met Phe Leu Tyr Leu Leu Gln Gly Asp Val Leu Asp Met Tyr
            2260                2265                2270
```

-continued

```
aac ctt aca gat agt tat tcg ctt gat gcc ccg gca tat gcg ggt acc      6864
Asn Leu Thr Asp Ser Tyr Ser Leu Asp Ala Pro Ala Tyr Ala Gly Thr
        2275                2280                2285

ctg gat ttg gaa ccg gag gat gta ata ccc agg ggg att tca ttc tca      6912
Leu Asp Leu Glu Pro Glu Asp Val Ile Pro Arg Gly Ile Ser Phe Ser
    2290                2295                2300

cgg gat ggc acg agt ctg ttt atg aca ggc gaa gac gtg gac cac att      6960
Arg Asp Gly Thr Ser Leu Phe Met Thr Gly Glu Asp Val Asp His Ile
2305                2310                2315                2320

cac gaa tat gca ttg aat gaa cca tgg gac ata cgc aat gcc ata ctt      7008
His Glu Tyr Ala Leu Asn Glu Pro Trp Asp Ile Arg Asn Ala Ile Leu
                2325                2330                2335

gca ggc tcc ctg tcc ata agc gca gtg aat ggt gca ccg cgg ggg ctg      7056
Ala Gly Ser Leu Ser Ile Ser Ala Val Asn Gly Ala Pro Arg Gly Leu
            2340                2345                2350

gat ata tcg gag gat ggc aca act gca cat act atg cgc ggg cgt gac      7104
Asp Ile Ser Glu Asp Gly Thr Thr Ala His Thr Met Arg Gly Arg Asp
        2355                2360                2365

ttt gac acg ggg ccc gca tcc ctg gta aac cac ata ttg cca ggc caa      7152
Phe Asp Thr Gly Pro Ala Ser Leu Val Asn His Ile Leu Pro Gly Gln
    2370                2375                2380

tat tcc ctg ctg acg gat gcg ccg gcg ttt gca tac ccc gtg gag gag      7200
Tyr Ser Leu Leu Thr Asp Ala Pro Ala Phe Ala Tyr Pro Val Glu Glu
2385                2390                2395                2400

gag ggt gca ccg ggg gat ctt gca ttc tcc gat gac ggc atg cgc atg      7248
Glu Gly Ala Pro Gly Asp Leu Ala Phe Ser Asp Asp Gly Met Arg Met
                2405                2410                2415

ttc gtg gcg ggc gta aac aac cat tta aga cag tac aac ctg ctg tcg      7296
Phe Val Ala Gly Val Asn Asn His Leu Arg Gln Tyr Asn Leu Leu Ser
            2420                2425                2430

ccg tat gac act gaa aat gca gaa cat ttc atc tcg acg gat ctg ctg      7344
Pro Tyr Asp Thr Glu Asn Ala Glu His Phe Ile Ser Thr Asp Leu Leu
        2435                2440                2445

act gcg gac agg ggc ccc acg ggt ctt gta ttt tca gat gag aac gac      7392
Thr Ala Asp Arg Gly Pro Thr Gly Leu Val Phe Ser Asp Glu Asn Asp
    2450                2455                2460

ttt ttc agc aca ggc gcc agg gcc caa ttt gtg cgc cag ttt acg aca      7440
Phe Phe Ser Thr Gly Ala Arg Ala Gln Phe Val Arg Gln Phe Thr Thr
2465                2470                2475                2480

aac cgc ccg tac gac gca tcc aca ata aca ctg agt gac aac gga ctg      7488
Asn Arg Pro Tyr Asp Ala Ser Thr Ile Thr Leu Ser Asp Asn Gly Leu
                2485                2490                2495

tac aag gtg agc gtg gac ggc ctg ccg tcc ggc ata cgg ttt acc ccc      7536
Tyr Lys Val Ser Val Asp Gly Leu Pro Ser Gly Ile Arg Phe Thr Pro
            2500                2505                2510

gac ggc atg aag atg ttc ata tcg ggc cag gag acg gcc atg ata tac      7584
Asp Gly Met Lys Met Phe Ile Ser Gly Gln Glu Thr Ala Met Ile Tyr
        2515                2520                2525

cag tat tcc ctg ccg tcc ccg tat gac aca tcc ggg gcg gtc agg gac      7632
Gln Tyr Ser Leu Pro Ser Pro Tyr Asp Thr Ser Gly Ala Val Arg Asp
    2530                2535                2540

agg gtt gag ata gtc gca ggg ctc ttt aga aat gca ggt ttg tcc gtc      7680
Arg Val Glu Ile Val Ala Gly Leu Phe Arg Asn Ala Gly Leu Ser Val
2545                2550                2555                2560

ggg ttg aac gag ccc agt cct tcc ggc ttt gac ttt tcg gag gac gga      7728
Gly Leu Asn Glu Pro Ser Pro Ser Gly Phe Asp Phe Ser Glu Asp Gly
                2565                2570                2575

atg gag ctg tac gtg acg ggg tcg ggc ctt gtt cac agg tat ttc ctg      7776
Met Glu Leu Tyr Val Thr Gly Ser Gly Leu Val His Arg Tyr Phe Leu
```

-continued

```
            2580                2585                2590

cca tcg cca tac ggc ctc gaa gat gca gcg tac ggg ggc agc ttc cac     7824
Pro Ser Pro Tyr Gly Leu Glu Asp Ala Ala Tyr Gly Gly Ser Phe His
        2595                2600                2605

acg ttc agg gag agc acg ccg ctg gga gtg gtg gtg cgg ggg gat gcc     7872
Thr Phe Arg Glu Ser Thr Pro Leu Gly Val Val Val Arg Gly Asp Ala
    2610                2615                2620

atg ttt gtg gcc ggg gac agt act gat tcc ata ttg aaa tat tcc ctg     7920
Met Phe Val Ala Gly Asp Ser Thr Asp Ser Ile Leu Lys Tyr Ser Leu
2625                2630                2635                2640

aac gca caa cct gtc ggc aac ata acc cat gcc gat acg cgc gcc ggg     7968
Asn Ala Gln Pro Val Gly Asn Ile Thr His Ala Asp Thr Arg Ala Gly
                2645                2650                2655

att gcc gac agg gcg gag atc gtg ttt ggg gca atg gca gat acg cgc     8016
Ile Ala Asp Arg Ala Glu Ile Val Phe Gly Ala Met Ala Asp Thr Arg
            2660                2665                2670

gcc gag att ctc gac ggc gcc gat gta gtt cat aag agt gtg aaa att     8064
Ala Glu Ile Leu Asp Gly Ala Asp Val Val His Lys Ser Val Lys Ile
        2675                2680                2685

gac gta ttc cca ata tcg gag ggc ata aca gtg ggc agg gca ctt tat     8112
Asp Val Phe Pro Ile Ser Glu Gly Ile Thr Val Gly Arg Ala Leu Tyr
    2690                2695                2700

cca gag gac gcc gcc ata ctt gat gac ggc gcg aat gcc acg cat aat     8160
Pro Glu Asp Ala Ala Ile Leu Asp Asp Gly Ala Asn Ala Thr His Asn
2705                2710                2715                2720

agg gtt gta atc att gtt cac gac ata aca gaa ggc gat gcg ccg tcc     8208
Arg Val Val Ile Ile Val His Asp Ile Thr Glu Gly Asp Ala Pro Ser
                2725                2730                2735

ata cat gat gag ccg att gcc gtg ggg att tac gcc ctc ggc cct atg     8256
Ile His Asp Glu Pro Ile Ala Val Gly Ile Tyr Ala Leu Gly Pro Met
            2740                2745                2750

gat aca atc gcc gtg gtt gat ctc cac cgc ctg gcc gta tcc gca tcc     8304
Asp Thr Ile Ala Val Val Asp Leu His Arg Leu Ala Val Ser Ala Ser
        2755                2760                2765

ttg tcc ggg ggt gat tcc ccg tcg gcc tca gat gca tcc gga gta gtg     8352
Leu Ser Gly Gly Asp Ser Pro Ser Ala Ser Asp Ala Ser Gly Val Val
    2770                2775                2780

gcc gag agc cgc aga aac gcg gtg gac agg cct ggc gtg gaa gag cgc     8400
Ala Glu Ser Arg Arg Asn Ala Val Asp Arg Pro Gly Val Glu Glu Arg
2785                2790                2795                2800

ata gga cat ggt gta tcc ctg gag gcg gcc gac agg cct gcc gtc gac     8448
Ile Gly His Gly Val Ser Leu Glu Ala Ala Asp Arg Pro Ala Val Asp
                2805                2810                2815

aac atg atg gat acg gat agt gcc ggc gtg tac gac cgc agt ccg gac     8496
Asn Met Met Asp Thr Asp Ser Ala Gly Val Tyr Asp Arg Ser Pro Asp
            2820                2825                2830

gac ggg ccc gcc gta tcc gac agg tcc gcg ctg ggg ctt gcc cgg atg     8544
Asp Gly Pro Ala Val Ser Asp Arg Ser Ala Leu Gly Leu Ala Arg Met
        2835                2840                2845

gca gcc gac agg cct gca gtc gat gac atg atg gat acg gat agt gcc     8592
Ala Ala Asp Arg Pro Ala Val Asp Asp Met Met Asp Thr Asp Ser Ala
    2850                2855                2860

ggc gtg tac gac cgc agc ccg gac gac ggg ccc gcc ata tcc gac agg     8640
Gly Val Tyr Asp Arg Ser Pro Asp Asp Gly Pro Ala Ile Ser Asp Arg
2865                2870                2875                2880

tcc gcg ctg ggg ctt gcc cgg atg gca gcc gac agg cct gca gtc gac     8688
Ser Ala Leu Gly Leu Ala Arg Met Ala Ala Asp Arg Pro Ala Val Asp
                2885                2890                2895

gac atg atg gat acg ggc agt gcc ggc gtg tac gac cgc agc ccg gac     8736
```

-continued

```
Asp Met Met Asp Thr Gly Ser Ala Gly Val Tyr Asp Arg Ser Pro Asp
            2900                2905                2910

gac ggg ccc gcc ata tcc gac agg tcc gcg ctg ggg ctt gcc cgg atg     8784
Asp Gly Pro Ala Ile Ser Asp Arg Ser Ala Leu Gly Leu Ala Arg Met
        2915                2920                2925

gca gcc gac agg cct gca gtc gat gac atg atg gat acg ggc agt gag     8832
Ala Ala Asp Arg Pro Ala Val Asp Asp Met Met Asp Thr Gly Ser Glu
    2930                2935                2940

agc acg agc agg ctt gga ccg gtt gac agg cca gaa ata gtc gag cgc     8880
Ser Thr Ser Arg Leu Gly Pro Val Asp Arg Pro Glu Ile Val Glu Arg
2945                2950                2955                2960

cac agc ctg gcc gcg tct gta tac ctg tcc ggg ggc gat tcc ccg tcg     8928
His Ser Leu Ala Ala Ser Val Tyr Leu Ser Gly Gly Asp Ser Pro Ser
                2965                2970                2975

gtc gca gac ggt cat gat gtg gag tcc gag ggc cgc aga gac ggg ggg     8976
Val Ala Asp Gly His Asp Val Glu Ser Glu Gly Arg Arg Asp Gly Gly
            2980                2985                2990

gac agg cct ggc atc gac gag cgt ata gtc atc aag atc tcg tac agc     9024
Asp Arg Pro Gly Ile Asp Glu Arg Ile Val Ile Lys Ile Ser Tyr Ser
        2995                3000                3005

cgc ggc gca gcc gat gcg ccc aga gtg gag gat gca atg gag act tcc     9072
Arg Gly Ala Ala Asp Ala Pro Arg Val Glu Asp Ala Met Glu Thr Ser
    3010                3015                3020

ggc gtg acc gcg tac agc cgc ggc gca gcc gat gcg ccc aga gtg gag     9120
Gly Val Thr Ala Tyr Ser Arg Gly Ala Ala Asp Ala Pro Arg Val Glu
3025                3030                3035                3040

gat gca atg gag act tcc ggc gtg acc gtc ccc agg cgc agt acc atg     9168
Asp Ala Met Glu Thr Ser Gly Val Thr Val Pro Arg Arg Ser Thr Met
                3045                3050                3055

gac gcg ccc aca gtg gcc gat gac cac agc ctg gcc cgg acc gca tcc     9216
Asp Ala Pro Thr Val Ala Asp Asp His Ser Leu Ala Arg Thr Ala Ser
            3060                3065                3070

ata tcc gaa ggc gat tcc ccg aca ttt gca gag gcg cgc cgc gcg gat     9264
Ile Ser Glu Gly Asp Ser Pro Thr Phe Ala Glu Ala Arg Arg Ala Asp
        3075                3080                3085

acc gtt ggg gat ata gac gag gtg gac gcg ccc aca gtg gcc gat gac     9312
Thr Val Gly Asp Ile Asp Glu Val Asp Ala Pro Thr Val Ala Asp Asp
    3090                3095                3100

cac agt ctg gcc cgg gcc gca tcc ata tcc gaa ggc gat tcc ccg aca     9360
His Ser Leu Ala Arg Ala Ala Ser Ile Ser Glu Gly Asp Ser Pro Thr
3105                3110                3115                3120

ttt gca gag gtg cgc cgc gcg gat acc gtt ggg gat ata gac gag gtg     9408
Phe Ala Glu Val Arg Arg Ala Asp Thr Val Gly Asp Ile Asp Glu Val
                3125                3130                3135

gac gcg ccc gcc gtg gcc gag agg ctc ctg gca gtc ctc ggc ctg cag     9456
Asp Ala Pro Ala Val Ala Glu Arg Leu Leu Ala Val Leu Gly Leu Gln
            3140                3145                3150

gcc cct gat tcg ccg gga gtg tgg gat act gta gga ata gat cac tcg     9504
Ala Pro Asp Ser Pro Gly Val Trp Asp Thr Val Gly Ile Asp His Ser
        3155                3160                3165

gag att tca ggc gat cct gtg ccg gag cca aga gta gtg ccc agg ggc     9552
Glu Ile Ser Gly Asp Pro Val Pro Glu Pro Arg Val Val Pro Arg Gly
    3170                3175                3180

ggt ggc ggt ggg gga ggc ggt tct tcg aac cgc ggc ctt gaa ccg cat     9600
Gly Gly Gly Gly Gly Gly Gly Ser Ser Asn Arg Gly Leu Glu Pro His
3185                3190                3195                3200

ggc ggc ggg tat gag att gac ttt gag ttc cgc ata gac ggc agg ctg     9648
Gly Gly Gly Tyr Glu Ile Asp Phe Glu Phe Arg Ile Asp Gly Arg Leu
                3205                3210                3215
```

-continued

```
gtg ctc ttc aat ggg aca gac gtg cta gcc gaa tcc ggc aag gac ctg     9696
Val Leu Phe Asn Gly Thr Asp Val Leu Ala Glu Ser Gly Lys Asp Leu
            3220                3225                3230

ctc atc cgt ccg gtg ttc cgg ccg gag ggg agt ttc aac ata ttt gat     9744
Leu Ile Arg Pro Val Phe Arg Pro Glu Gly Ser Phe Asn Ile Phe Asp
        3235                3240                3245

atg gag gtg ttg ttt acc gcc ccc ggc ggg gag ata tcg act gcc tac     9792
Met Glu Val Leu Phe Thr Ala Pro Gly Gly Glu Ile Ser Thr Ala Tyr
    3250                3255                3260

tac aac agg gct gga atc ctc atg ggg att gac tgc ggc gag ctg att     9840
Tyr Asn Arg Ala Gly Ile Leu Met Gly Ile Asp Cys Gly Glu Leu Ile
3265                3270                3275                3280

atg acc gat acg acg tat tca tgc gac atg ctg gac ata ttc gga gat     9888
Met Thr Asp Thr Thr Tyr Ser Cys Asp Met Leu Asp Ile Phe Gly Asp
                3285                3290                3295

gag ata tac cat gtg gag agg ctt gac gca ttc aac ggc atg gtc atc     9936
Glu Ile Tyr His Val Glu Arg Leu Asp Ala Phe Asn Gly Met Val Ile
            3300                3305                3310

tcc ttg gac ggc ccc ctc gac ggg acg gtc agt gta tcg ctt cgt gac     9984
Ser Leu Asp Gly Pro Leu Asp Gly Thr Val Ser Val Ser Leu Arg Asp
        3315                3320                3325

aac cac ggc atc ccg ctg gcg cag cat cgg ctg cat aaa tac gag att    10032
Asn His Gly Ile Pro Leu Ala Gln His Arg Leu His Lys Tyr Glu Ile
    3330                3335                3340

ttg att ttg gac gcc gct gaa aac aga ccc ctg tca gtc tcg acg gac    10080
Leu Ile Leu Asp Ala Ala Glu Asn Arg Pro Leu Ser Val Ser Thr Asp
3345                3350                3355                3360

ccc aag ccc gtg gag gat cca tcg ccc gtg cag cat ata gag tcc ctc    10128
Pro Lys Pro Val Glu Asp Pro Ser Pro Val Gln His Ile Glu Ser Leu
                3365                3370                3375

cag atg gat ccg gag ccc gtg gag tcc gag ccc ctc ccg atg gac tcc    10176
Gln Met Asp Pro Glu Pro Val Glu Ser Glu Pro Leu Pro Met Asp Ser
            3380                3385                3390

gag ccc gtg gag gat ctg gaa cct gtg cag cat cta gag tcc ctc ccg    10224
Glu Pro Val Glu Asp Leu Glu Pro Val Gln His Leu Glu Ser Leu Pro
        3395                3400                3405

atg gac ccc gag ccc gtg gag gat ctg gaa cct gtg cag cat ctc gag    10272
Met Asp Pro Glu Pro Val Glu Asp Leu Glu Pro Val Gln His Leu Glu
    3410                3415                3420

ccc gtg cag gga tcc ccg ccc gtg cag gga ggg ccg gag tcc gtg gag    10320
Pro Val Gln Gly Ser Pro Pro Val Gln Gly Gly Pro Glu Ser Val Glu
3425                3430                3435                3440

tca ggc ata gca tac acg cta tgg cag ttc ctt tca gga ctg ctg gat    10368
Ser Gly Ile Ala Tyr Thr Leu Trp Gln Phe Leu Ser Gly Leu Leu Asp
                3445                3450                3455

gcc ctg ggt ctt gcc gac ccg gat gtc gga tct gtc caa aaa acg tcc    10416
Ala Leu Gly Leu Ala Asp Pro Asp Val Gly Ser Val Gln Lys Thr Ser
            3460                3465                3470

tga                                                                10419


<210> SEQ ID NO 4
<211> LENGTH: 3472
<212> TYPE: PRT
<213> ORGANISM: Cenarchaeum symbiosum

<400> SEQUENCE: 4

Met Pro Ala Pro Pro Gly Glu Gly Ser Leu Gly Gly Val Ala Ile Ser
 1               5                  10                  15

Asp Asp Gly Arg Tyr Met Tyr Ala Ile Gly Arg Asp Leu Leu Thr Val
            20                  25                  30
```

-continued

```
Tyr Arg Tyr Thr Met Asn Pro Pro His Asp Ile Ala Ser Ala Ala Leu
        35                  40                  45

Gly Ala Gln Ser Phe Ser Leu Pro Gly Gly Ile Ser Pro Ala Pro Gly
    50                  55                  60

Ala Pro Thr Gly Leu Asp Ile Ser Asp Asp Gly Arg His Leu Tyr Val
65                  70                  75                  80

Pro Asp Glu Asn Gly Val Val Tyr Arg Phe Asp Leu Glu Ser Pro Tyr
                85                  90                  95

Arg Leu Asp Gly Gly Thr Phe Gly Ser Ser Val Tyr Val Gly Ser Asp
            100                 105                 110

Val Ala Ala Pro Arg Gly Val Tyr Val Ala Pro Gly Gly Ser Leu Met
        115                 120                 125

Leu Val Ser Asp Ser Ala Asp Gly Thr Ile His Arg Tyr Glu Leu Ala
    130                 135                 140

Ser Pro Tyr Glu Pro Ala Gly Ala Ala Asn Arg Gly Ser Phe Asp Val
145                 150                 155                 160

Ser Asp Met Asp Gly Ser Pro Val Gly Ala Gly Phe Ala Gly Gly Leu
                165                 170                 175

His Met Tyr Val Ala Gly Asn Asp Thr Gly Arg Val Tyr Gln Tyr Pro
            180                 185                 190

Ala Gly Thr His Gln Ile Gln Glu Ala Ala Ala Gly Pro Arg Leu Leu
        195                 200                 205

Ser Ala Val Leu Asp Lys Asp Gly Thr Leu Arg Ala Ala Phe Asp Gly
    210                 215                 220

Thr Val Asp Ala Gly Ser Val Gln Pro Gly Met Ile Thr Ile Arg Asp
225                 230                 235                 240

Gly His Gly Ser Asn Thr Gly Ile Pro Leu Leu Leu Ala Gly Gly Ala
                245                 250                 255

Ala Asp Ser Asp Val Met Thr Phe Val Val Pro Glu Lys Asp Arg Ala
            260                 265                 270

Glu Ala Ala Ala Tyr Gly Asp Gln Ser Leu His Val Pro Ala Ala Ala
        275                 280                 285

Leu Ala Gly Thr Gly Gly Gly Pro Phe Val Pro Asp Phe Ser Gly Gly
    290                 295                 300

Ser Leu Leu Ala Ser Leu Tyr Arg His Glu Arg Pro Phe Gln Gly Glu
305                 310                 315                 320

Glu Met Ala Arg Thr Glu Arg Ser Asp Arg Tyr Ala Leu Thr Val Thr
                325                 330                 335

Ala Gly Gly Ser Gln Met His Val Gly Gly Ala Gly Gly Asn Ile Thr
            340                 345                 350

Trp Tyr Asp Leu Gly Thr Pro His Asp Ile Thr Thr Gly Val Arg Ala
        355                 360                 365

Gly Ser Asp Ile Leu Pro Ala Tyr Pro Ser Ala Gly Arg Asn Val Val
    370                 375                 380

Pro Ser Ile Thr Gly Ile Ala Phe Ser Asp Asp Gly Met Arg Leu Phe
385                 390                 395                 400

Ala Ala Asn Arg Gly Asp Arg Ile Pro Met Tyr Gln Leu Asp Ser Pro
                405                 410                 415

Tyr Asp Ile Gly Ser Ala Ser Leu Glu Gly Thr Leu Phe Thr Gly Phe
            420                 425                 430

Gln Ser Gly Ile Ala Phe Ser Asp Asp Gly Thr Arg Met Phe Ala Ala
        435                 440                 445
```

-continued

```
Leu Leu Thr Glu Asn Ala Ile Arg Gln Tyr Asp Leu Glu Gly Pro Tyr
    450                 455                 460

Asp Ile Arg Gly Ala Gly Asn Ala Gly Gln Tyr Asp Leu Asp Ile Pro
465                 470                 475                 480

Leu His Pro Gly Leu Leu Phe Leu Leu Thr Ser Gly Val His Phe Ser
                485                 490                 495

Pro Asp Gly Thr Arg Met Phe Val Gly Glu Gly Ile Ser Asp Ala Glu
            500                 505                 510

Asp Ala Asn Ala Asn Arg Asp Val Asn Val Asn Leu Trp His Arg Phe
        515                 520                 525

Asp Leu Ser Thr Pro Phe Asp Val Leu Thr Ala Glu Arg Val Asp Thr
    530                 535                 540

Tyr Glu Tyr Ser Thr Gly Pro Ala Gly Asp Leu Glu Asp Leu Ser Leu
545                 550                 555                 560

Ser Pro Asp Gly Arg Arg Leu Tyr Thr Leu Ser Ser Glu Arg Val Ser
                565                 570                 575

Ser Ser Glu Tyr Thr Ile Thr Arg Ala Gln Tyr Trp Leu Pro Glu Pro
            580                 585                 590

Tyr Asp Val Thr Pro Pro Tyr His Val Pro Ser Phe Asn Ala Ser Gln
        595                 600                 605

Gly Gly Asn Leu Ala Asp Pro Tyr Gly Met Ala Phe Ser Pro Asp Gly
    610                 615                 620

Thr Arg Leu Leu Val Thr Gly His Gly Gln Thr Asn Ala Lys Leu Phe
625                 630                 635                 640

His Leu Asn Pro Pro Phe Asp Val Gly Thr Ala Val Phe His Asp His
                645                 650                 655

Gly Arg Phe Arg Pro Gly Gly Pro Ala Ser Glu Ile Glu Ala Ser Gly
            660                 665                 670

Ile Ser Leu Ser Ala Asp Gly Ser Arg Met Phe Leu Ser Asp Arg Gly
        675                 680                 685

Arg Gly Ala Ile Ser Gln Tyr Thr Leu Val Ala Pro Phe Asp Val Glu
    690                 695                 700

Phe Ala Ser Asp Val Ser Ala Asp Gly Gln Leu Asp Val Gly Ala Gln
705                 710                 715                 720

Asp Ala Leu Pro Gly Gly Leu Ala Phe Ser Pro Gly Gly Thr Arg Leu
                725                 730                 735

Phe Met Val Gly Gly Met Asp Arg Ser Val His Met Tyr Ser Leu Asn
            740                 745                 750

Thr Pro Phe Asp Leu Gly Gly Ala Glu His Ala Ala Ser Phe Gly Val
        755                 760                 765

Gly Asp Arg Val Ser Asp Pro Leu Gly Ile Ala Phe Gly Asn Gly Gly
    770                 775                 780

Thr Lys Met Leu Ile Ala Asp Thr Thr Gly Phe Val His Gly Tyr Asp
785                 790                 795                 800

Leu Gly Ala Pro Tyr Asp Ile Ser Gly Pro Ala Tyr Ser Gly Ile Phe
                805                 810                 815

Asp Ala Gly Gly Ser Ile Arg Asp Val Ala Val Gly Gly Gly Ser Met
            820                 825                 830

Phe Ile Leu Glu Gly Glu Thr Asp Arg Val Tyr Glu His Arg Pro Gly
        835                 840                 845

Ile Tyr Pro Val Val Ser Ala Leu Asp Gly Pro Ala Leu Val Ser Ala
    850                 855                 860

Ala Ala Asp Ala Arg Val Gly Ala Ala Glu Val Leu Phe Asp Arg Ala
```

-continued

```
865                 870                 875                 880

Val Asp Val Gly Gly Ile Asp Pro Gly Gly Val Arg Ile Val Asp Ala
                885                 890                 895

Ala Gly Pro Leu Pro Gly Val Val Ile Ser Asp Ala Val Ile Pro Gly
            900                 905                 910

Glu Asp Pro Gly Val Ala Arg Phe Ser Leu Ser Asp Ala Glu Val Leu
        915                 920                 925

Ala Val Ser Gly Tyr Ala Glu Pro Ser Leu Val Phe Gly Arg His Ala
    930                 935                 940

Val Pro Gly Ala Ala Gly Gly Thr Phe Pro Ser Gln Ile Gly Asn Ala
945                 950                 955                 960

Thr Glu Leu Val Gly Ser Ile Pro Asn Pro Thr Leu Asp Phe Gly Thr
                965                 970                 975

Thr Leu Thr Gly Ala Ala Phe Ser Ala Asp Gly Thr Val Val Phe Leu
            980                 985                 990

Ser Asp Gly Pro Thr Gly Arg Val Tyr Pro Tyr Ser Leu Asn Ile Pro
        995                 1000                1005

Phe Asp Ile Ser Ser Ala Ala Pro Gly Gly Phe Val Ile Val Pro Val
    1010                1015                1020

Gly Val Ser Asp Ile Ala Phe Ser Ala Asp Gly Arg Asn Met Leu Val
1025                1030                1035                1040

Ala Asp Glu Thr Gly Gly Ile His Arg Tyr Leu Ala Arg Ser Pro Tyr
                1045                1050                1055

Glu Ile Gly Thr Asp Phe Ile Lys Ser Ser Leu Gly Glu Phe Val Glu
            1060                1065                1070

Thr Phe Ser Ala Ala Pro Arg Val Gln Asp Leu Ala Gly Ile Ala Phe
        1075                1080                1085

Ser His Asp Gly Met Ile Met Leu Ala Ala Gly Gly Ser Gly Ser Val
    1090                1095                1100

His Arg Tyr Ser Leu Pro Ser Pro Tyr Ala Val Ser Gly Ala Lys Tyr
1105                1110                1115                1120

Glu Glu Thr Ala Met Ile Gly Gly Ser Pro Ser Gly Leu Glu Phe Ser
                1125                1130                1135

Ser Asp Gly Leu Arg Met Phe Val Pro Asp Ala Gly Ser Glu Thr Ala
            1140                1145                1150

Ala Val Tyr Gly Leu Ala Ala Pro Tyr Gly Ile Gly Glu Ala Glu Pro
        1155                1160                1165

Leu Pro Pro Leu Phe Leu Gly Val Gly Ala Glu Glu Ala Thr Leu Ser
    1170                1175                1180

Pro Asp Gly Arg His Ile Leu Val Pro Gly Arg Pro Gly Leu Ser Gln
1185                1190                1195                1200

Tyr Ser Leu Phe Ser Thr Asn Leu Glu Leu Cys Ala Glu Pro Arg Gly
                1205                1210                1215

Ile Asp Gly Gly Ser Cys Glu Asp Gly Ile Tyr Ala Phe Glu Ser Pro
            1220                1225                1230

Gly Arg Gly Glu Gly Val Ser Leu Ala Ala Ser Ile Thr Ala Ala Asp
        1235                1240                1245

Gly Pro Gly Ile Gly Glu Leu His Gly Phe Ala Gly Pro Pro Met Pro
    1250                1255                1260

Ala Pro Val Met Glu Gln Val Thr Leu Asp Ser Arg Glu Gly Thr Leu
1265                1270                1275                1280

Arg Val Arg Leu Asp Arg Thr Val Asp Val Asp Thr Val Arg Pro Tyr
                1285                1290                1295
```

-continued

```
Lys Met Trp Val Glu Asp Ser Asp Gly Ser Gln Thr Thr Leu Ala Asn
            1300                1305                1310

Ser Thr Leu Leu Asn Ala Glu Asn Ser Asn Ile Leu Leu Phe Arg Leu
        1315                1320                1325

Asp Asp Ala Ala Ala Gly Lys Ile Ser Gly Tyr Thr Ser Pro Val Phe
    1330                1335                1340

Arg Thr Trp Ser Ser Pro Phe Leu Gly Thr Asp Gly Ala Thr Arg Pro
1345                1350                1355                1360

His Thr Leu Gly Phe Gly Asp Val Arg Leu Ala Asp Ile Tyr Asp Ala
                1365                1370                1375

Ser Gly Asp Val Pro Ser Pro Ser Gly Ile Glu Phe Ser Asp Asp Gly
            1380                1385                1390

Met Arg Met Phe Val Thr Gly Ile Gly Thr Pro Gly Ile Asn Ile Phe
        1395                1400                1405

Thr Leu Ser Ala Pro Phe Asp Ile Thr Leu Pro Lys His Ser Gly Ser
    1410                1415                1420

Thr Asn Ile Gly Gly Leu Ser Val Ser Asp Leu Ala Phe Ala Asn Asn
1425                1430                1435                1440

Gly Asn Ser Leu Thr Val Leu Asp Val Asp Gly Val Leu Arg Val Tyr
                1445                1450                1455

Ala Leu Gly Asp Asp Tyr Asn Val Val Thr Gly Thr Thr Gln Lys Phe
            1460                1465                1470

Arg Ile Thr Leu Asp Thr Thr Gln Gly Ile Pro Asn Ser Ile Tyr Thr
        1475                1480                1485

Ser Pro Asp Gly Leu Ser Gln Phe Val Ala Tyr Asp Asp Arg Ile Asp
    1490                1495                1500

Leu Tyr Val Leu Gly Ser Pro Asn Asp Ile Ser Ser Thr Thr Glu Ile
1505                1510                1515                1520

Ile Pro Tyr Ser Leu Pro Arg Pro Asp Pro Pro Thr Gly Met Asp Phe
                1525                1530                1535

Thr Pro Asp Gly Arg Arg Met Phe Leu Ser Thr Glu Asn Gly Ile Asp
            1540                1545                1550

Gln Tyr Leu Leu Ser Glu Pro Phe Ala Val Thr Thr Ser Val Phe Leu
        1555                1560                1565

Arg Thr Ile Pro Ile Asp Gly Gly Ala Glu Gly Ile Arg Phe Val Asp
    1570                1575                1580

Asn Gly Arg Gly Leu Phe Val Pro Gly Ala Asp Gly Ile Ile Gln Arg
1585                1590                1595                1600

His Glu Leu Ile Tyr Pro Tyr Gly Ala Ser Thr Ser Leu Leu Glu Thr
                1605                1610                1615

Val Arg Asp Gly Val Thr Asp Gly Gly Pro Gly Glu Asn Pro Ala Ala
            1620                1625                1630

Gly Glu Ile Arg Leu Ala Gly Thr Phe Asn Ala Ser Asp Asn Val Gln
        1635                1640                1645

Ser Pro Ser Gly Ile Glu Phe Ser Gly Asp Gly Thr Gly Met Phe Val
    1650                1655                1660

Thr Gly Phe Gly Ala Ala Gly Val Asn Glu Phe Ser Leu Ser Ala Pro
1665                1670                1675                1680

Phe Asp Thr Thr Leu Pro Val His Val Glu Leu His Asp Ile Gly Gly
                1685                1690                1695

Gln Pro Ala Val Asp Leu Ala Phe Ala Glu Asp Gly Arg Thr Leu Leu
            1700                1705                1710
```

-continued

```
Leu Leu Ala Ala Asp Gly Thr Leu Asp Phe Tyr Ser Leu Ala Gly Asp
        1715                1720                1725

Ala Tyr Asp Ile Gly Glu Ala Ser Arg Thr Phe Gln Val Pro Phe Glu
    1730                1735                1740

Asp Ala Ala Gly Ala Val Pro Gly Ala Phe Tyr Gln Pro Pro Asp Gly
1745                1750                1755                1760

Ser Ser Ile Ile Ala Ala Phe Asp Gly Arg Ile Asp Gln Tyr Val Val
                1765                1770                1775

Ile Pro Phe Glu Phe Val Ser Tyr Pro Leu Thr Arg Pro Gly Thr Pro
            1780                1785                1790

Thr Gly Ile Asp Phe Ala Pro Asp Gly Arg Trp Met Phe Leu Ser Thr
        1795                1800                1805

Glu Asn Gly Ile Asp Gln Tyr Leu Leu Ser Ile Pro Phe Asp Val Arg
    1810                1815                1820

Ser Leu Thr Tyr Thr Gly Thr Ile Pro Val Asp Gly Val Glu Gly Met
1825                1830                1835                1840

Gln Phe Ala Asp Asn Gly Arg Ala Leu Phe Leu Ala Asp Ser Glu Gly
                1845                1850                1855

Leu Ile Tyr Asn Tyr Asp Leu Glu Asp Pro Tyr Ala Leu Asp Gly Asn
            1860                1865                1870

Thr Ile Ser Val Glu Phe Ser Phe Asp Gly Ser Val Met Tyr Val Leu
        1875                1880                1885

Glu Tyr Asp Thr Lys Arg Val Val Ser Tyr Glu Leu Glu Phe Pro Phe
    1890                1895                1900

Asp Val Ser Ser Arg Thr Arg Ala Asp Thr Leu Asp Ile Pro Gln Ile
1905                1910                1915                1920

Asp Ser Pro Arg His Val Ala Val Ser Met Pro Gly Asn His Leu Tyr
                1925                1930                1935

Ile Thr Asn Ser Val Phe Gly Glu Asp Asp Thr Ile His Ser Tyr Gly
            1940                1945                1950

Ile Ser Asn Asn Asp Ile Ser Ser Ala Ser Tyr Ile Gly Glu Glu Gly
        1955                1960                1965

Ile Pro Glu Pro Val Ile Asn Gly Ile Asp Phe Ser Asn Asn Gly Arg
    1970                1975                1980

Arg Met Phe Leu Ile Gly Gly Asn Gly Phe Asp Tyr Gln Val Ile His
1985                1990                1995                2000

Asp Tyr Met Leu Gly Thr Arg Tyr Asp Ile Ser Ser Arg Ser Leu Leu
                2005                2010                2015

Asp Thr Tyr Ala Ile Pro Gly Pro Val Val Phe Pro Ala Gly Leu Asp
            2020                2025                2030

Phe Ser Phe Asp Arg Leu Ser Met Phe Ile Ile Ser Thr Ala Gly Ser
        2035                2040                2045

Val Tyr Arg Tyr Gly Leu Asp Asp Pro Phe Ile Val Glu Thr Met Asp
    2050                2055                2060

Tyr Gln Glu Ser Phe Arg Leu Pro Val Pro Ser Ala Ala Asp Asn Ser
2065                2070                2075                2080

Ile Ser Asp Leu Ala Phe Gly Ser Ser Gly Leu Asn Ala Val Ile Ser
                2085                2090                2095

His Glu Gly Leu Asp Thr Leu Tyr Ser Phe Val Leu Asp Ile Pro Tyr
            2100                2105                2110

Gly Ala Glu Leu Asp Ile Asp Arg Leu Glu Leu Pro Leu Val Gly Val
        2115                2120                2125

Pro Thr Gly Phe Glu Phe Ser Asp Asn Gly Arg Gln Leu Tyr Ile Gly
```

-continued

```
    2130                2135                2140

Ala Phe Arg Asp Ser Gln Ser Ser Pro Gly Thr Leu Pro Ala Gly Leu
2145                2150                2155                2160

Gln Arg Tyr Glu Leu Gly Ile Pro Tyr Asp Leu Ala Ser Ala Val Phe
                2165                2170                2175

Ala Gln Ser Leu Gly Ile Phe Asp Phe Pro Pro Phe Asn Gly Met Arg
            2180                2185                2190

Ala Asn Gly Ser Leu Ala Gly Leu His Val Pro Pro Asp Gly Ser Ile
        2195                2200                2205

Leu Phe Arg Ala Gly Asn Ala Glu Arg Thr Val Ile Ser Tyr Asp Met
    2210                2215                2220

Asp Ser His Asp Leu Asp Thr Leu Ser Phe Arg Glu Ser Phe Lys Pro
2225                2230                2235                2240

Asp Val Gly Gln Ser Thr Pro Asn Ile Arg Asp Met Asp Ile Ser Pro
                2245                2250                2255

Asp Gly Met Phe Leu Tyr Leu Leu Gln Gly Asp Val Leu Asp Met Tyr
            2260                2265                2270

Asn Leu Thr Asp Ser Tyr Ser Leu Asp Ala Pro Ala Tyr Ala Gly Thr
        2275                2280                2285

Leu Asp Leu Glu Pro Glu Asp Val Ile Pro Arg Gly Ile Ser Phe Ser
    2290                2295                2300

Arg Asp Gly Thr Ser Leu Phe Met Thr Gly Glu Asp Val Asp His Ile
2305                2310                2315                2320

His Glu Tyr Ala Leu Asn Glu Pro Trp Asp Ile Arg Asn Ala Ile Leu
                2325                2330                2335

Ala Gly Ser Leu Ser Ile Ser Ala Val Asn Gly Ala Pro Arg Gly Leu
            2340                2345                2350

Asp Ile Ser Glu Asp Gly Thr Thr Ala His Thr Met Arg Gly Arg Asp
        2355                2360                2365

Phe Asp Thr Gly Pro Ala Ser Leu Val Asn His Ile Leu Pro Gly Gln
    2370                2375                2380

Tyr Ser Leu Leu Thr Asp Ala Pro Ala Phe Ala Tyr Pro Val Glu Glu
2385                2390                2395                2400

Glu Gly Ala Pro Gly Asp Leu Ala Phe Ser Asp Asp Gly Met Arg Met
                2405                2410                2415

Phe Val Ala Gly Val Asn Asn His Leu Arg Gln Tyr Asn Leu Leu Ser
            2420                2425                2430

Pro Tyr Asp Thr Glu Asn Ala Glu His Phe Ile Ser Thr Asp Leu Leu
        2435                2440                2445

Thr Ala Asp Arg Gly Pro Thr Gly Leu Val Phe Ser Asp Glu Asn Asp
    2450                2455                2460

Phe Phe Ser Thr Gly Ala Arg Ala Gln Phe Val Arg Gln Phe Thr Thr
2465                2470                2475                2480

Asn Arg Pro Tyr Asp Ala Ser Thr Ile Thr Leu Ser Asp Asn Gly Leu
                2485                2490                2495

Tyr Lys Val Ser Val Asp Gly Leu Pro Ser Gly Ile Arg Phe Thr Pro
            2500                2505                2510

Asp Gly Met Lys Met Phe Ile Ser Gly Gln Glu Thr Ala Met Ile Tyr
        2515                2520                2525

Gln Tyr Ser Leu Pro Ser Pro Tyr Asp Thr Ser Gly Ala Val Arg Asp
    2530                2535                2540

Arg Val Glu Ile Val Ala Gly Leu Phe Arg Asn Ala Gly Leu Ser Val
2545                2550                2555                2560
```

-continued

```
Gly Leu Asn Glu Pro Ser Pro Ser Gly Phe Asp Phe Ser Glu Asp Gly
                2565                2570                2575

Met Glu Leu Tyr Val Thr Gly Ser Gly Leu Val His Arg Tyr Phe Leu
            2580                2585                2590

Pro Ser Pro Tyr Gly Leu Glu Asp Ala Ala Tyr Gly Gly Ser Phe His
        2595                2600                2605

Thr Phe Arg Glu Ser Thr Pro Leu Gly Val Val Val Arg Gly Asp Ala
    2610                2615                2620

Met Phe Val Ala Gly Asp Ser Thr Asp Ser Ile Leu Lys Tyr Ser Leu
2625                2630                2635                2640

Asn Ala Gln Pro Val Gly Asn Ile Thr His Ala Asp Thr Arg Ala Gly
                2645                2650                2655

Ile Ala Asp Arg Ala Glu Ile Val Phe Gly Ala Met Ala Asp Thr Arg
            2660                2665                2670

Ala Glu Ile Leu Asp Gly Ala Asp Val Val His Lys Ser Val Lys Ile
        2675                2680                2685

Asp Val Phe Pro Ile Ser Glu Gly Ile Thr Val Gly Arg Ala Leu Tyr
    2690                2695                2700

Pro Glu Asp Ala Ala Ile Leu Asp Asp Gly Ala Asn Ala Thr His Asn
2705                2710                2715                2720

Arg Val Val Ile Ile Val His Asp Ile Thr Glu Gly Asp Ala Pro Ser
                2725                2730                2735

Ile His Asp Glu Pro Ile Ala Val Gly Ile Tyr Ala Leu Gly Pro Met
            2740                2745                2750

Asp Thr Ile Ala Val Val Asp Leu His Arg Leu Ala Val Ser Ala Ser
        2755                2760                2765

Leu Ser Gly Gly Asp Ser Pro Ser Ala Ser Asp Ala Ser Gly Val Val
    2770                2775                2780

Ala Glu Ser Arg Arg Asn Ala Val Asp Arg Pro Gly Val Glu Glu Arg
2785                2790                2795                2800

Ile Gly His Gly Val Ser Leu Glu Ala Ala Asp Arg Pro Ala Val Asp
                2805                2810                2815

Asn Met Met Asp Thr Asp Ser Ala Gly Val Tyr Asp Arg Ser Pro Asp
            2820                2825                2830

Asp Gly Pro Ala Val Ser Asp Arg Ser Ala Leu Gly Leu Ala Arg Met
        2835                2840                2845

Ala Ala Asp Arg Pro Ala Val Asp Asp Met Met Asp Thr Asp Ser Ala
    2850                2855                2860

Gly Val Tyr Asp Arg Ser Pro Asp Asp Gly Pro Ala Ile Ser Asp Arg
2865                2870                2875                2880

Ser Ala Leu Gly Leu Ala Arg Met Ala Ala Asp Arg Pro Ala Val Asp
                2885                2890                2895

Asp Met Met Asp Thr Gly Ser Ala Gly Val Tyr Asp Arg Ser Pro Asp
            2900                2905                2910

Asp Gly Pro Ala Ile Ser Asp Arg Ser Ala Leu Gly Leu Ala Arg Met
        2915                2920                2925

Ala Ala Asp Arg Pro Ala Val Asp Asp Met Met Asp Thr Gly Ser Glu
    2930                2935                2940

Ser Thr Ser Arg Leu Gly Pro Val Asp Arg Pro Glu Ile Val Glu Arg
2945                2950                2955                2960

His Ser Leu Ala Ala Ser Val Tyr Leu Ser Gly Gly Asp Ser Pro Ser
                2965                2970                2975
```

-continued

```
Val Ala Asp Gly His Asp Val Glu Ser Glu Gly Arg Arg Asp Gly Gly
            2980                2985                2990

Asp Arg Pro Gly Ile Asp Glu Arg Ile Val Ile Lys Ile Ser Tyr Ser
        2995                3000                3005

Arg Gly Ala Ala Asp Ala Pro Arg Val Glu Asp Ala Met Glu Thr Ser
    3010                3015                3020

Gly Val Thr Ala Tyr Ser Arg Gly Ala Ala Asp Ala Pro Arg Val Glu
3025                3030                3035                3040

Asp Ala Met Glu Thr Ser Gly Val Thr Val Pro Arg Arg Ser Thr Met
                3045                3050                3055

Asp Ala Pro Thr Val Ala Asp Asp His Ser Leu Ala Arg Thr Ala Ser
            3060                3065                3070

Ile Ser Glu Gly Asp Ser Pro Thr Phe Ala Glu Ala Arg Arg Ala Asp
        3075                3080                3085

Thr Val Gly Asp Ile Asp Glu Val Asp Ala Pro Thr Val Ala Asp Asp
    3090                3095                3100

His Ser Leu Ala Arg Ala Ala Ser Ile Ser Glu Gly Asp Ser Pro Thr
3105                3110                3115                3120

Phe Ala Glu Val Arg Arg Ala Asp Thr Val Gly Asp Ile Asp Glu Val
                3125                3130                3135

Asp Ala Pro Ala Val Ala Glu Arg Leu Leu Ala Val Leu Gly Leu Gln
            3140                3145                3150

Ala Pro Asp Ser Pro Gly Val Trp Asp Thr Val Gly Ile Asp His Ser
        3155                3160                3165

Glu Ile Ser Gly Asp Pro Val Pro Glu Pro Arg Val Val Pro Arg Gly
    3170                3175                3180

Gly Gly Gly Gly Gly Gly Gly Ser Ser Asn Arg Gly Leu Glu Pro His
3185                3190                3195                3200

Gly Gly Gly Tyr Glu Ile Asp Phe Glu Phe Arg Ile Asp Gly Arg Leu
                3205                3210                3215

Val Leu Phe Asn Gly Thr Asp Val Leu Ala Glu Ser Gly Lys Asp Leu
            3220                3225                3230

Leu Ile Arg Pro Val Phe Arg Pro Glu Gly Ser Phe Asn Ile Phe Asp
        3235                3240                3245

Met Glu Val Leu Phe Thr Ala Pro Gly Gly Glu Ile Ser Thr Ala Tyr
    3250                3255                3260

Tyr Asn Arg Ala Gly Ile Leu Met Gly Ile Asp Cys Gly Glu Leu Ile
3265                3270                3275                3280

Met Thr Asp Thr Thr Tyr Ser Cys Asp Met Leu Asp Ile Phe Gly Asp
                3285                3290                3295

Glu Ile Tyr His Val Glu Arg Leu Asp Ala Phe Asn Gly Met Val Ile
            3300                3305                3310

Ser Leu Asp Gly Pro Leu Asp Gly Thr Val Ser Val Ser Leu Arg Asp
        3315                3320                3325

Asn His Gly Ile Pro Leu Ala Gln His Arg Leu His Lys Tyr Glu Ile
    3330                3335                3340

Leu Ile Leu Asp Ala Ala Glu Asn Arg Pro Leu Ser Val Ser Thr Asp
3345                3350                3355                3360

Pro Lys Pro Val Glu Asp Pro Ser Pro Val Gln His Ile Glu Ser Leu
                3365                3370                3375

Gln Met Asp Pro Glu Pro Val Glu Ser Glu Pro Leu Pro Met Asp Ser
            3380                3385                3390

Glu Pro Val Glu Asp Leu Glu Pro Val Gln His Leu Glu Ser Leu Pro
```

-continued

```
        3395                3400                3405

Met Asp Pro Glu Pro Val Glu Asp Leu Glu Pro Val Gln His Leu Glu
    3410                3415                3420

Pro Val Gln Gly Ser Pro Pro Val Gln Gly Gly Pro Glu Ser Val Glu
3425                3430                3435                3440

Ser Gly Ile Ala Tyr Thr Leu Trp Gln Phe Leu Ser Gly Leu Leu Asp
                3445                3450                3455

Ala Leu Gly Leu Ala Asp Pro Asp Val Gly Ser Val Gln Lys Thr Ser
            3460                3465                3470


<210> SEQ ID NO 5
<211> LENGTH: 819
<212> TYPE: DNA
<213> ORGANISM: Cenarchaeum symbiosum
<220> FEATURE:
<221> NAME/KEY: CDS
<222> LOCATION: (1)...(810)

<400> SEQUENCE: 5

atg cat ggg atc gag ggc ggc cgg gga gat atg tcg gag aat ttt gtg       48
Met His Gly Ile Glu Gly Gly Arg Gly Asp Met Ser Glu Asn Phe Val
 1               5                  10                  15

gcg ttt tgc gtg gcg tgc gcc agg gga gtc aca aag gac gag atg aag       96
Ala Phe Cys Val Ala Cys Ala Arg Gly Val Thr Lys Asp Glu Met Lys
            20                  25                  30

tat gta gac ggg agg gtc ttc cac aaa gag tgc cat gca agg cac ggc      144
Tyr Val Asp Gly Arg Val Phe His Lys Glu Cys His Ala Arg His Gly
        35                  40                  45

ggg cag atc cgc ttc ccc aac cca gag gtc gag cag cgc gtg gcc gag      192
Gly Gln Ile Arg Phe Pro Asn Pro Glu Val Glu Gln Arg Val Ala Glu
     50                  55                  60

ctg aag gtg gac ctg ata cag atg aga aac cag ctg gcc gag atg aac      240
Leu Lys Val Asp Leu Ile Gln Met Arg Asn Gln Leu Ala Glu Met Asn
 65                  70                  75                  80

agg gcg tcg ggg gac gga ggg gtg cat tcc agc gcc acc tct gcg gcc      288
Arg Ala Ser Gly Asp Gly Gly Val His Ser Ser Ala Thr Ser Ala Ala
                 85                  90                  95

gag gcc gag cag cac agg gcc gag cta aag gta cag ctg gtg cag atg      336
Glu Ala Glu Gln His Arg Ala Glu Leu Lys Val Gln Leu Val Gln Met
            100                 105                 110

aga aac cag ctg gcc gag atg aac agg aag gcc ccc gga aag ccg gca      384
Arg Asn Gln Leu Ala Glu Met Asn Arg Lys Ala Pro Gly Lys Pro Ala
        115                 120                 125

cgg aaa aag gcc gca ggc aag act gca cgg aga aag agc ggc aag aag      432
Arg Lys Lys Ala Ala Gly Lys Thr Ala Arg Arg Lys Ser Gly Lys Lys
    130                 135                 140

acg gtg cgc agg aag acc ggc aag agg act gcc ggt aag aag gcc ggg      480
Thr Val Arg Arg Lys Thr Gly Lys Arg Thr Ala Gly Lys Lys Ala Gly
145                 150                 155                 160

gcg cgg agg aag act acg gtc aag agg acg gcg cgg agg aag acc acg      528
Ala Arg Arg Lys Thr Thr Val Lys Arg Thr Ala Arg Arg Lys Thr Thr
                165                 170                 175

gca aag aag gca gcc ggc aga aag gcc ggg gcg cgc aga aag gcc aca      576
Ala Lys Lys Ala Ala Gly Arg Lys Ala Gly Ala Arg Arg Lys Ala Thr
            180                 185                 190

gtc aag agg acg gtg cac aaa aag att gga gtg cgg agg aag act acg      624
Val Lys Arg Thr Val His Lys Lys Ile Gly Val Arg Arg Lys Thr Thr
        195                 200                 205

gca agg agg acg gcc ggt aag agt acg gtg cgc agg aag agc aca gtc      672
Ala Arg Arg Thr Ala Gly Lys Ser Thr Val Arg Arg Lys Ser Thr Val
```

-continued

```
    210                 215                 220

aag agg acg gtg cac agg aag acc ggc aag aag gca gta gta cgc agg      720
Lys Arg Thr Val His Arg Lys Thr Gly Lys Lys Ala Val Val Arg Arg
225                 230                 235                 240

aag agc aca gtc aag agg acg gca cgg agg ccg gcc ggc aga aag acc      768
Lys Ser Thr Val Lys Arg Thr Ala Arg Arg Pro Ala Gly Arg Lys Thr
                245                 250                 255

ccc gga agg gcc gcg cgc agg gcc ggc gca aag agg cgc tag              810
Pro Gly Arg Ala Ala Arg Arg Ala Gly Ala Lys Arg Arg
            260                 265

cctgctgat                                                            819


<210> SEQ ID NO 6
<211> LENGTH: 269
<212> TYPE: PRT
<213> ORGANISM: Cenarchaeum symbiosum

<400> SEQUENCE: 6

Met His Gly Ile Glu Gly Gly Arg Gly Asp Met Ser Glu Asn Phe Val
 1               5                  10                  15

Ala Phe Cys Val Ala Cys Ala Arg Gly Val Thr Lys Asp Glu Met Lys
            20                  25                  30

Tyr Val Asp Gly Arg Val Phe His Lys Glu Cys His Ala Arg His Gly
        35                  40                  45

Gly Gln Ile Arg Phe Pro Asn Pro Glu Val Glu Gln Arg Val Ala Glu
    50                  55                  60

Leu Lys Val Asp Leu Ile Gln Met Arg Asn Gln Leu Ala Glu Met Asn
65                  70                  75                  80

Arg Ala Ser Gly Asp Gly Gly Val His Ser Ser Ala Thr Ser Ala Ala
                85                  90                  95

Glu Ala Glu Gln His Arg Ala Glu Leu Lys Val Gln Leu Val Gln Met
            100                 105                 110

Arg Asn Gln Leu Ala Glu Met Asn Arg Lys Ala Pro Gly Lys Pro Ala
        115                 120                 125

Arg Lys Lys Ala Ala Gly Lys Thr Ala Arg Arg Lys Ser Gly Lys Lys
    130                 135                 140

Thr Val Arg Arg Lys Thr Gly Lys Arg Thr Ala Gly Lys Lys Ala Gly
145                 150                 155                 160

Ala Arg Arg Lys Thr Thr Val Lys Arg Thr Ala Arg Arg Lys Thr Thr
                165                 170                 175

Ala Lys Lys Ala Ala Gly Arg Lys Ala Gly Ala Arg Arg Lys Ala Thr
            180                 185                 190

Val Lys Arg Thr Val His Lys Lys Ile Gly Val Arg Arg Lys Thr Thr
        195                 200                 205

Ala Arg Arg Thr Ala Gly Lys Ser Thr Val Arg Arg Lys Ser Thr Val
    210                 215                 220

Lys Arg Thr Val His Arg Lys Thr Gly Lys Lys Ala Val Val Arg Arg
225                 230                 235                 240

Lys Ser Thr Val Lys Arg Thr Ala Arg Arg Pro Ala Gly Arg Lys Thr
                245                 250                 255

Pro Gly Arg Ala Ala Arg Arg Ala Gly Ala Lys Arg Arg
            260                 265


<210> SEQ ID NO 7
<211> LENGTH: 1569
<212> TYPE: DNA
```

-continued

<213> ORGANISM: Cenarchaeum symbiosum
<220> FEATURE:
<221> NAME/KEY: CDS
<222> LOCATION: (1)...(1569)

<400> SEQUENCE: 7 atg cag tcg ctt gga cgg cta gac gag gcg tgc gcg gag ata tcg cgc 48
Met Gln Ser Leu Gly Arg Leu Asp Glu Ala Cys Ala Glu Ile Ser Arg
1 5 10 15 agc ctg ctt gaa tac gag tcc ccc acc gcc ggt gat gtc cgg acg gag 96
Ser Leu Leu Glu Tyr Glu Ser Pro Thr Ala Gly Asp Val Arg Thr Glu
20 25 30 atc aga agg gca tgc aca aag tac tcg ctc cgg agg atc cca aag aac 144
Ile Arg Arg Ala Cys Thr Lys Tyr Ser Leu Arg Arg Ile Pro Lys Asn
35 40 45 cgc gag ata ctg gcc acc gcc agg ggt cag gac ttt gac agg ctg cgc 192
Arg Glu Ile Leu Ala Thr Ala Arg Gly Gln Asp Phe Asp Arg Leu Arg
50 55 60 ccc ctg ctg ctc aaa aag ccc gta aag acc gca tcc ggg gtg gcc gtg 240
Pro Leu Leu Leu Lys Lys Pro Val Lys Thr Ala Ser Gly Val Ala Val
65 70 75 80 ata gca gtc atg ccc atg ccg tac gcg tgc ccc cac ggc aga tgc aca 288
Ile Ala Val Met Pro Met Pro Tyr Ala Cys Pro His Gly Arg Cys Thr
85 90 95 tac tgc ccc ggc ggg gag gcg tcg aac aca ccc aac agc tat acc ggc 336
Tyr Cys Pro Gly Gly Glu Ala Ser Asn Thr Pro Asn Ser Tyr Thr Gly
100 105 110 ggc gag ccc ata gcg gcg ggc gcc atg aac agc ggg tac gac ccg gaa 384
Gly Glu Pro Ile Ala Ala Gly Ala Met Asn Ser Gly Tyr Asp Pro Glu
115 120 125 gag cag gtc cgc gcg ggt ctg gcc cgg ctg cgc gcg cac ggc cac gat 432
Glu Gln Val Arg Ala Gly Leu Ala Arg Leu Arg Ala His Gly His Asp
130 135 140 gta gcc aag ctg gag ata gta ata gtg ggc ggc aca ttc ctg ttc atg 480
Val Ala Lys Leu Glu Ile Val Ile Val Gly Gly Thr Phe Leu Phe Met
145 150 155 160 ccg cag gag tac cag gag tgg ttc gtc aag tcc tgt tat gac gcg ctc 528
Pro Gln Glu Tyr Gln Glu Trp Phe Val Lys Ser Cys Tyr Asp Ala Leu
165 170 175 aac ggg tcc gct tcc gcg ggg atg gag gag gcc aag cac cga aat gaa 576
Asn Gly Ser Ala Ser Ala Gly Met Glu Glu Ala Lys His Arg Asn Glu
180 185 190 act gcc gtg cac aga aac gtg ggc ctc acc ata gag acc aag ccg gac 624
Thr Ala Val His Arg Asn Val Gly Leu Thr Ile Glu Thr Lys Pro Asp
195 200 205 tat tgc agg aca gag cat gtg gac gcg atg ctc ggc ttt ggg gcc acg 672
Tyr Cys Arg Thr Glu His Val Asp Ala Met Leu Gly Phe Gly Ala Thr
210 215 220 cgc gtg gag ata ggc gtg cag agc ctc cgg gag gag gtc tac ttg agg 720
Arg Val Glu Ile Gly Val Gln Ser Leu Arg Glu Glu Val Tyr Leu Arg
225 230 235 240 gtc aac cgg ggg cac ggc tac cag gat gtg aca gag tcg ttt gcc gcc 768
Val Asn Arg Gly His Gly Tyr Gln Asp Val Thr Glu Ser Phe Ala Ala
245 250 255 gcc agg gat gca ggc tac aag gtg gct gcc cac atg atg cca gga ctc 816
Ala Arg Asp Ala Gly Tyr Lys Val Ala Ala His Met Met Pro Gly Leu
260 265 270 ccg ggg gcc acc ccg gaa ggc gac atc gag gat ctg cgc atg ctg ttt 864
Pro Gly Ala Thr Pro Glu Gly Asp Ile Glu Asp Leu Arg Met Leu Phe
275 280 285

-continued

```
gag gat ccc gcg ctc agg ccg gac atg ctc aag gtg tac ccc gcg cta       912
Glu Asp Pro Ala Leu Arg Pro Asp Met Leu Lys Val Tyr Pro Ala Leu
    290                 295                 300

gta gta agg ggc acc ccc atg tat gag gag tat tcg agg ggc gag tat       960
Val Val Arg Gly Thr Pro Met Tyr Glu Glu Tyr Ser Arg Gly Glu Tyr
305                 310                 315                 320

tcc ccg tat acg gaa gag gag gtc atc cgg gtg ctc tcc gag gcc aag      1008
Ser Pro Tyr Thr Glu Glu Glu Val Ile Arg Val Leu Ser Glu Ala Lys
                325                 330                 335

gcg cgc gtg ccc agg tgg gcg agg ata atg cgc gtg cag cgc gag ata      1056
Ala Arg Val Pro Arg Trp Ala Arg Ile Met Arg Val Gln Arg Glu Ile
            340                 345                 350

cac ccc gac gag ata gtg gcc ggg ccg agg agc ggc aac ctc cgc cag      1104
His Pro Asp Glu Ile Val Ala Gly Pro Arg Ser Gly Asn Leu Arg Gln
        355                 360                 365

ctg gtg cac aag agg ctc caa gag cag ggc cgc cga tgc cgc tgc ata      1152
Leu Val His Lys Arg Leu Gln Glu Gln Gly Arg Arg Cys Arg Cys Ile
    370                 375                 380

cgg tgc agg gag gcg ggg ctc gcg ggg agg acc gtg ccg cag aag ctc      1200
Arg Cys Arg Glu Ala Gly Leu Ala Gly Arg Thr Val Pro Gln Lys Leu
385                 390                 395                 400

cgt att gac agg gcg gac tat tcg gcc tcg ggg ggg aga gaa tcg ttt      1248
Arg Ile Asp Arg Ala Asp Tyr Ser Ala Ser Gly Gly Arg Glu Ser Phe
                405                 410                 415

atc tcg ctt gta gac ggg gat gat gcc atc tat ggc ttt gtg cgc ctg      1296
Ile Ser Leu Val Asp Gly Asp Asp Ala Ile Tyr Gly Phe Val Arg Leu
            420                 425                 430

cgc aag ccc tcc gga gca gca cac agg ccg gag gtc aca ccg gaa tcc      1344
Arg Lys Pro Ser Gly Ala Ala His Arg Pro Glu Val Thr Pro Glu Ser
        435                 440                 445

tgc ata ata cgc gag ctg cac gta tac ggc agg tcg ctt ggc ctc ggc      1392
Cys Ile Ile Arg Glu Leu His Val Tyr Gly Arg Ser Leu Gly Leu Gly
    450                 455                 460

gag agg ggc ggc ata cag cac tcg ggt cta ggc aga agg ctc gtc tca      1440
Glu Arg Gly Gly Ile Gln His Ser Gly Leu Gly Arg Arg Leu Val Ser
465                 470                 475                 480

gaa gca gag tct gcc gcc cgt gag ctt ggc gcg ggc agg ctc ctt gtg      1488
Glu Ala Glu Ser Ala Ala Arg Glu Leu Gly Ala Gly Arg Leu Leu Val
                485                 490                 495

ata agc gcc gtc ggg aca agg ggt tac tat cgc agg ctc gga tat tca      1536
Ile Ser Ala Val Gly Thr Arg Gly Tyr Tyr Arg Arg Leu Gly Tyr Ser
            500                 505                 510

cgc acg ggc ccc tac atg ggg aag gtg ctc tga                          1569
Arg Thr Gly Pro Tyr Met Gly Lys Val Leu
        515                 520


<210> SEQ ID NO 8
<211> LENGTH: 522
<212> TYPE: PRT
<213> ORGANISM: Cenarchaeum symbiosum

<400> SEQUENCE: 8

Met Gln Ser Leu Gly Arg Leu Asp Glu Ala Cys Ala Glu Ile Ser Arg
 1               5                  10                  15

Ser Leu Leu Glu Tyr Glu Ser Pro Thr Ala Gly Asp Val Arg Thr Glu
            20                  25                  30

Ile Arg Arg Ala Cys Thr Lys Tyr Ser Leu Arg Arg Ile Pro Lys Asn
        35                  40                  45

Arg Glu Ile Leu Ala Thr Ala Arg Gly Gln Asp Phe Asp Arg Leu Arg
    50                  55                  60
```

-continued

```
Pro Leu Leu Leu Lys Lys Pro Val Lys Thr Ala Ser Gly Val Ala Val
65                  70                  75                  80

Ile Ala Val Met Pro Met Pro Tyr Ala Cys Pro His Gly Arg Cys Thr
                85                  90                  95

Tyr Cys Pro Gly Gly Glu Ala Ser Asn Thr Pro Asn Ser Tyr Thr Gly
            100                 105                 110

Gly Glu Pro Ile Ala Ala Gly Ala Met Asn Ser Gly Tyr Asp Pro Glu
        115                 120                 125

Glu Gln Val Arg Ala Gly Leu Ala Arg Leu Arg Ala His Gly His Asp
    130                 135                 140

Val Ala Lys Leu Glu Ile Val Ile Val Gly Gly Thr Phe Leu Phe Met
145                 150                 155                 160

Pro Gln Glu Tyr Gln Glu Trp Phe Val Lys Ser Cys Tyr Asp Ala Leu
                165                 170                 175

Asn Gly Ser Ala Ser Ala Gly Met Glu Glu Ala Lys His Arg Asn Glu
            180                 185                 190

Thr Ala Val His Arg Asn Val Gly Leu Thr Ile Glu Thr Lys Pro Asp
        195                 200                 205

Tyr Cys Arg Thr Glu His Val Asp Ala Met Leu Gly Phe Gly Ala Thr
    210                 215                 220

Arg Val Glu Ile Gly Val Gln Ser Leu Arg Glu Glu Val Tyr Leu Arg
225                 230                 235                 240

Val Asn Arg Gly His Gly Tyr Gln Asp Val Thr Glu Ser Phe Ala Ala
                245                 250                 255

Ala Arg Asp Ala Gly Tyr Lys Val Ala Ala His Met Met Pro Gly Leu
            260                 265                 270

Pro Gly Ala Thr Pro Glu Gly Asp Ile Glu Asp Leu Arg Met Leu Phe
        275                 280                 285

Glu Asp Pro Ala Leu Arg Pro Asp Met Leu Lys Val Tyr Pro Ala Leu
    290                 295                 300

Val Val Arg Gly Thr Pro Met Tyr Glu Glu Tyr Ser Arg Gly Glu Tyr
305                 310                 315                 320

Ser Pro Tyr Thr Glu Glu Glu Val Ile Arg Val Leu Ser Glu Ala Lys
                325                 330                 335

Ala Arg Val Pro Arg Trp Ala Arg Ile Met Arg Val Gln Arg Glu Ile
            340                 345                 350

His Pro Asp Glu Ile Val Ala Gly Pro Arg Ser Gly Asn Leu Arg Gln
        355                 360                 365

Leu Val His Lys Arg Leu Gln Glu Gln Gly Arg Arg Cys Arg Cys Ile
    370                 375                 380

Arg Cys Arg Glu Ala Gly Leu Ala Gly Arg Thr Val Pro Gln Lys Leu
385                 390                 395                 400

Arg Ile Asp Arg Ala Asp Tyr Ser Ala Ser Gly Gly Arg Glu Ser Phe
                405                 410                 415

Ile Ser Leu Val Asp Gly Asp Asp Ala Ile Tyr Gly Phe Val Arg Leu
            420                 425                 430

Arg Lys Pro Ser Gly Ala Ala His Arg Pro Glu Val Thr Pro Glu Ser
        435                 440                 445

Cys Ile Ile Arg Glu Leu His Val Tyr Gly Arg Ser Leu Gly Leu Gly
    450                 455                 460

Glu Arg Gly Gly Ile Gln His Ser Gly Leu Gly Arg Arg Leu Val Ser
465                 470                 475                 480
```

-continued

```
Glu Ala Glu Ser Ala Ala Arg Glu Leu Gly Ala Gly Arg Leu Leu Val
            485                 490                 495

Ile Ser Ala Val Gly Thr Arg Gly Tyr Tyr Arg Arg Leu Gly Tyr Ser
            500                 505                 510

Arg Thr Gly Pro Tyr Met Gly Lys Val Leu
        515                 520


<210> SEQ ID NO 9
<211> LENGTH: 1575
<212> TYPE: DNA
<213> ORGANISM: Cenarchaeum symbiosum
<220> FEATURE:
<221> NAME/KEY: CDS
<222> LOCATION: (1)...(1575)

<400> SEQUENCE: 9

atg gag acg ata ggc cgc ggc acc tgg ata gac aag ctg gcg cat gaa        48
Met Glu Thr Ile Gly Arg Gly Thr Trp Ile Asp Lys Leu Ala His Glu
 1               5                  10                  15

ctg gta gag cgc gaa gag gcc ctc ggc cgg gat aca gag atg ata aac        96
Leu Val Glu Arg Glu Glu Ala Leu Gly Arg Asp Thr Glu Met Ile Asn
            20                  25                  30

gtc gag agc ggc ctt ggc gcg tcc ggg ata ccc cac atg ggg agc ctc       144
Val Glu Ser Gly Leu Gly Ala Ser Gly Ile Pro His Met Gly Ser Leu
        35                  40                  45

ggg gat gca gtc agg gcg tac ggc gtg ggg ctc gcc gtc ggc gac atg       192
Gly Asp Ala Val Arg Ala Tyr Gly Val Gly Leu Ala Val Gly Asp Met
    50                  55                  60

ggg cac agc ttc cgg ctc ata gcg tac ttt gac gac ctc gac ggg ctc       240
Gly His Ser Phe Arg Leu Ile Ala Tyr Phe Asp Asp Leu Asp Gly Leu
 65                  70                  75                  80

cgc aag gtc ccc gag ggc atg cca tcc tcg cta gaa gag cac ata gcc       288
Arg Lys Val Pro Glu Gly Met Pro Ser Ser Leu Glu Glu His Ile Ala
                85                  90                  95

cgt ccc gtc tcg gcg ata ccc gac ccc tac ggg tgc cac gat tcc tac       336
Arg Pro Val Ser Ala Ile Pro Asp Pro Tyr Gly Cys His Asp Ser Tyr
            100                 105                 110

ggc atg cac atg agc ggc ctg ctg cta gag ggg ctc gac gca ctg ggc       384
Gly Met His Met Ser Gly Leu Leu Leu Glu Gly Leu Asp Ala Leu Gly
        115                 120                 125

ata gag tat gac ttt agg cgg gca agg gac acg tac cgc gac ggc ctg       432
Ile Glu Tyr Asp Phe Arg Arg Ala Arg Asp Thr Tyr Arg Asp Gly Leu
    130                 135                 140

ctc gca gaa cag atc cac agg ata cta tcg aac agc tcg gta ata ggg       480
Leu Ala Glu Gln Ile His Arg Ile Leu Ser Asn Ser Ser Val Ile Gly
145                 150                 155                 160

gag aag ata gcc gag atg gtg ggc cag gaa aag ttt cgc agc agc ctg       528
Glu Lys Ile Ala Glu Met Val Gly Gln Glu Lys Phe Arg Ser Ser Leu
                165                 170                 175

ccg tac ttt gca gtc tgt gaa cag tgc ggg aag atg tac acg gcc gag       576
Pro Tyr Phe Ala Val Cys Glu Gln Cys Gly Lys Met Tyr Thr Ala Glu
            180                 185                 190

tcc gtt gaa tac ctg gca gac agc cgc aag gtg cgg tac agg tgc ggc       624
Ser Val Glu Tyr Leu Ala Asp Ser Arg Lys Val Arg Tyr Arg Cys Gly
        195                 200                 205

gac gcc gag gta ggc gga aga aag atc gcc ggc tgc ggg cac gag ggc       672
Asp Ala Glu Val Gly Gly Arg Lys Ile Ala Gly Cys Gly His Glu Gly
    210                 215                 220

gag gcg gac acg ggc gga gcc ggc ggc aag ctc gcc tgg aag gtg gag       720
Glu Ala Asp Thr Gly Gly Ala Gly Gly Lys Leu Ala Trp Lys Val Glu
225                 230                 235                 240
```

-continued

```
ttt gcc gca agg tgg cag gcg ttt gat gta cgc ttt gag gca tac ggc      768
Phe Ala Ala Arg Trp Gln Ala Phe Asp Val Arg Phe Glu Ala Tyr Gly
                245                 250                 255

aag gac atc atg gac tct gta agg ata aac gac tgg gtc tcc gac gag      816
Lys Asp Ile Met Asp Ser Val Arg Ile Asn Asp Trp Val Ser Asp Glu
            260                 265                 270

ata cta tcc agc ccg cac ccc cac cat aca agg tac gag atg ttc ctc      864
Ile Leu Ser Ser Pro His Pro His His Thr Arg Tyr Glu Met Phe Leu
        275                 280                 285

gac aag ggc ggc aaa aag ata tca aag tcg tca gga aac gtg gtc acg      912
Asp Lys Gly Gly Lys Lys Ile Ser Lys Ser Ser Gly Asn Val Val Thr
    290                 295                 300

ccg cag aaa tgg ctc agg tac ggc acc ccc cag tcg ata ctg ctc ctc      960
Pro Gln Lys Trp Leu Arg Tyr Gly Thr Pro Gln Ser Ile Leu Leu Leu
305                 310                 315                 320

atg tac aag cgc atc acg ggg gcg cgg gag ctt ggc ctc gag gat gtg     1008
Met Tyr Lys Arg Ile Thr Gly Ala Arg Glu Leu Gly Leu Glu Asp Val
                325                 330                 335

cca tcc ctg atg gac gag tac ggc gat ctt cag cgc gag tac ttt gcg     1056
Pro Ser Leu Met Asp Glu Tyr Gly Asp Leu Gln Arg Glu Tyr Phe Ala
            340                 345                 350

gga ggg ggc agg ggc ggg aaa gcc cgc gag gcc aag aac agg ggg cta     1104
Gly Gly Gly Arg Gly Gly Lys Ala Arg Glu Ala Lys Asn Arg Gly Leu
        355                 360                 365

ttc gag tat acg aac ctg ctg gag gca cag gag ggg ccg cgg ccg cat     1152
Phe Glu Tyr Thr Asn Leu Leu Glu Ala Gln Glu Gly Pro Arg Pro His
    370                 375                 380

gcg ggc tac cgg ctg cta gtc gag ctc tcc agg ctg ttc agg gag aat     1200
Ala Gly Tyr Arg Leu Leu Val Glu Leu Ser Arg Leu Phe Arg Glu Asn
385                 390                 395                 400

agg acc gag cgc gtc aca aaa aag ctc gtc gag tac ggg gta att gac     1248
Arg Thr Glu Arg Val Thr Lys Lys Leu Val Glu Tyr Gly Val Ile Asp
                405                 410                 415

ggg ccc tcg ccc ggg atc gag cgg ctc ata gca ctg gcc gga aac tat     1296
Gly Pro Ser Pro Gly Ile Glu Arg Leu Ile Ala Leu Ala Gly Asn Tyr
            420                 425                 430

gca gac gac atg tat tct gcc gag aga aca gag gtg gag ctt gac ggg     1344
Ala Asp Asp Met Tyr Ser Ala Glu Arg Thr Glu Val Glu Leu Asp Gly
        435                 440                 445

gcc aca agg ggg gcc ctc tcg gag ctg gca gaa atg ctc ggt tcc gcc     1392
Ala Thr Arg Gly Ala Leu Ser Glu Leu Ala Glu Met Leu Gly Ser Ala
    450                 455                 460

ccg gag ggc gga ctg cag gat gtc ata tac ggc gtg gcc aag tcc cac     1440
Pro Glu Gly Gly Leu Gln Asp Val Ile Tyr Gly Val Ala Lys Ser His
465                 470                 475                 480

ggg gtg ccc ccg cgc gac ttt ttc aag gcg ctg tac agg ata ata ctg     1488
Gly Val Pro Pro Arg Asp Phe Phe Lys Ala Leu Tyr Arg Ile Ile Leu
                485                 490                 495

gat gca tcc agc ggg ccg agg ata ggc ccc ttc ata gag gac ata ggc     1536
Asp Ala Ser Ser Gly Pro Arg Ile Gly Pro Phe Ile Glu Asp Ile Gly
            500                 505                 510

agg gag aag gtg gca ggt atg ata cgg ggg cgc ctc tga                 1575
Arg Glu Lys Val Ala Gly Met Ile Arg Gly Arg Leu
        515                 520
```

<210> SEQ ID NO 10
<211> LENGTH: 524
<212> TYPE: PRT
<213> ORGANISM: Cenarchaeum symbiosum -continued

<400> SEQUENCE: 10

```
Met Glu Thr Ile Gly Arg Gly Thr Trp Ile Asp Lys Leu Ala His Glu
 1               5                  10                  15

Leu Val Glu Arg Glu Glu Ala Leu Gly Arg Asp Thr Glu Met Ile Asn
            20                  25                  30

Val Glu Ser Gly Leu Gly Ala Ser Gly Ile Pro His Met Gly Ser Leu
        35                  40                  45

Gly Asp Ala Val Arg Ala Tyr Gly Val Gly Leu Ala Val Gly Asp Met
    50                  55                  60

Gly His Ser Phe Arg Leu Ile Ala Tyr Phe Asp Asp Leu Asp Gly Leu
65                  70                  75                  80

Arg Lys Val Pro Glu Gly Met Pro Ser Ser Leu Glu Glu His Ile Ala
                85                  90                  95

Arg Pro Val Ser Ala Ile Pro Asp Pro Tyr Gly Cys His Asp Ser Tyr
            100                 105                 110

Gly Met His Met Ser Gly Leu Leu Leu Glu Gly Leu Asp Ala Leu Gly
        115                 120                 125

Ile Glu Tyr Asp Phe Arg Arg Ala Arg Asp Thr Tyr Arg Asp Gly Leu
    130                 135                 140

Leu Ala Glu Gln Ile His Arg Ile Leu Ser Asn Ser Ser Val Ile Gly
145                 150                 155                 160

Glu Lys Ile Ala Glu Met Val Gly Gln Glu Lys Phe Arg Ser Ser Leu
                165                 170                 175

Pro Tyr Phe Ala Val Cys Glu Gln Cys Gly Lys Met Tyr Thr Ala Glu
            180                 185                 190

Ser Val Glu Tyr Leu Ala Asp Ser Arg Lys Val Arg Tyr Arg Cys Gly
        195                 200                 205

Asp Ala Glu Val Gly Gly Arg Lys Ile Ala Gly Cys Gly His Glu Gly
    210                 215                 220

Glu Ala Asp Thr Gly Gly Ala Gly Gly Lys Leu Ala Trp Lys Val Glu
225                 230                 235                 240

Phe Ala Ala Arg Trp Gln Ala Phe Asp Val Arg Phe Glu Ala Tyr Gly
                245                 250                 255

Lys Asp Ile Met Asp Ser Val Arg Ile Asn Asp Trp Val Ser Asp Glu
            260                 265                 270

Ile Leu Ser Ser Pro His Pro His His Thr Arg Tyr Glu Met Phe Leu
        275                 280                 285

Asp Lys Gly Gly Lys Lys Ile Ser Lys Ser Ser Gly Asn Val Val Thr
    290                 295                 300

Pro Gln Lys Trp Leu Arg Tyr Gly Thr Pro Gln Ser Ile Leu Leu Leu
305                 310                 315                 320

Met Tyr Lys Arg Ile Thr Gly Ala Arg Glu Leu Gly Leu Glu Asp Val
                325                 330                 335

Pro Ser Leu Met Asp Glu Tyr Gly Asp Leu Gln Arg Glu Tyr Phe Ala
            340                 345                 350

Gly Gly Gly Arg Gly Gly Lys Ala Arg Glu Ala Lys Asn Arg Gly Leu
        355                 360                 365

Phe Glu Tyr Thr Asn Leu Leu Glu Ala Gln Glu Gly Pro Arg Pro His
    370                 375                 380

Ala Gly Tyr Arg Leu Leu Val Glu Leu Ser Arg Leu Phe Arg Glu Asn
385                 390                 395                 400

Arg Thr Glu Arg Val Thr Lys Lys Leu Val Glu Tyr Gly Val Ile Asp
                405                 410                 415
```

-continued

```
Gly Pro Ser Pro Gly Ile Glu Arg Leu Ile Ala Leu Ala Gly Asn Tyr
            420                 425                 430

Ala Asp Asp Met Tyr Ser Ala Glu Arg Thr Glu Val Glu Leu Asp Gly
        435                 440                 445

Ala Thr Arg Gly Ala Leu Ser Glu Leu Ala Glu Met Leu Gly Ser Ala
    450                 455                 460

Pro Glu Gly Gly Leu Gln Asp Val Ile Tyr Gly Val Ala Lys Ser His
465                 470                 475                 480

Gly Val Pro Pro Arg Asp Phe Phe Lys Ala Leu Tyr Arg Ile Ile Leu
                485                 490                 495

Asp Ala Ser Ser Gly Pro Arg Ile Gly Pro Phe Ile Glu Asp Ile Gly
            500                 505                 510

Arg Glu Lys Val Ala Gly Met Ile Arg Gly Arg Leu
        515                 520


<210> SEQ ID NO 11
<211> LENGTH: 885
<212> TYPE: DNA
<213> ORGANISM: Cenarchaeum sybiosum
<220> FEATURE:
<221> NAME/KEY: CDS
<222> LOCATION: (1)...(885)

<400> SEQUENCE: 11

atg gag tca gcc ggt gag cag gca cct ggt gtg gta ctt cac gac tat       48
Met Glu Ser Ala Gly Glu Gln Ala Pro Gly Val Val Leu His Asp Tyr
 1               5                  10                  15

ctt tca aaa ttg caa cag tat tcg ggg agg gac aca att cta tat gcg       96
Leu Ser Lys Leu Gln Gln Tyr Ser Gly Arg Asp Thr Ile Leu Tyr Ala
            20                  25                  30

acc aac tgg atg acg gac gaa ccg cat acg cct aat gaa gct ctc ata      144
Thr Asn Trp Met Thr Asp Glu Pro His Thr Pro Asn Glu Ala Leu Ile
        35                  40                  45

aca aat ggt gac ctg tat gga ttt atg agg atg atg cgt gat tta aag      192
Thr Asn Gly Asp Leu Tyr Gly Phe Met Arg Met Met Arg Asp Leu Lys
    50                  55                  60

act aaa aaa ttg gat ctg ata ctc cac agt cct gga ggt tct gcc gag      240
Thr Lys Lys Leu Asp Leu Ile Leu His Ser Pro Gly Gly Ser Ala Glu
65                  70                  75                  80

tct gca gaa tcg att gtc aca tac ctt cat gcg aaa tat gat gat att      288
Ser Ala Glu Ser Ile Val Thr Tyr Leu His Ala Lys Tyr Asp Asp Ile
                85                  90                  95

cgg gtc atc ata ccg tat gcc gca atg tca gca gcc tcg atg ctt gct      336
Arg Val Ile Ile Pro Tyr Ala Ala Met Ser Ala Ala Ser Met Leu Ala
            100                 105                 110

tgc gca tca aat tcc ctg gta atg ggc aaa cac tcg tct ata gga ccc      384
Cys Ala Ser Asn Ser Leu Val Met Gly Lys His Ser Ser Ile Gly Pro
        115                 120                 125

gct gat ccc caa ttt att ttc cca acc aag att ggc atg caa ata atg      432
Ala Asp Pro Gln Phe Ile Phe Pro Thr Lys Ile Gly Met Gln Ile Met
    130                 135                 140

tct gca cag ctt cta att gac gag ttg caa gaa gtg cag gtg gta tct      480
Ser Ala Gln Leu Leu Ile Asp Glu Leu Gln Glu Val Gln Val Val Ser
145                 150                 155                 160

gaa aaa cat ccg ggc agg ctt ggc gca tgg ctt cca ttg tta gga caa      528
Glu Lys His Pro Gly Arg Leu Gly Ala Trp Leu Pro Leu Leu Gly Gln
                165                 170                 175

tat cct cct gga ctg gtt caa aaa tgc att agc agc cag aaa cta gct      576
Tyr Pro Pro Gly Leu Val Gln Lys Cys Ile Ser Ser Gln Lys Leu Ala
```

-continued

```
            180                 185                 190

gaa gtg ctt gta caa aaa tgg ctg gaa gac cac atg ttt gct ggc gag      624
Glu Val Leu Val Gln Lys Trp Leu Glu Asp His Met Phe Ala Gly Glu
        195                 200                 205

tct gat gcg gca gaa aaa tca aaa aaa ata tct gga atg tta gct tct      672
Ser Asp Ala Ala Glu Lys Ser Lys Lys Ile Ser Gly Met Leu Ala Ser
    210                 215                 220

cct gga aaa tat tac agt cat ggg aga tac ata tcg cga gag gag tgt      720
Pro Gly Lys Tyr Tyr Ser His Gly Arg Tyr Ile Ser Arg Glu Glu Cys
225                 230                 235                 240

agg ggc atc ggt ttg aaa ata act gat cta gaa gcc gac caa gaa ttt      768
Arg Gly Ile Gly Leu Lys Ile Thr Asp Leu Glu Ala Asp Gln Glu Phe
                245                 250                 255

cag gat ctg aca ttg tcg gta tct cat gca gcg gat atc ctg tct caa      816
Gln Asp Leu Thr Leu Ser Val Ser His Ala Ala Asp Ile Leu Ser Gln
            260                 265                 270

ttt act cca atc aac aaa atc atc gcg aat cac ctc ggt aat tca gtt      864
Phe Thr Pro Ile Asn Lys Ile Ile Ala Asn His Leu Gly Asn Ser Val
        275                 280                 285

atc agc aaa cca tca aca tag                                          885
Ile Ser Lys Pro Ser Thr
    290


<210> SEQ ID NO 12
<211> LENGTH: 294
<212> TYPE: PRT
<213> ORGANISM: Cenarchaeum sybiosum

<400> SEQUENCE: 12

Met Glu Ser Ala Gly Glu Gln Ala Pro Gly Val Val Leu His Asp Tyr
 1               5                  10                  15

Leu Ser Lys Leu Gln Gln Tyr Ser Gly Arg Asp Thr Ile Leu Tyr Ala
            20                  25                  30

Thr Asn Trp Met Thr Asp Glu Pro His Thr Pro Asn Glu Ala Leu Ile
        35                  40                  45

Thr Asn Gly Asp Leu Tyr Gly Phe Met Arg Met Met Arg Asp Leu Lys
    50                  55                  60

Thr Lys Lys Leu Asp Leu Ile Leu His Ser Pro Gly Gly Ser Ala Glu
65                  70                  75                  80

Ser Ala Glu Ser Ile Val Thr Tyr Leu His Ala Lys Tyr Asp Asp Ile
                85                  90                  95

Arg Val Ile Ile Pro Tyr Ala Ala Met Ser Ala Ala Ser Met Leu Ala
            100                 105                 110

Cys Ala Ser Asn Ser Leu Val Met Gly Lys His Ser Ser Ile Gly Pro
        115                 120                 125

Ala Asp Pro Gln Phe Ile Phe Pro Thr Lys Ile Gly Met Gln Ile Met
    130                 135                 140

Ser Ala Gln Leu Leu Ile Asp Glu Leu Gln Glu Val Gln Val Val Ser
145                 150                 155                 160

Glu Lys His Pro Gly Arg Leu Gly Ala Trp Leu Pro Leu Leu Gly Gln
                165                 170                 175

Tyr Pro Pro Gly Leu Val Gln Lys Cys Ile Ser Ser Gln Lys Leu Ala
            180                 185                 190

Glu Val Leu Val Gln Lys Trp Leu Glu Asp His Met Phe Ala Gly Glu
        195                 200                 205

Ser Asp Ala Ala Glu Lys Ser Lys Lys Ile Ser Gly Met Leu Ala Ser
    210                 215                 220
```

-continued

```
Pro Gly Lys Tyr Tyr Ser His Gly Arg Tyr Ile Ser Arg Glu Glu Cys
225                 230                 235                 240

Arg Gly Ile Gly Leu Lys Ile Thr Asp Leu Glu Ala Asp Gln Glu Phe
                245                 250                 255

Gln Asp Leu Thr Leu Ser Val Ser His Ala Ala Asp Ile Leu Ser Gln
            260                 265                 270

Phe Thr Pro Ile Asn Lys Ile Ile Ala Asn His Leu Gly Asn Ser Val
        275                 280                 285

Ile Ser Lys Pro Ser Thr
    290


<210> SEQ ID NO 13
<211> LENGTH: 1305
<212> TYPE: DNA
<213> ORGANISM: Cenarchaem symbiosum
<220> FEATURE:
<221> NAME/KEY: CDS
<222> LOCATION: (1)...(1305)

<400> SEQUENCE: 13

gtg gat cta gag cgc gag tac agg gca aag acc agg ggc tcg gcg ggg       48
Met Asp Leu Glu Arg Glu Tyr Arg Ala Lys Thr Arg Gly Ser Ala Gly
 1               5                  10                  15

ata ttt gcc cgg tcg aga agg tac cat gta ggg ggg gtc agc cac aac       96
Ile Phe Ala Arg Ser Arg Arg Tyr His Val Gly Gly Val Ser His Asn
            20                  25                  30

ata agg tac tat gag ccg tac ccg ttt gtt aca agg tcg gcg cgc ggc      144
Ile Arg Tyr Tyr Glu Pro Tyr Pro Phe Val Thr Arg Ser Ala Arg Gly
        35                  40                  45

aag cac ctt gtg gac gtc gac ggg aac aag tat acc gac tat tgg atg      192
Lys His Leu Val Asp Val Asp Gly Asn Lys Tyr Thr Asp Tyr Trp Met
    50                  55                  60

ggg cac tgg agc ctg ata ctc ggc cac gcg ccg gcg caa gta agg tcg      240
Gly His Trp Ser Leu Ile Leu Gly His Ala Pro Ala Gln Val Arg Ser
 65                  70                  75                  80

gca gtg gag ggg cag ctg cgc cgc ggc tgg ata cac ggg acc gca aac      288
Ala Val Glu Gly Gln Leu Arg Arg Gly Trp Ile His Gly Thr Ala Asn
                85                  90                  95

gag ccc acc atg cgg ctc tcg gag atc ata cgc ggg gcg gta aag gcg      336
Glu Pro Thr Met Arg Leu Ser Glu Ile Ile Arg Gly Ala Val Lys Ala
            100                 105                 110

gca gag aag ata agg tat gtt aca tcc ggc acg gag gcc gtc atg tat      384
Ala Glu Lys Ile Arg Tyr Val Thr Ser Gly Thr Glu Ala Val Met Tyr
        115                 120                 125

gcg gca agg atg gcg cgc gca cgc acg gga aaa aaa gtg ata gca aag      432
Ala Ala Arg Met Ala Arg Ala Arg Thr Gly Lys Lys Val Ile Ala Lys
    130                 135                 140

gtc gac ggc ggc tgg cac gga tac gcg tcg ggg ctg cta aag tcg gtc      480
Val Asp Gly Gly Trp His Gly Tyr Ala Ser Gly Leu Leu Lys Ser Val
145                 150                 155                 160

aac tgg ccg tac gat gtg ccc gag agc ggg ggg ctc gtc gac gag gag      528
Asn Trp Pro Tyr Asp Val Pro Glu Ser Gly Gly Leu Val Asp Glu Glu
                165                 170                 175

cac acc gtg tcc atc ccg tac aac aat ctg gag gga tcc ctg gag gcg      576
His Thr Val Ser Ile Pro Tyr Asn Asn Leu Glu Gly Ser Leu Glu Ala
            180                 185                 190

cta agg cgc gca ggg ggc gac ctt gca tgt gtc ata gtc gag ccg atg      624
Leu Arg Arg Ala Gly Gly Asp Leu Ala Cys Val Ile Val Glu Pro Met
        195                 200                 205
```

-continued

```
ctt ggc ggc ggc ggc tgc ata ccg gca gaa ccg gac tat ctc cgc ggc       672
Leu Gly Gly Gly Gly Cys Ile Pro Ala Glu Pro Asp Tyr Leu Arg Gly
    210                 215                 220

ata cag gag ttt gtg cat tcg aag ggt gca ctg ttc att ctc gac gag       720
Ile Gln Glu Phe Val His Ser Lys Gly Ala Leu Phe Ile Leu Asp Glu
225                 230                 235                 240

ata gtc acg ggg ttc cgg ttc gac ttt ggc tgc gcg tac aag aaa atg       768
Ile Val Thr Gly Phe Arg Phe Asp Phe Gly Cys Ala Tyr Lys Lys Met
                245                 250                 255

ggg ctg gac ccc gac gtg gtg gcg ctg gga aag ata gtc ggg ggc gga       816
Gly Leu Asp Pro Asp Val Val Ala Leu Gly Lys Ile Val Gly Gly Gly
            260                 265                 270

ttc ccc ata ggt gtg gtg tgc ggc aag gac gag gtg atg tgc atc tcc       864
Phe Pro Ile Gly Val Val Cys Gly Lys Asp Glu Val Met Cys Ile Ser
        275                 280                 285

gat acc ggc gcg cat gca aga acc gag agg gcg tac att ggc ggc ggc       912
Asp Thr Gly Ala His Ala Arg Thr Glu Arg Ala Tyr Ile Gly Gly Gly
    290                 295                 300

acc ttt tct gca aac ccc gcg acg atg act gcg ggt gcc gcg gca ctc       960
Thr Phe Ser Ala Asn Pro Ala Thr Met Thr Ala Gly Ala Ala Ala Leu
305                 310                 315                 320

ggt gca ctc agg gag aga agg ggc aca cta tac ccc aga ata aac tcc      1008
Gly Ala Leu Arg Glu Arg Arg Gly Thr Leu Tyr Pro Arg Ile Asn Ser
                325                 330                 335

atg ggg gac gac gca agg gcg cgg ctc tcg agg ata ttc gac ggc agg      1056
Met Gly Asp Asp Ala Arg Ala Arg Leu Ser Arg Ile Phe Asp Gly Arg
            340                 345                 350

gtt gca gtg acc ggc agg ggc tcg ctg ttc atg acg cac ttt aca ccg      1104
Val Ala Val Thr Gly Arg Gly Ser Leu Phe Met Thr His Phe Thr Pro
        355                 360                 365

gat ggg gcc cgc agg ata tcc agc gcg gca gat gct gcc gcc tgc gat      1152
Asp Gly Ala Arg Arg Ile Ser Ser Ala Ala Asp Ala Ala Ala Cys Asp
    370                 375                 380

gtg cat ctg ctg cac agg tac cac ctg gac atg att aca agg gac ggc      1200
Val His Leu Leu His Arg Tyr His Leu Asp Met Ile Thr Arg Asp Gly
385                 390                 395                 400

ata ttc ttt ctg cca ggc aag ctg ggg gcc ata tct gcc gcc cac tca      1248
Ile Phe Phe Leu Pro Gly Lys Leu Gly Ala Ile Ser Ala Ala His Ser
                405                 410                 415

agg gcg gac ctt ggg gcc atg tat tcg gcg tct gag cgc ttt gcg ggg      1296
Arg Ala Asp Leu Gly Ala Met Tyr Ser Ala Ser Glu Arg Phe Ala Gly
            420                 425                 430

gga ctg tga                                                          1305
Gly Leu


<210> SEQ ID NO 14
<211> LENGTH: 434
<212> TYPE: PRT
<213> ORGANISM: Cenarchaem symbiosum

<400> SEQUENCE: 14

Met Asp Leu Glu Arg Glu Tyr Arg Ala Lys Thr Arg Gly Ser Ala Gly
 1               5                  10                  15

Ile Phe Ala Arg Ser Arg Arg Tyr His Val Gly Gly Val Ser His Asn
            20                  25                  30

Ile Arg Tyr Tyr Glu Pro Tyr Pro Phe Val Thr Arg Ser Ala Arg Gly
        35                  40                  45

Lys His Leu Val Asp Val Asp Gly Asn Lys Tyr Thr Asp Tyr Trp Met
    50                  55                  60
```

-continued

```
Gly His Trp Ser Leu Ile Leu Gly His Ala Pro Ala Gln Val Arg Ser
65                  70                  75                  80

Ala Val Glu Gly Gln Leu Arg Arg Gly Trp Ile His Gly Thr Ala Asn
                85                  90                  95

Glu Pro Thr Met Arg Leu Ser Glu Ile Ile Arg Gly Ala Val Lys Ala
            100                 105                 110

Ala Glu Lys Ile Arg Tyr Val Thr Ser Gly Thr Glu Ala Val Met Tyr
        115                 120                 125

Ala Ala Arg Met Ala Arg Ala Arg Thr Gly Lys Lys Val Ile Ala Lys
    130                 135                 140

Val Asp Gly Gly Trp His Gly Tyr Ala Ser Gly Leu Leu Lys Ser Val
145                 150                 155                 160

Asn Trp Pro Tyr Asp Val Pro Glu Ser Gly Gly Leu Val Asp Glu Glu
                165                 170                 175

His Thr Val Ser Ile Pro Tyr Asn Asn Leu Glu Gly Ser Leu Glu Ala
            180                 185                 190

Leu Arg Arg Ala Gly Gly Asp Leu Ala Cys Val Ile Val Glu Pro Met
        195                 200                 205

Leu Gly Gly Gly Gly Cys Ile Pro Ala Glu Pro Asp Tyr Leu Arg Gly
    210                 215                 220

Ile Gln Glu Phe Val His Ser Lys Gly Ala Leu Phe Ile Leu Asp Glu
225                 230                 235                 240

Ile Val Thr Gly Phe Arg Phe Asp Phe Gly Cys Ala Tyr Lys Lys Met
                245                 250                 255

Gly Leu Asp Pro Asp Val Val Ala Leu Gly Lys Ile Val Gly Gly Gly
            260                 265                 270

Phe Pro Ile Gly Val Val Cys Gly Lys Asp Glu Val Met Cys Ile Ser
        275                 280                 285

Asp Thr Gly Ala His Ala Arg Thr Glu Arg Ala Tyr Ile Gly Gly Gly
    290                 295                 300

Thr Phe Ser Ala Asn Pro Ala Thr Met Thr Ala Gly Ala Ala Ala Leu
305                 310                 315                 320

Gly Ala Leu Arg Glu Arg Arg Gly Thr Leu Tyr Pro Arg Ile Asn Ser
                325                 330                 335

Met Gly Asp Asp Ala Arg Ala Arg Leu Ser Arg Ile Phe Asp Gly Arg
            340                 345                 350

Val Ala Val Thr Gly Arg Gly Ser Leu Phe Met Thr His Phe Thr Pro
        355                 360                 365

Asp Gly Ala Arg Arg Ile Ser Ser Ala Ala Asp Ala Ala Ala Cys Asp
    370                 375                 380

Val His Leu Leu His Arg Tyr His Leu Asp Met Ile Thr Arg Asp Gly
385                 390                 395                 400

Ile Phe Phe Leu Pro Gly Lys Leu Gly Ala Ile Ser Ala Ala His Ser
                405                 410                 415

Arg Ala Asp Leu Gly Ala Met Tyr Ser Ala Ser Glu Arg Phe Ala Gly
            420                 425                 430

Gly Leu

<210> SEQ ID NO 15
<211> LENGTH: 816
<212> TYPE: DNA
<213> ORGANISM: Cenarchaeum symbiosum
<220> FEATURE:
<221> NAME/KEY: CDS
<222> LOCATION: (1)...(816)
```

-continued

<400> SEQUENCE: 15

```
atg ata ctc ttc ggc aag agc gac ccc tcc gac ctg ctc cgc cag gcc       48
Met Ile Leu Phe Gly Lys Ser Asp Pro Ser Asp Leu Leu Arg Gln Ala
 1               5                  10                  15

gat ctt ttg tgc agt ggg aac aag tac aag gcg gca gtg ggc ctg tac       96
Asp Leu Leu Cys Ser Gly Asn Lys Tyr Lys Ala Ala Val Gly Leu Tyr
            20                  25                  30

agc agg ata ctc aag gac gac ccg cag aac agg atg gtc ctg cag aga      144
Ser Arg Ile Leu Lys Asp Asp Pro Gln Asn Arg Met Val Leu Gln Arg
        35                  40                  45

aag ggc ctc gcc ctc aac agg ata aga agg tac tct gat gcc ata acg      192
Lys Gly Leu Ala Leu Asn Arg Ile Arg Arg Tyr Ser Asp Ala Ile Thr
    50                  55                  60

tgc ttt gat ctg ctg ctc gag ctg gat gat ggc gac gcg cct gca tac      240
Cys Phe Asp Leu Leu Leu Glu Leu Asp Asp Gly Asp Ala Pro Ala Tyr
65                  70                  75                  80

aac aac aag gcc ata gcc cag gcc gag ctg ggc gat acg gca tcc gcc      288
Asn Asn Lys Ala Ile Ala Gln Ala Glu Leu Gly Asp Thr Ala Ser Ala
                85                  90                  95

ctg gag aac tat ggc agg gcc atc gaa gcc agc ccc agg tac gcg ccg      336
Leu Glu Asn Tyr Gly Arg Ala Ile Glu Ala Ser Pro Arg Tyr Ala Pro
            100                 105                 110

gcg tac ttt aac agg gcc gtc ctg ctc gac agg ctc ggc gag cac gaa      384
Ala Tyr Phe Asn Arg Ala Val Leu Leu Asp Arg Leu Gly Glu His Glu
        115                 120                 125

gac gcg ctg ccg gac ctc gac aag gcg aca agg ctg gac agg gac aag      432
Asp Ala Leu Pro Asp Leu Asp Lys Ala Thr Arg Leu Asp Arg Asp Lys
    130                 135                 140

gcc aac ccg agg ttc tac aag ggg ata gtc ctg gga aag atg ggc cgg      480
Ala Asn Pro Arg Phe Tyr Lys Gly Ile Val Leu Gly Lys Met Gly Arg
145                 150                 155                 160

cat gca gag gcg ctg tcc tgc ttc aag gag gtg tgc agg gcg gac cac      528
His Ala Glu Ala Leu Ser Cys Phe Lys Glu Val Cys Arg Ala Asp His
                165                 170                 175

ggc cac gcc gac tca cag ttc cac gtg gcg ata gag gta gcc gag ctc      576
Gly His Ala Asp Ser Gln Phe His Val Ala Ile Glu Val Ala Glu Leu
            180                 185                 190

ggc aaa cac gcc gaa gcc ctc ggt gag ctt gcg gca ctg ccc gca gag      624
Gly Lys His Ala Glu Ala Leu Gly Glu Leu Ala Ala Leu Pro Ala Glu
        195                 200                 205

tac cgc gag aac gca aac gtt ctc tac gcc cgg gcg cgc agc ctc gcc      672
Tyr Arg Glu Asn Ala Asn Val Leu Tyr Ala Arg Ala Arg Ser Leu Ala
    210                 215                 220

ggc ctg gac agg tac gac gag tcc att gca cac ctg caa aag gcc gcc      720
Gly Leu Asp Arg Tyr Asp Glu Ser Ile Ala His Leu Gln Lys Ala Ala
225                 230                 235                 240

aga aag gac tcc aag aca ata aaa aag tgg gcc cgc gcc gag aag gcc      768
Arg Lys Asp Ser Lys Thr Ile Lys Lys Trp Ala Arg Ala Glu Lys Ala
                245                 250                 255

ttt gat cat ata cgg gat gat ccc agg ttc aaa aag ata gcc ggg taa      816
Phe Asp His Ile Arg Asp Asp Pro Arg Phe Lys Lys Ile Ala Gly
            260                 265                 270
```

<210> SEQ ID NO 16
<211> LENGTH: 271
<212> TYPE: PRT
<213> ORGANISM: Cenarchaeum symbiosum

<400> SEQUENCE: 16

-continued

Met Ile Leu Phe Gly Lys Ser Asp Pro Ser Asp Leu Leu Arg Gln Ala
1 5 10 15

Asp Leu Leu Cys Ser Gly Asn Lys Tyr Lys Ala Ala Val Gly Leu Tyr
20 25 30

Ser Arg Ile Leu Lys Asp Asp Pro Gln Asn Arg Met Val Leu Gln Arg
35 40 45

Lys Gly Leu Ala Leu Asn Arg Ile Arg Arg Tyr Ser Asp Ala Ile Thr
50 55 60

Cys Phe Asp Leu Leu Leu Glu Leu Asp Asp Gly Asp Ala Pro Ala Tyr
65 70 75 80

Asn Asn Lys Ala Ile Ala Gln Ala Glu Leu Gly Asp Thr Ala Ser Ala
85 90 95

Leu Glu Asn Tyr Gly Arg Ala Ile Glu Ala Ser Pro Arg Tyr Ala Pro
100 105 110

Ala Tyr Phe Asn Arg Ala Val Leu Leu Asp Arg Leu Gly Glu His Glu
115 120 125

Asp Ala Leu Pro Asp Leu Asp Lys Ala Thr Arg Leu Asp Arg Asp Lys
130 135 140

Ala Asn Pro Arg Phe Tyr Lys Gly Ile Val Leu Gly Lys Met Gly Arg
145 150 155 160

His Ala Glu Ala Leu Ser Cys Phe Lys Glu Val Cys Arg Ala Asp His
165 170 175

Gly His Ala Asp Ser Gln Phe His Val Ala Ile Glu Val Ala Glu Leu
180 185 190

Gly Lys His Ala Glu Ala Leu Gly Glu Leu Ala Ala Leu Pro Ala Glu
195 200 205

Tyr Arg Glu Asn Ala Asn Val Leu Tyr Ala Arg Ala Arg Ser Leu Ala
210 215 220

Gly Leu Asp Arg Tyr Asp Glu Ser Ile Ala His Leu Gln Lys Ala Ala
225 230 235 240

Arg Lys Asp Ser Lys Thr Ile Lys Lys Trp Ala Arg Ala Glu Lys Ala
245 250 255

Phe Asp His Ile Arg Asp Asp Pro Arg Phe Lys Lys Ile Ala Gly
260 265 270

<210> SEQ ID NO 17
<211> LENGTH: 696
<212> TYPE: DNA
<213> ORGANISM: Cenarchaeum symbiosum
<220> FEATURE:
<221> NAME/KEY: CDS
<222> LOCATION: (1)...(696)

<400> SEQUENCE: 17 gtg act gac aag aca agg atc atc gtc ctg cgc aac gcc atg act gaa 48
Met Thr Asp Lys Thr Arg Ile Ile Val Leu Arg Asn Ala Met Thr Glu
1 5 10 15 cag tcc gcc cgg gcc atg atc gag gca aaa aag acg ggg cca ttc agg 96
Gln Ser Ala Arg Ala Met Ile Glu Ala Lys Lys Thr Gly Pro Phe Arg
20 25 30 gcc atg atg agg gcg ccc cca aag gag gac gtc cat gta cat tcc gta 144
Ala Met Met Arg Ala Pro Pro Lys Glu Asp Val His Val His Ser Val
35 40 45 agg ctc gtc cac gag gcg ctc atc cgc gtc tcc gcc cgg tac tcg gcc 192
Arg Leu Val His Glu Ala Leu Ile Arg Val Ser Ala Arg Tyr Ser Ala
50 55 60 gac ttt ttc aga agg gcc gtg cac ccg atc aag gtg gat cag aac gtg 240

-continued

```
Asp Phe Phe Arg Arg Ala Val His Pro Ile Lys Val Asp Gln Asn Val
 65                 70                  75                  80

atc gag gtg gtg ctg ggc gac ggc gtc ttc ccg ata agg tca aag tcg       288
Ile Glu Val Val Leu Gly Asp Gly Val Phe Pro Ile Arg Ser Lys Ser
                 85                  90                  95

cgc ata cgc aag acc ctg tcc gcc ggg cgc ggc aag aac agg gtc gat       336
Arg Ile Arg Lys Thr Leu Ser Ala Gly Arg Gly Lys Asn Arg Val Asp
            100                 105                 110

ctg gaa ctc gag gag cac gta tac gcg gaa tca gag ggc gtg atg tgc       384
Leu Glu Leu Glu Glu His Val Tyr Ala Glu Ser Glu Gly Val Met Cys
        115                 120                 125

ctt gac cgg cac ggc ggg gag acc ggc ttt ccc tac aag acg ggg acc       432
Leu Asp Arg His Gly Gly Glu Thr Gly Phe Pro Tyr Lys Thr Gly Thr
    130                 135                 140

ggc gcg gtc gag ccg tac ccg cgg cgc atg ctt gat tcg tcg gag aat       480
Gly Ala Val Glu Pro Tyr Pro Arg Arg Met Leu Asp Ser Ser Glu Asn
145                 150                 155                 160

gtg cgg cgc ccg gag ata gac acc ggg gtg gcg ctg gaa aaa ctc cgg       528
Val Arg Arg Pro Glu Ile Asp Thr Gly Val Ala Leu Glu Lys Leu Arg
                165                 170                 175

gta aag ctc cgc ggg ccc ccg cct gac ggc atg cgc gac ctc cgg gag       576
Val Lys Leu Arg Gly Pro Pro Pro Asp Gly Met Arg Asp Leu Arg Glu
            180                 185                 190

gag ttt gca gtc aga tcg gtc gaa gaa gtg tat gcc cct gtc tac gag       624
Glu Phe Ala Val Arg Ser Val Glu Glu Val Tyr Ala Pro Val Tyr Glu
        195                 200                 205

tcg cgg ctt gtg ggg ccc aaa aaa aag gtc cgg ata atg cgg ata gac       672
Ser Arg Leu Val Gly Pro Lys Lys Lys Val Arg Ile Met Arg Ile Asp
    210                 215                 220

gcg gca aga aaa aag atg ctg tag                                       696
Ala Ala Arg Lys Lys Met Leu
225                 230


<210> SEQ ID NO 18
<211> LENGTH: 231
<212> TYPE: PRT
<213> ORGANISM: Cenarchaeum symbiosum

<400> SEQUENCE: 18

Met Thr Asp Lys Thr Arg Ile Ile Val Leu Arg Asn Ala Met Thr Glu
 1               5                  10                  15

Gln Ser Ala Arg Ala Met Ile Glu Ala Lys Lys Thr Gly Pro Phe Arg
            20                  25                  30

Ala Met Met Arg Ala Pro Pro Lys Glu Asp Val His Val His Ser Val
        35                  40                  45

Arg Leu Val His Glu Ala Leu Ile Arg Val Ser Ala Arg Tyr Ser Ala
    50                  55                  60

Asp Phe Phe Arg Arg Ala Val His Pro Ile Lys Val Asp Gln Asn Val
65                  70                  75                  80

Ile Glu Val Val Leu Gly Asp Gly Val Phe Pro Ile Arg Ser Lys Ser
                85                  90                  95

Arg Ile Arg Lys Thr Leu Ser Ala Gly Arg Gly Lys Asn Arg Val Asp
            100                 105                 110

Leu Glu Leu Glu Glu His Val Tyr Ala Glu Ser Glu Gly Val Met Cys
        115                 120                 125

Leu Asp Arg His Gly Gly Glu Thr Gly Phe Pro Tyr Lys Thr Gly Thr
    130                 135                 140

Gly Ala Val Glu Pro Tyr Pro Arg Arg Met Leu Asp Ser Ser Glu Asn
```

-continued

```
145                 150                 155                 160

Val Arg Arg Pro Glu Ile Asp Thr Gly Val Ala Leu Glu Lys Leu Arg
                165                 170                 175

Val Lys Leu Arg Gly Pro Pro Pro Asp Gly Met Arg Asp Leu Arg Glu
            180                 185                 190

Glu Phe Ala Val Arg Ser Val Glu Glu Val Tyr Ala Pro Val Tyr Glu
        195                 200                 205

Ser Arg Leu Val Gly Pro Lys Lys Lys Val Arg Ile Met Arg Ile Asp
    210                 215                 220

Ala Ala Arg Lys Lys Met Leu
225                 230


<210> SEQ ID NO 19
<211> LENGTH: 378
<212> TYPE: DNA
<213> ORGANISM: Cenarchaeum symbiosum
<220> FEATURE:
<221> NAME/KEY: CDS
<222> LOCATION: (1)...(378)

<400> SEQUENCE: 19

atg agg tca gaa gag agg ccg ggt cac att gaa aag ttc cta aag agg       48
Met Arg Ser Glu Glu Arg Pro Gly His Ile Glu Lys Phe Leu Lys Arg
 1               5                  10                  15

gcg gac aag gcg atc gac agc gcg gtc gag cag ggc gtc aag agg gcc       96
Ala Asp Lys Ala Ile Asp Ser Ala Val Glu Gln Gly Val Lys Arg Ala
            20                  25                  30

gac gag ata cta gac gat gca gtc gag ctc ggc aag att acg gtg ggc      144
Asp Glu Ile Leu Asp Asp Ala Val Glu Leu Gly Lys Ile Thr Val Gly
        35                  40                  45

gag gcg cag agg agg agc gat gtg ctg ctc aaa cag gcc gag cgg gag      192
Glu Ala Gln Arg Arg Ser Asp Val Leu Leu Lys Gln Ala Glu Arg Glu
    50                  55                  60

agc agg cgg ctc aag tcc aag ggc gcc aaa aag ctc gaa aag ggc ata      240
Ser Arg Arg Leu Lys Ser Lys Gly Ala Lys Lys Leu Glu Lys Gly Ile
 65                  70                  75                  80

ggc gcc gca aaa aag atg gca gca ggc aag ggc gac gcg ctc gag acg      288
Gly Ala Ala Lys Lys Met Ala Ala Gly Lys Gly Asp Ala Leu Glu Thr
                85                  90                  95

ctc gca aag ctc ggc gag ctc aga aag gcg ggg atc ata acg gag aaa      336
Leu Ala Lys Leu Gly Glu Leu Arg Lys Ala Gly Ile Ile Thr Glu Lys
            100                 105                 110

gag ttt cgc gcc aaa aag aaa aag ctc ctc gca gag atc tga              378
Glu Phe Arg Ala Lys Lys Lys Lys Leu Leu Ala Glu Ile
        115                 120                 125


<210> SEQ ID NO 20
<211> LENGTH: 125
<212> TYPE: PRT
<213> ORGANISM: Cenarchaeum symbiosum

<400> SEQUENCE: 20

Met Arg Ser Glu Glu Arg Pro Gly His Ile Glu Lys Phe Leu Lys Arg
 1               5                  10                  15

Ala Asp Lys Ala Ile Asp Ser Ala Val Glu Gln Gly Val Lys Arg Ala
            20                  25                  30

Asp Glu Ile Leu Asp Asp Ala Val Glu Leu Gly Lys Ile Thr Val Gly
        35                  40                  45

Glu Ala Gln Arg Arg Ser Asp Val Leu Leu Lys Gln Ala Glu Arg Glu
    50                  55                  60
```

-continued

```
Ser Arg Arg Leu Lys Ser Lys Gly Ala Lys Lys Leu Glu Lys Gly Ile
65                  70                  75                  80

Gly Ala Ala Lys Lys Met Ala Ala Gly Lys Gly Asp Ala Leu Glu Thr
                85                  90                  95

Leu Ala Lys Leu Gly Glu Leu Arg Lys Ala Gly Ile Ile Thr Glu Lys
            100                 105                 110

Glu Phe Arg Ala Lys Lys Lys Lys Leu Leu Ala Glu Ile
        115                 120                 125


<210> SEQ ID NO 21
<211> LENGTH: 600
<212> TYPE: DNA
<213> ORGANISM: Cenarchaeum symbiosum
<220> FEATURE:
<221> NAME/KEY: CDS
<222> LOCATION: (1)...(600)

<400> SEQUENCE: 21

atg tcc cag acg ggg gcc ccg ggc ggg cat gcc tgc acg cca tac acg       48
Met Ser Gln Thr Gly Ala Pro Gly Gly His Ala Cys Thr Pro Tyr Thr
 1               5                  10                  15

cac gat cac gcc tcg atc gag ctc aag gac gcg tgg gcc tcg tcg agg       96
His Asp His Ala Ser Ile Glu Leu Lys Asp Ala Trp Ala Ser Ser Arg
            20                  25                  30

aac gtc cgc gag atg tac ttt gtg acc gcc acg ttc tcg tcc gag agc      144
Asn Val Arg Glu Met Tyr Phe Val Thr Ala Thr Phe Ser Ser Glu Ser
        35                  40                  45

cag ccg tac ttt gca ccg cag gcc aac cac tac ctg ctg gca agg ttc      192
Gln Pro Tyr Phe Ala Pro Gln Ala Asn His Tyr Leu Leu Ala Arg Phe
    50                  55                  60

aag gac gcc ccc aga atg atc aag gcg gtg ggc cgg ggg gag ggc gca      240
Lys Asp Ala Pro Arg Met Ile Lys Ala Val Gly Arg Gly Glu Gly Ala
 65                  70                  75                  80

tcc tat gtg ttt agc atg gac gag gac ata ttc gag agg gag tcc ccc      288
Ser Tyr Val Phe Ser Met Asp Glu Asp Ile Phe Glu Arg Glu Ser Pro
                85                  90                  95

ggg gtg agc tat gta tcg gtg tac tat ctg gag tac ggc gat tcc gag      336
Gly Val Ser Tyr Val Ser Val Tyr Tyr Leu Glu Tyr Gly Asp Ser Glu
            100                 105                 110

ag gac ata tgc gag gtg gcg tcc gtg gtg ggg aga aag gag aag ata      384
Glu Asp Ile Cys Glu Val Ala Ser Val Val Gly Arg Lys Glu Lys Ile
        115                 120                 125

ggc agg gcg gga ata ggg cgc atg gac gtc tgc tcg agg gtg ccg cca      432
Gly Arg Ala Gly Ile Gly Arg Met Asp Val Cys Ser Arg Val Pro Pro
    130                 135                 140

aag ttt gcc ttt ccg tac agc ggg aac ata ata gtc ctc gag gtc tcc      480
Lys Phe Ala Phe Pro Tyr Ser Gly Asn Ile Ile Val Leu Glu Val Ser
145                 150                 155                 160

agc gag aag agc tac cag agc gtc aac aag tac tgc gag aag acg cgg      528
Ser Glu Lys Ser Tyr Gln Ser Val Asn Lys Tyr Cys Glu Lys Thr Arg
                165                 170                 175

cgc gag gtc atc cgc aag ggg ata acg atg acc aac ctt gtg agc ctg      576
Arg Glu Val Ile Arg Lys Gly Ile Thr Met Thr Asn Leu Val Ser Leu
            180                 185                 190

tcc ata ctg gag cgg cta aag tag                                      600
Ser Ile Leu Glu Arg Leu Lys
        195


<210> SEQ ID NO 22
<211> LENGTH: 199
```

-continued

<212> TYPE: PRT
<213> ORGANISM: Cenarchaeum symbiosum

<400> SEQUENCE: 22

```
Met Ser Gln Thr Gly Ala Pro Gly Gly His Ala Cys Thr Pro Tyr Thr
 1               5                  10                  15

His Asp His Ala Ser Ile Glu Leu Lys Asp Ala Trp Ala Ser Ser Arg
            20                  25                  30

Asn Val Arg Glu Met Tyr Phe Val Thr Ala Thr Phe Ser Ser Glu Ser
        35                  40                  45

Gln Pro Tyr Phe Ala Pro Gln Ala Asn His Tyr Leu Leu Ala Arg Phe
    50                  55                  60

Lys Asp Ala Pro Arg Met Ile Lys Ala Val Gly Arg Gly Glu Gly Ala
65                  70                  75                  80

Ser Tyr Val Phe Ser Met Asp Glu Asp Ile Phe Glu Arg Glu Ser Pro
                85                  90                  95

Gly Val Ser Tyr Val Ser Val Tyr Tyr Leu Glu Tyr Gly Asp Ser Glu
            100                 105                 110

Glu Asp Ile Cys Glu Val Ala Ser Val Val Gly Arg Lys Glu Lys Ile
        115                 120                 125

Gly Arg Ala Gly Ile Gly Arg Met Asp Val Cys Ser Arg Val Pro Pro
    130                 135                 140

Lys Phe Ala Phe Pro Tyr Ser Gly Asn Ile Ile Val Leu Glu Val Ser
145                 150                 155                 160

Ser Glu Lys Ser Tyr Gln Ser Val Asn Lys Tyr Cys Glu Lys Thr Arg
                165                 170                 175

Arg Glu Val Ile Arg Lys Gly Ile Thr Met Thr Asn Leu Val Ser Leu
            180                 185                 190

Ser Ile Leu Glu Arg Leu Lys
        195
```

<210> SEQ ID NO 23
<211> LENGTH: 810
<212> TYPE: DNA
<213> ORGANISM: Cenarchaeum symbiosum
<220> FEATURE:
<221> NAME/KEY: CDS
<222> LOCATION: (1)...(810)

<400> SEQUENCE: 23

```
ttg gct cgg cgc tac aag ccc cgg ata aag cag gtc cta cgc gag gtg       48
Met Ala Arg Arg Tyr Lys Pro Arg Ile Lys Gln Val Leu Arg Glu Val
 1               5                  10                  15

ccc ctc aag aac gtg cac gtg tgg aag gac gcg cag gca agg agg ctg       96
Pro Leu Lys Asn Val His Val Trp Lys Asp Ala Gln Ala Arg Arg Leu
            20                  25                  30

gac agg tcc agg gtg agg gag att gca aag tcg atc agg tcc gag ggc      144
Asp Arg Ser Arg Val Arg Glu Ile Ala Lys Ser Ile Arg Ser Glu Gly
        35                  40                  45

ctg cag aac ccg ccc gta ata cag agg ggc ggc agg ggg ctg tac ctg      192
Leu Gln Asn Pro Pro Val Ile Gln Arg Gly Gly Arg Gly Leu Tyr Leu
    50                  55                  60

ctc ata tcg ggg aac cac agg ctt gcg gcc cta aag cat ctg ggc gca      240
Leu Ile Ser Gly Asn His Arg Leu Ala Ala Leu Lys His Leu Gly Ala
65                  70                  75                  80

aaa aag tcc aag ttt ctt gtg ata acc aag gat acg gag tac ggc ctg      288
Lys Lys Ser Lys Phe Leu Val Ile Thr Lys Asp Thr Glu Tyr Gly Leu
                85                  90                  95
```

-continued

```
gag gac gca aag gcg gca tcg gtc gtg gag aac ctg cac cgg atg cag      336
Glu Asp Ala Lys Ala Ala Ser Val Val Glu Asn Leu His Arg Met Gln
            100                 105                 110

atg agc ccc cgg gag ctc gcc gac gcg tgc agg ttt ctc gcc gag cag      384
Met Ser Pro Arg Glu Leu Ala Asp Ala Cys Arg Phe Leu Ala Glu Gln
        115                 120                 125

atg acc cgc gcc gag gcc gca agg aag ctc ggc atg tcg atg ccc acg      432
Met Thr Arg Ala Glu Ala Ala Arg Lys Leu Gly Met Ser Met Pro Thr
    130                 135                 140

ttc aaa aag tac cac ggc ttt gcg ggc gtg ccg gag aag atc aag gcg      480
Phe Lys Lys Tyr His Gly Phe Ala Gly Val Pro Glu Lys Ile Lys Ala
145                 150                 155                 160

cta gtc ccc ggg acc ata tcc cgg gac gag gcg aca aag ctg tac cag      528
Leu Val Pro Gly Thr Ile Ser Arg Asp Glu Ala Thr Lys Leu Tyr Gln
                165                 170                 175

gcc gtc ccg acc gtc tcc cag gcg ctc aag gtg gcg ctg aac ata tca      576
Ala Val Pro Thr Val Ser Gln Ala Leu Lys Val Ala Leu Asn Ile Ser
            180                 185                 190

agg ctt gat cgg ccg tcg agg cgg atc tac ctg agg ctg cta gcc cag      624
Arg Leu Asp Arg Pro Ser Arg Arg Ile Tyr Leu Arg Leu Leu Ala Gln
        195                 200                 205

agc ccc cgc tcg ggc cac agg atc ctg cta aag agg gtg cgc aag acg      672
Ser Pro Arg Ser Gly His Arg Ile Leu Leu Lys Arg Val Arg Lys Thr
    210                 215                 220

ggc gtc agg aag aag atc ccc ata gag ctc ggc aag aac ggc gca aga      720
Gly Val Arg Lys Lys Ile Pro Ile Glu Leu Gly Lys Asn Gly Ala Arg
225                 230                 235                 240

aag ctt gcc cgg gtg gcc gag cgc gag ggc acc gac gag acc cgg ctt      768
Lys Leu Ala Arg Val Ala Glu Arg Glu Gly Thr Asp Glu Thr Arg Leu
                245                 250                 255

gcc aac agg ata gtc cgg gag tac ctg agg aag cag cga tga              810
Ala Asn Arg Ile Val Arg Glu Tyr Leu Arg Lys Gln Arg
            260                 265


<210> SEQ ID NO 24
<211> LENGTH: 269
<212> TYPE: PRT
<213> ORGANISM: Cenarchaeum symbiosum

<400> SEQUENCE: 24

Met Ala Arg Arg Tyr Lys Pro Arg Ile Lys Gln Val Leu Arg Glu Val
 1               5                  10                  15

Pro Leu Lys Asn Val His Val Trp Lys Asp Ala Gln Ala Arg Arg Leu
            20                  25                  30

Asp Arg Ser Arg Val Arg Glu Ile Ala Lys Ser Ile Arg Ser Glu Gly
        35                  40                  45

Leu Gln Asn Pro Pro Val Ile Gln Arg Gly Gly Arg Gly Leu Tyr Leu
    50                  55                  60

Leu Ile Ser Gly Asn His Arg Leu Ala Ala Leu Lys His Leu Gly Ala
65                  70                  75                  80

Lys Lys Ser Lys Phe Leu Val Ile Thr Lys Asp Thr Glu Tyr Gly Leu
                85                  90                  95

Glu Asp Ala Lys Ala Ala Ser Val Val Glu Asn Leu His Arg Met Gln
            100                 105                 110

Met Ser Pro Arg Glu Leu Ala Asp Ala Cys Arg Phe Leu Ala Glu Gln
        115                 120                 125

Met Thr Arg Ala Glu Ala Ala Arg Lys Leu Gly Met Ser Met Pro Thr
    130                 135                 140
```

-continued

```
Phe Lys Lys Tyr His Gly Phe Ala Gly Val Pro Glu Lys Ile Lys Ala
145                 150                 155                 160

Leu Val Pro Gly Thr Ile Ser Arg Asp Glu Ala Thr Lys Leu Tyr Gln
                165                 170                 175

Ala Val Pro Thr Val Ser Gln Ala Leu Lys Val Ala Leu Asn Ile Ser
            180                 185                 190

Arg Leu Asp Arg Pro Ser Arg Arg Ile Tyr Leu Arg Leu Leu Ala Gln
        195                 200                 205

Ser Pro Arg Ser Gly His Arg Ile Leu Leu Lys Arg Val Arg Lys Thr
    210                 215                 220

Gly Val Arg Lys Lys Ile Pro Ile Glu Leu Gly Lys Asn Gly Ala Arg
225                 230                 235                 240

Lys Leu Ala Arg Val Ala Glu Arg Glu Gly Thr Asp Glu Thr Arg Leu
                245                 250                 255

Ala Asn Arg Ile Val Arg Glu Tyr Leu Arg Lys Gln Arg
            260                 265


<210> SEQ ID NO 25
<211> LENGTH: 837
<212> TYPE: DNA
<213> ORGANISM: Cenarchaeum symbiosum
<220> FEATURE:
<221> NAME/KEY: CDS
<222> LOCATION: (1)...(837)

<400> SEQUENCE: 25

ttg tta act gtg ttt ggt aag ttt atc aca aca att agg tta gat aga       48
Met Leu Thr Val Phe Gly Lys Phe Ile Thr Thr Ile Arg Leu Asp Arg
 1               5                  10                  15

gct gtt ccc ccg cag gcc ccc gtg cac gta ctc tat cgc gca gcc ccc       96
Ala Val Pro Pro Gln Ala Pro Val His Val Leu Tyr Arg Ala Ala Pro
            20                  25                  30

cgg ggg aca gcc gga acc ggg ggc tgc cgg ggc ggg atc ccg ggc gtc      144
Arg Gly Thr Ala Gly Thr Gly Gly Cys Arg Gly Gly Ile Pro Gly Val
        35                  40                  45

gat aga ata aat acg cgc ggg gcc gcg gtg cga tcg ccc gtg ctg ata      192
Asp Arg Ile Asn Thr Arg Gly Ala Ala Val Arg Ser Pro Val Leu Ile
     50                  55                  60

ata aac tgc aaa aac tat gag gag gcc gcc ggc ggc agg atc cgc ggg      240
Ile Asn Cys Lys Asn Tyr Glu Glu Ala Ala Gly Gly Arg Ile Arg Gly
 65                  70                  75                  80

ctg gca gat gcc gcg gcc ggg gct gcc gcc agg tac ggc gtc agg ata      288
Leu Ala Asp Ala Ala Ala Gly Ala Ala Ala Arg Tyr Gly Val Arg Ile
                 85                  90                  95

gcg ata gcc ccg ccg cag cac ctg ctg ggc att ata gca ggc cgg gat      336
Ala Ile Ala Pro Pro Gln His Leu Leu Gly Ile Ile Ala Gly Arg Asp
            100                 105                 110

ctt ggc gtg ctg gcc cag cat gtc gac gac aag ggg acg ggg agc acc      384
Leu Gly Val Leu Ala Gln His Val Asp Asp Lys Gly Thr Gly Ser Thr
        115                 120                 125

aca ggg tat gtc gtc ccg gag ctg cta aaa cag tcg ggg gtc tcc ggg      432
Thr Gly Tyr Val Val Pro Glu Leu Leu Lys Gln Ser Gly Val Ser Gly
    130                 135                 140

gcc ata atc aac cac agc gag cac cgc gta ccc gcg gac cag gtg gcg      480
Ala Ile Ile Asn His Ser Glu His Arg Val Pro Ala Asp Gln Val Ala
145                 150                 155                 160

ggc ctg gta cca agg ctc agg ggc ctt ggc atg gtc tcg gtg gtc tgc      528
Gly Leu Val Pro Arg Leu Arg Gly Leu Gly Met Val Ser Val Val Cys
                165                 170                 175
```

-continued

```
gtc agg gat ccc gcc gag gcc gcc gat ctc tcc cgg tat tgc ccc gac      576
Val Arg Asp Pro Ala Glu Ala Ala Asp Leu Ser Arg Tyr Cys Pro Asp
            180                 185                 190

tac ata gcg ata gag cct ccc gag ctg ata ggt tcc ggc agg tcc gtc      624
Tyr Ile Ala Ile Glu Pro Pro Glu Leu Ile Gly Ser Gly Arg Ser Val
        195                 200                 205

tcg aca gag agg ccc cag gtc ata caa gag gcc gca gag gcc atc agg      672
Ser Thr Glu Arg Pro Gln Val Ile Gln Glu Ala Ala Glu Ala Ile Arg
    210                 215                 220

ggg gct ggc ggc gta aag ctg ctc tgc ggg gcg ggc ata acc tcc ggg      720
Gly Ala Gly Gly Val Lys Leu Leu Cys Gly Ala Gly Ile Thr Ser Gly
225                 230                 235                 240

gcg gac gtg cgc agg gcc ctc gag ctt ggc tcc gag ggc att ctt gtg      768
Ala Asp Val Arg Arg Ala Leu Glu Leu Gly Ser Glu Gly Ile Leu Val
                245                 250                 255

gca agc ggg gtc gta aag tcg gca gac ccc gca ggg gcc atc ggg gag      816
Ala Ser Gly Val Val Lys Ser Ala Asp Pro Ala Gly Ala Ile Gly Glu
            260                 265                 270

ctt gcc cgg gcc atg tcc tga                                          837
Leu Ala Arg Ala Met Ser
        275


<210> SEQ ID NO 26
<211> LENGTH: 278
<212> TYPE: PRT
<213> ORGANISM: Cenarchaeum symbiosum

<400> SEQUENCE: 26

Met Leu Thr Val Phe Gly Lys Phe Ile Thr Thr Ile Arg Leu Asp Arg
 1               5                  10                  15

Ala Val Pro Pro Gln Ala Pro Val His Val Leu Tyr Arg Ala Ala Pro
            20                  25                  30

Arg Gly Thr Ala Gly Thr Gly Gly Cys Arg Gly Gly Ile Pro Gly Val
        35                  40                  45

Asp Arg Ile Asn Thr Arg Gly Ala Ala Val Arg Ser Pro Val Leu Ile
    50                  55                  60

Ile Asn Cys Lys Asn Tyr Glu Glu Ala Ala Gly Gly Arg Ile Arg Gly
65                  70                  75                  80

Leu Ala Asp Ala Ala Ala Gly Ala Ala Ala Arg Tyr Gly Val Arg Ile
                85                  90                  95

Ala Ile Ala Pro Pro Gln His Leu Leu Gly Ile Ile Ala Gly Arg Asp
            100                 105                 110

Leu Gly Val Leu Ala Gln His Val Asp Asp Lys Gly Thr Gly Ser Thr
        115                 120                 125

Thr Gly Tyr Val Val Pro Glu Leu Leu Lys Gln Ser Gly Val Ser Gly
    130                 135                 140

Ala Ile Ile Asn His Ser Glu His Arg Val Pro Ala Asp Gln Val Ala
145                 150                 155                 160

Gly Leu Val Pro Arg Leu Arg Gly Leu Gly Met Val Ser Val Val Cys
                165                 170                 175

Val Arg Asp Pro Ala Glu Ala Ala Asp Leu Ser Arg Tyr Cys Pro Asp
            180                 185                 190

Tyr Ile Ala Ile Glu Pro Pro Glu Leu Ile Gly Ser Gly Arg Ser Val
        195                 200                 205

Ser Thr Glu Arg Pro Gln Val Ile Gln Glu Ala Ala Glu Ala Ile Arg
    210                 215                 220

Gly Ala Gly Gly Val Lys Leu Leu Cys Gly Ala Gly Ile Thr Ser Gly
```

-continued

```
225                 230                 235                 240

Ala Asp Val Arg Arg Ala Leu Glu Leu Gly Ser Glu Gly Ile Leu Val
                245                 250                 255

Ala Ser Gly Val Val Lys Ser Ala Asp Pro Ala Gly Ala Ile Gly Glu
            260                 265                 270

Leu Ala Arg Ala Met Ser
        275
```

<210> SEQ ID NO 27
<211> LENGTH: 549
<212> TYPE: DNA
<213> ORGANISM: Cenarchaeum symbiosum
<220> FEATURE:
<221> NAME/KEY: CDS
<222> LOCATION: (1)...(549)

<400> SEQUENCE: 27

```
atg ctg gat cca agg aaa cgg ccc agg gtg gtc aac gtt gtg agt acc       48
Met Leu Asp Pro Arg Lys Arg Pro Arg Val Val Asn Val Val Ser Thr
 1               5                  10                  15

gcc gac ctg ggc cgg agg gtg ggc gca aaa aag atg gcc gcc atg cca       96
Ala Asp Leu Gly Arg Arg Val Gly Ala Lys Lys Met Ala Ala Met Pro
            20                  25                  30

tgc tgc atg tac gac gag gcg gta tac ggc ggc agg tgc ggc tat atc      144
Cys Cys Met Tyr Asp Glu Ala Val Tyr Gly Gly Arg Cys Gly Tyr Ile
        35                  40                  45

aaa aca ccc ggc atg cgg ggg cgc gtg acg gtg ttt ctc tcg ggc aag      192
Lys Thr Pro Gly Met Arg Gly Arg Val Thr Val Phe Leu Ser Gly Lys
    50                  55                  60

atg ata tcc gtc ggc gcc agc tcc gtg agg gca tcg ttt gcg cag ctg      240
Met Ile Ser Val Gly Ala Ser Ser Val Arg Ala Ser Phe Ala Gln Leu
 65                  70                  75                  80

cac gag gcc cgg ctg cac ctg ttc cgg aac ggg gcg gcg gcc ggc ggg      288
His Glu Ala Arg Leu His Leu Phe Arg Asn Gly Ala Ala Ala Gly Gly
                85                  90                  95

tgt aca agg ccc gtc gta cgc aat atg gtg gcg aca gtg gat gca gga      336
Cys Thr Arg Pro Val Val Arg Asn Met Val Ala Thr Val Asp Ala Gly
            100                 105                 110

cgg act gtt ccc ata gac agg ata tcg tcg cgg ata ccc ggc gcg gtg      384
Arg Thr Val Pro Ile Asp Arg Ile Ser Ser Arg Ile Pro Gly Ala Val
        115                 120                 125

tac gac ccg ggg tcg ttt ccc ggc atg ata cta aag ggg ctg ggc agc      432
Tyr Asp Pro Gly Ser Phe Pro Gly Met Ile Leu Lys Gly Leu Gly Ser
    130                 135                 140

tgc agc ttc ctt gtg ttt gcg tcg gga aag gtg gtg ata gcg ggc gcc      480
Cys Ser Phe Leu Val Phe Ala Ser Gly Lys Val Val Ile Ala Gly Ala
145                 150                 155                 160

cgg tcg cca ggc gag cta tac agg tcg tcg ttt gac ctg ctg gcg cgc      528
Arg Ser Pro Gly Glu Leu Tyr Arg Ser Ser Phe Asp Leu Leu Ala Arg
                165                 170                 175

ctc aac ggc gcg ggc gcc tag                                          549
Leu Asn Gly Ala Gly Ala
            180
```

<210> SEQ ID NO 28
<211> LENGTH: 182
<212> TYPE: PRT
<213> ORGANISM: Cenarchaeum symbiosum

<400> SEQUENCE: 28

```
Met Leu Asp Pro Arg Lys Arg Pro Arg Val Val Asn Val Val Ser Thr
```

-continued

```
 1               5                   10                  15

Ala Asp Leu Gly Arg Arg Val Gly Ala Lys Lys Met Ala Ala Met Pro
            20                  25                  30

Cys Cys Met Tyr Asp Glu Ala Val Tyr Gly Gly Arg Cys Gly Tyr Ile
        35                  40                  45

Lys Thr Pro Gly Met Arg Gly Arg Val Thr Val Phe Leu Ser Gly Lys
    50                  55                  60

Met Ile Ser Val Gly Ala Ser Ser Val Arg Ala Ser Phe Ala Gln Leu
65                  70                  75                  80

His Glu Ala Arg Leu His Leu Phe Arg Asn Gly Ala Ala Ala Gly Gly
                85                  90                  95

Cys Thr Arg Pro Val Val Arg Asn Met Val Ala Thr Val Asp Ala Gly
            100                 105                 110

Arg Thr Val Pro Ile Asp Arg Ile Ser Ser Arg Ile Pro Gly Ala Val
        115                 120                 125

Tyr Asp Pro Gly Ser Phe Pro Gly Met Ile Leu Lys Gly Leu Gly Ser
    130                 135                 140

Cys Ser Phe Leu Val Phe Ala Ser Gly Lys Val Val Ile Ala Gly Ala
145                 150                 155                 160

Arg Ser Pro Gly Glu Leu Tyr Arg Ser Ser Phe Asp Leu Leu Ala Arg
                165                 170                 175

Leu Asn Gly Ala Gly Ala
            180


<210> SEQ ID NO 29
<211> LENGTH: 2535
<212> TYPE: DNA
<213> ORGANISM: Cenarchaeum symbiosum
<220> FEATURE:
<221> NAME/KEY: CDS
<222> LOCATION: (1)...(2535)

<400> SEQUENCE: 29

gtg acg gtg caa gat gcc gta gag ata ccc ccg tcg ctg ctg gta tct       48
Met Thr Val Gln Asp Ala Val Glu Ile Pro Pro Ser Leu Leu Val Ser
 1               5                   10                  15

gca aca tac gac agc cag gca ggg gcg gtc gtc ctc aag ttt tac gag       96
Ala Thr Tyr Asp Ser Gln Ala Gly Ala Val Val Leu Lys Phe Tyr Glu
             20                  25                  30

ccg gaa tca caa aag atc gta cac tgg acg gac aat acg ggg cac aag      144
Pro Glu Ser Gln Lys Ile Val His Trp Thr Asp Asn Thr Gly His Lys
         35                  40                  45

ccc tac tgc tat acg agg cag ccc ccc tcc gag ctt ggg gag ctt gaa      192
Pro Tyr Cys Tyr Thr Arg Gln Pro Pro Ser Glu Leu Gly Glu Leu Glu
     50                  55                  60

ggc agg gag gat gtg cta gga acg gag cag gtc atg cgg cac gac ctg      240
Gly Arg Glu Asp Val Leu Gly Thr Glu Gln Val Met Arg His Asp Leu
 65                  70                  75                  80

ata gcc gac aag gat gtg ccc gtc acc aag ata act gtg gcc gac ccc      288
Ile Ala Asp Lys Asp Val Pro Val Thr Lys Ile Thr Val Ala Asp Pro
                 85                  90                  95

ctt gcc ata ggc ggg acc aac tcg gag aag agc atc cgc aac atc atg      336
Leu Ala Ile Gly Gly Thr Asn Ser Glu Lys Ser Ile Arg Asn Ile Met
            100                 105                 110

gac acg tgg gaa tcc gac ata aag tac tat gag aac tat ctg tac gac      384
Asp Thr Trp Glu Ser Asp Ile Lys Tyr Tyr Glu Asn Tyr Leu Tyr Asp
        115                 120                 125

aag agc ctg gtc gtg ggc agg tac tat tcg gta tcc ggc ggc aag gta      432
```

-continued

```
Lys Ser Leu Val Val Gly Arg Tyr Tyr Ser Val Ser Gly Gly Lys Val
    130                 135                 140

atc ccg cat gac atg ccc ata tcc gac gag gta aag ctg gcc ctc aag        480
Ile Pro His Asp Met Pro Ile Ser Asp Glu Val Lys Leu Ala Leu Lys
145                 150                 155                 160

agc ctc ctc tgg gac aag gtt gta gac gag ggc atg gcg gac aga aaa        528
Ser Leu Leu Trp Asp Lys Val Val Asp Glu Gly Met Ala Asp Arg Lys
                165                 170                 175

gag ttc cgc gag ttc ata gcg ggg tgg gcg gac ctg ctc aac cag ccc        576
Glu Phe Arg Glu Phe Ile Ala Gly Trp Ala Asp Leu Leu Asn Gln Pro
            180                 185                 190

ata ccc agg ata cgg cgc ctc agc ttt gat atc gag gtg gat tca gag        624
Ile Pro Arg Ile Arg Arg Leu Ser Phe Asp Ile Glu Val Asp Ser Glu
        195                 200                 205

gag ggc agg atc ccc gac ccc aag ata tcc gac agg agg gtt acg gcg        672
Glu Gly Arg Ile Pro Asp Pro Lys Ile Ser Asp Arg Arg Val Thr Ala
    210                 215                 220

gtg ggg ttt gcc gcc acc gac ggc cta aaa cag gta ttc gtc ctg agg        720
Val Gly Phe Ala Ala Thr Asp Gly Leu Lys Gln Val Phe Val Leu Arg
225                 230                 235                 240

agc ggc gca gaa gag ggc gag aac ggc gtg acc ccc ggt gtc gag gtg        768
Ser Gly Ala Glu Glu Gly Glu Asn Gly Val Thr Pro Gly Val Glu Val
                245                 250                 255

gta ttc tac gac aag gaa gct gac atg atc cgc gac gcg cta tcg gta        816
Val Phe Tyr Asp Lys Glu Ala Asp Met Ile Arg Asp Ala Leu Ser Val
            260                 265                 270

ata ggc tcg tac ccg ttt gtt ctg acg tac aac ggc gac gac ttt gac        864
Ile Gly Ser Tyr Pro Phe Val Leu Thr Tyr Asn Gly Asp Asp Phe Asp
        275                 280                 285

atg ccg tac atg ctc aac agg gca cgg cgc ctc gga gta tct gac tct        912
Met Pro Tyr Met Leu Asn Arg Ala Arg Arg Leu Gly Val Ser Asp Ser
    290                 295                 300

gac att cct ttg tac atg atg cgg gat tct gcc acg ctc cgg cac gga        960
Asp Ile Pro Leu Tyr Met Met Arg Asp Ser Ala Thr Leu Arg His Gly
305                 310                 315                 320

gtc cac ctg gac ctg tac agg acc ttc tcg aac agg tca ttc cag ctg       1008
Val His Leu Asp Leu Tyr Arg Thr Phe Ser Asn Arg Ser Phe Gln Leu
                325                 330                 335

tac gcc ttt gcg gca aag tac acg gac tat tcc ctt aac agc gtc aca       1056
Tyr Ala Phe Ala Ala Lys Tyr Thr Asp Tyr Ser Leu Asn Ser Val Thr
            340                 345                 350

aag gcg atg ctc ggc gag ggc aag gtc gac tat ggg gtc aaa ctg ggg       1104
Lys Ala Met Leu Gly Glu Gly Lys Val Asp Tyr Gly Val Lys Leu Gly
        355                 360                 365

gat ctc acc tta tac cag act gca aac tat tgc tat cac gac gcg cgc       1152
Asp Leu Thr Leu Tyr Gln Thr Ala Asn Tyr Cys Tyr His Asp Ala Arg
    370                 375                 380

ctg acg ctc gag ctt agc acc ttt ggc aac gag ata ctc atg gac ctg       1200
Leu Thr Leu Glu Leu Ser Thr Phe Gly Asn Glu Ile Leu Met Asp Leu
385                 390                 395                 400

ctg gtg gtg acc agc aga ata gcc cgg atg ccc atc gat gac atg tcc       1248
Leu Val Val Thr Ser Arg Ile Ala Arg Met Pro Ile Asp Asp Met Ser
                405                 410                 415

cgc atg ggc gtc tcg cag tgg ata cgc agc ctg ctg tac tat gag cac       1296
Arg Met Gly Val Ser Gln Trp Ile Arg Ser Leu Leu Tyr Tyr Glu His
            420                 425                 430

aga cag cga aac gcg ctc ata ccg cgg agg gac gag ctg gag ggc agg       1344
Arg Gln Arg Asn Ala Leu Ile Pro Arg Arg Asp Glu Leu Glu Gly Arg
        435                 440                 445
```

-continued

```
tcg cgc gag gtg agc aac gac gcg gta ata aag gat aaa aag ttc cgc      1392
Ser Arg Glu Val Ser Asn Asp Ala Val Ile Lys Asp Lys Lys Phe Arg
    450                 455                 460

ggg ggc ctt gtc gtc gag cct gaa gag ggc ata cac ttt gat gtt acg      1440
Gly Gly Leu Val Val Glu Pro Glu Glu Gly Ile His Phe Asp Val Thr
465                 470                 475                 480

gtg atg gac ttt gcg agc ctg tat ccc agt atc ata aag gtg agg aac      1488
Val Met Asp Phe Ala Ser Leu Tyr Pro Ser Ile Ile Lys Val Arg Asn
                485                 490                 495

ctc tcg tac gag acc gtc cgg tgc gtg cat gca gaa tgc aaa aag aac      1536
Leu Ser Tyr Glu Thr Val Arg Cys Val His Ala Glu Cys Lys Lys Asn
            500                 505                 510

acc atc ccc gat acc aac cac tgg gta tgt aca aaa aac aac ggc ctg      1584
Thr Ile Pro Asp Thr Asn His Trp Val Cys Thr Lys Asn Asn Gly Leu
        515                 520                 525

aca tcg atg ata atc ggc tcg ctg cgg gac ctg cgc gtc aac tat tac      1632
Thr Ser Met Ile Ile Gly Ser Leu Arg Asp Leu Arg Val Asn Tyr Tyr
    530                 535                 540

aag agc ctc tca aag agc aca tcc att acg gag gag cag cgg cag cag      1680
Lys Ser Leu Ser Lys Ser Thr Ser Ile Thr Glu Glu Gln Arg Gln Gln
545                 550                 555                 560

tat acc gta atc agc cag gcc ctc aag gtc gtg ctc aac gca agc tac      1728
Tyr Thr Val Ile Ser Gln Ala Leu Lys Val Val Leu Asn Ala Ser Tyr
                565                 570                 575

ggc gtg atg ggc gcc gag ata ttc ccg ctg tac ttt tta ccc gcg gca      1776
Gly Val Met Gly Ala Glu Ile Phe Pro Leu Tyr Phe Leu Pro Ala Ala
            580                 585                 590

gag gcc acc act gct gtc ggg cgc tat atc atc atg cag acg ata tcg      1824
Glu Ala Thr Thr Ala Val Gly Arg Tyr Ile Ile Met Gln Thr Ile Ser
        595                 600                 605

cac tgc gag cag atg gga gtg agg gtg ctg tac ggg gac acc gat tct      1872
His Cys Glu Gln Met Gly Val Arg Val Leu Tyr Gly Asp Thr Asp Ser
    610                 615                 620

ctg ttc ata aag gat ccc gaa gag agg cag atc cac gag ata gtc gag      1920
Leu Phe Ile Lys Asp Pro Glu Glu Arg Gln Ile His Glu Ile Val Glu
625                 630                 635                 640

cat gca aag aag gag cac ggt gtg gag ctc gaa gtg gac aaa gag tac      1968
His Ala Lys Lys Glu His Gly Val Glu Leu Glu Val Asp Lys Glu Tyr
                645                 650                 655

agg tat gtc gtg cta tcc aac agg aaa aaa aac tat ttc ggg gtg acc      2016
Arg Tyr Val Val Leu Ser Asn Arg Lys Lys Asn Tyr Phe Gly Val Thr
            660                 665                 670

cgg gca ggc aag gtc gac gtc aag ggg ctg acg ggc aaa aag tcg cac      2064
Arg Ala Gly Lys Val Asp Val Lys Gly Leu Thr Gly Lys Lys Ser His
        675                 680                 685

acg ccc ccg ttc ata aag gag ctc ttc tac tcg ctg ctc gac ata ctc      2112
Thr Pro Pro Phe Ile Lys Glu Leu Phe Tyr Ser Leu Leu Asp Ile Leu
    690                 695                 700

tca gga gtc gag agc gag gac gag ttc gag tca gcc aag atg agg atc      2160
Ser Gly Val Glu Ser Glu Asp Glu Phe Glu Ser Ala Lys Met Arg Ile
705                 710                 715                 720

tca aag gcg atc gcc gcg tgc ggc aag agg ctc gag gag agg cag atc      2208
Ser Lys Ala Ile Ala Ala Cys Gly Lys Arg Leu Glu Glu Arg Gln Ile
                725                 730                 735

ccc ctc gtg gac ctg gcg ttc aat gtg atg ata agc aag gcg ccc tcc      2256
Pro Leu Val Asp Leu Ala Phe Asn Val Met Ile Ser Lys Ala Pro Ser
            740                 745                 750

gaa tat gtc aag acc gtc ccg cag cac ata cgg gcg gca agg ctg ctg      2304
Glu Tyr Val Lys Thr Val Pro Gln His Ile Arg Ala Ala Arg Leu Leu
        755                 760                 765
```

-continued

```
gag aac gca agg gag gtc aaa aag ggc gac ata ata tcg tac gta aag      2352
Glu Asn Ala Arg Glu Val Lys Lys Gly Asp Ile Ile Ser Tyr Val Lys
    770                 775                 780

gtg atg aac aag acc ggc gtc aag ccg gtg gag atg gcc cgg gca ggc      2400
Val Met Asn Lys Thr Gly Val Lys Pro Val Glu Met Ala Arg Ala Gly
785                 790                 795                 800

gag gtg gac acg tca aag tac ctc gag ttc atg gag tcg acg ctc gac      2448
Glu Val Asp Thr Ser Lys Tyr Leu Glu Phe Met Glu Ser Thr Leu Asp
                805                 810                 815

cag ctc acc tcg tcc atg ggc ctt gac ttt gac gag ata ctc ggc aag      2496
Gln Leu Thr Ser Ser Met Gly Leu Asp Phe Asp Glu Ile Leu Gly Lys
            820                 825                 830

cca aag cag acc ggc atg gag cag ttc ttt ttc aaa tga                  2535
Pro Lys Gln Thr Gly Met Glu Gln Phe Phe Phe Lys
        835                 840
```

<210> SEQ ID NO 30
<211> LENGTH: 844
<212> TYPE: PRT
<213> ORGANISM: Cenarchaeum symbiosum

<400> SEQUENCE: 30

```
Met Thr Val Gln Asp Ala Val Glu Ile Pro Pro Ser Leu Leu Val Ser
 1               5                  10                  15

Ala Thr Tyr Asp Ser Gln Ala Gly Ala Val Val Leu Lys Phe Tyr Glu
            20                  25                  30

Pro Glu Ser Gln Lys Ile Val His Trp Thr Asp Asn Thr Gly His Lys
        35                  40                  45

Pro Tyr Cys Tyr Thr Arg Gln Pro Pro Ser Glu Leu Gly Glu Leu Glu
    50                  55                  60

Gly Arg Glu Asp Val Leu Gly Thr Glu Gln Val Met Arg His Asp Leu
65                  70                  75                  80

Ile Ala Asp Lys Asp Val Pro Val Thr Lys Ile Thr Val Ala Asp Pro
                85                  90                  95

Leu Ala Ile Gly Gly Thr Asn Ser Glu Lys Ser Ile Arg Asn Ile Met
            100                 105                 110

Asp Thr Trp Glu Ser Asp Ile Lys Tyr Tyr Glu Asn Tyr Leu Tyr Asp
        115                 120                 125

Lys Ser Leu Val Val Gly Arg Tyr Tyr Ser Val Ser Gly Gly Lys Val
    130                 135                 140

Ile Pro His Asp Met Pro Ile Ser Asp Glu Val Lys Leu Ala Leu Lys
145                 150                 155                 160

Ser Leu Leu Trp Asp Lys Val Val Asp Glu Gly Met Ala Asp Arg Lys
                165                 170                 175

Glu Phe Arg Glu Phe Ile Ala Gly Trp Ala Asp Leu Leu Asn Gln Pro
            180                 185                 190

Ile Pro Arg Ile Arg Arg Leu Ser Phe Asp Ile Glu Val Asp Ser Glu
        195                 200                 205

Glu Gly Arg Ile Pro Asp Pro Lys Ile Ser Asp Arg Arg Val Thr Ala
    210                 215                 220

Val Gly Phe Ala Ala Thr Asp Gly Leu Lys Gln Val Phe Val Leu Arg
225                 230                 235                 240

Ser Gly Ala Glu Glu Gly Glu Asn Gly Val Thr Pro Gly Val Glu Val
                245                 250                 255

Val Phe Tyr Asp Lys Glu Ala Asp Met Ile Arg Asp Ala Leu Ser Val
            260                 265                 270
```

-continued

```
Ile Gly Ser Tyr Pro Phe Val Leu Thr Tyr Asn Gly Asp Asp Phe Asp
        275                 280                 285

Met Pro Tyr Met Leu Asn Arg Ala Arg Arg Leu Gly Val Ser Asp Ser
    290                 295                 300

Asp Ile Pro Leu Tyr Met Met Arg Asp Ser Ala Thr Leu Arg His Gly
305                 310                 315                 320

Val His Leu Asp Leu Tyr Arg Thr Phe Ser Asn Arg Ser Phe Gln Leu
                325                 330                 335

Tyr Ala Phe Ala Ala Lys Tyr Thr Asp Tyr Ser Leu Asn Ser Val Thr
            340                 345                 350

Lys Ala Met Leu Gly Glu Gly Lys Val Asp Tyr Gly Val Lys Leu Gly
        355                 360                 365

Asp Leu Thr Leu Tyr Gln Thr Ala Asn Tyr Cys Tyr His Asp Ala Arg
    370                 375                 380

Leu Thr Leu Glu Leu Ser Thr Phe Gly Asn Glu Ile Leu Met Asp Leu
385                 390                 395                 400

Leu Val Val Thr Ser Arg Ile Ala Arg Met Pro Ile Asp Asp Met Ser
                405                 410                 415

Arg Met Gly Val Ser Gln Trp Ile Arg Ser Leu Leu Tyr Tyr Glu His
            420                 425                 430

Arg Gln Arg Asn Ala Leu Ile Pro Arg Arg Asp Glu Leu Glu Gly Arg
        435                 440                 445

Ser Arg Glu Val Ser Asn Asp Ala Val Ile Lys Asp Lys Lys Phe Arg
    450                 455                 460

Gly Gly Leu Val Val Glu Pro Glu Glu Gly Ile His Phe Asp Val Thr
465                 470                 475                 480

Val Met Asp Phe Ala Ser Leu Tyr Pro Ser Ile Ile Lys Val Arg Asn
                485                 490                 495

Leu Ser Tyr Glu Thr Val Arg Cys Val His Ala Glu Cys Lys Lys Asn
            500                 505                 510

Thr Ile Pro Asp Thr Asn His Trp Val Cys Thr Lys Asn Asn Gly Leu
        515                 520                 525

Thr Ser Met Ile Ile Gly Ser Leu Arg Asp Leu Arg Val Asn Tyr Tyr
    530                 535                 540

Lys Ser Leu Ser Lys Ser Thr Ser Ile Thr Glu Glu Gln Arg Gln Gln
545                 550                 555                 560

Tyr Thr Val Ile Ser Gln Ala Leu Lys Val Val Leu Asn Ala Ser Tyr
                565                 570                 575

Gly Val Met Gly Ala Glu Ile Phe Pro Leu Tyr Phe Leu Pro Ala Ala
            580                 585                 590

Glu Ala Thr Thr Ala Val Gly Arg Tyr Ile Ile Met Gln Thr Ile Ser
        595                 600                 605

His Cys Glu Gln Met Gly Val Arg Val Leu Tyr Gly Asp Thr Asp Ser
    610                 615                 620

Leu Phe Ile Lys Asp Pro Glu Glu Arg Gln Ile His Glu Ile Val Glu
625                 630                 635                 640

His Ala Lys Lys Glu His Gly Val Glu Leu Glu Val Asp Lys Glu Tyr
                645                 650                 655

Arg Tyr Val Val Leu Ser Asn Arg Lys Lys Asn Tyr Phe Gly Val Thr
            660                 665                 670

Arg Ala Gly Lys Val Asp Val Lys Gly Leu Thr Gly Lys Lys Ser His
        675                 680                 685
```

-continued

```
Thr Pro Pro Phe Ile Lys Glu Leu Phe Tyr Ser Leu Leu Asp Ile Leu
    690                 695                 700

Ser Gly Val Glu Ser Glu Asp Glu Phe Glu Ser Ala Lys Met Arg Ile
705                 710                 715                 720

Ser Lys Ala Ile Ala Ala Cys Gly Lys Arg Leu Glu Glu Arg Gln Ile
                725                 730                 735

Pro Leu Val Asp Leu Ala Phe Asn Val Met Ile Ser Lys Ala Pro Ser
            740                 745                 750

Glu Tyr Val Lys Thr Val Pro Gln His Ile Arg Ala Ala Arg Leu Leu
        755                 760                 765

Glu Asn Ala Arg Glu Val Lys Lys Gly Asp Ile Ile Ser Tyr Val Lys
    770                 775                 780

Val Met Asn Lys Thr Gly Val Lys Pro Val Glu Met Ala Arg Ala Gly
785                 790                 795                 800

Glu Val Asp Thr Ser Lys Tyr Leu Glu Phe Met Glu Ser Thr Leu Asp
                805                 810                 815

Gln Leu Thr Ser Ser Met Gly Leu Asp Phe Asp Glu Ile Leu Gly Lys
            820                 825                 830

Pro Lys Gln Thr Gly Met Glu Gln Phe Phe Phe Lys
        835                 840


<210> SEQ ID NO 31
<211> LENGTH: 555
<212> TYPE: DNA
<213> ORGANISM: Cenarchaeum symbiosum
<220> FEATURE:
<221> NAME/KEY: CDS
<222> LOCATION: (1)...(555)

<400> SEQUENCE: 31

atg ccg ggc ggg ggc agg ctg ccc gtg agc ggc ttt gag cgc cct acc       48
Met Pro Gly Gly Gly Arg Leu Pro Val Ser Gly Phe Glu Arg Pro Thr
 1               5                  10                  15

tgg gat gaa tat ttc atg ctg cag gcg gag ctt gca aag ctc cga tcc       96
Trp Asp Glu Tyr Phe Met Leu Gln Ala Glu Leu Ala Lys Leu Arg Ser
            20                  25                  30

aac tgt ata gtc cgc aag gtg ggg gcc gta ata gtg agg gac cac cgg      144
Asn Cys Ile Val Arg Lys Val Gly Ala Val Ile Val Arg Asp His Arg
        35                  40                  45

cag ctc gcc aca ggg tat aac ggg acg cct cct ggc gtc aag aac tgc      192
Gln Leu Ala Thr Gly Tyr Asn Gly Thr Pro Pro Gly Val Lys Asn Cys
    50                  55                  60

tac gag ggc ggc tgc gag agg tgt gcc gag cgc atc gag ggc agg atc      240
Tyr Glu Gly Gly Cys Glu Arg Cys Ala Glu Arg Ile Glu Gly Arg Ile
 65                  70                  75                  80

aag tca ggc gag gcc ctg gac cgg tgc ctg tgc aac cat gca gag gcc      288
Lys Ser Gly Glu Ala Leu Asp Arg Cys Leu Cys Asn His Ala Glu Ala
                85                  90                  95

aac gct ata atg cac tgt gcg ata ctc ggg ata ggc gcg ggg ggc ggg      336
Asn Ala Ile Met His Cys Ala Ile Leu Gly Ile Gly Ala Gly Gly Gly
            100                 105                 110

ggg gcc acc atg tac acc acg ttc tcg ccg tgt ctg gag tgt acc aag      384
Gly Ala Thr Met Tyr Thr Thr Phe Ser Pro Cys Leu Glu Cys Thr Lys
        115                 120                 125

atg gcc gta acg ata ggg atc agg cgg ttt gtc tgc ctt gat acc tac      432
Met Ala Val Thr Ile Gly Ile Arg Arg Phe Val Cys Leu Asp Thr Tyr
    130                 135                 140

ccc gag aac acc tcc cgg ctg gta aaa gag aca tcc tcc gag ata acc      480
Pro Glu Asn Thr Ser Arg Leu Val Lys Glu Thr Ser Ser Glu Ile Thr
```

-continued

```
145                 150                 155                 160

atg atg gac aag gaa aag atc tcg tac tgg gcg tca agg atg ccc gga      528
Met Met Asp Lys Glu Lys Ile Ser Tyr Trp Ala Ser Arg Met Pro Gly
                165                 170                 175

ggc agc aag gag gtg ccg gtg cgg tga                                  555
Gly Ser Lys Glu Val Pro Val Arg
            180


<210> SEQ ID NO 32
<211> LENGTH: 184
<212> TYPE: PRT
<213> ORGANISM: Cenarchaeum symbiosum

<400> SEQUENCE: 32

Met Pro Gly Gly Gly Arg Leu Pro Val Ser Gly Phe Glu Arg Pro Thr
 1               5                  10                  15

Trp Asp Glu Tyr Phe Met Leu Gln Ala Glu Leu Ala Lys Leu Arg Ser
            20                  25                  30

Asn Cys Ile Val Arg Lys Val Gly Ala Val Ile Val Arg Asp His Arg
        35                  40                  45

Gln Leu Ala Thr Gly Tyr Asn Gly Thr Pro Pro Gly Val Lys Asn Cys
    50                  55                  60

Tyr Glu Gly Gly Cys Glu Arg Cys Ala Glu Arg Ile Glu Gly Arg Ile
65                  70                  75                  80

Lys Ser Gly Glu Ala Leu Asp Arg Cys Leu Cys Asn His Ala Glu Ala
                85                  90                  95

Asn Ala Ile Met His Cys Ala Ile Leu Gly Ile Gly Ala Gly Gly Gly
            100                 105                 110

Gly Ala Thr Met Tyr Thr Thr Phe Ser Pro Cys Leu Glu Cys Thr Lys
        115                 120                 125

Met Ala Val Thr Ile Gly Ile Arg Arg Phe Val Cys Leu Asp Thr Tyr
    130                 135                 140

Pro Glu Asn Thr Ser Arg Leu Val Lys Glu Thr Ser Ser Glu Ile Thr
145                 150                 155                 160

Met Met Asp Lys Glu Lys Ile Ser Tyr Trp Ala Ser Arg Met Pro Gly
                165                 170                 175

Gly Ser Lys Glu Val Pro Val Arg
            180


<210> SEQ ID NO 33
<211> LENGTH: 1509
<212> TYPE: DNA
<213> ORGANISM: Cenarchaeum symbiosum
<220> FEATURE:
<221> NAME/KEY: CDS
<222> LOCATION: (1)...(1509)

<400> SEQUENCE: 33

gtg gag act ggg cac ata acg ggc agg tac atc gag ccc ggt gcc gtc       48
Met Glu Thr Gly His Ile Thr Gly Arg Tyr Ile Glu Pro Gly Ala Val
 1               5                  10                  15

gag agg cgc gac tac cag gtg ggc ctg gcg gaa cag gcc ata cgg gag       96
Glu Arg Arg Asp Tyr Gln Val Gly Leu Ala Glu Gln Ala Ile Arg Glu
            20                  25                  30

aac tgt atc gtg gtg ctc ccg acg ggc ctc ggc aag act gcc gtc gcc      144
Asn Cys Ile Val Val Leu Pro Thr Gly Leu Gly Lys Thr Ala Val Ala
        35                  40                  45

ctc cag gtg atc gcc cac tat ctc gac gag ggc cgc ggg gcg ctc ttc      192
Leu Gln Val Ile Ala His Tyr Leu Asp Glu Gly Arg Gly Ala Leu Phe
```

-continued

```
    50                  55                  60

ctt gcc cct aca agg gtc ctg gta aac cag cac cgc cag ttc ctg ggc      240
Leu Ala Pro Thr Arg Val Leu Val Asn Gln His Arg Gln Phe Leu Gly
 65                  70                  75                  80

agg gcc ctt acc ata tcc gat att aca ctg gtc acg gga gag gac acc      288
Arg Ala Leu Thr Ile Ser Asp Ile Thr Leu Val Thr Gly Glu Asp Thr
                 85                  90                  95

att ccc cgg cgc aaa aag gcg tgg gga ggc agc gtg atc tgc gcc acg      336
Ile Pro Arg Arg Lys Lys Ala Trp Gly Gly Ser Val Ile Cys Ala Thr
            100                 105                 110

ccc gag ata gca aga aat gat ata gag cgc ggc ctg gtc ccg ctc gaa      384
Pro Glu Ile Ala Arg Asn Asp Ile Glu Arg Gly Leu Val Pro Leu Glu
        115                 120                 125

cag ttc ggc ctg gtc ata ttc gac gag gcc cac agg gcg gtg ggc gac      432
Gln Phe Gly Leu Val Ile Phe Asp Glu Ala His Arg Ala Val Gly Asp
    130                 135                 140

tat gcc tat tct tcc ata gcg cgg gcg gta ggg gat aac tcc agg atg      480
Tyr Ala Tyr Ser Ser Ile Ala Arg Ala Val Gly Asp Asn Ser Arg Met
145                 150                 155                 160

gtg ggc atg act gcg acg ctt ccc agc gag agg gag aag gca gac gag      528
Val Gly Met Thr Ala Thr Leu Pro Ser Glu Arg Glu Lys Ala Asp Glu
                165                 170                 175

ata atg ggc acc ctg ctc tcc agg agc ata gcc cag agg aca gaa gac      576
Ile Met Gly Thr Leu Leu Ser Arg Ser Ile Ala Gln Arg Thr Glu Asp
            180                 185                 190

gac ccg gac gta aag ccc tat gta cag gag act gcc acc gag tgg ata      624
Asp Pro Asp Val Lys Pro Tyr Val Gln Glu Thr Ala Thr Glu Trp Ile
        195                 200                 205

aag gtg gat ctt ccc ccc gag atg aag gag ata cag agg ctc ctc aag      672
Lys Val Asp Leu Pro Pro Glu Met Lys Glu Ile Gln Arg Leu Leu Lys
    210                 215                 220

ctg gcc ctc gac gag agg tat tcc tcc ctc aag agg tgc ggg tac gat      720
Leu Ala Leu Asp Glu Arg Tyr Ser Ser Leu Lys Arg Cys Gly Tyr Asp
225                 230                 235                 240

ctt ggc tcg aac agg tcg ctc tcg gcg ctg ctc cgg ctg cgc atg gtg      768
Leu Gly Ser Asn Arg Ser Leu Ser Ala Leu Leu Arg Leu Arg Met Val
                245                 250                 255

gtg ctt ggc ggc aac agg cgc gcg gcc aag ccg ctg ttc act gcg ata      816
Val Leu Gly Gly Asn Arg Arg Ala Ala Lys Pro Leu Phe Thr Ala Ile
            260                 265                 270

cgc ata acg tac gcg cta aac ata ttc gag gcg cac ggg gtc acg ccc      864
Arg Ile Thr Tyr Ala Leu Asn Ile Phe Glu Ala His Gly Val Thr Pro
        275                 280                 285

ttt cta aag ttc tgc gag agg acc tcc aag aaa aag ggc gtc ggc gtg      912
Phe Leu Lys Phe Cys Glu Arg Thr Ser Lys Lys Lys Gly Val Gly Val
    290                 295                 300

gcg gag ctg ttc gaa cag gac cgg aac ttt aca ggg gcc atc gcg cgc      960
Ala Glu Leu Phe Glu Gln Asp Arg Asn Phe Thr Gly Ala Ile Ala Arg
305                 310                 315                 320

gca aag gcc gcg cag gcg gca ggc atg gag cat ccc aag ata cca aag     1008
Ala Lys Ala Ala Gln Ala Ala Gly Met Glu His Pro Lys Ile Pro Lys
                325                 330                 335

ctc gag gat gcc gtc cgc ggg gcc cgg gga aag gcg ctg gtc ttt acg     1056
Leu Glu Asp Ala Val Arg Gly Ala Arg Gly Lys Ala Leu Val Phe Thr
            340                 345                 350

agc tat cgt gat tct gtc gac ctc ata cac tca aga ctc aag gcg gcc     1104
Ser Tyr Arg Asp Ser Val Asp Leu Ile His Ser Arg Leu Lys Ala Ala
        355                 360                 365

ggg ata aac tcg ggc atc ctg ata gga aag gcg gga gaa aag ggc cta     1152
```

-continued

```
Gly Ile Asn Ser Gly Ile Leu Ile Gly Lys Ala Gly Glu Lys Gly Leu
    370                 375                 380

aag cag aga aaa cag gtg gag act gtg gca aag ttc cgt gac ggc ggg     1200
Lys Gln Arg Lys Gln Val Glu Thr Val Ala Lys Phe Arg Asp Gly Gly
385                 390                 395                 400

tac gac gtg ctg gta tcg acg agg gtc ggc gag gag ggg ctc gac ata     1248
Tyr Asp Val Leu Val Ser Thr Arg Val Gly Glu Glu Gly Leu Asp Ile
                405                 410                 415

tcg gag gtc aac ctg gtg ata ttc tat gac aat gtg cca agc tcg atc     1296
Ser Glu Val Asn Leu Val Ile Phe Tyr Asp Asn Val Pro Ser Ser Ile
            420                 425                 430

agg tac gtg cag agg agg ggg aga aca ggc aga aag gac gcc ggc agg     1344
Arg Tyr Val Gln Arg Arg Gly Arg Thr Gly Arg Lys Asp Ala Gly Arg
        435                 440                 445

ctg ata gta ttg atg gca aag ggg acg ata gac gag gca tac tat tgg     1392
Leu Ile Val Leu Met Ala Lys Gly Thr Ile Asp Glu Ala Tyr Tyr Trp
    450                 455                 460

att ggt cgg cgc aag atg agc gcc gcc aag ggc atg ggt gag agg atg     1440
Ile Gly Arg Arg Lys Met Ser Ala Ala Lys Gly Met Gly Glu Arg Met
465                 470                 475                 480

aac cgg tcg ctg gcg gca ggc ggg gct gct gcc aag gcc gct cca aag     1488
Asn Arg Ser Leu Ala Ala Gly Gly Ala Ala Ala Lys Ala Ala Pro Lys
                485                 490                 495

gga ctc gag ggg tac ttt tag                                         1509
Gly Leu Glu Gly Tyr Phe
            500


<210> SEQ ID NO 34
<211> LENGTH: 502
<212> TYPE: PRT
<213> ORGANISM: Cenarchaeum symbiosum

<400> SEQUENCE: 34

Met Glu Thr Gly His Ile Thr Gly Arg Tyr Ile Glu Pro Gly Ala Val
 1               5                  10                  15

Glu Arg Arg Asp Tyr Gln Val Gly Leu Ala Glu Gln Ala Ile Arg Glu
            20                  25                  30

Asn Cys Ile Val Val Leu Pro Thr Gly Leu Gly Lys Thr Ala Val Ala
        35                  40                  45

Leu Gln Val Ile Ala His Tyr Leu Asp Glu Gly Arg Gly Ala Leu Phe
    50                  55                  60

Leu Ala Pro Thr Arg Val Leu Val Asn Gln His Arg Gln Phe Leu Gly
65                  70                  75                  80

Arg Ala Leu Thr Ile Ser Asp Ile Thr Leu Val Thr Gly Glu Asp Thr
                85                  90                  95

Ile Pro Arg Arg Lys Lys Ala Trp Gly Gly Ser Val Ile Cys Ala Thr
            100                 105                 110

Pro Glu Ile Ala Arg Asn Asp Ile Glu Arg Gly Leu Val Pro Leu Glu
        115                 120                 125

Gln Phe Gly Leu Val Ile Phe Asp Glu Ala His Arg Ala Val Gly Asp
    130                 135                 140

Tyr Ala Tyr Ser Ser Ile Ala Arg Ala Val Gly Asp Asn Ser Arg Met
145                 150                 155                 160

Val Gly Met Thr Ala Thr Leu Pro Ser Glu Arg Glu Lys Ala Asp Glu
                165                 170                 175

Ile Met Gly Thr Leu Leu Ser Arg Ser Ile Ala Gln Arg Thr Glu Asp
            180                 185                 190
```

-continued

```
Asp Pro Asp Val Lys Pro Tyr Val Gln Glu Thr Ala Thr Glu Trp Ile
        195                 200                 205

Lys Val Asp Leu Pro Pro Glu Met Lys Glu Ile Gln Arg Leu Leu Lys
    210                 215                 220

Leu Ala Leu Asp Glu Arg Tyr Ser Ser Leu Lys Arg Cys Gly Tyr Asp
225                 230                 235                 240

Leu Gly Ser Asn Arg Ser Leu Ser Ala Leu Leu Arg Leu Arg Met Val
                245                 250                 255

Val Leu Gly Gly Asn Arg Arg Ala Ala Lys Pro Leu Phe Thr Ala Ile
            260                 265                 270

Arg Ile Thr Tyr Ala Leu Asn Ile Phe Glu Ala His Gly Val Thr Pro
        275                 280                 285

Phe Leu Lys Phe Cys Glu Arg Thr Ser Lys Lys Lys Gly Val Gly Val
    290                 295                 300

Ala Glu Leu Phe Glu Gln Asp Arg Asn Phe Thr Gly Ala Ile Ala Arg
305                 310                 315                 320

Ala Lys Ala Ala Gln Ala Ala Gly Met Glu His Pro Lys Ile Pro Lys
                325                 330                 335

Leu Glu Asp Ala Val Arg Gly Ala Arg Gly Lys Ala Leu Val Phe Thr
            340                 345                 350

Ser Tyr Arg Asp Ser Val Asp Leu Ile His Ser Arg Leu Lys Ala Ala
        355                 360                 365

Gly Ile Asn Ser Gly Ile Leu Ile Gly Lys Ala Gly Glu Lys Gly Leu
    370                 375                 380

Lys Gln Arg Lys Gln Val Glu Thr Val Ala Lys Phe Arg Asp Gly Gly
385                 390                 395                 400

Tyr Asp Val Leu Val Ser Thr Arg Val Gly Glu Glu Gly Leu Asp Ile
                405                 410                 415

Ser Glu Val Asn Leu Val Ile Phe Tyr Asp Asn Val Pro Ser Ser Ile
            420                 425                 430

Arg Tyr Val Gln Arg Arg Gly Arg Thr Gly Arg Lys Asp Ala Gly Arg
        435                 440                 445

Leu Ile Val Leu Met Ala Lys Gly Thr Ile Asp Glu Ala Tyr Tyr Trp
    450                 455                 460

Ile Gly Arg Arg Lys Met Ser Ala Ala Lys Gly Met Gly Glu Arg Met
465                 470                 475                 480

Asn Arg Ser Leu Ala Ala Gly Gly Ala Ala Ala Lys Ala Ala Pro Lys
                485                 490                 495

Gly Leu Glu Gly Tyr Phe
            500


<210> SEQ ID NO 35
<211> LENGTH: 402
<212> TYPE: DNA
<213> ORGANISM: Cenarchaeum symbiosum
<220> FEATURE:
<221> NAME/KEY: CDS
<222> LOCATION: (1)...(402)

<400> SEQUENCE: 35

gtg tca tcg tac ttt acc ata aag acc gcc aac ctg gcc ctg ccc gac       48
Met Ser Ser Tyr Phe Thr Ile Lys Thr Ala Asn Leu Ala Leu Pro Asp
 1               5                  10                  15

gtg gtc aaa aag tac aac cac gtc ctg gca tgc aag agc gag gtg atg       96
Val Val Lys Lys Tyr Asn His Val Leu Ala Cys Lys Ser Glu Val Met
            20                  25                  30
```

-continued

```
agg gcc gag aag cag atc cag acg tcc atc tcc tcg tct agc ggg ctc      144
Arg Ala Glu Lys Gln Ile Gln Thr Ser Ile Ser Ser Ser Ser Gly Leu
        35                  40                  45

gac aag tac tcg gag ctc aag caa cag ttc aac tcc cgg ata acc gag      192
Asp Lys Tyr Ser Glu Leu Lys Gln Gln Phe Asn Ser Arg Ile Thr Glu
    50                  55                  60

ttc tac cgc tcg ata gaa gag ctg gaa aag acc ggt gcg gtg gtc aag      240
Phe Tyr Arg Ser Ile Glu Glu Leu Glu Lys Thr Gly Ala Val Val Lys
 65                  70                  75                  80

agc ata gac gag ggc ctg ctg gac ttt ccc gca aag cgc ttt ggg gac      288
Ser Ile Asp Glu Gly Leu Leu Asp Phe Pro Ala Lys Arg Phe Gly Asp
                 85                  90                  95

gac atc tgg ctg tgc tgg aag aca ggc gag cgc gag atc aag ttc tgg      336
Asp Ile Trp Leu Cys Trp Lys Thr Gly Glu Arg Glu Ile Lys Phe Trp
            100                 105                 110

cat gaa aag gac tct ggt ttt ggc gga aga aag ccc ata gag gta agt      384
His Glu Lys Asp Ser Gly Phe Gly Gly Arg Lys Pro Ile Glu Val Ser
        115                 120                 125

gac gag tca cta gtg tag                                              402
Asp Glu Ser Leu Val
    130


<210> SEQ ID NO 36
<211> LENGTH: 133
<212> TYPE: PRT
<213> ORGANISM: Cenarchaeum symbiosum

<400> SEQUENCE: 36

Met Ser Ser Tyr Phe Thr Ile Lys Thr Ala Asn Leu Ala Leu Pro Asp
1               5                   10                  15

Val Val Lys Lys Tyr Asn His Val Leu Ala Cys Lys Ser Glu Val Met
            20                  25                  30

Arg Ala Glu Lys Gln Ile Gln Thr Ser Ile Ser Ser Ser Ser Gly Leu
        35                  40                  45

Asp Lys Tyr Ser Glu Leu Lys Gln Gln Phe Asn Ser Arg Ile Thr Glu
    50                  55                  60

Phe Tyr Arg Ser Ile Glu Glu Leu Glu Lys Thr Gly Ala Val Val Lys
65                  70                  75                  80

Ser Ile Asp Glu Gly Leu Leu Asp Phe Pro Ala Lys Arg Phe Gly Asp
                85                  90                  95

Asp Ile Trp Leu Cys Trp Lys Thr Gly Glu Arg Glu Ile Lys Phe Trp
            100                 105                 110

His Glu Lys Asp Ser Gly Phe Gly Gly Arg Lys Pro Ile Glu Val Ser
        115                 120                 125

Asp Glu Ser Leu Val
    130


<210> SEQ ID NO 37
<211> LENGTH: 879
<212> TYPE: DNA
<213> ORGANISM: Cenarchaeum symbiosum
<220> FEATURE:
<221> NAME/KEY: CDS
<222> LOCATION: (1)...(879)

<400> SEQUENCE: 37

atg ctc tcc gcc tgg ttg cgc gta ata cgc gtc cgc ttc ctg ctc gcg       48
Met Leu Ser Ala Trp Leu Arg Val Ile Arg Val Arg Phe Leu Leu Ala
 1               5                  10                  15

tcg gtg ata gcc gtc tcg gcg ggc ctc gcc ctc tcc tgg tgg cac ggc       96
```

-continued

```
Ser Val Ile Ala Val Ser Ala Gly Leu Ala Leu Ser Trp Trp His Gly
            20                  25                  30

cac gaa ata gac gca ttc tcc gcc gcg ctc acc atg gcc ggc gtg gcc      144
His Glu Ile Asp Ala Phe Ser Ala Ala Leu Thr Met Ala Gly Val Ala
        35                  40                  45

gcg ctc cac gca agc gtg gac atg ctc aac gat tat tcg gac tac aag      192
Ala Leu His Ala Ser Val Asp Met Leu Asn Asp Tyr Ser Asp Tyr Lys
    50                  55                  60

cgc ggc ata gat acc ata acc aag agg acc ccg atg agc ggc gga aca      240
Arg Gly Ile Asp Thr Ile Thr Lys Arg Thr Pro Met Ser Gly Gly Thr
65                  70                  75                  80

ggg gtg ctg cca gaa ggc ctg ctt acc ccc ggc cag gtg cac cgc gcc      288
Gly Val Leu Pro Glu Gly Leu Leu Thr Pro Gly Gln Val His Arg Ala
                85                  90                  95

ggc atc ata tcg ctg gtc ctg ggc tct gct gtc ggc gcg tac ttt gtg      336
Gly Ile Ile Ser Leu Val Leu Gly Ser Ala Val Gly Ala Tyr Phe Val
            100                 105                 110

gtc aca acg ggg ccc gtc ata gcc atg ata ctc ggc ttt gcc gta gtc      384
Val Thr Thr Gly Pro Val Ile Ala Met Ile Leu Gly Phe Ala Val Val
        115                 120                 125

tcg ata tac ttt tac tcg acg agg att gta gac tcg ggc ctc tcc gag      432
Ser Ile Tyr Phe Tyr Ser Thr Arg Ile Val Asp Ser Gly Leu Ser Glu
    130                 135                 140

gtc ttt gtg gcc gtc aag ggg gcg atg atc gtc ctt ggc gcc tac tac      480
Val Phe Val Ala Val Lys Gly Ala Met Ile Val Leu Gly Ala Tyr Tyr
145                 150                 155                 160

ata cag gcg ccc gag ata acg cct gcc gcc gtt ctg gtg ggg gcg gcc      528
Ile Gln Ala Pro Glu Ile Thr Pro Ala Ala Val Leu Val Gly Ala Ala
                165                 170                 175

gtg ggc gcc ctc tcg tcg gcg gtc ctc ttt gtg gcg tcg ttt cca gac      576
Val Gly Ala Leu Ser Ser Ala Val Leu Phe Val Ala Ser Phe Pro Asp
            180                 185                 190

cac gat gcg gac aag tcc cgc ggc aga aag acg ctt gtt ata atc ctg      624
His Asp Ala Asp Lys Ser Arg Gly Arg Lys Thr Leu Val Ile Ile Leu
        195                 200                 205

ggc aag gag agg gcc tcg cgg atc ctc tgg gtg ttc ccc gca gtg gca      672
Gly Lys Glu Arg Ala Ser Arg Ile Leu Trp Val Phe Pro Ala Val Ala
    210                 215                 220

tac tcg tcc gtt ata acg ggg gtc atc ctg cag ttc ctg ccg gtg cat      720
Tyr Ser Ser Val Ile Thr Gly Val Ile Leu Gln Phe Leu Pro Val His
225                 230                 235                 240

gca cta acc atg ctg ctt gca gcc ccc ctt gca gta att gcg gca aaa      768
Ala Leu Thr Met Leu Leu Ala Ala Pro Leu Ala Val Ile Ala Ala Lys
                245                 250                 255

ggc ctt gcc agg gag tac ggc ggg gac ggg atc ata cgg gtc atg cgc      816
Gly Leu Ala Arg Glu Tyr Gly Gly Asp Gly Ile Ile Arg Val Met Arg
            260                 265                 270

ggc acg ctg cgg ttt agc agg gtt gca ggc gcc ctg ctg gtg ttg ggc      864
Gly Thr Leu Arg Phe Ser Arg Val Ala Gly Ala Leu Leu Val Leu Gly
        275                 280                 285

att ctg ttg ggc tga                                                  879
Ile Leu Leu Gly
    290


<210> SEQ ID NO 38
<211> LENGTH: 292
<212> TYPE: PRT
<213> ORGANISM: Cenarchaeum symbiosum

<400> SEQUENCE: 38
```

-continued

```
Met Leu Ser Ala Trp Leu Arg Val Ile Arg Val Arg Phe Leu Leu Ala
 1               5                  10                  15

Ser Val Ile Ala Val Ser Ala Gly Leu Ala Leu Ser Trp Trp His Gly
            20                  25                  30

His Glu Ile Asp Ala Phe Ser Ala Ala Leu Thr Met Ala Gly Val Ala
        35                  40                  45

Ala Leu His Ala Ser Val Asp Met Leu Asn Asp Tyr Ser Asp Tyr Lys
    50                  55                  60

Arg Gly Ile Asp Thr Ile Thr Lys Arg Thr Pro Met Ser Gly Gly Thr
65                  70                  75                  80

Gly Val Leu Pro Glu Gly Leu Leu Thr Pro Gly Gln Val His Arg Ala
                85                  90                  95

Gly Ile Ile Ser Leu Val Leu Gly Ser Ala Val Gly Ala Tyr Phe Val
            100                 105                 110

Val Thr Thr Gly Pro Val Ile Ala Met Ile Leu Gly Phe Ala Val Val
        115                 120                 125

Ser Ile Tyr Phe Tyr Ser Thr Arg Ile Val Asp Ser Gly Leu Ser Glu
    130                 135                 140

Val Phe Val Ala Val Lys Gly Ala Met Ile Val Leu Gly Ala Tyr Tyr
145                 150                 155                 160

Ile Gln Ala Pro Glu Ile Thr Pro Ala Ala Val Leu Val Gly Ala Ala
                165                 170                 175

Val Gly Ala Leu Ser Ser Ala Val Leu Phe Val Ala Ser Phe Pro Asp
            180                 185                 190

His Asp Ala Asp Lys Ser Arg Gly Arg Lys Thr Leu Val Ile Ile Leu
        195                 200                 205

Gly Lys Glu Arg Ala Ser Arg Ile Leu Trp Val Phe Pro Ala Val Ala
    210                 215                 220

Tyr Ser Ser Val Ile Thr Gly Val Ile Leu Gln Phe Leu Pro Val His
225                 230                 235                 240

Ala Leu Thr Met Leu Leu Ala Ala Pro Leu Ala Val Ile Ala Ala Lys
                245                 250                 255

Gly Leu Ala Arg Glu Tyr Gly Gly Asp Gly Ile Ile Arg Val Met Arg
            260                 265                 270

Gly Thr Leu Arg Phe Ser Arg Val Ala Gly Ala Leu Leu Val Leu Gly
        275                 280                 285

Ile Leu Leu Gly
    290


<210> SEQ ID NO 39
<211> LENGTH: 1119
<212> TYPE: DNA
<213> ORGANISM: Cenarchaeum symbiosum
<220> FEATURE:
<221> NAME/KEY: CDS
<222> LOCATION: (1)...(1119)

<400> SEQUENCE: 39

atg atc agc ggg cac gcc acg gcc gag ggt aca cgc agg ata gcc gag       48
Met Ile Ser Gly His Ala Thr Ala Glu Gly Thr Arg Arg Ile Ala Glu
 1               5                  10                  15

atg tcg ggc gcc cat atc gac aac tac aag atg gtc gac ggg ctg cac       96
Met Ser Gly Ala His Ile Asp Asn Tyr Lys Met Val Asp Gly Leu His
            20                  25                  30

ctc tcc aac gtg ggg atg ggc acc tac ctt ggc gac gcg gat gac gcc      144
Leu Ser Asn Val Gly Met Gly Thr Tyr Leu Gly Asp Ala Asp Asp Ala
        35                  40                  45
```

-continued

```
acc gac agg gcc gtc acg gac gca gtc aag agg tcc gtc aaa aca ggc      192
Thr Asp Arg Ala Val Thr Asp Ala Val Lys Arg Ser Val Lys Thr Gly
     50                  55                  60

ata aac gtc ata gat acg gcg ata aac tac cgc ctc cag agg gcc gag      240
Ile Asn Val Ile Asp Thr Ala Ile Asn Tyr Arg Leu Gln Arg Ala Glu
 65                  70                  75                  80

cgc tct gtc ggc agg gcc gtc acg gag ctc tca gaa gag ggg ctc gta      288
Arg Ser Val Gly Arg Ala Val Thr Glu Leu Ser Glu Glu Gly Leu Val
                 85                  90                  95

tca agg gac caa ata ttc ata tcg aca aag gcg ggc tat gta aca aac      336
Ser Arg Asp Gln Ile Phe Ile Ser Thr Lys Ala Gly Tyr Val Thr Asn
            100                 105                 110

gac tcc gag gtc tcg ctt gac ttt tgg gag tat gtg aaa aaa gag tac      384
Asp Ser Glu Val Ser Leu Asp Phe Trp Glu Tyr Val Lys Lys Glu Tyr
        115                 120                 125

gtc ggg ggc ggc gtg atc cag gca ggc gac ata tcc tcc gga tac cac      432
Val Gly Gly Gly Val Ile Gln Ala Gly Asp Ile Ser Ser Gly Tyr His
    130                 135                 140

tgc atg aag ccc gcc tat cta gag gac cag ctg aag agg agc ctt gca      480
Cys Met Lys Pro Ala Tyr Leu Glu Asp Gln Leu Lys Arg Ser Leu Ala
145                 150                 155                 160

aac atg ggc ctc gac tgt atc gac ctt gtc tac gtg cac aac ccc gtc      528
Asn Met Gly Leu Asp Cys Ile Asp Leu Val Tyr Val His Asn Pro Val
                165                 170                 175

gag ggg cag atc aag gac cgc ccc ata ccg gag atc ctc gac tgt ata      576
Glu Gly Gln Ile Lys Asp Arg Pro Ile Pro Glu Ile Leu Asp Cys Ile
            180                 185                 190

gga gag gcc ttt gcc atg tac gag aag gca agg gag gat ggc cgc atc      624
Gly Glu Ala Phe Ala Met Tyr Glu Lys Ala Arg Glu Asp Gly Arg Ile
        195                 200                 205

aga tac tat ggg ctc gcc acg tgg gag tgc ttt cgt gtt gca ggg gac      672
Arg Tyr Tyr Gly Leu Ala Thr Trp Glu Cys Phe Arg Val Ala Gly Asp
    210                 215                 220

aac ccg cag aat gtc cag ctc gaa gac gtt gta aag aag gcc aaa gac      720
Asn Pro Gln Asn Val Gln Leu Glu Asp Val Val Lys Lys Ala Lys Asp
225                 230                 235                 240

gca ggc ggg gac aac cac gga ttc aag ttc ata cag ctg ccc ttc aac      768
Ala Gly Gly Asp Asn His Gly Phe Lys Phe Ile Gln Leu Pro Phe Asn
                245                 250                 255

cag tac ttt gac cag gct tac atg cta aag aac cag acg gtg gac ggc      816
Gln Tyr Phe Asp Gln Ala Tyr Met Leu Lys Asn Gln Thr Val Asp Gly
            260                 265                 270

aga aag ctg tcc ata ctg gat gcg gca gta tcc ctt ggc gtc ggt gtg      864
Arg Lys Leu Ser Ile Leu Asp Ala Ala Val Ser Leu Gly Val Gly Val
        275                 280                 285

ttc acg agt gtc ccg ttc atg caa ggc aag ctg ctc gag cct ggc ctg      912
Phe Thr Ser Val Pro Phe Met Gln Gly Lys Leu Leu Glu Pro Gly Leu
    290                 295                 300

ctg ccg gag ttt ggc ggg ctc tcc ccc gcc ctg cga tcc ctg cag ttt      960
Leu Pro Glu Phe Gly Gly Leu Ser Pro Ala Leu Arg Ser Leu Gln Phe
305                 310                 315                 320

atc agg tct aca cca ggc gtg ctt gcc ccc ctg ccg ggg cac aac tca     1008
Ile Arg Ser Thr Pro Gly Val Leu Ala Pro Leu Pro Gly His Asn Ser
                325                 330                 335

gct gcg cat aca gac gag aac ctc aag atc atg ggc gtg ccc ccc atc     1056
Ala Ala His Thr Asp Glu Asn Leu Lys Ile Met Gly Val Pro Pro Ile
            340                 345                 350

ccg cct gac aag ttc ggg gag ctt gtg gcc agc ctc acc tcg tgg tcg     1104
Pro Pro Asp Lys Phe Gly Glu Leu Val Ala Ser Leu Thr Ser Trp Ser
```

-continued

```
        355                 360                 365

ccc ggt cag aaa tag                                                 1119
Pro Gly Gln Lys
    370


<210> SEQ ID NO 40
<211> LENGTH: 372
<212> TYPE: PRT
<213> ORGANISM: Cenarchaeum symbiosum

<400> SEQUENCE: 40

Met Ile Ser Gly His Ala Thr Ala Glu Gly Thr Arg Arg Ile Ala Glu
 1               5                  10                  15

Met Ser Gly Ala His Ile Asp Asn Tyr Lys Met Val Asp Gly Leu His
            20                  25                  30

Leu Ser Asn Val Gly Met Gly Thr Tyr Leu Gly Asp Ala Asp Asp Ala
        35                  40                  45

Thr Asp Arg Ala Val Thr Asp Ala Val Lys Arg Ser Val Lys Thr Gly
    50                  55                  60

Ile Asn Val Ile Asp Thr Ala Ile Asn Tyr Arg Leu Gln Arg Ala Glu
65                  70                  75                  80

Arg Ser Val Gly Arg Ala Val Thr Glu Leu Ser Glu Glu Gly Leu Val
                85                  90                  95

Ser Arg Asp Gln Ile Phe Ile Ser Thr Lys Ala Gly Tyr Val Thr Asn
            100                 105                 110

Asp Ser Glu Val Ser Leu Asp Phe Trp Glu Tyr Val Lys Lys Glu Tyr
        115                 120                 125

Val Gly Gly Gly Val Ile Gln Ala Gly Asp Ile Ser Ser Gly Tyr His
    130                 135                 140

Cys Met Lys Pro Ala Tyr Leu Glu Asp Gln Leu Lys Arg Ser Leu Ala
145                 150                 155                 160

Asn Met Gly Leu Asp Cys Ile Asp Leu Val Tyr Val His Asn Pro Val
                165                 170                 175

Glu Gly Gln Ile Lys Asp Arg Pro Ile Pro Glu Ile Leu Asp Cys Ile
            180                 185                 190

Gly Glu Ala Phe Ala Met Tyr Glu Lys Ala Arg Glu Asp Gly Arg Ile
        195                 200                 205

Arg Tyr Tyr Gly Leu Ala Thr Trp Glu Cys Phe Arg Val Ala Gly Asp
    210                 215                 220

Asn Pro Gln Asn Val Gln Leu Glu Asp Val Val Lys Lys Ala Lys Asp
225                 230                 235                 240

Ala Gly Gly Asp Asn His Gly Phe Lys Phe Ile Gln Leu Pro Phe Asn
                245                 250                 255

Gln Tyr Phe Asp Gln Ala Tyr Met Leu Lys Asn Gln Thr Val Asp Gly
            260                 265                 270

Arg Lys Leu Ser Ile Leu Asp Ala Ala Val Ser Leu Gly Val Gly Val
        275                 280                 285

Phe Thr Ser Val Pro Phe Met Gln Gly Lys Leu Leu Glu Pro Gly Leu
    290                 295                 300

Leu Pro Glu Phe Gly Gly Leu Ser Pro Ala Leu Arg Ser Leu Gln Phe
305                 310                 315                 320

Ile Arg Ser Thr Pro Gly Val Leu Ala Pro Leu Pro Gly His Asn Ser
                325                 330                 335

Ala Ala His Thr Asp Glu Asn Leu Lys Ile Met Gly Val Pro Pro Ile
            340                 345                 350
```

-continued

```
Pro Pro Asp Lys Phe Gly Glu Leu Val Ala Ser Leu Thr Ser Trp Ser
        355                 360                 365

Pro Gly Gln Lys
    370


<210> SEQ ID NO 41
<211> LENGTH: 1107
<212> TYPE: DNA
<213> ORGANISM: Cenarchaeum symbiosum
<220> FEATURE:
<221> NAME/KEY: CDS
<222> LOCATION: (1)...(1107)

<400> SEQUENCE: 41

atg gca cgg ggg cct atc ttg agt gaa aag ttc cag ata ctg cag ggc       48
Met Ala Arg Gly Pro Ile Leu Ser Glu Lys Phe Gln Ile Leu Gln Gly
 1               5                  10                  15

gac gcc cgg gag gtg ctg ccg cgg ctg gca aag aat aca gcc gag cgc       96
Asp Ala Arg Glu Val Leu Pro Arg Leu Ala Lys Asn Thr Ala Glu Arg
            20                  25                  30

ggc agg tac aga ctg gcg gta aca tcc cct ccc tat tac ggg cac aga      144
Gly Arg Tyr Arg Leu Ala Val Thr Ser Pro Pro Tyr Tyr Gly His Arg
        35                  40                  45

aag tac ggg tcg gag ccc tcc gag ctg ggc cag gaa aag acg cca gac      192
Lys Tyr Gly Ser Glu Pro Ser Glu Leu Gly Gln Glu Lys Thr Pro Asp
    50                  55                  60

gag ttc atc gag gag ctg gca gga gta ttc aag agc tgc atg gac ctg      240
Glu Phe Ile Glu Glu Leu Ala Gly Val Phe Lys Ser Cys Met Asp Leu
 65                  70                  75                  80

cta aca gac gac ggg agc ctc ttc ata gtg ata ggt gat acc agg agg      288
Leu Thr Asp Asp Gly Ser Leu Phe Ile Val Ile Gly Asp Thr Arg Arg
                85                  90                  95

cgg cgc cac aag ctg atg gtc ccg cac cgg ctc gcg cta agg ctg gtg      336
Arg Arg His Lys Leu Met Val Pro His Arg Leu Ala Leu Arg Leu Val
            100                 105                 110

gat ctt ggg tac cat ttc cag gag gat ata atc tgg tac aag cga aac      384
Asp Leu Gly Tyr His Phe Gln Glu Asp Ile Ile Trp Tyr Lys Arg Asn
        115                 120                 125

gcc atc tcg caa agc tcg cgg caa aac ctg acg cag gcg tac gag ttt      432
Ala Ile Ser Gln Ser Ser Arg Gln Asn Leu Thr Gln Ala Tyr Glu Phe
    130                 135                 140

gtt ctg gtc ctc tca aag tcg gat acc ccc gcc tat gac ata aac ccg      480
Val Leu Val Leu Ser Lys Ser Asp Thr Pro Ala Tyr Asp Ile Asn Pro
145                 150                 155                 160

ata cgc gtc cag ggc aac gag gcc ctg agc ggg ata aac agc aaa ccc      528
Ile Arg Val Gln Gly Asn Glu Ala Leu Ser Gly Ile Asn Ser Lys Pro
                165                 170                 175

gca aat gac cgg ctg cag ttc gcc ccc ggg aag agg gat ccc gag gca      576
Ala Asn Asp Arg Leu Gln Phe Ala Pro Gly Lys Arg Asp Pro Glu Ala
            180                 185                 190

ata ggg agg att gca gcc gtg ata cac ggc tca acg cct ggt acg ccg      624
Ile Gly Arg Ile Ala Ala Val Ile His Gly Ser Thr Pro Gly Thr Pro
        195                 200                 205

ttt gac gag ctg cca acc acc ggg gaa ata tca tgg gcc cac ggc tat      672
Phe Asp Glu Leu Pro Thr Thr Gly Glu Ile Ser Trp Ala His Gly Tyr
    210                 215                 220

gac ccc gaa aag tac tgc ccc acg tgc tat cgc aag ttc cgg agg cat      720
Asp Pro Glu Lys Tyr Cys Pro Thr Cys Tyr Arg Lys Phe Arg Arg His
225                 230                 235                 240

gcg acg cgc aag agg ata ggg ggc cac gag cac tat ccg ata ttt gcc      768
```

-continued

```
Ala Thr Arg Lys Arg Ile Gly Gly His Glu His Tyr Pro Ile Phe Ala
                245                 250                 255

gca tgc aac ccg cgg ggc aag aac ccg ggg aac gtc tgg gag ata tcc      816
Ala Cys Asn Pro Arg Gly Lys Asn Pro Gly Asn Val Trp Glu Ile Ser
            260                 265                 270

aca aag gcg cac cat gga aac gag cac ttt gcg gta ttc cca gaa gac      864
Thr Lys Ala His His Gly Asn Glu His Phe Ala Val Phe Pro Glu Asp
        275                 280                 285

ctt gta tcc agg ata gta aag ttt gcc aca aaa gag ggc gat tac gtg      912
Leu Val Ser Arg Ile Val Lys Phe Ala Thr Lys Glu Gly Asp Tyr Val
    290                 295                 300

ctg gac ccg ttt gca ggc agg ggg acc acg gga ata gtc tct gca tgc      960
Leu Asp Pro Phe Ala Gly Arg Gly Thr Thr Gly Ile Val Ser Ala Cys
305                 310                 315                 320

ctc aag agg ggc ttt acc ggg ata gac ctg tat cct gcc aac gtg gca     1008
Leu Lys Arg Gly Phe Thr Gly Ile Asp Leu Tyr Pro Ala Asn Val Ala
                325                 330                 335

agg gcc cgg cgc aac gtg cag gat tcc gcc gat tca cgg ctc tca aaa     1056
Arg Ala Arg Arg Asn Val Gln Asp Ser Ala Asp Ser Arg Leu Ser Lys
            340                 345                 350

aag gtg ctc gac cag ata atg ccc gag agg cag ctg acc ggc tat ttc     1104
Lys Val Leu Asp Gln Ile Met Pro Glu Arg Gln Leu Thr Gly Tyr Phe
        355                 360                 365

tga                                                                 1107


<210> SEQ ID NO 42
<211> LENGTH: 368
<212> TYPE: PRT
<213> ORGANISM: Cenarchaeum symbiosum

<400> SEQUENCE: 42

Met Ala Arg Gly Pro Ile Leu Ser Glu Lys Phe Gln Ile Leu Gln Gly
 1               5                  10                  15

Asp Ala Arg Glu Val Leu Pro Arg Leu Ala Lys Asn Thr Ala Glu Arg
            20                  25                  30

Gly Arg Tyr Arg Leu Ala Val Thr Ser Pro Pro Tyr Tyr Gly His Arg
        35                  40                  45

Lys Tyr Gly Ser Glu Pro Ser Glu Leu Gly Gln Glu Lys Thr Pro Asp
    50                  55                  60

Glu Phe Ile Glu Glu Leu Ala Gly Val Phe Lys Ser Cys Met Asp Leu
65                  70                  75                  80

Leu Thr Asp Asp Gly Ser Leu Phe Ile Val Ile Gly Asp Thr Arg Arg
                85                  90                  95

Arg Arg His Lys Leu Met Val Pro His Arg Leu Ala Leu Arg Leu Val
            100                 105                 110

Asp Leu Gly Tyr His Phe Gln Glu Asp Ile Ile Trp Tyr Lys Arg Asn
        115                 120                 125

Ala Ile Ser Gln Ser Ser Arg Gln Asn Leu Thr Gln Ala Tyr Glu Phe
    130                 135                 140

Val Leu Val Leu Ser Lys Ser Asp Thr Pro Ala Tyr Asp Ile Asn Pro
145                 150                 155                 160

Ile Arg Val Gln Gly Asn Glu Ala Leu Ser Gly Ile Asn Ser Lys Pro
                165                 170                 175

Ala Asn Asp Arg Leu Gln Phe Ala Pro Gly Lys Arg Asp Pro Glu Ala
            180                 185                 190

Ile Gly Arg Ile Ala Ala Val Ile His Gly Ser Thr Pro Gly Thr Pro
        195                 200                 205
```

-continued

Phe Asp Glu Leu Pro Thr Thr Gly Glu Ile Ser Trp Ala His Gly Tyr
    210                 215                 220

Asp Pro Glu Lys Tyr Cys Pro Thr Cys Tyr Arg Lys Phe Arg Arg His
225                 230                 235                 240

Ala Thr Arg Lys Arg Ile Gly Gly His Glu His Tyr Pro Ile Phe Ala
                245                 250                 255

Ala Cys Asn Pro Arg Gly Lys Asn Pro Gly Asn Val Trp Glu Ile Ser
            260                 265                 270

Thr Lys Ala His His Gly Asn Glu His Phe Ala Val Phe Pro Glu Asp
        275                 280                 285

Leu Val Ser Arg Ile Val Lys Phe Ala Thr Lys Glu Gly Asp Tyr Val
    290                 295                 300

Leu Asp Pro Phe Ala Gly Arg Gly Thr Thr Gly Ile Val Ser Ala Cys
305                 310                 315                 320

Leu Lys Arg Gly Phe Thr Gly Ile Asp Leu Tyr Pro Ala Asn Val Ala
                325                 330                 335

Arg Ala Arg Arg Asn Val Gln Asp Ser Ala Asp Ser Arg Leu Ser Lys
            340                 345                 350

Lys Val Leu Asp Gln Ile Met Pro Glu Arg Gln Leu Thr Gly Tyr Phe
        355                 360                 365

<210> SEQ ID NO 43
<211> LENGTH: 933
<212> TYPE: DNA
<213> ORGANISM: Cenarchaeum symbiosum
<220> FEATURE:
<221> NAME/KEY: CDS
<222> LOCATION: (1)...(933)

<400> SEQUENCE: 43 atg cct agt tac gca gaa ata gca aac gac gta ctt cga cta atg gag      48
Met Pro Ser Tyr Ala Glu Ile Ala Asn Asp Val Leu Arg Leu Met Glu
 1               5                  10                  15 tca gtc ggt gag cag gca cct ggt gta gta ctt cac gac tat ctt tca      96
Ser Val Gly Glu Gln Ala Pro Gly Val Val Leu His Asp Tyr Leu Ser
            20                  25                  30 aaa ttg caa cag tat tcg ggg agg gat aca ata ctg tat gcg acc aac     144
Lys Leu Gln Gln Tyr Ser Gly Arg Asp Thr Ile Leu Tyr Ala Thr Asn
        35                  40                  45 tgg ata acg gac gaa gcg cat acg tct aat gaa gct ctc ata aca aat     192
Trp Ile Thr Asp Glu Ala His Thr Ser Asn Glu Ala Leu Ile Thr Asn
     50                  55                  60 ggt gac ctg tat gga ttt atg agg atg atg cgt gat tta aag act aag     240
Gly Asp Leu Tyr Gly Phe Met Arg Met Met Arg Asp Leu Lys Thr Lys
 65                  70                  75                  80 aaa tta gat tta ata ctc cac agt ccg ggg ggc tcc gtc gag tcc acc     288
Lys Leu Asp Leu Ile Leu His Ser Pro Gly Gly Ser Val Glu Ser Thr
                 85                  90                  95 gaa gca atc gtc tca tac ata cgt gca aaa ttt aaa aat gtc cgg atc     336
Glu Ala Ile Val Ser Tyr Ile Arg Ala Lys Phe Lys Asn Val Arg Ile
            100                 105                 110 att atc cca tat gcc gcg atg tcg gca gct gcg atg ctt gca tgc tca     384
Ile Ile Pro Tyr Ala Ala Met Ser Ala Ala Ala Met Leu Ala Cys Ser
        115                 120                 125 tcg aat tgc ctg gta atg ggt aaa cac tca tcg ata ggt ccc acc gac     432
Ser Asn Cys Leu Val Met Gly Lys His Ser Ser Ile Gly Pro Thr Asp
    130                 135                 140 ccc caa ttt att att cca acc agg acc ggc atg cac ata atg tct gca     480

-continued

```
Pro Gln Phe Ile Ile Pro Thr Arg Thr Gly Met His Ile Met Ser Ala
145                 150                 155                 160

cag ttt cta att agc gag ttt caa gaa gca cag tcg gtg tca gaa aaa      528
Gln Phe Leu Ile Ser Glu Phe Gln Glu Ala Gln Ser Val Ser Glu Lys
                165                 170                 175

cac ccg ggg agg ctc ggc gca tgg ctt cca ctg tta ggg caa tat cct      576
His Pro Gly Arg Leu Gly Ala Trp Leu Pro Leu Leu Gly Gln Tyr Pro
            180                 185                 190

ccc ggg cta att caa aaa tgc att agc agc cag aag cta agt gtg gaa      624
Pro Gly Leu Ile Gln Lys Cys Ile Ser Ser Gln Lys Leu Ser Val Glu
        195                 200                 205

ctt gta caa aaa tgg ctg gct aga tac atg ttt gag aac gag tct gca      672
Leu Val Gln Lys Trp Leu Ala Arg Tyr Met Phe Glu Asn Glu Ser Ala
    210                 215                 220

gcg gta aaa aag tca aaa aaa ata tca gaa ata atg tct tcc tct aaa      720
Ala Val Lys Lys Ser Lys Lys Ile Ser Glu Ile Met Ser Ser Ser Lys
225                 230                 235                 240

aaa tat cac agt cat gga agg cgc ata tcg aga gaa gaa tgt aaa agg      768
Lys Tyr His Ser His Gly Arg Arg Ile Ser Arg Glu Glu Cys Lys Arg
                245                 250                 255

att ggc tta aaa gta act gat ctg gaa gat gaa caa gaa ttt caa gat      816
Ile Gly Leu Lys Val Thr Asp Leu Glu Asp Glu Gln Glu Phe Gln Asp
            260                 265                 270

ctg gtg ctg tca gta ttt cat gcg gca aat acc atg ttt cag tat act      864
Leu Val Leu Ser Val Phe His Ala Ala Asn Thr Met Phe Gln Tyr Thr
        275                 280                 285

cca gtc aac aaa att atc atg aat cac ctc ggt aat acc gtc gtt gag      912
Pro Val Asn Lys Ile Ile Met Asn His Leu Gly Asn Thr Val Val Glu
    290                 295                 300

aca ctg cca aca cca cgg taa                                          933
Thr Leu Pro Thr Pro Arg
305                 310


<210> SEQ ID NO 44
<211> LENGTH: 310
<212> TYPE: PRT
<213> ORGANISM: Cenarchaeum symbiosum

<400> SEQUENCE: 44

Met Pro Ser Tyr Ala Glu Ile Ala Asn Asp Val Leu Arg Leu Met Glu
 1               5                  10                  15

Ser Val Gly Glu Gln Ala Pro Gly Val Val Leu His Asp Tyr Leu Ser
            20                  25                  30

Lys Leu Gln Gln Tyr Ser Gly Arg Asp Thr Ile Leu Tyr Ala Thr Asn
        35                  40                  45

Trp Ile Thr Asp Glu Ala His Thr Ser Asn Glu Ala Leu Ile Thr Asn
    50                  55                  60

Gly Asp Leu Tyr Gly Phe Met Arg Met Met Arg Asp Leu Lys Thr Lys
65                  70                  75                  80

Lys Leu Asp Leu Ile Leu His Ser Pro Gly Gly Ser Val Glu Ser Thr
                85                  90                  95

Glu Ala Ile Val Ser Tyr Ile Arg Ala Lys Phe Lys Asn Val Arg Ile
            100                 105                 110

Ile Ile Pro Tyr Ala Ala Met Ser Ala Ala Ala Met Leu Ala Cys Ser
        115                 120                 125

Ser Asn Cys Leu Val Met Gly Lys His Ser Ser Ile Gly Pro Thr Asp
    130                 135                 140

Pro Gln Phe Ile Ile Pro Thr Arg Thr Gly Met His Ile Met Ser Ala
```

-continued

```
145                 150                 155                 160

Gln Phe Leu Ile Ser Glu Phe Gln Glu Ala Gln Ser Val Ser Glu Lys
                165                 170                 175

His Pro Gly Arg Leu Gly Ala Trp Leu Pro Leu Leu Gly Gln Tyr Pro
            180                 185                 190

Pro Gly Leu Ile Gln Lys Cys Ile Ser Ser Gln Lys Leu Ser Val Glu
        195                 200                 205

Leu Val Gln Lys Trp Leu Ala Arg Tyr Met Phe Glu Asn Glu Ser Ala
    210                 215                 220

Ala Val Lys Lys Ser Lys Lys Ile Ser Glu Ile Met Ser Ser Ser Lys
225                 230                 235                 240

Lys Tyr His Ser His Gly Arg Arg Ile Ser Arg Glu Glu Cys Lys Arg
                245                 250                 255

Ile Gly Leu Lys Val Thr Asp Leu Glu Asp Glu Gln Glu Phe Gln Asp
            260                 265                 270

Leu Val Leu Ser Val Phe His Ala Ala Asn Thr Met Phe Gln Tyr Thr
        275                 280                 285

Pro Val Asn Lys Ile Ile Met Asn His Leu Gly Asn Thr Val Val Glu
    290                 295                 300

Thr Leu Pro Thr Pro Arg
305                 310


<210> SEQ ID NO 45
<211> LENGTH: 1305
<212> TYPE: DNA
<213> ORGANISM: Cenarchaeum symbiosum
<220> FEATURE:
<221> NAME/KEY: CDS
<222> LOCATION: (1)...(1305)

<400> SEQUENCE: 45

gtg gat ctg gaa cgc gag tac agg gca aag acc ggc ggc tcg gcc cgg       48
Met Asp Leu Glu Arg Glu Tyr Arg Ala Lys Thr Gly Gly Ser Ala Arg
 1               5                  10                  15

atc ttt gcc agg tcg aaa aag tac cac gtc ggc ggg gtc agc cac aac       96
Ile Phe Ala Arg Ser Lys Lys Tyr His Val Gly Gly Val Ser His Asn
            20                  25                  30

ata agg ttc tac gag ccg tat ccg ttt gtg aca agg tcc gcg agc ggc      144
Ile Arg Phe Tyr Glu Pro Tyr Pro Phe Val Thr Arg Ser Ala Ser Gly
        35                  40                  45

aag cac ctc gtc gac gtg gac ggg aac aag tat gta gac tac tgg atg      192
Lys His Leu Val Asp Val Asp Gly Asn Lys Tyr Val Asp Tyr Trp Met
    50                  55                  60

ggg cac tgg agc ctg ata ctg ggg cac gcg ccg gcg cca gtc agg tcg      240
Gly His Trp Ser Leu Ile Leu Gly His Ala Pro Ala Pro Val Arg Ser
 65                  70                  75                  80

gca gta gag ggg cag ctt cgc cgc ggc tgg atc cac ggg acc gtc aac      288
Ala Val Glu Gly Gln Leu Arg Arg Gly Trp Ile His Gly Thr Val Asn
                85                  90                  95

gag cag acg atg aat ctc tcg gag ata ata cgc ggc gcg gta agc gtg      336
Glu Gln Thr Met Asn Leu Ser Glu Ile Ile Arg Gly Ala Val Ser Val
            100                 105                 110

gca gaa aag aca agg tac gtc acg tcg ggg acg gag gcc gtc atg tat      384
Ala Glu Lys Thr Arg Tyr Val Thr Ser Gly Thr Glu Ala Val Met Tyr
        115                 120                 125

gcg gca agg ctg gcg cgc gcg cat acg ggc aga aaa ata ata gca aag      432
Ala Ala Arg Leu Ala Arg Ala His Thr Gly Arg Lys Ile Ile Ala Lys
    130                 135                 140
```

-continued

```
gcg gac ggc ggc tgg cac ggg tac gcg tcg ggg ctg ctc aag tcg gtc      480
Ala Asp Gly Gly Trp His Gly Tyr Ala Ser Gly Leu Leu Lys Ser Val
145                 150                 155                 160

aac tgg ccg tat gat gtg ccc gag agc ggg ggg ctc gtc gac gaa gag      528
Asn Trp Pro Tyr Asp Val Pro Glu Ser Gly Gly Leu Val Asp Glu Glu
                165                 170                 175

cac tct ata tcc att ccg tac aac gat ctt gaa ggt tcc ctg gat gtt      576
His Ser Ile Ser Ile Pro Tyr Asn Asp Leu Glu Gly Ser Leu Asp Val
            180                 185                 190

ctt ggg cgc gca ggc gac gac ttg gca tgc gtg ata atc gag ccg ctg      624
Leu Gly Arg Ala Gly Asp Asp Leu Ala Cys Val Ile Ile Glu Pro Leu
        195                 200                 205

ctg ggc ggc ggc ggc tgc ata ccg gcg gat gag gac tat ctg cgc ggc      672
Leu Gly Gly Gly Gly Cys Ile Pro Ala Asp Glu Asp Tyr Leu Arg Gly
    210                 215                 220

ata cag gag ttt gtg cat tca agg ggc gcg ctg ctt gtc ctc gac gag      720
Ile Gln Glu Phe Val His Ser Arg Gly Ala Leu Leu Val Leu Asp Glu
225                 230                 235                 240

ata gtg aca ggg ttc cgg ttt agg ttt ggc tgc gcg tat gct gca gca      768
Ile Val Thr Gly Phe Arg Phe Arg Phe Gly Cys Ala Tyr Ala Ala Ala
                245                 250                 255

ggg ctg gac ccc gat ata gtg gcg ctc ggc aag ata gtc ggg ggc gga      816
Gly Leu Asp Pro Asp Ile Val Ala Leu Gly Lys Ile Val Gly Gly Gly
            260                 265                 270

ttc ccc ata ggg gtg ata tgc ggc aag gac gag gtg atg gaa atc tcc      864
Phe Pro Ile Gly Val Ile Cys Gly Lys Asp Glu Val Met Glu Ile Ser
        275                 280                 285

aac act ata tcg cat gca aag tcc gac agg gcg tac atc ggc ggc ggc      912
Asn Thr Ile Ser His Ala Lys Ser Asp Arg Ala Tyr Ile Gly Gly Gly
    290                 295                 300

aca ttc tct gca aac ccc gcc acg atg aca gcg ggc gcg gca gcg ctc      960
Thr Phe Ser Ala Asn Pro Ala Thr Met Thr Ala Gly Ala Ala Ala Leu
305                 310                 315                 320

ggg gag ctc aaa aag aga aag ggc aca ata tac ccg agg ata aac tcc     1008
Gly Glu Leu Lys Lys Arg Lys Gly Thr Ile Tyr Pro Arg Ile Asn Ser
                325                 330                 335

atg ggg gac gac gca agg gac aag ctc tca aag ata ttt ggg aac agg     1056
Met Gly Asp Asp Ala Arg Asp Lys Leu Ser Lys Ile Phe Gly Asn Arg
            340                 345                 350

gta tcc gtg acc gga agg ggc tcg ctg ttc atg act cac ttt gtt caa     1104
Val Ser Val Thr Gly Arg Gly Ser Leu Phe Met Thr His Phe Val Gln
        355                 360                 365

gat ggc gcc ggc agg gtc tca aat gct gca gat gcg gca gcc tgc gat     1152
Asp Gly Ala Gly Arg Val Ser Asn Ala Ala Asp Ala Ala Ala Cys Asp
    370                 375                 380

gtt gag ctg ctg cac agg tac cac ctg gac atg atc acc cgg gac ggc     1200
Val Glu Leu Leu His Arg Tyr His Leu Asp Met Ile Thr Arg Asp Gly
385                 390                 395                 400

ata ttc ttt ctg ccg ggc aag ctg ggg gcc ata tcg gcg gcg cac tca     1248
Ile Phe Phe Leu Pro Gly Lys Leu Gly Ala Ile Ser Ala Ala His Ser
                405                 410                 415

aag gcc gac ctc aag acc atg tat tcc gca tca gag cgc ttt gca gaa     1296
Lys Ala Asp Leu Lys Thr Met Tyr Ser Ala Ser Glu Arg Phe Ala Glu
            420                 425                 430

ggc cta tga                                                         1305
Gly Leu
```

<210> SEQ ID NO 46
<211> LENGTH: 434
<212> TYPE: PRT

-continued

<213> ORGANISM: Cenarchaeum symbiosum

<400> SEQUENCE: 46

```
Met Asp Leu Glu Arg Glu Tyr Arg Ala Lys Thr Gly Gly Ser Ala Arg
 1               5                  10                  15

Ile Phe Ala Arg Ser Lys Lys Tyr His Val Gly Gly Val Ser His Asn
            20                  25                  30

Ile Arg Phe Tyr Glu Pro Tyr Pro Phe Val Thr Arg Ser Ala Ser Gly
        35                  40                  45

Lys His Leu Val Asp Val Asp Gly Asn Lys Tyr Val Asp Tyr Trp Met
    50                  55                  60

Gly His Trp Ser Leu Ile Leu Gly His Ala Pro Ala Pro Val Arg Ser
65                  70                  75                  80

Ala Val Glu Gly Gln Leu Arg Arg Gly Trp Ile His Gly Thr Val Asn
                85                  90                  95

Glu Gln Thr Met Asn Leu Ser Glu Ile Ile Arg Gly Ala Val Ser Val
            100                 105                 110

Ala Glu Lys Thr Arg Tyr Val Thr Ser Gly Thr Glu Ala Val Met Tyr
        115                 120                 125

Ala Ala Arg Leu Ala Arg Ala His Thr Gly Arg Lys Ile Ile Ala Lys
    130                 135                 140

Ala Asp Gly Gly Trp His Gly Tyr Ala Ser Gly Leu Leu Lys Ser Val
145                 150                 155                 160

Asn Trp Pro Tyr Asp Val Pro Glu Ser Gly Gly Leu Val Asp Glu Glu
                165                 170                 175

His Ser Ile Ser Ile Pro Tyr Asn Asp Leu Glu Gly Ser Leu Asp Val
            180                 185                 190

Leu Gly Arg Ala Gly Asp Asp Leu Ala Cys Val Ile Ile Glu Pro Leu
        195                 200                 205

Leu Gly Gly Gly Gly Cys Ile Pro Ala Asp Glu Asp Tyr Leu Arg Gly
    210                 215                 220

Ile Gln Glu Phe Val His Ser Arg Gly Ala Leu Leu Val Leu Asp Glu
225                 230                 235                 240

Ile Val Thr Gly Phe Arg Phe Arg Phe Gly Cys Ala Tyr Ala Ala Ala
                245                 250                 255

Gly Leu Asp Pro Asp Ile Val Ala Leu Gly Lys Ile Val Gly Gly Gly
            260                 265                 270

Phe Pro Ile Gly Val Ile Cys Gly Lys Asp Glu Val Met Glu Ile Ser
        275                 280                 285

Asn Thr Ile Ser His Ala Lys Ser Asp Arg Ala Tyr Ile Gly Gly Gly
    290                 295                 300

Thr Phe Ser Ala Asn Pro Ala Thr Met Thr Ala Gly Ala Ala Ala Leu
305                 310                 315                 320

Gly Glu Leu Lys Lys Arg Lys Gly Thr Ile Tyr Pro Arg Ile Asn Ser
                325                 330                 335

Met Gly Asp Asp Ala Arg Asp Lys Leu Ser Lys Ile Phe Gly Asn Arg
            340                 345                 350

Val Ser Val Thr Gly Arg Gly Ser Leu Phe Met Thr His Phe Val Gln
        355                 360                 365

Asp Gly Ala Gly Arg Val Ser Asn Ala Ala Asp Ala Ala Ala Cys Asp
    370                 375                 380

Val Glu Leu Leu His Arg Tyr His Leu Asp Met Ile Thr Arg Asp Gly
385                 390                 395                 400
```

-continued

```
Ile Phe Phe Leu Pro Gly Lys Leu Gly Ala Ile Ser Ala Ala His Ser
            405                 410                 415

Lys Ala Asp Leu Lys Thr Met Tyr Ser Ala Ser Glu Arg Phe Ala Glu
            420                 425                 430

Gly Leu


<210> SEQ ID NO 47
<211> LENGTH: 807
<212> TYPE: DNA
<213> ORGANISM: Cenarchaeum symbiosum
<220> FEATURE:
<221> NAME/KEY: CDS
<222> LOCATION: (1)...(807)

<400> SEQUENCE: 47

atg ata ctc ttc ggc aag agc gac ccc gcc gag ctg gtg cgc cag gcg       48
Met Ile Leu Phe Gly Lys Ser Asp Pro Ala Glu Leu Val Arg Gln Ala
 1               5                  10                  15

gac ctc ctg tgc agc aag aac cag ttc agg gcg gca ata ggc ctg tac       96
Asp Leu Leu Cys Ser Lys Asn Gln Phe Arg Ala Ala Ile Gly Leu Tyr
            20                  25                  30

ggg aaa atc ctc aag gac gac ccg cag aac agg ggc gtc ctg cac aaa      144
Gly Lys Ile Leu Lys Asp Asp Pro Gln Asn Arg Gly Val Leu His Lys
        35                  40                  45

aag ggg ctg gcc cag aac agg gca aaa aag tac tct gat gcg atc acg      192
Lys Gly Leu Ala Gln Asn Arg Ala Lys Lys Tyr Ser Asp Ala Ile Thr
    50                  55                  60

tgc ttt gac cgg ctg ctc gag ctt gac aac aag gac gcg ccc gcg tac      240
Cys Phe Asp Arg Leu Leu Glu Leu Asp Asn Lys Asp Ala Pro Ala Tyr
 65                  70                  75                  80

aac aac aag gcc ata gcc cag gcc gag ctc gga gac acg gca tcc gcg      288
Asn Asn Lys Ala Ile Ala Gln Ala Glu Leu Gly Asp Thr Ala Ser Ala
                85                  90                  95

ctg gaa aac tac ggc agg gcc atc gag gcc gac ccg cgg tac gcg ccg      336
Leu Glu Asn Tyr Gly Arg Ala Ile Glu Ala Asp Pro Arg Tyr Ala Pro
            100                 105                 110

gcg cgc ttc aac agg gcc gtg ctg ctc gac agg ctg ggc gag cat gag      384
Ala Arg Phe Asn Arg Ala Val Leu Leu Asp Arg Leu Gly Glu His Glu
        115                 120                 125

gag gcg ctg ccg gac ctc gac agg gca gcc gag ctg gac cga cgc aag      432
Glu Ala Leu Pro Asp Leu Asp Arg Ala Ala Glu Leu Asp Arg Arg Lys
    130                 135                 140

ccg aac ccg agg ttc tac aag ggg ata gtg ctc ggc aag atg ggc agg      480
Pro Asn Pro Arg Phe Tyr Lys Gly Ile Val Leu Gly Lys Met Gly Arg
145                 150                 155                 160

cac gaa gag gcg ctg gcc tgc ttc aag ggc gtg tgc aag agg cat ccc      528
His Glu Glu Ala Leu Ala Cys Phe Lys Gly Val Cys Lys Arg His Pro
                165                 170                 175

ggc cac gcc gac tca cag ttc cac gtg ggg ata gag ctt acc gag ctt      576
Gly His Ala Asp Ser Gln Phe His Val Gly Ile Glu Leu Thr Glu Leu
            180                 185                 190

ggc agg cac gcc gag gcc ctc ggg gag ctt gca tca ctg ccc gcg gag      624
Gly Arg His Ala Glu Ala Leu Gly Glu Leu Ala Ser Leu Pro Ala Glu
        195                 200                 205

cac cgc gag aac gcc aat gta ttg tat gcc agg gcg cgc agc ctc tcg      672
His Arg Glu Asn Ala Asn Val Leu Tyr Ala Arg Ala Arg Ser Leu Ser
    210                 215                 220

ggc ctt ggc agg gag gac gaa tcc ata gcg cac ctg caa aag gcg gcc      720
Gly Leu Gly Arg Glu Asp Glu Ser Ile Ala His Leu Gln Lys Ala Ala
225                 230                 235                 240
```

-continued

```
aaa aaa gat tcc aag acg ata aaa aag tgg gcc cgc gca gaa aag gcc      768
Lys Lys Asp Ser Lys Thr Ile Lys Lys Trp Ala Arg Ala Glu Lys Ala
                245                 250                 255

ttt gac gga ata cgg gac gat ccc ggt tca aaa aga tag                  807
Phe Asp Gly Ile Arg Asp Asp Pro Gly Ser Lys Arg
            260                 265
```

<210> SEQ ID NO 48
<211> LENGTH: 268
<212> TYPE: PRT
<213> ORGANISM: Cenarchaeum symbiosum

<400> SEQUENCE: 48

```
Met Ile Leu Phe Gly Lys Ser Asp Pro Ala Glu Leu Val Arg Gln Ala
 1               5                  10                  15

Asp Leu Leu Cys Ser Lys Asn Gln Phe Arg Ala Ala Ile Gly Leu Tyr
            20                  25                  30

Gly Lys Ile Leu Lys Asp Asp Pro Gln Asn Arg Gly Val Leu His Lys
        35                  40                  45

Lys Gly Leu Ala Gln Asn Arg Ala Lys Lys Tyr Ser Asp Ala Ile Thr
    50                  55                  60

Cys Phe Asp Arg Leu Leu Glu Leu Asp Asn Lys Asp Ala Pro Ala Tyr
65                  70                  75                  80

Asn Asn Lys Ala Ile Ala Gln Ala Glu Leu Gly Asp Thr Ala Ser Ala
                85                  90                  95

Leu Glu Asn Tyr Gly Arg Ala Ile Glu Ala Asp Pro Arg Tyr Ala Pro
            100                 105                 110

Ala Arg Phe Asn Arg Ala Val Leu Leu Asp Arg Leu Gly Glu His Glu
        115                 120                 125

Glu Ala Leu Pro Asp Leu Asp Arg Ala Ala Glu Leu Asp Arg Arg Lys
    130                 135                 140

Pro Asn Pro Arg Phe Tyr Lys Gly Ile Val Leu Gly Lys Met Gly Arg
145                 150                 155                 160

His Glu Glu Ala Leu Ala Cys Phe Lys Gly Val Cys Lys Arg His Pro
                165                 170                 175

Gly His Ala Asp Ser Gln Phe His Val Gly Ile Glu Leu Thr Glu Leu
            180                 185                 190

Gly Arg His Ala Glu Ala Leu Gly Glu Leu Ala Ser Leu Pro Ala Glu
        195                 200                 205

His Arg Glu Asn Ala Asn Val Leu Tyr Ala Arg Ala Arg Ser Leu Ser
    210                 215                 220

Gly Leu Gly Arg Glu Asp Glu Ser Ile Ala His Leu Gln Lys Ala Ala
225                 230                 235                 240

Lys Lys Asp Ser Lys Thr Ile Lys Lys Trp Ala Arg Ala Glu Lys Ala
                245                 250                 255

Phe Asp Gly Ile Arg Asp Asp Pro Gly Ser Lys Arg
            260                 265
```

<210> SEQ ID NO 49
<211> LENGTH: 708
<212> TYPE: DNA
<213> ORGANISM: Cenarchaeum symbiosum
<220> FEATURE:
<221> NAME/KEY: CDS
<222> LOCATION: (1)...(708)

<400> SEQUENCE: 49

```
gtg cgg cag ggg atg act gga aag acc agg acg gcg gtc ctg cgg aac       48
```

-continued

```
Met Arg Gln Gly Met Thr Gly Lys Thr Arg Thr Ala Val Leu Arg Asn
 1               5                  10                  15

gcc atg act gag gag tcg gct cgg gcc atg ata gag gca aag aag acg       96
Ala Met Thr Glu Glu Ser Ala Arg Ala Met Ile Glu Ala Lys Lys Thr
            20                  25                  30

ggt gcc ttt agg gcc ctt atg agg gcc ccg cgg aaa gaa gac gtc cat      144
Gly Ala Phe Arg Ala Leu Met Arg Ala Pro Arg Lys Glu Asp Val His
        35                  40                  45

gtg cat tct gta aag ctg gtc cac gag gcg ctg atc cgg gtc tcc gcc      192
Val His Ser Val Lys Leu Val His Glu Ala Leu Ile Arg Val Ser Ala
    50                  55                  60

agg tac tct gcg gat ttt ttc aga aag gcg gtt cac ccg atc aag gtg      240
Arg Tyr Ser Ala Asp Phe Phe Arg Lys Ala Val His Pro Ile Lys Val
 65                  70                  75                  80

gac cag aac gtg atc gag gtg gtg cta ggc gac ggc gtc ttt ccc ata      288
Asp Gln Asn Val Ile Glu Val Val Leu Gly Asp Gly Val Phe Pro Ile
                85                  90                  95

agg tcc aag tcg cgc ata cac aag acg ctc tcg gca ggg ctc ggc aag      336
Arg Ser Lys Ser Arg Ile His Lys Thr Leu Ser Ala Gly Leu Gly Lys
            100                 105                 110

aac agg gtc gac ctc gag cta gaa gag cat gtc ttt gcg gaa tca gaa      384
Asn Arg Val Asp Leu Glu Leu Glu Glu His Val Phe Ala Glu Ser Glu
        115                 120                 125

ggg atg atg tgc ctt gac cgg cac ggc ggc gag acg gac ttt ccc tac      432
Gly Met Met Cys Leu Asp Arg His Gly Gly Glu Thr Asp Phe Pro Tyr
    130                 135                 140

aag acg ggg ccc ggc gcg gtg gag ccg tac ccg cgg agg ata ctc gat      480
Lys Thr Gly Pro Gly Ala Val Glu Pro Tyr Pro Arg Arg Ile Leu Asp
145                 150                 155                 160

gcg tca gag aat gtg cgg agc ccc gag gtg gag aca gaa gag gcg ctc      528
Ala Ser Glu Asn Val Arg Ser Pro Glu Val Glu Thr Glu Glu Ala Leu
                165                 170                 175

tca aaa cta aaa gag aag ctg cgc ggg ccc ccg cct gac ggc atg cgc      576
Ser Lys Leu Lys Glu Lys Leu Arg Gly Pro Pro Pro Asp Gly Met Arg
            180                 185                 190

gac ctg cgg gag gag ttt gcc gca aag gcg gtg gag gtg gtc tat gta      624
Asp Leu Arg Glu Glu Phe Ala Ala Lys Ala Val Glu Val Val Tyr Val
        195                 200                 205

cca gtc tat gaa tcg cga ctt gtg ggg ccc aaa aaa aag gtc cgc atg      672
Pro Val Tyr Glu Ser Arg Leu Val Gly Pro Lys Lys Lys Val Arg Met
    210                 215                 220

atg cgg att gac gcg gca aga aaa aag atc ctc tag                      708
Met Arg Ile Asp Ala Ala Arg Lys Lys Ile Leu
225                 230                 235


<210> SEQ ID NO 50
<211> LENGTH: 235
<212> TYPE: PRT
<213> ORGANISM: Cenarchaeum symbiosum

<400> SEQUENCE: 50

Met Arg Gln Gly Met Thr Gly Lys Thr Arg Thr Ala Val Leu Arg Asn
 1               5                  10                  15

Ala Met Thr Glu Glu Ser Ala Arg Ala Met Ile Glu Ala Lys Lys Thr
            20                  25                  30

Gly Ala Phe Arg Ala Leu Met Arg Ala Pro Arg Lys Glu Asp Val His
        35                  40                  45

Val His Ser Val Lys Leu Val His Glu Ala Leu Ile Arg Val Ser Ala
    50                  55                  60
```

-continued

```
Arg Tyr Ser Ala Asp Phe Phe Arg Lys Ala Val His Pro Ile Lys Val
65                  70                  75                  80

Asp Gln Asn Val Ile Glu Val Val Leu Gly Asp Gly Val Phe Pro Ile
                85                  90                  95

Arg Ser Lys Ser Arg Ile His Lys Thr Leu Ser Ala Gly Leu Gly Lys
            100                 105                 110

Asn Arg Val Asp Leu Glu Leu Glu Glu His Val Phe Ala Glu Ser Glu
        115                 120                 125

Gly Met Met Cys Leu Asp Arg His Gly Gly Glu Thr Asp Phe Pro Tyr
    130                 135                 140

Lys Thr Gly Pro Gly Ala Val Glu Pro Tyr Pro Arg Arg Ile Leu Asp
145                 150                 155                 160

Ala Ser Glu Asn Val Arg Ser Pro Glu Val Glu Thr Glu Glu Ala Leu
                165                 170                 175

Ser Lys Leu Lys Glu Lys Leu Arg Gly Pro Pro Pro Asp Gly Met Arg
            180                 185                 190

Asp Leu Arg Glu Glu Phe Ala Ala Lys Ala Val Glu Val Val Tyr Val
        195                 200                 205

Pro Val Tyr Glu Ser Arg Leu Val Gly Pro Lys Lys Lys Val Arg Met
    210                 215                 220

Met Arg Ile Asp Ala Ala Arg Lys Lys Ile Leu
225                 230                 235


<210> SEQ ID NO 51
<211> LENGTH: 378
<212> TYPE: DNA
<213> ORGANISM: Cenarchaeum symbiosum
<220> FEATURE:
<221> NAME/KEY: CDS
<222> LOCATION: (1)...(378)

<400> SEQUENCE: 51

atg agg tcg gag ggc agg ccc gga tac atc gaa aag ttc cta aag agg       48
Met Arg Ser Glu Gly Arg Pro Gly Tyr Ile Glu Lys Phe Leu Lys Arg
 1               5                  10                  15

gcg gac aag gcg ata gac aat gca gtc gag cag ggc gtc aag agg gca       96
Ala Asp Lys Ala Ile Asp Asn Ala Val Glu Gln Gly Val Lys Arg Ala
            20                  25                  30

gac gag ata cta gat gac gca gtc gag ctc ggc aag atc acc gtg ggc      144
Asp Glu Ile Leu Asp Asp Ala Val Glu Leu Gly Lys Ile Thr Val Gly
        35                  40                  45

gag gcg caa aaa aga agc gat gtg ctg ctc aag cag gcc gag cgg gag      192
Glu Ala Gln Lys Arg Ser Asp Val Leu Leu Lys Gln Ala Glu Arg Glu
     50                  55                  60

agc aag cgg ctc aag tca agg ggc gcc aaa aag ctc gaa aag ggc ata      240
Ser Lys Arg Leu Lys Ser Arg Gly Ala Lys Lys Leu Glu Lys Gly Ile
 65                  70                  75                  80

ggg gcg gca aaa aag atg gca gcc ggc aag ggc gac gcg cta gag acc      288
Gly Ala Ala Lys Lys Met Ala Ala Gly Lys Gly Asp Ala Leu Glu Thr
                 85                  90                  95

ctg gca aag ctc ggc gag ctg aga aag gcg ggg atc ata acg gag aag      336
Leu Ala Lys Leu Gly Glu Leu Arg Lys Ala Gly Ile Ile Thr Glu Lys
            100                 105                 110

gag ttt cgc gcc aag aaa aag aag ctt ctc gcg gag atc tga              378
Glu Phe Arg Ala Lys Lys Lys Lys Leu Leu Ala Glu Ile
        115                 120                 125


<210> SEQ ID NO 52
<211> LENGTH: 125
```

-continued

<212> TYPE: PRT
<213> ORGANISM: Cenarchaeum symbiosum

<400> SEQUENCE: 52

```
Met Arg Ser Glu Gly Arg Pro Gly Tyr Ile Glu Lys Phe Leu Lys Arg
 1               5                  10                  15

Ala Asp Lys Ala Ile Asp Asn Ala Val Glu Gln Gly Val Lys Arg Ala
            20                  25                  30

Asp Glu Ile Leu Asp Asp Ala Val Glu Leu Gly Lys Ile Thr Val Gly
        35                  40                  45

Glu Ala Gln Lys Arg Ser Asp Val Leu Leu Lys Gln Ala Glu Arg Glu
    50                  55                  60

Ser Lys Arg Leu Lys Ser Arg Gly Ala Lys Lys Leu Glu Lys Gly Ile
65                  70                  75                  80

Gly Ala Ala Lys Lys Met Ala Ala Gly Lys Gly Asp Ala Leu Glu Thr
                85                  90                  95

Leu Ala Lys Leu Gly Glu Leu Arg Lys Ala Gly Ile Ile Thr Glu Lys
            100                 105                 110

Glu Phe Arg Ala Lys Lys Lys Lys Leu Leu Ala Glu Ile
        115                 120                 125
```

<210> SEQ ID NO 53
<211> LENGTH: 606
<212> TYPE: DNA
<213> ORGANISM: Cenarchaeum symbiosum
<220> FEATURE:
<221> NAME/KEY: CDS
<222> LOCATION: (1)...(606)

<400> SEQUENCE: 53

```
atg tcc aag acg gag gcc tcc ccg ggg gga tat gcc tgc acg cca tac       48
Met Ser Lys Thr Glu Ala Ser Pro Gly Gly Tyr Ala Cys Thr Pro Tyr
 1               5                  10                  15

acg cac gac cat gcc tcg ata gag ctc aag gag gaa tgg tcc tcg tcg       96
Thr His Asp His Ala Ser Ile Glu Leu Lys Glu Glu Trp Ser Ser Ser
            20                  25                  30

agg aac gta ggc gag atg tac ttt gtg acc gcc act ttc tcg tcc aaa      144
Arg Asn Val Gly Glu Met Tyr Phe Val Thr Ala Thr Phe Ser Ser Lys
        35                  40                  45

agc aag ccg tac ttt gag cag cag gcc agc cac tac ctg ctg gca agg      192
Ser Lys Pro Tyr Phe Glu Gln Gln Ala Ser His Tyr Leu Leu Ala Arg
    50                  55                  60

ttc aaa aac ggc ccc aaa atg ata aag gcg gtg gag ggc cgc ggg ggc      240
Phe Lys Asn Gly Pro Lys Met Ile Lys Ala Val Glu Gly Arg Gly Gly
 65                  70                  75                  80

ggc cct tcc tat tta ttc agc atg gac gag gag ata ttc gaa agg gaa      288
Gly Pro Ser Tyr Leu Phe Ser Met Asp Glu Glu Ile Phe Glu Arg Glu
                85                  90                  95

tcc ccc ggg atg agc tat gta tcc atg tac tat ctg gaa tac gga gat      336
Ser Pro Gly Met Ser Tyr Val Ser Met Tyr Tyr Leu Glu Tyr Gly Asp
            100                 105                 110

tcc gag gag gac ata cgc gag gtg gcg tcg gta gtg gca aga aag gag      384
Ser Glu Glu Asp Ile Arg Glu Val Ala Ser Val Val Ala Arg Lys Glu
        115                 120                 125

aag ata ggc agg gcg gga ata ggg cgc atg gat gta tgc tcg agg att      432
Lys Ile Gly Arg Ala Gly Ile Gly Arg Met Asp Val Cys Ser Arg Ile
    130                 135                 140

ccg cca aag ttt gcc ttc ccg tac agc ggg aac att gtg gtg ctc gag      480
Pro Pro Lys Phe Ala Phe Pro Tyr Ser Gly Asn Ile Val Val Leu Glu
145                 150                 155                 160
```

-continued

```
gta tcc agc gaa aag agc cac cag agc gtc aac aag tac tgc gaa aag      528
Val Ser Ser Glu Lys Ser His Gln Ser Val Asn Lys Tyr Cys Glu Lys
                165                 170                 175

act aga agg gaa gtg atc cgc aag ggg ata acg atg acc aac ctt gta      576
Thr Arg Arg Glu Val Ile Arg Lys Gly Ile Thr Met Thr Asn Leu Val
            180                 185                 190

agc ctg tcg ata ctg gag agg ctc aaa taa                              606
Ser Leu Ser Ile Leu Glu Arg Leu Lys
        195                 200


<210> SEQ ID NO 54
<211> LENGTH: 201
<212> TYPE: PRT
<213> ORGANISM: Cenarchaeum symbiosum

<400> SEQUENCE: 54

Met Ser Lys Thr Glu Ala Ser Pro Gly Gly Tyr Ala Cys Thr Pro Tyr
 1               5                  10                  15

Thr His Asp His Ala Ser Ile Glu Leu Lys Glu Glu Trp Ser Ser Ser
            20                  25                  30

Arg Asn Val Gly Glu Met Tyr Phe Val Thr Ala Thr Phe Ser Ser Lys
        35                  40                  45

Ser Lys Pro Tyr Phe Glu Gln Gln Ala Ser His Tyr Leu Leu Ala Arg
    50                  55                  60

Phe Lys Asn Gly Pro Lys Met Ile Lys Ala Val Glu Gly Arg Gly Gly
65                  70                  75                  80

Gly Pro Ser Tyr Leu Phe Ser Met Asp Glu Glu Ile Phe Glu Arg Glu
                85                  90                  95

Ser Pro Gly Met Ser Tyr Val Ser Met Tyr Tyr Leu Glu Tyr Gly Asp
            100                 105                 110

Ser Glu Glu Asp Ile Arg Glu Val Ala Ser Val Val Ala Arg Lys Glu
        115                 120                 125

Lys Ile Gly Arg Ala Gly Ile Gly Arg Met Asp Val Cys Ser Arg Ile
    130                 135                 140

Pro Pro Lys Phe Ala Phe Pro Tyr Ser Gly Asn Ile Val Val Leu Glu
145                 150                 155                 160

Val Ser Ser Glu Lys Ser His Gln Ser Val Asn Lys Tyr Cys Glu Lys
                165                 170                 175

Thr Arg Arg Glu Val Ile Arg Lys Gly Ile Thr Met Thr Asn Leu Val
            180                 185                 190

Ser Leu Ser Ile Leu Glu Arg Leu Lys
        195                 200


<210> SEQ ID NO 55
<211> LENGTH: 822
<212> TYPE: DNA
<213> ORGANISM: Cenarchaeum symbiosum
<220> FEATURE:
<221> NAME/KEY: CDS
<222> LOCATION: (1)...(822)

<400> SEQUENCE: 55

ttg aaa agt acg ttg gtt cgg cgc tac aag ccc aag ata aag cag acc       48
Met Lys Ser Thr Leu Val Arg Arg Tyr Lys Pro Lys Ile Lys Gln Thr
 1               5                  10                  15

ctc cgc gag gtg ccc ctc aaa aat gtg cat gtg tgg aag gag gcg cag       96
Leu Arg Glu Val Pro Leu Lys Asn Val His Val Trp Lys Glu Ala Gln
            20                  25                  30
```

-continued

```
gca agg agg ctg gac agg tcc cgg gtg cgg gat atc gca aag tcg atc      144
Ala Arg Arg Leu Asp Arg Ser Arg Val Arg Asp Ile Ala Lys Ser Ile
        35                  40                  45

aga tca gag ggg ctg cag aac ccg ccc gtc ata cag agg ggc ggc agg      192
Arg Ser Glu Gly Leu Gln Asn Pro Pro Val Ile Gln Arg Gly Gly Arg
    50                  55                  60

ggg ctg tac ctc ctc ata tcg ggg cac cac cgg ctt gcg gcc ctc aag      240
Gly Leu Tyr Leu Leu Ile Ser Gly His His Arg Leu Ala Ala Leu Lys
 65                  70                  75                  80

tac ctg ggc gca aaa aag tcc aag ttt ctg gtg ata acc aag gat aca      288
Tyr Leu Gly Ala Lys Lys Ser Lys Phe Leu Val Ile Thr Lys Asp Thr
                 85                  90                  95

gag tac ggc ctg gat gat gca aag gcc gca tcg gtt gta gag aac ctg      336
Glu Tyr Gly Leu Asp Asp Ala Lys Ala Ala Ser Val Val Glu Asn Leu
            100                 105                 110

cac cgt ctc cag atg agc ccg cgg gag ctt gca gac gca tgc aag ttc      384
His Arg Leu Gln Met Ser Pro Arg Glu Leu Ala Asp Ala Cys Lys Phe
        115                 120                 125

ctg gcc gag cag acg aca aaa tcc gag gcc gca aaa aag ctc ggc atg      432
Leu Ala Glu Gln Thr Thr Lys Ser Glu Ala Ala Lys Lys Leu Gly Met
    130                 135                 140

tcg atg ccc acg ttc aag aaa tac cac ggc ttt gcg ggc gta ccg gac      480
Ser Met Pro Thr Phe Lys Lys Tyr His Gly Phe Ala Gly Val Pro Asp
145                 150                 155                 160

aag atc aag gcg atg gta ccg ggc acc ata tcc cgg gac gag gcg aca      528
Lys Ile Lys Ala Met Val Pro Gly Thr Ile Ser Arg Asp Glu Ala Thr
                165                 170                 175

agg ctc tac cag gcg gtg ccg acc ata tcc cag gcg ctc aag gtg gta      576
Arg Leu Tyr Gln Ala Val Pro Thr Ile Ser Gln Ala Leu Lys Val Val
            180                 185                 190

tca aag ata gca aag ctc gac agg ccg tcg agg cgg atc tac ctg agg      624
Ser Lys Ile Ala Lys Leu Asp Arg Pro Ser Arg Arg Ile Tyr Leu Arg
        195                 200                 205

ttg ctt gcc cag agc ccc cgc tcc ggc cac aag ata ata cta aag agg      672
Leu Leu Ala Gln Ser Pro Arg Ser Gly His Lys Ile Ile Leu Lys Arg
    210                 215                 220

atg cgc aag gtg ggc atc aag aaa aag ata cca ata gag ctg ggc aag      720
Met Arg Lys Val Gly Ile Lys Lys Lys Ile Pro Ile Glu Leu Gly Lys
225                 230                 235                 240

aac ggc gca aga aag ctc tcc agg ctg gcc gag cgc gag ggg aca gac      768
Asn Gly Ala Arg Lys Leu Ser Arg Leu Ala Glu Arg Glu Gly Thr Asp
                245                 250                 255

gag acc cgg ctt gcc aac agg ata gtc cgg gaa tac ctg agg aag cgg      816
Glu Thr Arg Leu Ala Asn Arg Ile Val Arg Glu Tyr Leu Arg Lys Arg
            260                 265                 270

cga tga                                                              822
Arg


<210> SEQ ID NO 56
<211> LENGTH: 273
<212> TYPE: PRT
<213> ORGANISM: Cenarchaeum symbiosum

<400> SEQUENCE: 56

Met Lys Ser Thr Leu Val Arg Arg Tyr Lys Pro Lys Ile Lys Gln Thr
 1               5                  10                  15

Leu Arg Glu Val Pro Leu Lys Asn Val His Val Trp Lys Glu Ala Gln
            20                  25                  30

Ala Arg Arg Leu Asp Arg Ser Arg Val Arg Asp Ile Ala Lys Ser Ile
        35                  40                  45
```

-continued

```
Arg Ser Glu Gly Leu Gln Asn Pro Pro Val Ile Gln Arg Gly Gly Arg
    50                  55                  60

Gly Leu Tyr Leu Leu Ile Ser Gly His His Arg Leu Ala Ala Leu Lys
65                  70                  75                  80

Tyr Leu Gly Ala Lys Lys Ser Lys Phe Leu Val Ile Thr Lys Asp Thr
                85                  90                  95

Glu Tyr Gly Leu Asp Asp Ala Lys Ala Ala Ser Val Val Glu Asn Leu
            100                 105                 110

His Arg Leu Gln Met Ser Pro Arg Glu Leu Ala Asp Ala Cys Lys Phe
        115                 120                 125

Leu Ala Glu Gln Thr Thr Lys Ser Glu Ala Ala Lys Lys Leu Gly Met
    130                 135                 140

Ser Met Pro Thr Phe Lys Lys Tyr His Gly Phe Ala Gly Val Pro Asp
145                 150                 155                 160

Lys Ile Lys Ala Met Val Pro Gly Thr Ile Ser Arg Asp Glu Ala Thr
                165                 170                 175

Arg Leu Tyr Gln Ala Val Pro Thr Ile Ser Gln Ala Leu Lys Val Val
            180                 185                 190

Ser Lys Ile Ala Lys Leu Asp Arg Pro Ser Arg Arg Ile Tyr Leu Arg
        195                 200                 205

Leu Leu Ala Gln Ser Pro Arg Ser Gly His Lys Ile Ile Leu Lys Arg
    210                 215                 220

Met Arg Lys Val Gly Ile Lys Lys Lys Ile Pro Ile Glu Leu Gly Lys
225                 230                 235                 240

Asn Gly Ala Arg Lys Leu Ser Arg Leu Ala Glu Arg Glu Gly Thr Asp
                245                 250                 255

Glu Thr Arg Leu Ala Asn Arg Ile Val Arg Glu Tyr Leu Arg Lys Arg
            260                 265                 270

Arg


<210> SEQ ID NO 57
<211> LENGTH: 669
<212> TYPE: DNA
<213> ORGANISM: Cenarchaeum symbiosum
<220> FEATURE:
<221> NAME/KEY: CDS
<222> LOCATION: (1)...(669)

<400> SEQUENCE: 57

gtg gcg cga tcg ccc gtg ctg ata ata aac tgc aaa aac tac aag gag       48
Met Ala Arg Ser Pro Val Leu Ile Ile Asn Cys Lys Asn Tyr Lys Glu
 1               5                  10                  15

gcg gcc ggc ggc aga att gac agc cta gcg gcg gca gcc gcc ggg gcg       96
Ala Ala Gly Gly Arg Ile Asp Ser Leu Ala Ala Ala Ala Ala Gly Ala
             20                  25                  30

gcc gca aaa tac ggc gtc agg ata gct ctt gcc ccg ccg cag cac ctg      144
Ala Ala Lys Tyr Gly Val Arg Ile Ala Leu Ala Pro Pro Gln His Leu
        35                  40                  45

ctg ggc gca gta aag ggg gaa gat ctt aca gtt ctg gcg cag cat ata      192
Leu Gly Ala Val Lys Gly Glu Asp Leu Thr Val Leu Ala Gln His Ile
     50                  55                  60

gac gac aag ggg gtt gga agc acc aca gga tat gtc gtg ccg gag ctg      240
Asp Asp Lys Gly Val Gly Ser Thr Thr Gly Tyr Val Val Pro Glu Leu
 65                  70                  75                  80

ctg gga gaa tcc ggc gtc tct ggc gcg ctc atc aac cac agc gag cac      288
Leu Gly Glu Ser Gly Val Ser Gly Ala Leu Ile Asn His Ser Glu His
                 85                  90                  95
```

-continued

```
cgc gta tca gct gac cag gtg gca agc ctt gtg ccc agg ctc agg ggt      336
Arg Val Ser Ala Asp Gln Val Ala Ser Leu Val Pro Arg Leu Arg Gly
            100                 105                 110

ctg gat atg atc tcc gtg gtc tgt gta aag gat tcc gcc gag gcg gca      384
Leu Asp Met Ile Ser Val Val Cys Val Lys Asp Ser Ala Glu Ala Ala
        115                 120                 125

aat ctc tcc cgg cac cgg ccc gac tac ata gct atc gag cct ccc gag      432
Asn Leu Ser Arg His Arg Pro Asp Tyr Ile Ala Ile Glu Pro Pro Glu
    130                 135                 140

ctg ata ggc tcg ggc agg tcc gtc tca tcg gag agg ccc gag ctg ata      480
Leu Ile Gly Ser Gly Arg Ser Val Ser Ser Glu Arg Pro Glu Leu Ile
145                 150                 155                 160

ggg gag gca gca gag gcc atc agg ggg gcg gat gga aca aag ctg ctc      528
Gly Glu Ala Ala Glu Ala Ile Arg Gly Ala Asp Gly Thr Lys Leu Leu
                165                 170                 175

tgc ggg gcg ggc ata aca tca ggc gct gat gtg cgc aag gcc ctc gag      576
Cys Gly Ala Gly Ile Thr Ser Gly Ala Asp Val Arg Lys Ala Leu Glu
            180                 185                 190

ctc ggc tcc aag ggg atc ctc gtg gca agc ggg gtg gta aaa tca tca      624
Leu Gly Ser Lys Gly Ile Leu Val Ala Ser Gly Val Val Lys Ser Ser
        195                 200                 205

gac ccc gct gcg gcc ata gcc gag ctg gca cag gcc atg tcc tga          669
Asp Pro Ala Ala Ala Ile Ala Glu Leu Ala Gln Ala Met Ser
    210                 215                 220
```

<210> SEQ ID NO 58
<211> LENGTH: 222
<212> TYPE: PRT
<213> ORGANISM: Cenarchaeum symbiosum

<400> SEQUENCE: 58

```
Met Ala Arg Ser Pro Val Leu Ile Ile Asn Cys Lys Asn Tyr Lys Glu
 1               5                  10                  15

Ala Ala Gly Gly Arg Ile Asp Ser Leu Ala Ala Ala Ala Ala Gly Ala
            20                  25                  30

Ala Ala Lys Tyr Gly Val Arg Ile Ala Leu Ala Pro Pro Gln His Leu
        35                  40                  45

Leu Gly Ala Val Lys Gly Glu Asp Leu Thr Val Leu Ala Gln His Ile
    50                  55                  60

Asp Asp Lys Gly Val Gly Ser Thr Thr Gly Tyr Val Val Pro Glu Leu
65                  70                  75                  80

Leu Gly Glu Ser Gly Val Ser Gly Ala Leu Ile Asn His Ser Glu His
                85                  90                  95

Arg Val Ser Ala Asp Gln Val Ala Ser Leu Val Pro Arg Leu Arg Gly
            100                 105                 110

Leu Asp Met Ile Ser Val Val Cys Val Lys Asp Ser Ala Glu Ala Ala
        115                 120                 125

Asn Leu Ser Arg His Arg Pro Asp Tyr Ile Ala Ile Glu Pro Pro Glu
    130                 135                 140

Leu Ile Gly Ser Gly Arg Ser Val Ser Ser Glu Arg Pro Glu Leu Ile
145                 150                 155                 160

Gly Glu Ala Ala Glu Ala Ile Arg Gly Ala Asp Gly Thr Lys Leu Leu
                165                 170                 175

Cys Gly Ala Gly Ile Thr Ser Gly Ala Asp Val Arg Lys Ala Leu Glu
            180                 185                 190

Leu Gly Ser Lys Gly Ile Leu Val Ala Ser Gly Val Val Lys Ser Ser
        195                 200                 205
```

-continued

```
Asp Pro Ala Ala Ala Ile Ala Glu Leu Ala Gln Ala Met Ser
    210                 215                 220


<210> SEQ ID NO 59
<211> LENGTH: 549
<212> TYPE: DNA
<213> ORGANISM: Cenarchaeum symbiosum
<220> FEATURE:
<221> NAME/KEY: CDS
<222> LOCATION: (1)...(548)

<400> SEQUENCE: 59

atg ctg gat ccc cgg acg cgg ccc cgg gtc gtc aat gtc gtc agc aca       48
Met Leu Asp Pro Arg Thr Arg Pro Arg Val Val Asn Val Val Ser Thr
 1               5                  10                  15

tca gac ctt gta caa agg gtg agc gca aaa aag atg gcc gcc atg ccg       96
Ser Asp Leu Val Gln Arg Val Ser Ala Lys Lys Met Ala Ala Met Pro
            20                  25                  30

tgc tgc atg tat gat gag gcc gta tac ggc ggc agg tgc ggc tac ata      144
Cys Cys Met Tyr Asp Glu Ala Val Tyr Gly Gly Arg Cys Gly Tyr Ile
        35                  40                  45

aag acg ccc ggc atg cag ggg agg gtg act gta ttc att tct ggc aag      192
Lys Thr Pro Gly Met Gln Gly Arg Val Thr Val Phe Ile Ser Gly Lys
     50                  55                  60

atg ata tcc gtc ggc gcc aga tcc gtg agg gcc tcg ttt ggg cag ctg      240
Met Ile Ser Val Gly Ala Arg Ser Val Arg Ala Ser Phe Gly Gln Leu
 65                  70                  75                  80

cac gag gcg cgg ctc cac ctg gtg cgc aac ggg gct gcc ggc gac tgc      288
His Glu Ala Arg Leu His Leu Val Arg Asn Gly Ala Ala Gly Asp Cys
                85                  90                  95

aag ata agg ccc gtc gtg cgc aat att gta gcc acg gtg gat gcc ggt      336
Lys Ile Arg Pro Val Val Arg Asn Ile Val Ala Thr Val Asp Ala Gly
            100                 105                 110

agg aat gtt ccc ata gac agg ata tcg tcg cgc atg cct ggc gct gta      384
Arg Asn Val Pro Ile Asp Arg Ile Ser Ser Arg Met Pro Gly Ala Val
        115                 120                 125

tat gat ccc ggg tcg ttt ccc ggg atg ata ctc aag ggg ctg gac agc      432
Tyr Asp Pro Gly Ser Phe Pro Gly Met Ile Leu Lys Gly Leu Asp Ser
    130                 135                 140

tgc agc ttt cta gtc ttt gcg tcg gga aag atg gtg ata gcg ggc gcc      480
Cys Ser Phe Leu Val Phe Ala Ser Gly Lys Met Val Ile Ala Gly Ala
145                 150                 155                 160

aag tcg ccg gat gag ctg cgc agg tcg tcg ttt gac ctg ctg acg cgc      528
Lys Ser Pro Asp Glu Leu Arg Arg Ser Ser Phe Asp Leu Leu Thr Arg
                165                 170                 175

ctc aat aac gcg ggg gcc ta g                                         549
Leu Asn Asn Ala Gly Ala
            180


<210> SEQ ID NO 60
<211> LENGTH: 182
<212> TYPE: PRT
<213> ORGANISM: Cenarchaeum symbiosum

<400> SEQUENCE: 60

Met Leu Asp Pro Arg Thr Arg Pro Arg Val Val Asn Val Val Ser Thr
 1               5                  10                  15

Ser Asp Leu Val Gln Arg Val Ser Ala Lys Lys Met Ala Ala Met Pro
            20                  25                  30

Cys Cys Met Tyr Asp Glu Ala Val Tyr Gly Gly Arg Cys Gly Tyr Ile
        35                  40                  45
```

-continued

```
Lys Thr Pro Gly Met Gln Gly Arg Val Thr Val Phe Ile Ser Gly Lys
    50                  55                  60

Met Ile Ser Val Gly Ala Arg Ser Val Arg Ala Ser Phe Gly Gln Leu
65                  70                  75                  80

His Glu Ala Arg Leu His Leu Val Arg Asn Gly Ala Ala Gly Asp Cys
                85                  90                  95

Lys Ile Arg Pro Val Val Arg Asn Ile Val Ala Thr Val Asp Ala Gly
            100                 105                 110

Arg Asn Val Pro Ile Asp Arg Ile Ser Ser Arg Met Pro Gly Ala Val
        115                 120                 125

Tyr Asp Pro Gly Ser Phe Pro Gly Met Ile Leu Lys Gly Leu Asp Ser
    130                 135                 140

Cys Ser Phe Leu Val Phe Ala Ser Gly Lys Met Val Ile Ala Gly Ala
145                 150                 155                 160

Lys Ser Pro Asp Glu Leu Arg Arg Ser Ser Phe Asp Leu Leu Thr Arg
                165                 170                 175

Leu Asn Asn Ala Gly Ala
            180
```

<210> SEQ ID NO 61
<211> LENGTH: 2538
<212> TYPE: DNA
<213> ORGANISM: Cenarchaeum symbiosum
<220> FEATURE:
<221> NAME/KEY: CDS
<222> LOCATION: (1)...(2538)

<400> SEQUENCE: 61

```
ctg act gca cag gat gaa gag att ccc ccg tca ctg ctt gta tct gca       48
Met Thr Ala Gln Asp Glu Glu Ile Pro Pro Ser Leu Leu Val Ser Ala
 1               5                  10                  15

acc tat gat ggc cag gca agg gcc gtg gtc ctc aag ttc tac gag tcg       96
Thr Tyr Asp Gly Gln Ala Arg Ala Val Val Leu Lys Phe Tyr Glu Ser
            20                  25                  30

gaa tcg caa aag atc atc cac tgg acg gac aac acg ggg cac aag ccc      144
Glu Ser Gln Lys Ile Ile His Trp Thr Asp Asn Thr Gly His Lys Pro
        35                  40                  45

tac tgt tat acg agg ctg ccg ccc tcc gag ctc ggc ttt ctt ggg ggc      192
Tyr Cys Tyr Thr Arg Leu Pro Pro Ser Glu Leu Gly Phe Leu Gly Gly
     50                  55                  60

agg gag gac gtg ctc ggg ata gag cag gtc atg cgg cac gac ctg ata      240
Arg Glu Asp Val Leu Gly Ile Glu Gln Val Met Arg His Asp Leu Ile
 65                  70                  75                  80

gcc gac aag gag gtg ccc gtc tcc aag ata acc gtc tct gat cct ctt      288
Ala Asp Lys Glu Val Pro Val Ser Lys Ile Thr Val Ser Asp Pro Leu
                 85                  90                  95

gcg ata ggc ggg acc cac tcg gag aag agc atc aga aac gtg ata gac      336
Ala Ile Gly Gly Thr His Ser Glu Lys Ser Ile Arg Asn Val Ile Asp
            100                 105                 110

acg tgg gaa tcc gac ata aag tat tac gag aac tat ctg tat gac gcg      384
Thr Trp Glu Ser Asp Ile Lys Tyr Tyr Glu Asn Tyr Leu Tyr Asp Ala
        115                 120                 125

ggc ctg gta gtg ggc agg tac tat tcg gta tca ggc ggg gag gtg att      432
Gly Leu Val Val Gly Arg Tyr Tyr Ser Val Ser Gly Gly Glu Val Ile
    130                 135                 140

ccg cat gac atg cca ata tcc gac gag gta aaa ctg gcc ctc aag agc      480
Pro His Asp Met Pro Ile Ser Asp Glu Val Lys Leu Ala Leu Lys Ser
145                 150                 155                 160
```

-continued

```
ctt ctc tgg gac aag ctc ata gac gag ggc atg gcc gac agg aaa gag      528
Leu Leu Trp Asp Lys Leu Ile Asp Glu Gly Met Ala Asp Arg Lys Glu
            165                 170                 175

ttc cgc gag ttc ata gcg ggg tgg gcg gac ctg ctc aac cag ccc ata      576
Phe Arg Glu Phe Ile Ala Gly Trp Ala Asp Leu Leu Asn Gln Pro Ile
        180                 185                 190

ccc cgg ata agg cgc ctc agc ttt gac atc gag gtg gat tca gag gag      624
Pro Arg Ile Arg Arg Leu Ser Phe Asp Ile Glu Val Asp Ser Glu Glu
    195                 200                 205

ggc agg atc ccc gat gcc aag atc tcg gac agg agg gtc aca gca gtg      672
Gly Arg Ile Pro Asp Ala Lys Ile Ser Asp Arg Arg Val Thr Ala Val
210                 215                 220

ggg ttt gcc gcc acc gac ggc ctc aga aag gtc ctt gtc ctg aag agc      720
Gly Phe Ala Ala Thr Asp Gly Leu Arg Lys Val Leu Val Leu Lys Ser
225                 230                 235                 240

ggc gcg gac gag ggc gca aac gat gtg acc ccc ggg gtc gag gtg gtg      768
Gly Ala Asp Glu Gly Ala Asn Asp Val Thr Pro Gly Val Glu Val Val
                245                 250                 255

ttc tac gac gag gac aag gag gcg gac atg atc cgc gac gcg cta gca      816
Phe Tyr Asp Glu Asp Lys Glu Ala Asp Met Ile Arg Asp Ala Leu Ala
            260                 265                 270

ata ata ggc tcg tac ccg ttt gtg ctt aca tac aac ggg gac gac ttt      864
Ile Ile Gly Ser Tyr Pro Phe Val Leu Thr Tyr Asn Gly Asp Asp Phe
        275                 280                 285

gac atg ccg tac atg tac aat cgg gcc cgg cgc ctc ggc gtg gcg gat      912
Asp Met Pro Tyr Met Tyr Asn Arg Ala Arg Arg Leu Gly Val Ala Asp
    290                 295                 300

tcc gac ata ccc ctg tac atg atg cgg gat tcg gcc acg ctc cgg cac      960
Ser Asp Ile Pro Leu Tyr Met Met Arg Asp Ser Ala Thr Leu Arg His
305                 310                 315                 320

ggc gtc cat ctg gac ctg tac agg acc ttc tcg aac agg tcg ttc cag     1008
Gly Val His Leu Asp Leu Tyr Arg Thr Phe Ser Asn Arg Ser Phe Gln
                325                 330                 335

ctg tat gca ttt gcg gca aag tat aca gat tac tcc ctg aac agc gtg     1056
Leu Tyr Ala Phe Ala Ala Lys Tyr Thr Asp Tyr Ser Leu Asn Ser Val
            340                 345                 350

tcc aag gcg atg ctc ggc gag ggc aag gtc gat tat ggc gtg tct ctc     1104
Ser Lys Ala Met Leu Gly Glu Gly Lys Val Asp Tyr Gly Val Ser Leu
        355                 360                 365

ggg gat ctc act cta tac cag act gca aac tat tgc tat cat gac gcg     1152
Gly Asp Leu Thr Leu Tyr Gln Thr Ala Asn Tyr Cys Tyr His Asp Ala
    370                 375                 380

cgc ctg acg ctg gag ctt agc acc ttt ggg aac gag ata ctg atg gac     1200
Arg Leu Thr Leu Glu Leu Ser Thr Phe Gly Asn Glu Ile Leu Met Asp
385                 390                 395                 400

ctc ctg gtg gtg acc agc agg att gcc cgg atg ccc atc gat gat atg     1248
Leu Leu Val Val Thr Ser Arg Ile Ala Arg Met Pro Ile Asp Asp Met
                405                 410                 415

tcc cgc atg ggc gtc tcg cag tgg ata agg agc ctg ctg tac tat gag     1296
Ser Arg Met Gly Val Ser Gln Trp Ile Arg Ser Leu Leu Tyr Tyr Glu
            420                 425                 430

cac agg cag cgc aac gcg ctg ata ccc cgc agg gac gag ctg gaa aag     1344
His Arg Gln Arg Asn Ala Leu Ile Pro Arg Arg Asp Glu Leu Glu Lys
        435                 440                 445

agg tct caa cag gta agc aac gac gcc gta atc aag gac aaa aag ttc     1392
Arg Ser Gln Gln Val Ser Asn Asp Ala Val Ile Lys Asp Lys Lys Phe
    450                 455                 460

cgc ggt ggt ctc gta gtc gag cct gaa gag ggc ata cac ttt gat gtt     1440
Arg Gly Gly Leu Val Val Glu Pro Glu Glu Gly Ile His Phe Asp Val
465                 470                 475                 480
```

-continued

```
aca gtt atg gat ttt gca agc ctg tat cct agc ata ata aag gtg cga      1488
Thr Val Met Asp Phe Ala Ser Leu Tyr Pro Ser Ile Ile Lys Val Arg
                485                 490                 495

aac ctc tcg tac gag acc gtc agg tgc gtt cat ccc gaa tgc aga aag      1536
Asn Leu Ser Tyr Glu Thr Val Arg Cys Val His Pro Glu Cys Arg Lys
            500                 505                 510

aac acc atc ccc gat acc aac cac tgg gta tgc acg aaa aac aac ggg      1584
Asn Thr Ile Pro Asp Thr Asn His Trp Val Cys Thr Lys Asn Asn Gly
        515                 520                 525

ctt aca tcg atg ata ata gga tcg ctc cgc gac ctg cgc gtc aac tat      1632
Leu Thr Ser Met Ile Ile Gly Ser Leu Arg Asp Leu Arg Val Asn Tyr
    530                 535                 540

tac aag agc ctc tca aag agc cag tct ata acg gag gag cag cgg cag      1680
Tyr Lys Ser Leu Ser Lys Ser Gln Ser Ile Thr Glu Glu Gln Arg Gln
545                 550                 555                 560

cag tat act gtg atc agc cag gcc ctc aag gtg gtg cta aac gca agc      1728
Gln Tyr Thr Val Ile Ser Gln Ala Leu Lys Val Val Leu Asn Ala Ser
                565                 570                 575

tac ggg gtg atg ggc gcc gag ata ttc ccg ctg tac ttt ctg cct gcc      1776
Tyr Gly Val Met Gly Ala Glu Ile Phe Pro Leu Tyr Phe Leu Pro Ala
            580                 585                 590

gcc gag gcc acc acg gcg gtc ggg cgc tat atc atc atg cag acc ata      1824
Ala Glu Ala Thr Thr Ala Val Gly Arg Tyr Ile Ile Met Gln Thr Ile
        595                 600                 605

tcg cac tgc gag cag atg ggc gta aag gtg ctg tac ggg gac acc gat      1872
Ser His Cys Glu Gln Met Gly Val Lys Val Leu Tyr Gly Asp Thr Asp
    610                 615                 620

tcg ctg ttc ata aag aat cca gag gag cgg cag atc cat gat ata gtc      1920
Ser Leu Phe Ile Lys Asn Pro Glu Glu Arg Gln Ile His Asp Ile Val
625                 630                 635                 640

gag cac gcc aaa aag gag cac ggc gtc gag ctc gag gtg gac aaa gag      1968
Glu His Ala Lys Lys Glu His Gly Val Glu Leu Glu Val Asp Lys Glu
                645                 650                 655

tac agg tat gtc gtg cta tct aac agg aag aaa aac tat ttc ggg gtg      2016
Tyr Arg Tyr Val Val Leu Ser Asn Arg Lys Lys Asn Tyr Phe Gly Val
            660                 665                 670

aca aag tcc ggc aag gtc gac gtc aag ggc ctg acg ggg aaa aag tcg      2064
Thr Lys Ser Gly Lys Val Asp Val Lys Gly Leu Thr Gly Lys Lys Ser
        675                 680                 685

cac acg ccc ccg ttc ata aag gag ctg ttc tat tcg ctg ctc gac ata      2112
His Thr Pro Pro Phe Ile Lys Glu Leu Phe Tyr Ser Leu Leu Asp Ile
    690                 695                 700

ctg tcg gct gta cag acc gag gac gag ttt gaa tcg gca aag cta aag      2160
Leu Ser Ala Val Gln Thr Glu Asp Glu Phe Glu Ser Ala Lys Leu Lys
705                 710                 715                 720

atc tca aag gcc ata gcg gca tcc ggg aag agg ctg gag gag agg ggg      2208
Ile Ser Lys Ala Ile Ala Ala Ser Gly Lys Arg Leu Glu Glu Arg Gly
                725                 730                 735

gtc ccg ctg gcg gat ctg gcg ttc aat gtg atg ata agc aag gcg ccc      2256
Val Pro Leu Ala Asp Leu Ala Phe Asn Val Met Ile Ser Lys Ala Pro
            740                 745                 750

tct gaa tac gta aag acc gtc ccg cag cac ata cgg gcg gcc aga ctg      2304
Ser Glu Tyr Val Lys Thr Val Pro Gln His Ile Arg Ala Ala Arg Leu
        755                 760                 765

ctc gag aac gca agg gag gtc aaa aaa ggc gac ata ata tcg tac gta      2352
Leu Glu Asn Ala Arg Glu Val Lys Lys Gly Asp Ile Ile Ser Tyr Val
    770                 775                 780

aag gtg atg aac aag aca ggc gtc aag cct gtc gag atg gcc cag gca      2400
Lys Val Met Asn Lys Thr Gly Val Lys Pro Val Glu Met Ala Gln Ala
```

-continued

```
785                 790                 795                 800

gga gag gtg gac acg tca aag tat cta gag ttc atg gag tct act ctg      2448
Gly Glu Val Asp Thr Ser Lys Tyr Leu Glu Phe Met Glu Ser Thr Leu
                805                 810                 815

gac cag ctc acc tcg tcc atg ggc ctt gac ttt gac gag atg ctg ggc      246
Asp Gln Leu Thr Ser Ser Met Gly Leu Asp Phe Asp Glu Met Leu Gly
            820                 825                 830

aag cca aag cag act gga atg gag cag ttc ttt ttc aaa tga              2538
Lys Pro Lys Gln Thr Gly Met Glu Gln Phe Phe Phe Lys
        835                 840                 845


<210> SEQ ID NO 62
<211> LENGTH: 845
<212> TYPE: PRT
<213> ORGANISM: Cenarchaeum symbiosum

<400> SEQUENCE: 62

Met Thr Ala Gln Asp Glu Glu Ile Pro Pro Ser Leu Leu Val Ser Ala
1               5                   10                  15

Thr Tyr Asp Gly Gln Ala Arg Ala Val Val Leu Lys Phe Tyr Glu Ser
            20                  25                  30

Glu Ser Gln Lys Ile Ile His Trp Thr Asp Asn Thr Gly His Lys Pro
        35                  40                  45

Tyr Cys Tyr Thr Arg Leu Pro Pro Ser Glu Leu Gly Phe Leu Gly Gly
    50                  55                  60

Arg Glu Asp Val Leu Gly Ile Glu Gln Val Met Arg His Asp Leu Ile
65                  70                  75                  80

Ala Asp Lys Glu Val Pro Val Ser Lys Ile Thr Val Ser Asp Pro Leu
                85                  90                  95

Ala Ile Gly Gly Thr His Ser Glu Lys Ser Ile Arg Asn Val Ile Asp
            100                 105                 110

Thr Trp Glu Ser Asp Ile Lys Tyr Tyr Glu Asn Tyr Leu Tyr Asp Ala
        115                 120                 125

Gly Leu Val Val Gly Arg Tyr Tyr Ser Val Ser Gly Gly Glu Val Ile
    130                 135                 140

Pro His Asp Met Pro Ile Ser Asp Glu Val Lys Leu Ala Leu Lys Ser
145                 150                 155                 160

Leu Leu Trp Asp Lys Leu Ile Asp Glu Gly Met Ala Asp Arg Lys Glu
                165                 170                 175

Phe Arg Glu Phe Ile Ala Gly Trp Ala Asp Leu Leu Asn Gln Pro Ile
            180                 185                 190

Pro Arg Ile Arg Arg Leu Ser Phe Asp Ile Glu Val Asp Ser Glu Glu
        195                 200                 205

Gly Arg Ile Pro Asp Ala Lys Ile Ser Asp Arg Arg Val Thr Ala Val
    210                 215                 220

Gly Phe Ala Ala Thr Asp Gly Leu Arg Lys Val Leu Val Leu Lys Ser
225                 230                 235                 240

Gly Ala Asp Glu Gly Ala Asn Asp Val Thr Pro Gly Val Glu Val Val
                245                 250                 255

Phe Tyr Asp Glu Asp Lys Glu Ala Asp Met Ile Arg Asp Ala Leu Ala
            260                 265                 270

Ile Ile Gly Ser Tyr Pro Phe Val Leu Thr Tyr Asn Gly Asp Asp Phe
        275                 280                 285

Asp Met Pro Tyr Met Tyr Asn Arg Ala Arg Arg Leu Gly Val Ala Asp
    290                 295                 300
```

-continued

```
Ser Asp Ile Pro Leu Tyr Met Met Arg Asp Ser Ala Thr Leu Arg His
305                 310                 315                 320

Gly Val His Leu Asp Leu Tyr Arg Thr Phe Ser Asn Arg Ser Phe Gln
                325                 330                 335

Leu Tyr Ala Phe Ala Ala Lys Tyr Thr Asp Tyr Ser Leu Asn Ser Val
            340                 345                 350

Ser Lys Ala Met Leu Gly Glu Gly Lys Val Asp Tyr Gly Val Ser Leu
        355                 360                 365

Gly Asp Leu Thr Leu Tyr Gln Thr Ala Asn Tyr Cys Tyr His Asp Ala
    370                 375                 380

Arg Leu Thr Leu Glu Leu Ser Thr Phe Gly Asn Glu Ile Leu Met Asp
385                 390                 395                 400

Leu Leu Val Val Thr Ser Arg Ile Ala Arg Met Pro Ile Asp Asp Met
                405                 410                 415

Ser Arg Met Gly Val Ser Gln Trp Ile Arg Ser Leu Leu Tyr Tyr Glu
            420                 425                 430

His Arg Gln Arg Asn Ala Leu Ile Pro Arg Arg Asp Glu Leu Glu Lys
        435                 440                 445

Arg Ser Gln Gln Val Ser Asn Asp Ala Val Ile Lys Asp Lys Lys Phe
    450                 455                 460

Arg Gly Gly Leu Val Val Glu Pro Glu Glu Gly Ile His Phe Asp Val
465                 470                 475                 480

Thr Val Met Asp Phe Ala Ser Leu Tyr Pro Ser Ile Ile Lys Val Arg
                485                 490                 495

Asn Leu Ser Tyr Glu Thr Val Arg Cys Val His Pro Glu Cys Arg Lys
            500                 505                 510

Asn Thr Ile Pro Asp Thr Asn His Trp Val Cys Thr Lys Asn Asn Gly
        515                 520                 525

Leu Thr Ser Met Ile Ile Gly Ser Leu Arg Asp Leu Arg Val Asn Tyr
    530                 535                 540

Tyr Lys Ser Leu Ser Lys Ser Gln Ser Ile Thr Glu Glu Gln Arg Gln
545                 550                 555                 560

Gln Tyr Thr Val Ile Ser Gln Ala Leu Lys Val Val Leu Asn Ala Ser
                565                 570                 575

Tyr Gly Val Met Gly Ala Glu Ile Phe Pro Leu Tyr Phe Leu Pro Ala
            580                 585                 590

Ala Glu Ala Thr Thr Ala Val Gly Arg Tyr Ile Ile Met Gln Thr Ile
        595                 600                 605

Ser His Cys Glu Gln Met Gly Val Lys Val Leu Tyr Gly Asp Thr Asp
    610                 615                 620

Ser Leu Phe Ile Lys Asn Pro Glu Glu Arg Gln Ile His Asp Ile Val
625                 630                 635                 640

Glu His Ala Lys Lys Glu His Gly Val Glu Leu Glu Val Asp Lys Glu
                645                 650                 655

Tyr Arg Tyr Val Val Leu Ser Asn Arg Lys Lys Asn Tyr Phe Gly Val
            660                 665                 670

Thr Lys Ser Gly Lys Val Asp Val Lys Gly Leu Thr Gly Lys Lys Ser
        675                 680                 685

His Thr Pro Pro Phe Ile Lys Glu Leu Phe Tyr Ser Leu Leu Asp Ile
    690                 695                 700

Leu Ser Ala Val Gln Thr Glu Asp Glu Phe Glu Ser Ala Lys Leu Lys
705                 710                 715                 720

Ile Ser Lys Ala Ile Ala Ala Ser Gly Lys Arg Leu Glu Glu Arg Gly
```

-continued

```
                725                 730                 735

Val Pro Leu Ala Asp Leu Ala Phe Asn Val Met Ile Ser Lys Ala Pro
            740                 745                 750

Ser Glu Tyr Val Lys Thr Val Pro Gln His Ile Arg Ala Ala Arg Leu
        755                 760                 765

Leu Glu Asn Ala Arg Glu Val Lys Lys Gly Asp Ile Ile Ser Tyr Val
    770                 775                 780

Lys Val Met Asn Lys Thr Gly Val Lys Pro Val Glu Met Ala Gln Ala
785                 790                 795                 800

Gly Glu Val Asp Thr Ser Lys Tyr Leu Glu Phe Met Glu Ser Thr Leu
                805                 810                 815

Asp Gln Leu Thr Ser Ser Met Gly Leu Asp Phe Asp Glu Met Leu Gly
            820                 825                 830

Lys Pro Lys Gln Thr Gly Met Glu Gln Phe Phe Phe Lys
        835                 840                 845


<210> SEQ ID NO 63
<211> LENGTH: 642
<212> TYPE: DNA
<213> ORGANISM: Cenarchaeum symbiosum
<220> FEATURE:
<221> NAME/KEY: CDS
<222> LOCATION: (1)...(642)

<400> SEQUENCE: 63

ttg ccc gtt atg tgt gcg gtc tcc acg cgc ggc cct gac gcg gcc tgt       48
Met Pro Val Met Cys Ala Val Ser Thr Arg Gly Pro Asp Ala Ala Cys
 1               5                  10                  15

tgt ttt atg gtt tcg tac acc ggg gca tat acc ata ata tgc cgg gcg       96
Cys Phe Met Val Ser Tyr Thr Gly Ala Tyr Thr Ile Ile Cys Arg Ala
            20                  25                  30

gtg gca cca tgg ccg ttg agc ggt ttt gag cgc ccg tcc tgg gac gaa      144
Val Ala Pro Trp Pro Leu Ser Gly Phe Glu Arg Pro Ser Trp Asp Glu
        35                  40                  45

tat ttc atg ctg cag gcg gag ctg gca aag ctc cga tcc aac tgc atg      192
Tyr Phe Met Leu Gln Ala Glu Leu Ala Lys Leu Arg Ser Asn Cys Met
    50                  55                  60

gtc aga aag gtg ggg gcc gtc ata gtc agg gat cac agg cag ctg gcc      240
Val Arg Lys Val Gly Ala Val Ile Val Arg Asp His Arg Gln Leu Ala
 65                  70                  75                  80

aca gga tac aac ggg acg ccc ccc ggc gta aag aac tgc ttc gag ggc      288
Thr Gly Tyr Asn Gly Thr Pro Pro Gly Val Lys Asn Cys Phe Glu Gly
                85                  90                  95

ggg tgc gaa agg tgc ata gag cgc atg gag ggc aag atc cgc tca ggc      336
Gly Cys Glu Arg Cys Ile Glu Arg Met Glu Gly Lys Ile Arg Ser Gly
            100                 105                 110

gag ggc ctg gac cgg tgc ctg tgc aac cat gca gag gcc aac gcg ata      384
Glu Gly Leu Asp Arg Cys Leu Cys Asn His Ala Glu Ala Asn Ala Ile
        115                 120                 125

atg cac tgt gcg ata ctg gga ata ggc gca ggg gga ggc aac gcc acc      432
Met His Cys Ala Ile Leu Gly Ile Gly Ala Gly Gly Gly Asn Ala Thr
    130                 135                 140

atg tat acg acg ttc tct ccg tgt tta gag tgc aca aag atg gcg gtg      480
Met Tyr Thr Thr Phe Ser Pro Cys Leu Glu Cys Thr Lys Met Ala Val
145                 150                 155                 160

acc ata gga atc agg cgg ttt gtc tgc ctg gat aca tat ccg gag aac      528
Thr Ile Gly Ile Arg Arg Phe Val Cys Leu Asp Thr Tyr Pro Glu Asn
                165                 170                 175

gcc tcc aag ctg gta aaa gat gca tcg gcc agc ata acc atg atg gac      576
```

-continued

```
Ala Ser Lys Leu Val Lys Asp Ala Ser Ala Ser Ile Thr Met Met Asp
            180                 185                 190

aag gag aag atc aca tac tgg gcg tca agg atg ccc ggg gga aca aag      624
Lys Glu Lys Ile Thr Tyr Trp Ala Ser Arg Met Pro Gly Gly Thr Lys
        195                 200                 205

gag gtg ccg gtg cgc tga                                              642
Glu Val Pro Val Arg
    210


<210> SEQ ID NO 64
<211> LENGTH: 213
<212> TYPE: PRT
<213> ORGANISM: Cenarchaeum symbiosum

<400> SEQUENCE: 64

Met Pro Val Met Cys Ala Val Ser Thr Arg Gly Pro Asp Ala Ala Cys
 1               5                  10                  15

Cys Phe Met Val Ser Tyr Thr Gly Ala Tyr Thr Ile Ile Cys Arg Ala
            20                  25                  30

Val Ala Pro Trp Pro Leu Ser Gly Phe Glu Arg Pro Ser Trp Asp Glu
        35                  40                  45

Tyr Phe Met Leu Gln Ala Glu Leu Ala Lys Leu Arg Ser Asn Cys Met
    50                  55                  60

Val Arg Lys Val Gly Ala Val Ile Val Arg Asp His Arg Gln Leu Ala
65                  70                  75                  80

Thr Gly Tyr Asn Gly Thr Pro Pro Gly Val Lys Asn Cys Phe Glu Gly
                85                  90                  95

Gly Cys Glu Arg Cys Ile Glu Arg Met Glu Gly Lys Ile Arg Ser Gly
            100                 105                 110

Glu Gly Leu Asp Arg Cys Leu Cys Asn His Ala Glu Ala Asn Ala Ile
        115                 120                 125

Met His Cys Ala Ile Leu Gly Ile Gly Ala Gly Gly Gly Asn Ala Thr
    130                 135                 140

Met Tyr Thr Thr Phe Ser Pro Cys Leu Glu Cys Thr Lys Met Ala Val
145                 150                 155                 160

Thr Ile Gly Ile Arg Arg Phe Val Cys Leu Asp Thr Tyr Pro Glu Asn
                165                 170                 175

Ala Ser Lys Leu Val Lys Asp Ala Ser Ala Ser Ile Thr Met Met Asp
            180                 185                 190

Lys Glu Lys Ile Thr Tyr Trp Ala Ser Arg Met Pro Gly Gly Thr Lys
        195                 200                 205

Glu Val Pro Val Arg
    210


<210> SEQ ID NO 65
<211> LENGTH: 1512
<212> TYPE: DNA
<213> ORGANISM: Cenarchaeum symbiosum
<220> FEATURE:
<221> NAME/KEY: CDS
<222> LOCATION: (1)...(1512)

<400> SEQUENCE: 65

gtg gag acc gca cac ata acg ggc aaa tac gta gag ccc ggc gcc gtc       48
Met Glu Thr Ala His Ile Thr Gly Lys Tyr Val Glu Pro Gly Ala Val
 1               5                  10                  15

gag agg cgc gac tac cag gtg ggc ctt gcc gag cag gcc ata cgg gaa       96
Glu Arg Arg Asp Tyr Gln Val Gly Leu Ala Glu Gln Ala Ile Arg Glu
            20                  25                  30
```

-continued

```
aac tgc ata gtg gtg ctg cct acc ggc ctc ggc aag acg gcc gtg gcc      144
Asn Cys Ile Val Val Leu Pro Thr Gly Leu Gly Lys Thr Ala Val Ala
         35                  40                  45

ctg cag gtg atc tcc cac tat ttg gac gaa ggc agg ggg gct ctc ttc      192
Leu Gln Val Ile Ser His Tyr Leu Asp Glu Gly Arg Gly Ala Leu Phe
     50                  55                  60

ctt gcg ccg aca agg gtg ctg gta aac cag cac cgc cag ttc ctg ggc      240
Leu Ala Pro Thr Arg Val Leu Val Asn Gln His Arg Gln Phe Leu Gly
 65                  70                  75                  80

agg gcc ctt acc ata tcc gat att acc ctg gtc aca ggc gag gac acc      288
Arg Ala Leu Thr Ile Ser Asp Ile Thr Leu Val Thr Gly Glu Asp Thr
                 85                  90                  95

gtc ccg agg cgc aaa aaa gct tgg ggc ggc agc gtg atc tgc gcc acc      336
Val Pro Arg Arg Lys Lys Ala Trp Gly Gly Ser Val Ile Cys Ala Thr
            100                 105                 110

ccc gag ata aca aga aac gac ata gcg cgc gga atg gtc ccg ctc gaa      384
Pro Glu Ile Thr Arg Asn Asp Ile Ala Arg Gly Met Val Pro Leu Glu
        115                 120                 125

cag ttc ggc ctg gtt gtg ttc gac gag gcc cac agg gcg gtg ggc gac      432
Gln Phe Gly Leu Val Val Phe Asp Glu Ala His Arg Ala Val Gly Asp
    130                 135                 140

tat gcc tat tcc gca ata gcg cgt gca gtg ggg gag aac tct aga atg      480
Tyr Ala Tyr Ser Ala Ile Ala Arg Ala Val Gly Glu Asn Ser Arg Met
145                 150                 155                 160

atc ggc atg act gcg acc ctt cca agc gag agg gag aaa gcc gac gag      528
Ile Gly Met Thr Ala Thr Leu Pro Ser Glu Arg Glu Lys Ala Asp Glu
                165                 170                 175

ata atg ggc act ctt ctc tca aag agc ata gca caa agg acc gaa gac      576
Ile Met Gly Thr Leu Leu Ser Lys Ser Ile Ala Gln Arg Thr Glu Asp
            180                 185                 190

gac ccg gat gta aag ccc tac gtg cag gag acc gaa act gaa tgg ata      624
Asp Pro Asp Val Lys Pro Tyr Val Gln Glu Thr Glu Thr Glu Trp Ile
        195                 200                 205

aag gtg gag ctg ccc ccg gag atg aag gag atc caa aag ctc ctg aag      672
Lys Val Glu Leu Pro Pro Glu Met Lys Glu Ile Gln Lys Leu Leu Lys
    210                 215                 220

atg gcc ctc gac gaa aga tat gcg gcc ctc aag agg tgc ggc tat gat      720
Met Ala Leu Asp Glu Arg Tyr Ala Ala Leu Lys Arg Cys Gly Tyr Asp
225                 230                 235                 240

ctc ggc tcg aac agg tcg ctc tcg gct ctg ctc cgc ctt cgc atg gtc      768
Leu Gly Ser Asn Arg Ser Leu Ser Ala Leu Leu Arg Leu Arg Met Val
                245                 250                 255

gtt cta agc ggc aac agg cgg gcg gca aag cct ttg ttt act gcg ata      816
Val Leu Ser Gly Asn Arg Arg Ala Ala Lys Pro Leu Phe Thr Ala Ile
            260                 265                 270

cgc atc aca tac gcg ctc aac ata ttc gag gcc cac ggg gtc acg ccg      864
Arg Ile Thr Tyr Ala Leu Asn Ile Phe Glu Ala His Gly Val Thr Pro
        275                 280                 285

ttt cta aag ttc tgc gag agg acc gtc aag aaa aag ggc gcc ggt gtt      912
Phe Leu Lys Phe Cys Glu Arg Thr Val Lys Lys Lys Gly Ala Gly Val
    290                 295                 300

gca gag ctg ttc gag gag gac aga aac ttt aca ggg gcc atg gcg cgc      960
Ala Glu Leu Phe Glu Glu Asp Arg Asn Phe Thr Gly Ala Met Ala Arg
305                 310                 315                 320

gca aag gcg gcg cag gca gcc ggc atg gag cat cca aag ata cca aag     1008
Ala Lys Ala Ala Gln Ala Ala Gly Met Glu His Pro Lys Ile Pro Lys
                325                 330                 335

ttg gaa gag gct gtg cgc ggg gcc aaa ggg aag gcg ctg gtc ttt aca     1056
Leu Glu Glu Ala Val Arg Gly Ala Lys Gly Lys Ala Leu Val Phe Thr
```

-continued

```
            340                 345                 350

agc tac agg gac tct gtc gat tta ata cac tca aag ctg cag gct gcc      1104
Ser Tyr Arg Asp Ser Val Asp Leu Ile His Ser Lys Leu Gln Ala Ala
        355                 360                 365

ggg ata aac tcg ggg atc ctc ata gga aag gcg gga gaa aag ggc ctc      1152
Gly Ile Asn Ser Gly Ile Leu Ile Gly Lys Ala Gly Glu Lys Gly Leu
    370                 375                 380

aag cag aaa aaa cag gta gag act gtc gcc aag ttc cgc gac ggg gga      1200
Lys Gln Lys Lys Gln Val Glu Thr Val Ala Lys Phe Arg Asp Gly Gly
385                 390                 395                 400

tac gac gtg ctc gta tct aca aga gtg ggc gag gag ggc ctc gac ata      1248
Tyr Asp Val Leu Val Ser Thr Arg Val Gly Glu Glu Gly Leu Asp Ile
                405                 410                 415

tcg gag gta aac ctt gtg gta ttc tat gac aat gtc cca agc tcg ata      1296
Ser Glu Val Asn Leu Val Val Phe Tyr Asp Asn Val Pro Ser Ser Ile
            420                 425                 430

agg tat gtg cag aga agg ggc agg acc ggc agg aag gac gcg ggc aag      1344
Arg Tyr Val Gln Arg Arg Gly Arg Thr Gly Arg Lys Asp Ala Gly Lys
        435                 440                 445

ctg gtg gta ctg atg gca aag ggg act ata gac gag gca tac tac tgg      1392
Leu Val Val Leu Met Ala Lys Gly Thr Ile Asp Glu Ala Tyr Tyr Trp
    450                 455                 460

ata ggc cgg cgc aag att act gcc gcc agg ggc atg ggg gac agg atg      1440
Ile Gly Arg Arg Lys Ile Thr Ala Ala Arg Gly Met Gly Asp Arg Met
465                 470                 475                 480

aac aag tcg ctt gca gcg ggg ggc cct gcg cca aag gca gcc cca aaa      1488
Asn Lys Ser Leu Ala Ala Gly Gly Pro Ala Pro Lys Ala Ala Pro Lys
                485                 490                 495

aag ggg ctc gag ggc tat ttc tag                                      1512
Lys Gly Leu Glu Gly Tyr Phe
            500


<210> SEQ ID NO 66
<211> LENGTH: 503
<212> TYPE: PRT
<213> ORGANISM: Cenarchaeum symbiosum

<400> SEQUENCE: 66

Met Glu Thr Ala His Ile Thr Gly Lys Tyr Val Glu Pro Gly Ala Val
 1               5                  10                  15

Glu Arg Arg Asp Tyr Gln Val Gly Leu Ala Glu Gln Ala Ile Arg Glu
            20                  25                  30

Asn Cys Ile Val Val Leu Pro Thr Gly Leu Gly Lys Thr Ala Val Ala
        35                  40                  45

Leu Gln Val Ile Ser His Tyr Leu Asp Glu Gly Arg Gly Ala Leu Phe
    50                  55                  60

Leu Ala Pro Thr Arg Val Leu Val Asn Gln His Arg Gln Phe Leu Gly
65                  70                  75                  80

Arg Ala Leu Thr Ile Ser Asp Ile Thr Leu Val Thr Gly Glu Asp Thr
                85                  90                  95

Val Pro Arg Arg Lys Lys Ala Trp Gly Gly Ser Val Ile Cys Ala Thr
            100                 105                 110

Pro Glu Ile Thr Arg Asn Asp Ile Ala Arg Gly Met Val Pro Leu Glu
        115                 120                 125

Gln Phe Gly Leu Val Val Phe Asp Glu Ala His Arg Ala Val Gly Asp
    130                 135                 140

Tyr Ala Tyr Ser Ala Ile Ala Arg Ala Val Gly Glu Asn Ser Arg Met
145                 150                 155                 160
```

-continued

```
Ile Gly Met Thr Ala Thr Leu Pro Ser Glu Arg Glu Lys Ala Asp Glu
                165                 170                 175

Ile Met Gly Thr Leu Leu Ser Lys Ser Ile Ala Gln Arg Thr Glu Asp
            180                 185                 190

Asp Pro Asp Val Lys Pro Tyr Val Gln Glu Thr Glu Thr Glu Trp Ile
        195                 200                 205

Lys Val Glu Leu Pro Pro Glu Met Lys Glu Ile Gln Lys Leu Leu Lys
    210                 215                 220

Met Ala Leu Asp Glu Arg Tyr Ala Ala Leu Lys Arg Cys Gly Tyr Asp
225                 230                 235                 240

Leu Gly Ser Asn Arg Ser Leu Ser Ala Leu Leu Arg Leu Arg Met Val
                245                 250                 255

Val Leu Ser Gly Asn Arg Arg Ala Ala Lys Pro Leu Phe Thr Ala Ile
            260                 265                 270

Arg Ile Thr Tyr Ala Leu Asn Ile Phe Glu Ala His Gly Val Thr Pro
        275                 280                 285

Phe Leu Lys Phe Cys Glu Arg Thr Val Lys Lys Lys Gly Ala Gly Val
    290                 295                 300

Ala Glu Leu Phe Glu Glu Asp Arg Asn Phe Thr Gly Ala Met Ala Arg
305                 310                 315                 320

Ala Lys Ala Ala Gln Ala Ala Gly Met Glu His Pro Lys Ile Pro Lys
                325                 330                 335

Leu Glu Glu Ala Val Arg Gly Ala Lys Gly Lys Ala Leu Val Phe Thr
            340                 345                 350

Ser Tyr Arg Asp Ser Val Asp Leu Ile His Ser Lys Leu Gln Ala Ala
        355                 360                 365

Gly Ile Asn Ser Gly Ile Leu Ile Gly Lys Ala Gly Glu Lys Gly Leu
    370                 375                 380

Lys Gln Lys Lys Gln Val Glu Thr Val Ala Lys Phe Arg Asp Gly Gly
385                 390                 395                 400

Tyr Asp Val Leu Val Ser Thr Arg Val Gly Glu Glu Gly Leu Asp Ile
                405                 410                 415

Ser Glu Val Asn Leu Val Val Phe Tyr Asp Asn Val Pro Ser Ser Ile
            420                 425                 430

Arg Tyr Val Gln Arg Arg Gly Arg Thr Gly Arg Lys Asp Ala Gly Lys
        435                 440                 445

Leu Val Val Leu Met Ala Lys Gly Thr Ile Asp Glu Ala Tyr Tyr Trp
    450                 455                 460

Ile Gly Arg Arg Lys Ile Thr Ala Ala Arg Gly Met Gly Asp Arg Met
465                 470                 475                 480

Asn Lys Ser Leu Ala Ala Gly Gly Pro Ala Pro Lys Ala Ala Pro Lys
                485                 490                 495

Lys Gly Leu Glu Gly Tyr Phe
            500
```

<210> SEQ ID NO 67
<211> LENGTH: 279
<212> TYPE: DNA
<213> ORGANISM: Cenarchaeum symbiosum
<220> FEATURE:
<221> NAME/KEY: CDS
<222> LOCATION: (1)...(279)

<400> SEQUENCE: 67

```
atg gcg gac aag ata aag tgc tcg cac ata ctg gta aaa aag cag ggc       48
```

-continued

```
Met Ala Asp Lys Ile Lys Cys Ser His Ile Leu Val Lys Lys Gln Gly
 1               5                  10                  15

gag gcg ctc gca gtg caa gag cgc ctc aag gcg ggc gaa aag ttt gga       96
Glu Ala Leu Ala Val Gln Glu Arg Leu Lys Ala Gly Glu Lys Phe Gly
             20                  25                  30

aag ctg gca aag gag ctc tcg ata gac ggg ggc agc gca aag agg gac      144
Lys Leu Ala Lys Glu Leu Ser Ile Asp Gly Gly Ser Ala Lys Arg Asp
         35                  40                  45

ggc agc ttg ggc tac ttt ggc agg ggc aag atg gta aag ccg ttt gag      192
Gly Ser Leu Gly Tyr Phe Gly Arg Gly Lys Met Val Lys Pro Phe Glu
     50                  55                  60

gat gcc gcg ttc cgc ctg cag gta ggc gag gta tcc gag ccg gta aaa      240
Asp Ala Ala Phe Arg Leu Gln Val Gly Glu Val Ser Glu Pro Val Lys
 65                  70                  75                  80

tcc gag ttt ggc tac cac gtg ata aag cgc ctg gga taa                  279
Ser Glu Phe Gly Tyr His Val Ile Lys Arg Leu Gly
                 85                  90


<210> SEQ ID NO 68
<211> LENGTH: 92
<212> TYPE: PRT
<213> ORGANISM: Cenarchaeum symbiosum

<400> SEQUENCE: 68

Met Ala Asp Lys Ile Lys Cys Ser His Ile Leu Val Lys Lys Gln Gly
 1               5                  10                  15

Glu Ala Leu Ala Val Gln Glu Arg Leu Lys Ala Gly Glu Lys Phe Gly
             20                  25                  30

Lys Leu Ala Lys Glu Leu Ser Ile Asp Gly Gly Ser Ala Lys Arg Asp
         35                  40                  45

Gly Ser Leu Gly Tyr Phe Gly Arg Gly Lys Met Val Lys Pro Phe Glu
     50                  55                  60

Asp Ala Ala Phe Arg Leu Gln Val Gly Glu Val Ser Glu Pro Val Lys
65                  70                  75                  80

Ser Glu Phe Gly Tyr His Val Ile Lys Arg Leu Gly
                85                  90


<210> SEQ ID NO 69
<211> LENGTH: 402
<212> TYPE: DNA
<213> ORGANISM: Cenarchaeum symbiosum
<220> FEATURE:
<221> NAME/KEY: CDS
<222> LOCATION: (1)...(402)

<400> SEQUENCE: 69

atg tct ttg tat ttt acg ata aag acg gcc aac ctg gcc ctg ccc gac       48
Met Ser Leu Tyr Phe Thr Ile Lys Thr Ala Asn Leu Ala Leu Pro Asp
 1               5                  10                  15

gtg gta aag agg tac aac cac gtc ctg gcg tgc aag agc gag gtg atg       96
Val Val Lys Arg Tyr Asn His Val Leu Ala Cys Lys Ser Glu Val Met
             20                  25                  30

agg gcc gag aag cag atc cag gtg tcc atc tcg tcg tcg ggc ggt ctg      144
Arg Ala Glu Lys Gln Ile Gln Val Ser Ile Ser Ser Ser Gly Gly Leu
         35                  40                  45

gac aag tac gcg gag ctc aag cag cag ttc aac tcg agg ata acc gag      192
Asp Lys Tyr Ala Glu Leu Lys Gln Gln Phe Asn Ser Arg Ile Thr Glu
     50                  55                  60

ttc tac cgc tcg ata gag gag ctg gag aag acg ggc gtg gtg gtc aag      240
Phe Tyr Arg Ser Ile Glu Glu Leu Glu Lys Thr Gly Val Val Val Lys
 65                  70                  75                  80
```

-continued

```
agc ata gac gag ggg ctc ctg gac ttt ccc gca aag cgc ttt ggg gac      288
Ser Ile Asp Glu Gly Leu Leu Asp Phe Pro Ala Lys Arg Phe Gly Asp
                 85                  90                  95

gac atc tgg ctg tgc tgg aag gtg ggc gag cgc gag atc aag ttc tgg      336
Asp Ile Trp Leu Cys Trp Lys Val Gly Glu Arg Glu Ile Lys Phe Trp
            100                 105                 110

cat gaa aag gac tcg ggg ttt gac gga aga aag ccc ata gag gta agt      384
His Glu Lys Asp Ser Gly Phe Asp Gly Arg Lys Pro Ile Glu Val Ser
        115                 120                 125

gac gag tca cta gtg tag                                              402
Asp Glu Ser Leu Val
    130


<210> SEQ ID NO 70
<211> LENGTH: 133
<212> TYPE: PRT
<213> ORGANISM: Cenarchaeum symbiosum

<400> SEQUENCE: 70

Met Ser Leu Tyr Phe Thr Ile Lys Thr Ala Asn Leu Ala Leu Pro Asp
 1               5                  10                  15

Val Val Lys Arg Tyr Asn His Val Leu Ala Cys Lys Ser Glu Val Met
            20                  25                  30

Arg Ala Glu Lys Gln Ile Gln Val Ser Ile Ser Ser Ser Gly Gly Leu
        35                  40                  45

Asp Lys Tyr Ala Glu Leu Lys Gln Gln Phe Asn Ser Arg Ile Thr Glu
    50                  55                  60

Phe Tyr Arg Ser Ile Glu Glu Leu Glu Lys Thr Gly Val Val Val Lys
65                  70                  75                  80

Ser Ile Asp Glu Gly Leu Leu Asp Phe Pro Ala Lys Arg Phe Gly Asp
                 85                  90                  95

Asp Ile Trp Leu Cys Trp Lys Val Gly Glu Arg Glu Ile Lys Phe Trp
            100                 105                 110

His Glu Lys Asp Ser Gly Phe Asp Gly Arg Lys Pro Ile Glu Val Ser
        115                 120                 125

Asp Glu Ser Leu Val
    130


<210> SEQ ID NO 71
<211> LENGTH: 879
<212> TYPE: DNA
<213> ORGANISM: Cenarchaeum symbiosum
<220> FEATURE:
<221> NAME/KEY: CDS
<222> LOCATION: (1)...(879)

<400> SEQUENCE: 71

atg ctc tcc tcc tgg ctg cgc gta ata cgc gtc cgg ttc ctg ctc gcg       48
Met Leu Ser Ser Trp Leu Arg Val Ile Arg Val Arg Phe Leu Leu Ala
 1               5                  10                  15

tcg gtg ata gcc gta tca gcg ggc ctt gcc ctc tcc tgg tgg cac ggc       96
Ser Val Ile Ala Val Ser Ala Gly Leu Ala Leu Ser Trp Trp His Gly
            20                  25                  30

cac gga ata gac gcg ctc aca gcg gca ctc acc atg gcc gga gtg gcc      144
His Gly Ile Asp Ala Leu Thr Ala Ala Leu Thr Met Ala Gly Val Ala
        35                  40                  45

gct ctt cat gca agc gtg gac atg ctc aac gac tac tgg gac tac aag      192
Ala Leu His Ala Ser Val Asp Met Leu Asn Asp Tyr Trp Asp Tyr Lys
    50                  55                  60
```

-continued

```
cgc ggc ata gat acg aga acc aag agg acc ccg atg agc ggg ggg aca      240
Arg Gly Ile Asp Thr Arg Thr Lys Arg Thr Pro Met Ser Gly Gly Thr
 65                  70                  75                  80

ggg gtg ctg cca gag ggc ctg ctg agc ccc cgc cag gtg tac cgc gcc      288
Gly Val Leu Pro Glu Gly Leu Leu Ser Pro Arg Gln Val Tyr Arg Ala
                85                  90                  95

ggc atc ata tca ctg gtg ctc ggg act gcc gcc ggc gca tac ttt gtg      336
Gly Ile Ile Ser Leu Val Leu Gly Thr Ala Ala Gly Ala Tyr Phe Val
            100                 105                 110

atc aca acg ggg ccc gtc ata gct gcg ata ctc ggc ttt gcg gtg gtc      384
Ile Thr Thr Gly Pro Val Ile Ala Ala Ile Leu Gly Phe Ala Val Val
        115                 120                 125

tcg att tac ttt tac tcg aca agg att gtg gac tcg ggc ctc tcc gag      432
Ser Ile Tyr Phe Tyr Ser Thr Arg Ile Val Asp Ser Gly Leu Ser Glu
    130                 135                 140

gtg ctc gtc ggg gtc aag ggg gcg atg atc gtc ctt ggc gcc tac tac      480
Val Leu Val Gly Val Lys Gly Ala Met Ile Val Leu Gly Ala Tyr Tyr
145                 150                 155                 160

ata cag gcg ccc gag atc acg ccg gcc gcc ctc ctc gtc ggc gcg gca      528
Ile Gln Ala Pro Glu Ile Thr Pro Ala Ala Leu Leu Val Gly Ala Ala
                165                 170                 175

gtg ggg gcg ctg tca tct gcg gtc ctc ttt gtg gcg tcg ttt ccg gac      576
Val Gly Ala Leu Ser Ser Ala Val Leu Phe Val Ala Ser Phe Pro Asp
            180                 185                 190

cac gac gca gac aag gag cgc ggc aga aaa acg ctg gtg ata ata ctg      624
His Asp Ala Asp Lys Glu Arg Gly Arg Lys Thr Leu Val Ile Ile Leu
        195                 200                 205

ggc aaa aag agg gcc tcg cgc ata ctc tgg gtc ttt cca gct gtg gcg      672
Gly Lys Lys Arg Ala Ser Arg Ile Leu Trp Val Phe Pro Ala Val Ala
    210                 215                 220

tat tca tcc gtg ata gcg ggg gtg att atc cag gtg ctg cca gtg tac      720
Tyr Ser Ser Val Ile Ala Gly Val Ile Ile Gln Val Leu Pro Val Tyr
225                 230                 235                 240

tcc ctc gcc atg ctg ctt gcc gcc ccc ctt gcg gca ata tcg gca agg      768
Ser Leu Ala Met Leu Leu Ala Ala Pro Leu Ala Ala Ile Ser Ala Arg
                245                 250                 255

ggc ctt gcc aaa gag tat gac ggg gac agg atc ata cgg gtc atg cgc      816
Gly Leu Ala Lys Glu Tyr Asp Gly Asp Arg Ile Ile Arg Val Met Arg
            260                 265                 270

ggc acg ctg cgg ttc agc agg act gca ggc gcg ctg ctg gtg ctg gga      864
Gly Thr Leu Arg Phe Ser Arg Thr Ala Gly Ala Leu Leu Val Leu Gly
        275                 280                 285

ata ctg ctt ggt tga                                                  879
Ile Leu Leu Gly
    290


<210> SEQ ID NO 72
<211> LENGTH: 292
<212> TYPE: PRT
<213> ORGANISM: Cenarchaeum symbiosum

<400> SEQUENCE: 72

Met Leu Ser Ser Trp Leu Arg Val Ile Arg Val Arg Phe Leu Leu Ala
 1               5                  10                  15

Ser Val Ile Ala Val Ser Ala Gly Leu Ala Leu Ser Trp Trp His Gly
            20                  25                  30

His Gly Ile Asp Ala Leu Thr Ala Ala Leu Thr Met Ala Gly Val Ala
        35                  40                  45

Ala Leu His Ala Ser Val Asp Met Leu Asn Asp Tyr Trp Asp Tyr Lys
    50                  55                  60
```

-continued

```
Arg Gly Ile Asp Thr Arg Thr Lys Arg Thr Pro Met Ser Gly Gly Thr
65                  70                  75                  80

Gly Val Leu Pro Glu Gly Leu Leu Ser Pro Arg Gln Val Tyr Arg Ala
                85                  90                  95

Gly Ile Ile Ser Leu Val Leu Gly Thr Ala Ala Gly Ala Tyr Phe Val
            100                 105                 110

Ile Thr Thr Gly Pro Val Ile Ala Ala Ile Leu Gly Phe Ala Val Val
        115                 120                 125

Ser Ile Tyr Phe Tyr Ser Thr Arg Ile Val Asp Ser Gly Leu Ser Glu
    130                 135                 140

Val Leu Val Gly Val Lys Gly Ala Met Ile Val Leu Gly Ala Tyr Tyr
145                 150                 155                 160

Ile Gln Ala Pro Glu Ile Thr Pro Ala Ala Leu Leu Val Gly Ala Ala
                165                 170                 175

Val Gly Ala Leu Ser Ser Ala Val Leu Phe Val Ala Ser Phe Pro Asp
            180                 185                 190

His Asp Ala Asp Lys Glu Arg Gly Arg Lys Thr Leu Val Ile Ile Leu
        195                 200                 205

Gly Lys Lys Arg Ala Ser Arg Ile Leu Trp Val Phe Pro Ala Val Ala
    210                 215                 220

Tyr Ser Ser Val Ile Ala Gly Val Ile Ile Gln Val Leu Pro Val Tyr
225                 230                 235                 240

Ser Leu Ala Met Leu Leu Ala Ala Pro Leu Ala Ala Ile Ser Ala Arg
                245                 250                 255

Gly Leu Ala Lys Glu Tyr Asp Gly Asp Arg Ile Ile Arg Val Met Arg
            260                 265                 270

Gly Thr Leu Arg Phe Ser Arg Thr Ala Gly Ala Leu Leu Val Leu Gly
        275                 280                 285

Ile Leu Leu Gly
    290
```

<210> SEQ ID NO 73
<211> LENGTH: 1227
<212> TYPE: DNA
<213> ORGANISM: Cenarchaeum symbiosum
<220> FEATURE:
<221> NAME/KEY: CDS
<222> LOCATION: (1)...(1227)

<400> SEQUENCE: 73

```
ttg agg ccc gcg gct gtg cct aca gca cgg gat att ggc gca gaa cgg       48
Met Arg Pro Ala Ala Val Pro Thr Ala Arg Asp Ile Gly Ala Glu Arg
 1               5                  10                  15

ggc aat ctc aca ctt tgt acc ctt cat aca cat aaa tcc cgc ttg gat       96
Gly Asn Leu Thr Leu Cys Thr Leu His Thr His Lys Ser Arg Leu Asp
            20                  25                  30

gtg cgg ctg cgc atg atc agc ggg cat gcc acg gcc gag ggt aca cag      144
Val Arg Leu Arg Met Ile Ser Gly His Ala Thr Ala Glu Gly Thr Gln
        35                  40                  45

agg ata gcc gag atg tcc ggc gca cac cat gac aac tac aag gtg gta      192
Arg Ile Ala Glu Met Ser Gly Ala His His Asp Asn Tyr Lys Val Val
     50                  55                  60

gac ggg ctg cac ctc tcc aac gtg ggg atg ggc acc tac ctt ggc gac      240
Asp Gly Leu His Leu Ser Asn Val Gly Met Gly Thr Tyr Leu Gly Asp
 65                  70                  75                  80

gcg gat gac gcc acc gac agg gcc gtc aca gac gcg gtc aag agg tca      288
Ala Asp Asp Ala Thr Asp Arg Ala Val Thr Asp Ala Val Lys Arg Ser
```

-continued

```
                 85                  90                  95

atc aag tcg ggg ata aac gtc ata gat acc gcg ata aac tac cgc ctc      336
Ile Lys Ser Gly Ile Asn Val Ile Asp Thr Ala Ile Asn Tyr Arg Leu
            100                 105                 110

cag agg gcc gag cgt tcc gtg ggc agg gcc gtt aca gag ctc tca gag      384
Gln Arg Ala Glu Arg Ser Val Gly Arg Ala Val Thr Glu Leu Ser Glu
        115                 120                 125

gag ggg ctg gta tcc agg gac cag ata ttc ata tcc aca aag gcg gga      432
Glu Gly Leu Val Ser Arg Asp Gln Ile Phe Ile Ser Thr Lys Ala Gly
    130                 135                 140

tac gtg acc aac gat tca gag gtc tcc ctc gac ttt tgg gag tat gta      480
Tyr Val Thr Asn Asp Ser Glu Val Ser Leu Asp Phe Trp Glu Tyr Val
145                 150                 155                 160

aaa aag gaa tac gtc ggt ggc ggc gtc ata cag tcc ggg gac ata tcc      528
Lys Lys Glu Tyr Val Gly Gly Gly Val Ile Gln Ser Gly Asp Ile Ser
                165                 170                 175

tcg gga tac cac tgc atg aag ccc gcg tat cta gag gac cag cta aag      576
Ser Gly Tyr His Cys Met Lys Pro Ala Tyr Leu Glu Asp Gln Leu Lys
            180                 185                 190

aga agc ctt gca aac atg aac gtc gac tgc ata gat ctt gtc tac gtg      624
Arg Ser Leu Ala Asn Met Asn Val Asp Cys Ile Asp Leu Val Tyr Val
        195                 200                 205

cac aac ccg gtg gag ggg cag atc aag gac cgc ccc gtg ccg gag atc      672
His Asn Pro Val Glu Gly Gln Ile Lys Asp Arg Pro Val Pro Glu Ile
    210                 215                 220

ctc gag ggg ata ggc gag gcc ttt gcc atg tac gag aaa atg cgg gag      720
Leu Glu Gly Ile Gly Glu Ala Phe Ala Met Tyr Glu Lys Met Arg Glu
225                 230                 235                 240

gct ggc cgc ata agg tat tac ggg ctc gcc acg tgg gag tgc ttc cgg      768
Ala Gly Arg Ile Arg Tyr Tyr Gly Leu Ala Thr Trp Glu Cys Phe Arg
                245                 250                 255

gtc gca gag ggc gac ccg cag agc atg cag ctc gaa gca gtg gta aaa      816
Val Ala Glu Gly Asp Pro Gln Ser Met Gln Leu Glu Ala Val Val Lys
            260                 265                 270

aag gcc aag gat gcc ggc ggg gag aac cac ggc ttt agg ttc ata cag      864
Lys Ala Lys Asp Ala Gly Gly Glu Asn His Gly Phe Arg Phe Ile Gln
        275                 280                 285

ctg cca ttc aac cag tac ttt gac cag gcc tac atg gta aag aac cag      912
Leu Pro Phe Asn Gln Tyr Phe Asp Gln Ala Tyr Met Val Lys Asn Gln
    290                 295                 300

ggg acg ggc ggc ggc aag tca tcc ata ctg gag gcg gca gcc gcg ctg      960
Gly Thr Gly Gly Gly Lys Ser Ser Ile Leu Glu Ala Ala Ala Ala Leu
305                 310                 315                 320

gac att ggc gtg ttc aca agc gtc ccg ttc atg cag ggc aag ctg ctc     1008
Asp Ile Gly Val Phe Thr Ser Val Pro Phe Met Gln Gly Lys Leu Leu
                325                 330                 335

gag cct ggc ctg ctg ccg gag ttt ggc ggg ctc tcg ccc gcc ctg cgg     1056
Glu Pro Gly Leu Leu Pro Glu Phe Gly Gly Leu Ser Pro Ala Leu Arg
            340                 345                 350

tcc ctg cag ttc atc agg tct aca ccg gga gtg ctt gcc ccc ctg ccg     1104
Ser Leu Gln Phe Ile Arg Ser Thr Pro Gly Val Leu Ala Pro Leu Pro
        355                 360                 365

ggg cac aag tcc agc ctg cat aca gac gag aac cta aag atc atg ggc     1152
Gly His Lys Ser Ser Leu His Thr Asp Glu Asn Leu Lys Ile Met Gly
    370                 375                 380

gtg ccc ccc att cct cct gac aag ttc ggg gag ctt gtg gcc agc ctt     1200
Val Pro Pro Ile Pro Pro Asp Lys Phe Gly Glu Leu Val Ala Ser Leu
385                 390                 395                 400

acc tca tgg tcg ccc ggc cag aaa tag                                 1227
```

-continued

```
Thr Ser Trp Ser Pro Gly Gln Lys
                405


<210> SEQ ID NO 74
<211> LENGTH: 408
<212> TYPE: PRT
<213> ORGANISM: Cenarchaeum symbiosum

<400> SEQUENCE: 74

Met Arg Pro Ala Ala Val Pro Thr Ala Arg Asp Ile Gly Ala Glu Arg
 1               5                  10                  15

Gly Asn Leu Thr Leu Cys Thr Leu His Thr His Lys Ser Arg Leu Asp
            20                  25                  30

Val Arg Leu Arg Met Ile Ser Gly His Ala Thr Ala Glu Gly Thr Gln
        35                  40                  45

Arg Ile Ala Glu Met Ser Gly Ala His His Asp Asn Tyr Lys Val Val
    50                  55                  60

Asp Gly Leu His Leu Ser Asn Val Gly Met Gly Thr Tyr Leu Gly Asp
65                  70                  75                  80

Ala Asp Asp Ala Thr Asp Arg Ala Val Thr Asp Ala Val Lys Arg Ser
                85                  90                  95

Ile Lys Ser Gly Ile Asn Val Ile Asp Thr Ala Ile Asn Tyr Arg Leu
            100                 105                 110

Gln Arg Ala Glu Arg Ser Val Gly Arg Ala Val Thr Glu Leu Ser Glu
        115                 120                 125

Glu Gly Leu Val Ser Arg Asp Gln Ile Phe Ile Ser Thr Lys Ala Gly
    130                 135                 140

Tyr Val Thr Asn Asp Ser Glu Val Ser Leu Asp Phe Trp Glu Tyr Val
145                 150                 155                 160

Lys Lys Glu Tyr Val Gly Gly Gly Val Ile Gln Ser Gly Asp Ile Ser
                165                 170                 175

Ser Gly Tyr His Cys Met Lys Pro Ala Tyr Leu Glu Asp Gln Leu Lys
            180                 185                 190

Arg Ser Leu Ala Asn Met Asn Val Asp Cys Ile Asp Leu Val Tyr Val
        195                 200                 205

His Asn Pro Val Glu Gly Gln Ile Lys Asp Arg Pro Val Pro Glu Ile
    210                 215                 220

Leu Glu Gly Ile Gly Glu Ala Phe Ala Met Tyr Glu Lys Met Arg Glu
225                 230                 235                 240

Ala Gly Arg Ile Arg Tyr Tyr Gly Leu Ala Thr Trp Glu Cys Phe Arg
                245                 250                 255

Val Ala Glu Gly Asp Pro Gln Ser Met Gln Leu Glu Ala Val Val Lys
            260                 265                 270

Lys Ala Lys Asp Ala Gly Gly Glu Asn His Gly Phe Arg Phe Ile Gln
        275                 280                 285

Leu Pro Phe Asn Gln Tyr Phe Asp Gln Ala Tyr Met Val Lys Asn Gln
    290                 295                 300

Gly Thr Gly Gly Gly Lys Ser Ser Ile Leu Glu Ala Ala Ala Ala Leu
305                 310                 315                 320

Asp Ile Gly Val Phe Thr Ser Val Pro Phe Met Gln Gly Lys Leu Leu
                325                 330                 335

Glu Pro Gly Leu Leu Pro Glu Phe Gly Gly Leu Ser Pro Ala Leu Arg
            340                 345                 350

Ser Leu Gln Phe Ile Arg Ser Thr Pro Gly Val Leu Ala Pro Leu Pro
        355                 360                 365
```

-continued

```
Gly His Lys Ser Ser Leu His Thr Asp Glu Asn Leu Lys Ile Met Gly
    370                 375                 380

Val Pro Pro Ile Pro Pro Asp Lys Phe Gly Glu Leu Val Ala Ser Leu
385                 390                 395                 400

Thr Ser Trp Ser Pro Gly Gln Lys
                405


<210> SEQ ID NO 75
<211> LENGTH: 1077
<212> TYPE: DNA
<213> ORGANISM: Cenarchaeum symbiosum
<220> FEATURE:
<221> NAME/KEY: CDS
<222> LOCATION: (1)...(1077)

<400> SEQUENCE: 75

atg aac aac cgg ttc cag gtt atc cgg ggg gat gcc cgg gcg gtg ctg       48
Met Asn Asn Arg Phe Gln Val Ile Arg Gly Asp Ala Arg Ala Val Leu
 1               5                  10                  15

ccc agg ctt gca aaa aag aat ggc gag cgc ggc agg tac agg ctg gcc       96
Pro Arg Leu Ala Lys Lys Asn Gly Glu Arg Gly Arg Tyr Arg Leu Ala
            20                  25                  30

gtc act tcc ccc ccg tat tac ggg cac aga aag tac ggg tcg gat ccc      144
Val Thr Ser Pro Pro Tyr Tyr Gly His Arg Lys Tyr Gly Ser Asp Pro
        35                  40                  45

tcc gag ctg ggc cag gag ggg acg cct gat gag ttc gtc gag gag ctg      192
Ser Glu Leu Gly Gln Glu Gly Thr Pro Asp Glu Phe Val Glu Glu Leu
    50                  55                  60

gca ggg gtg ttc aag agc tgc atg gac ctg ctt acc gac gac ggc agc      240
Ala Gly Val Phe Lys Ser Cys Met Asp Leu Leu Thr Asp Asp Gly Ser
 65                  70                  75                  80

ctc ttc ata gtg ata ggc gac acc cgg agg cgg cgc cgg aag ctg atg      288
Leu Phe Ile Val Ile Gly Asp Thr Arg Arg Arg Arg Arg Lys Leu Met
                85                  90                  95

gtc ccg cac cgg ctc gcg ctc aga ctt gta gac ctt ggg tac cac ttt      336
Val Pro His Arg Leu Ala Leu Arg Leu Val Asp Leu Gly Tyr His Phe
            100                 105                 110

caa gag gat ata gtc tgg tac aag aaa aac gcg cta tca cag agc tcg      384
Gln Glu Asp Ile Val Trp Tyr Lys Lys Asn Ala Leu Ser Gln Ser Ser
        115                 120                 125

aag cag aac ctt acg cag gcg tac gag ttt gtg ctg gtg cta tca aag      432
Lys Gln Asn Leu Thr Gln Ala Tyr Glu Phe Val Leu Val Leu Ser Lys
    130                 135                 140

tcg gaa tcc ccc gcc ttt gac ata gac ccg ata cgc gtc cag ggc aac      480
Ser Glu Ser Pro Ala Phe Asp Ile Asp Pro Ile Arg Val Gln Gly Asn
145                 150                 155                 160

gag gcc ctg agc ggg gtc aac agg aag ccg gag cgc gac cgg ctg cag      528
Glu Ala Leu Ser Gly Val Asn Arg Lys Pro Glu Arg Asp Arg Leu Gln
                165                 170                 175

ttc tcc ccc ggg agg agg gac cct gaa gcc ata ggg agg att gca gca      576
Phe Ser Pro Gly Arg Arg Asp Pro Glu Ala Ile Gly Arg Ile Ala Ala
            180                 185                 190

gtg ata cac ggc tcg tcc ccc gag acg ccg ttt gac gag ctg cca acc      624
Val Ile His Gly Ser Ser Pro Glu Thr Pro Phe Asp Glu Leu Pro Thr
        195                 200                 205

acc gag gag ata tcg cgg gcc cac ggg tat gac ccc gaa aag cac tgc      672
Thr Glu Glu Ile Ser Arg Ala His Gly Tyr Asp Pro Glu Lys His Cys
    210                 215                 220

ccg aca tgc tac cgc aag ttc aaa agg cat gcg acg cgc aag cgg ata      720
Pro Thr Cys Tyr Arg Lys Phe Lys Arg His Ala Thr Arg Lys Arg Ile
```

-continued

```
225                 230                 235                 240

ggg ggc cac gag cac tat ccg ata ttt gca gca tgc aac ccc cgg ggc      768
Gly Gly His Glu His Tyr Pro Ile Phe Ala Ala Cys Asn Pro Arg Gly
            245                 250                 255

aag aac cct ggg aac gtc tgg gag ata tcc aca aag gcg cac cac ggc      816
Lys Asn Pro Gly Asn Val Trp Glu Ile Ser Thr Lys Ala His His Gly
            260                 265                 270

aac gag cac ttt gcg gtg ttc cca gaa gac ctc gta tcc cgg ata gta      864
Asn Glu His Phe Ala Val Phe Pro Glu Asp Leu Val Ser Arg Ile Val
        275                 280                 285

aag ttt gcc aca aga gag ggc gac tat gtg ctg gat ccg ttt gcg gga      912
Lys Phe Ala Thr Arg Glu Gly Asp Tyr Val Leu Asp Pro Phe Ala Gly
    290                 295                 300

agg ggc aca acg ggg ata gtc tcg gcg tgc ctc aag agg ggc ttt acg      960
Arg Gly Thr Thr Gly Ile Val Ser Ala Cys Leu Lys Arg Gly Phe Thr
305                 310                 315                 320

gga ata gac ctg tat cct gcc aac gtg gac agg acc cgg cgc aat gtg     1008
Gly Ile Asp Leu Tyr Pro Ala Asn Val Asp Arg Thr Arg Arg Asn Val
            325                 330                 335

aaa gat tct gcg gac tcg aag ctg cca aaa aag gtg cta gac cag ata     1056
Lys Asp Ser Ala Asp Ser Lys Leu Pro Lys Lys Val Leu Asp Gln Ile
            340                 345                 350

atg ccc gag gga aca cgc tga                                         1077
Met Pro Glu Gly Thr Arg
        355


<210> SEQ ID NO 76
<211> LENGTH: 358
<212> TYPE: PRT
<213> ORGANISM: Cenarchaeum symbiosum

<400> SEQUENCE: 76

Met Asn Asn Arg Phe Gln Val Ile Arg Gly Asp Ala Arg Ala Val Leu
 1               5                  10                  15

Pro Arg Leu Ala Lys Lys Asn Gly Glu Arg Gly Arg Tyr Arg Leu Ala
            20                  25                  30

Val Thr Ser Pro Pro Tyr Tyr Gly His Arg Lys Tyr Gly Ser Asp Pro
        35                  40                  45

Ser Glu Leu Gly Gln Glu Gly Thr Pro Asp Glu Phe Val Glu Glu Leu
    50                  55                  60

Ala Gly Val Phe Lys Ser Cys Met Asp Leu Leu Thr Asp Asp Gly Ser
65                  70                  75                  80

Leu Phe Ile Val Ile Gly Asp Thr Arg Arg Arg Arg Arg Lys Leu Met
            85                  90                  95

Val Pro His Arg Leu Ala Leu Arg Leu Val Asp Leu Gly Tyr His Phe
            100                 105                 110

Gln Glu Asp Ile Val Trp Tyr Lys Lys Asn Ala Leu Ser Gln Ser Ser
        115                 120                 125

Lys Gln Asn Leu Thr Gln Ala Tyr Glu Phe Val Leu Val Leu Ser Lys
    130                 135                 140

Ser Glu Ser Pro Ala Phe Asp Ile Asp Pro Ile Arg Val Gln Gly Asn
145                 150                 155                 160

Glu Ala Leu Ser Gly Val Asn Arg Lys Pro Glu Arg Asp Arg Leu Gln
            165                 170                 175

Phe Ser Pro Gly Arg Arg Asp Pro Glu Ala Ile Gly Arg Ile Ala Ala
            180                 185                 190

Val Ile His Gly Ser Ser Pro Glu Thr Pro Phe Asp Glu Leu Pro Thr
```

-continued

```
        195                 200                 205

Thr Glu Glu Ile Ser Arg Ala His Gly Tyr Asp Pro Glu Lys His Cys
    210                 215                 220

Pro Thr Cys Tyr Arg Lys Phe Lys Arg His Ala Thr Arg Lys Arg Ile
225                 230                 235                 240

Gly Gly His Glu His Tyr Pro Ile Phe Ala Ala Cys Asn Pro Arg Gly
                245                 250                 255

Lys Asn Pro Gly Asn Val Trp Glu Ile Ser Thr Lys Ala His His Gly
            260                 265                 270

Asn Glu His Phe Ala Val Phe Pro Glu Asp Leu Val Ser Arg Ile Val
        275                 280                 285

Lys Phe Ala Thr Arg Glu Gly Asp Tyr Val Leu Asp Pro Phe Ala Gly
    290                 295                 300

Arg Gly Thr Thr Gly Ile Val Ser Ala Cys Leu Lys Arg Gly Phe Thr
305                 310                 315                 320

Gly Ile Asp Leu Tyr Pro Ala Asn Val Asp Arg Thr Arg Arg Asn Val
                325                 330                 335

Lys Asp Ser Ala Asp Ser Lys Leu Pro Lys Lys Val Leu Asp Gln Ile
            340                 345                 350

Met Pro Glu Gly Thr Arg
        355


<210> SEQ ID NO 77
<211> LENGTH: 468
<212> TYPE: DNA
<213> ORGANISM: Cenarchaeum symbiosum
<220> FEATURE:
<221> NAME/KEY: CDS
<222> LOCATION: (1)...(468)

<400> SEQUENCE: 77

atg cgg ctg ccc cgg cgc cga ctt aaa atc gtt gta gga tgc ggc gcc       48
Met Arg Leu Pro Arg Arg Arg Leu Lys Ile Val Val Gly Cys Gly Ala
 1               5                  10                  15

gca gat gca ttg ccc gcc tta tac acc gcc cgg gat cgg ccg cct tgc       96
Ala Asp Ala Leu Pro Ala Leu Tyr Thr Ala Arg Asp Arg Pro Pro Cys
            20                  25                  30

agc aca cgc agt ata aac ggg ggc ccg ggc ggc gcg tat cac atg tgg      144
Ser Thr Arg Ser Ile Asn Gly Gly Pro Gly Gly Ala Tyr His Met Trp
        35                  40                  45

ata aag gac gaa ttc ctc ggc ccg ggc aac aag atg agg ctg ctc tac      192
Ile Lys Asp Glu Phe Leu Gly Pro Gly Asn Lys Met Arg Leu Leu Tyr
     50                  55                  60

ctg ata ctg ccc atc tat ggg tat atc ttt ctg gag tac tat ccg ttc      240
Leu Ile Leu Pro Ile Tyr Gly Tyr Ile Phe Leu Glu Tyr Tyr Pro Phe
 65                  70                  75                  80

ttt ccc tgg atg gcc acc tac tgg tgg tca gta gct ctc agc ccc ccg      288
Phe Pro Trp Met Ala Thr Tyr Trp Trp Ser Val Ala Leu Ser Pro Pro
                 85                  90                  95

ata gtg ccc acg cat tat gcc ggg gag gcc ctg ggg cgg ctg atc ggg      336
Ile Val Pro Thr His Tyr Ala Gly Glu Ala Leu Gly Arg Leu Ile Gly
            100                 105                 110

gat cac gta ttg ttt ggc atc acc aca aag tac gtc tat gcg gca ata      384
Asp His Val Leu Phe Gly Ile Thr Thr Lys Tyr Val Tyr Ala Ala Ile
        115                 120                 125

tgg ctc ggc atg gcc cat ggg ata atc ctg ctg gca ggg cgc ctc cgg      432
Trp Leu Gly Met Ala His Gly Ile Ile Leu Leu Ala Gly Arg Leu Arg
    130                 135                 140
```

-continued

```
gga cct agg cag gcg cca cgg acg ggc atc cca tag                   468
Gly Pro Arg Gln Ala Pro Arg Thr Gly Ile Pro
145                 150                 155


<210> SEQ ID NO 78
<211> LENGTH: 155
<212> TYPE: PRT
<213> ORGANISM: Cenarchaeum symbiosum

<400> SEQUENCE: 78

Met Arg Leu Pro Arg Arg Arg Leu Lys Ile Val Val Gly Cys Gly Ala
 1               5                  10                  15

Ala Asp Ala Leu Pro Ala Leu Tyr Thr Ala Arg Asp Arg Pro Pro Cys
            20                  25                  30

Ser Thr Arg Ser Ile Asn Gly Gly Pro Gly Gly Ala Tyr His Met Trp
        35                  40                  45

Ile Lys Asp Glu Phe Leu Gly Pro Gly Asn Lys Met Arg Leu Leu Tyr
    50                  55                  60

Leu Ile Leu Pro Ile Tyr Gly Tyr Ile Phe Leu Glu Tyr Tyr Pro Phe
65                  70                  75                  80

Phe Pro Trp Met Ala Thr Tyr Trp Trp Ser Val Ala Leu Ser Pro Pro
                85                  90                  95

Ile Val Pro Thr His Tyr Ala Gly Glu Ala Leu Gly Arg Leu Ile Gly
            100                 105                 110

Asp His Val Leu Phe Gly Ile Thr Thr Lys Tyr Val Tyr Ala Ala Ile
        115                 120                 125

Trp Leu Gly Met Ala His Gly Ile Ile Leu Leu Ala Gly Arg Leu Arg
    130                 135                 140

Gly Pro Arg Gln Ala Pro Arg Thr Gly Ile Pro
145                 150                 155


<210> SEQ ID NO 79
<211> LENGTH: 1779
<212> TYPE: DNA
<213> ORGANISM: Cenarchaeum symbiosum
<220> FEATURE:
<221> NAME/KEY: CDS
<222> LOCATION: (1)...(1779)

<400> SEQUENCE: 79

ttg aag ctg caa ggc aag act gcc gtg atc acc ggc agt ggt acc ggg    48
Met Lys Leu Gln Gly Lys Thr Ala Val Ile Thr Gly Ser Gly Thr Gly
 1               5                  10                  15

atc ggg ctg gcg gtg gca agg aaa ttt gcc gag aac ggg gcc agc gtg    96
Ile Gly Leu Ala Val Ala Arg Lys Phe Ala Glu Asn Gly Ala Ser Val
            20                  25                  30

gta ata ctc gga agg aga aag gag ccc ctc gat gag gca gca gca gag   144
Val Ile Leu Gly Arg Arg Lys Glu Pro Leu Asp Glu Ala Ala Ala Glu
        35                  40                  45

ctc aaa aag ata gcg gaa tct gca ggc tgc ggg gcc tcg atc agg ata   192
Leu Lys Lys Ile Ala Glu Ser Ala Gly Cys Gly Ala Ser Ile Arg Ile
    50                  55                  60

ttc gcc ggg gtg gac gtg gcc gac gaa tcc gcg ata acg aaa atg ttc   240
Phe Ala Gly Val Asp Val Ala Asp Glu Ser Ala Ile Thr Lys Met Phe
65                  70                  75                  80

gac gag ctg tcc agc tca ggt gta acc gtg gac ata ctg gtg aac aat   288
Asp Glu Leu Ser Ser Ser Gly Val Thr Val Asp Ile Leu Val Asn Asn
                85                  90                  95

gcc ggc gtg tcg ggg ccc gtc acg tgc ttt gcc aac aat gat cta gaa   336
Ala Gly Val Ser Gly Pro Val Thr Cys Phe Ala Asn Asn Asp Leu Glu
```

-continued

```
            100                 105                 110

gag ttc cgc ggg gca gtc gac ata cac ctg acc ggc tcc ttc tgg aca      384
Glu Phe Arg Gly Ala Val Asp Ile His Leu Thr Gly Ser Phe Trp Thr
        115                 120                 125

tcg agg gag gcc ctc aag gtc atg aaa aag ggc tcc aag att gtc acc      432
Ser Arg Glu Ala Leu Lys Val Met Lys Lys Gly Ser Lys Ile Val Thr
    130                 135                 140

atg act acg ttt ttt gca gaa gag agg cca ctc gag cag agg ccg tac      480
Met Thr Thr Phe Phe Ala Glu Glu Arg Pro Leu Glu Gln Arg Pro Tyr
145                 150                 155                 160

agg ttc cgc gac ccg tat aca acc gca cag ggc gca aag aac agg ctc      528
Arg Phe Arg Asp Pro Tyr Thr Thr Ala Gln Gly Ala Lys Asn Arg Leu
                165                 170                 175

gcc gag gcg atg tcg tgg gat ctt tta gac cgc ggg ata aca tcg ata      576
Ala Glu Ala Met Ser Trp Asp Leu Leu Asp Arg Gly Ile Thr Ser Ile
            180                 185                 190

gcg acc aac ccc ggc ccc gtc cat tct gac agg ata tac aag acg gta      624
Ala Thr Asn Pro Gly Pro Val His Ser Asp Arg Ile Tyr Lys Thr Val
        195                 200                 205

tac ccg agg gcg gca ctc gag ttt gtc agg gtt tca ggg ttt gag gac      672
Tyr Pro Arg Ala Ala Leu Glu Phe Val Arg Val Ser Gly Phe Glu Asp
    210                 215                 220

ctg cag cca gaa gaa gtc gag gtg gca ggc ggc agg cta atc cac ctg      720
Leu Gln Pro Glu Glu Val Glu Val Ala Gly Gly Arg Leu Ile His Leu
225                 230                 235                 240

ctc ggc gcg gac gac gat gca aga aaa aaa ggc ata gca gag gcc gca      768
Leu Gly Ala Asp Asp Asp Ala Arg Lys Lys Gly Ile Ala Glu Ala Ala
                245                 250                 255

gag cac ttt gcc aag cta aag ccc gtg gat ccc gca aag cta gag gcc      816
Glu His Phe Ala Lys Leu Lys Pro Val Asp Pro Ala Lys Leu Glu Ala
            260                 265                 270

acc ctt gat gcc ctg ctc gca aag atc aag ggg ata gcc gaa aag ata      864
Thr Leu Asp Ala Leu Leu Ala Lys Ile Lys Gly Ile Ala Glu Lys Ile
        275                 280                 285

cag gcc aac act gca agg atg ata cca gac ggg gag ttt ctc tcc cag      912
Gln Ala Asn Thr Ala Arg Met Ile Pro Asp Gly Glu Phe Leu Ser Gln
    290                 295                 300

gac cag gtg gcc gag acg gta ctc gcc ctc tgc gat gac aag atg gcc      960
Asp Gln Val Ala Glu Thr Val Leu Ala Leu Cys Asp Asp Lys Met Ala
305                 310                 315                 320

aag acg gta aac ggc cgc gta atc ccc gcc gac agg gta ttc tac ccg     1008
Lys Thr Val Asn Gly Arg Val Ile Pro Ala Asp Arg Val Phe Tyr Pro
                325                 330                 335

gta agg gcg cat gtg gcc aat gcc gct ccg cgc gtg ccc ccg cac gac     1056
Val Arg Ala His Val Ala Asn Ala Ala Pro Arg Val Pro Pro His Asp
            340                 345                 350

tat tcc ggg gga tgc gtc cta ttc atg ata gat gca gca gac gac agg     1104
Tyr Ser Gly Gly Cys Val Leu Phe Met Ile Asp Ala Ala Asp Asp Arg
        355                 360                 365

gat gta gaa agg gcg acc gcc ctg gca tcc cat gtg gaa agc cac ggg     1152
Asp Val Glu Arg Ala Thr Ala Leu Ala Ser His Val Glu Ser His Gly
    370                 375                 380

ggc acg gca gtc tgc ata gtc tca gaa gac tcg ccc cgc gcg gca aag     1200
Gly Thr Ala Val Cys Ile Val Ser Glu Asp Ser Pro Arg Ala Ala Lys
385                 390                 395                 400

gag atg ata gcg tca aag ttc cac tcg cat gcg agc cac ata gac aag     1248
Glu Met Ile Ala Ser Lys Phe His Ser His Ala Ser His Ile Asp Lys
                405                 410                 415

gta gac gag ata aac agg tgg ctg agc gct gca tca aca aag ata ggc     1296
```

-continued

```
Val Asp Glu Ile Asn Arg Trp Leu Ser Ala Ala Ser Thr Lys Ile Gly
            420                 425                 430

ccc ata tct gca gtg gtc cac ctg tcc ggc agg atg cca aaa tcc ggc     1344
Pro Ile Ser Ala Val Val His Leu Ser Gly Arg Met Pro Lys Ser Gly
        435                 440                 445

agc cta atg gat ctc tcc aga aaa gaa tgg gac gcg ctg gtt gac agg     1392
Ser Leu Met Asp Leu Ser Arg Lys Glu Trp Asp Ala Leu Val Asp Arg
    450                 455                 460

ttc ata ggg acg ccg gct gcc gtc ctg cac agg tcg ctt gag cac ttt     1440
Phe Ile Gly Thr Pro Ala Ala Val Leu His Arg Ser Leu Glu His Phe
465                 470                 475                 480

gca ccc ggc ggg cgc aag gac ccc cgt ttg ttc aag ggc aag agc ggc     1488
Ala Pro Gly Gly Arg Lys Asp Pro Arg Leu Phe Lys Gly Lys Ser Gly
                485                 490                 495

gtc atc gtg ata ata ggc ccc gac ctg ccc gcg ggg aaa aag gcc tcc     1536
Val Ile Val Ile Ile Gly Pro Asp Leu Pro Ala Gly Lys Lys Ala Ser
            500                 505                 510

ggc gcc gag agg gca agg gcg gag atc ttc cgg ggt gcg ctc agg ccg     1584
Gly Ala Glu Arg Ala Arg Ala Glu Ile Phe Arg Gly Ala Leu Arg Pro
        515                 520                 525

ctg acg act aca gtc aac cag gag ctc agc gat gtg cta aag tca aac     1632
Leu Thr Thr Thr Val Asn Gln Glu Leu Ser Asp Val Leu Lys Ser Asn
    530                 535                 540

gtg cgc ctg ttt acc atc ctt ccc ggc agg gcg gac ggg ggc gag acc     1680
Val Arg Leu Phe Thr Ile Leu Pro Gly Arg Ala Asp Gly Gly Glu Thr
545                 550                 555                 560

gat gat tcc cgc ata tct gct gca atc gac tac ttt ctg acc ccc gag     1728
Asp Asp Ser Arg Ile Ser Ala Ala Ile Asp Tyr Phe Leu Thr Pro Glu
                565                 570                 575

gct gtc tcg tcc ggc gag gtc ata ttc tgc gta gac gag aac agg ggc     1776
Ala Val Ser Ser Gly Glu Val Ile Phe Cys Val Asp Glu Asn Arg Gly
            580                 585                 590

tag                                                                 1779


<210> SEQ ID NO 80
<211> LENGTH: 592
<212> TYPE: PRT
<213> ORGANISM: Cenarchaeum symbiosum

<400> SEQUENCE: 80

Met Lys Leu Gln Gly Lys Thr Ala Val Ile Thr Gly Ser Gly Thr Gly
 1               5                  10                  15

Ile Gly Leu Ala Val Ala Arg Lys Phe Ala Glu Asn Gly Ala Ser Val
            20                  25                  30

Val Ile Leu Gly Arg Arg Lys Glu Pro Leu Asp Glu Ala Ala Ala Glu
        35                  40                  45

Leu Lys Lys Ile Ala Glu Ser Ala Gly Cys Gly Ala Ser Ile Arg Ile
    50                  55                  60

Phe Ala Gly Val Asp Val Ala Asp Glu Ser Ala Ile Thr Lys Met Phe
65                  70                  75                  80

Asp Glu Leu Ser Ser Ser Gly Val Thr Val Asp Ile Leu Val Asn Asn
                85                  90                  95

Ala Gly Val Ser Gly Pro Val Thr Cys Phe Ala Asn Asn Asp Leu Glu
            100                 105                 110

Glu Phe Arg Gly Ala Val Asp Ile His Leu Thr Gly Ser Phe Trp Thr
        115                 120                 125

Ser Arg Glu Ala Leu Lys Val Met Lys Lys Gly Ser Lys Ile Val Thr
    130                 135                 140
```

-continued

```
Met Thr Thr Phe Phe Ala Glu Glu Arg Pro Leu Glu Gln Arg Pro Tyr
145                 150                 155                 160

Arg Phe Arg Asp Pro Tyr Thr Thr Ala Gln Gly Ala Lys Asn Arg Leu
                165                 170                 175

Ala Glu Ala Met Ser Trp Asp Leu Leu Asp Arg Gly Ile Thr Ser Ile
            180                 185                 190

Ala Thr Asn Pro Gly Pro Val His Ser Asp Arg Ile Tyr Lys Thr Val
        195                 200                 205

Tyr Pro Arg Ala Ala Leu Glu Phe Val Arg Val Ser Gly Phe Glu Asp
    210                 215                 220

Leu Gln Pro Glu Glu Val Glu Val Ala Gly Gly Arg Leu Ile His Leu
225                 230                 235                 240

Leu Gly Ala Asp Asp Asp Ala Arg Lys Lys Gly Ile Ala Glu Ala Ala
                245                 250                 255

Glu His Phe Ala Lys Leu Lys Pro Val Asp Pro Ala Lys Leu Glu Ala
            260                 265                 270

Thr Leu Asp Ala Leu Leu Ala Lys Ile Lys Gly Ile Ala Glu Lys Ile
        275                 280                 285

Gln Ala Asn Thr Ala Arg Met Ile Pro Asp Gly Glu Phe Leu Ser Gln
    290                 295                 300

Asp Gln Val Ala Glu Thr Val Leu Ala Leu Cys Asp Asp Lys Met Ala
305                 310                 315                 320

Lys Thr Val Asn Gly Arg Val Ile Pro Ala Asp Arg Val Phe Tyr Pro
                325                 330                 335

Val Arg Ala His Val Ala Asn Ala Ala Pro Arg Val Pro Pro His Asp
            340                 345                 350

Tyr Ser Gly Gly Cys Val Leu Phe Met Ile Asp Ala Ala Asp Asp Arg
        355                 360                 365

Asp Val Glu Arg Ala Thr Ala Leu Ala Ser His Val Glu Ser His Gly
    370                 375                 380

Gly Thr Ala Val Cys Ile Val Ser Glu Asp Ser Pro Arg Ala Ala Lys
385                 390                 395                 400

Glu Met Ile Ala Ser Lys Phe His Ser His Ala Ser His Ile Asp Lys
                405                 410                 415

Val Asp Glu Ile Asn Arg Trp Leu Ser Ala Ala Ser Thr Lys Ile Gly
            420                 425                 430

Pro Ile Ser Ala Val Val His Leu Ser Gly Arg Met Pro Lys Ser Gly
        435                 440                 445

Ser Leu Met Asp Leu Ser Arg Lys Glu Trp Asp Ala Leu Val Asp Arg
    450                 455                 460

Phe Ile Gly Thr Pro Ala Ala Val Leu His Arg Ser Leu Glu His Phe
465                 470                 475                 480

Ala Pro Gly Gly Arg Lys Asp Pro Arg Leu Phe Lys Gly Lys Ser Gly
                485                 490                 495

Val Ile Val Ile Ile Gly Pro Asp Leu Pro Ala Gly Lys Lys Ala Ser
            500                 505                 510

Gly Ala Glu Arg Ala Arg Ala Glu Ile Phe Arg Gly Ala Leu Arg Pro
        515                 520                 525

Leu Thr Thr Thr Val Asn Gln Glu Leu Ser Asp Val Leu Lys Ser Asn
    530                 535                 540

Val Arg Leu Phe Thr Ile Leu Pro Gly Arg Ala Asp Gly Gly Glu Thr
545                 550                 555                 560
```

-continued

```
Asp Asp Ser Arg Ile Ser Ala Ala Ile Asp Tyr Phe Leu Thr Pro Glu
                565                 570                 575

Ala Val Ser Ser Gly Glu Val Ile Phe Cys Val Asp Glu Asn Arg Gly
            580                 585                 590


<210> SEQ ID NO 81
<211> LENGTH: 40
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 81

aagctagact tttaattggg atccggcggg gcggcgcatg                            40


<210> SEQ ID NO 82
<211> LENGTH: 40
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 82

aagctaaact tttaattggg atccggcgag ccggcgcgtg                            40


<210> SEQ ID NO 83
<211> LENGTH: 41
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 83

ggaaactttg attatacggg cgtgctgccc cggggcccat g                          41


<210> SEQ ID NO 84
<211> LENGTH: 41
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 84

ggaaactttg attatacggg cgtacattcc cggggcccat g                          41


<210> SEQ ID NO 85
<211> LENGTH: 42
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 85

aaggcaaggt aataatagcc tgccgtctgt aacggccgta tg                         42


<210> SEQ ID NO 86
<211> LENGTH: 42
<212> TYPE: DNA
<213> ORGANISM: Cenarchaeum symbiosum
<220> FEATURE:
<221> NAME/KEY: TATA_signal
<222> LOCATION: (11)...(16)
```

<400> SEQUENCE: 86
acggcaaggt aataatagcc tgccgtccgt acctgccgta tg 42

<210> SEQ ID NO 87
<211> LENGTH: 42
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 87
catggaacta gatattaacc ggttccgcgg atcccatgca tg 42

<210> SEQ ID NO 88
<211> LENGTH: 42
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 88
catggaacta gataataacc ggtcccgcgg gtacaatgca tg 42

<210> SEQ ID NO 89
<211> LENGTH: 43
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 89
ataccgagaa gttatagcag ggtatggaat gtgcgcgcgc atg 43

<210> SEQ ID NO 90
<211> LENGTH: 43
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 90
agcacgacaa gttatagcag ggtacaaagg agcagcgcac atg 43

<210> SEQ ID NO 91
<211> LENGTH: 43
<212> TYPE: DNA
<213> ORGANISM: Cenarcheaum symbiosum
<220> FEATURE:
<221> NAME/KEY: TATA_signal
<222> LOCATION: (11)...(16)

<400> SEQUENCE: 91
atccgccctg attaaattat gggggggagcg gcctgctgcc gtg 43

<210> SEQ ID NO 92
<211> LENGTH: 43
<212> TYPE: DNA
<213> ORGANISM: Cenarchaeum symbiosum
<220> FEATURE:
<221> NAME/KEY: TATA_signal
<222> LOCATION: (11)...(16)

-continued

<400> SEQUENCE: 92
atccggcctc attaaattac gggggtaca acctgctgcc gtg 43

<210> SEQ ID NO 93
<211> LENGTH: 43
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 93
ccttcataca cataaatccc gcttggatgt gcggctgcgc atg 43

<210> SEQ ID NO 94
<211> LENGTH: 43
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 94
acttcataca cataaatccc gcctgaacgg tcgtccgcgc atg 43

<210> SEQ ID NO 95
<211> LENGTH: 43
<212> TYPE: DNA
<213> ORGANISM: Cenarchaeum symbiosum
<220> FEATURE:
<221> NAME/KEY: TATA_signal
<222> LOCATION: (10)...(15)

<400> SEQUENCE: 95
ggcatatacc ataatatgcc gggcggtggc accatggccg ttg 43

<210> SEQ ID NO 96
<211> LENGTH: 43
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 96
ccgcatatac cataatatgc cgggcggggg caggctgccc gtg 43

<210> SEQ ID NO 97
<211> LENGTH: 44
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 97
tgtacgaaac cataaaacaa caggccgcgt cagggccgcg cgtg 44

<210> SEQ ID NO 98
<211> LENGTH: 43
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 98

-continued gggtagaaac cataaaacaa caggccgcgg cagggcgcgc gtg 43

<210> SEQ ID NO 99
<211> LENGTH: 42
<212> TYPE: DNA
<213> ORGANISM: Cenarchaeum symbiosum
<220> FEATURE:
<221> NAME/KEY: TATA_signal
<222> LOCATION: (9)...(14)

<400> SEQUENCE: 99
acacgcagta taaacggggg cccgggcggc gcgtatcaca tg 42

<210> SEQ ID NO 100
<211> LENGTH: 43
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 100
atacacgtgg tataaacaga ggccggacgg cgcggaccac atg 43

<210> SEQ ID NO 101
<211> LENGTH: 44
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 101
gcgatagtta tttaaaacta ggatgccgat cacggatcgt ccca 44

<210> SEQ ID NO 102
<211> LENGTH: 44
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 102
gcgatagtta tttaaaacta ggatgccggg cacccgtcgt ccca 44

<210> SEQ ID NO 103
<211> LENGTH: 44
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 103
ccgggccccg gttaaaatag cgcacgggcg gatcctgacc aatg 44

<210> SEQ ID NO 104
<211> LENGTH: 45
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 104

-continued ccgggccccg gttaaaatag agtgcggccg ggcaccggat caatg 45

<210> SEQ ID NO 105
<211> LENGTH: 51
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 105
gcgtcgatag aataaatacg cgcagggggc cccgtggcgc gatcgcccgt g 51

<210> SEQ ID NO 106
<211> LENGTH: 47
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 106
gcgtcgatag aataaatacg cgcggggccg cggtgcgatc gcccgtg 47

<210> SEQ ID NO 107
<211> LENGTH: 60
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 107
atttcaacta cataaatgcc tagttacgca gaaatagcaa acgacgtact tcgactaatg 60

<210> SEQ ID NO 108
<211> LENGTH: 60
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 108
acttcaacta cataaatgcc tagctacgca gaaatatcaa acaaagtact tcgactaatg 60

<210> SEQ ID NO 109
<211> LENGTH: 67
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 109
acggcaggct attattacct tgccttgcgt tgtatagtat gccttatgcg gggtgcggca 60
ggggatg 67

<210> SEQ ID NO 110
<211> LENGTH: 66
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 110

-continued acggcaggct attattacct tgccgtgtgt acagggcatg ccggatgagg gggcctgccg 60
ggagtg 66

<210> SEQ ID NO 111
<211> LENGTH: 121
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 111
ctacaacgat tttaagtcgg cgccggggca gccgcataga atgtgtatga cccgtaggat 60
cgcgcggccc gcctgctgcg cagatctgtc cgtccagcct gatgtggggc aggcaacatg 120
a 121

<210> SEQ ID NO 112
<211> LENGTH: 98
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 112
ctacaaagat tttaagacgg cgcgggtgcc gcggtacaag atgaatacga cttgtcggat 60
cgcgcagggg cagatggatg gcacgggggc ctatcttg 98

<210> SEQ ID NO 113
<211> LENGTH: 236
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 113
tcggcgatgg tttatatgcc catggacggg ccgatccgat cgtacgtgac gcaagagcgg 60
cgcttgcgat gaatgcatgg tattgtacca tattgtgatt cgctggcctc cagttacgca 120
cacagaatga gggtatgatc gaagggtcat atctgagatg tgaagattat gtgcattctg 180
ttcaattcca aaagtacaag cgtacttaac aaaaaaaaaa taatccaatt atgaat 236

<210> SEQ ID NO 114
<211> LENGTH: 235
<212> TYPE: DNA
<213> ORGANISM: Cenarchaeum symbiosum
<220> FEATURE:
<221> NAME/KEY: TATA_signal
<222> LOCATION: (11)...(16)

<400> SEQUENCE: 114
ccggcgatgg tttatatgcc catggacaag gcgatccgat cgtacgtgac gcaagagcgg 60
cgcttgcgat gaagccatgg tattgtacca ttttgtgatt cgcaggcctc cagttacgca 120
cacagaatga ggatctgatc gaagggtcat atctgagatg tgaagattat gtgcattccg 180
ttcaattcca aaagtacagg cgtactttga aaaaaaaaat aatccaaata agaat 235

<210> SEQ ID NO 115
<211> LENGTH: 20
<212> TYPE: DNA

-continued

```
<213> ORGANISM: Artificial Sequence
<220> FEATURE:
<223> OTHER INFORMATION: Oligonucleotide

<400> SEQUENCE: 115

gtgctccccc gccaattcct                                             20


<210> SEQ ID NO 116
<211> LENGTH: 15
<212> TYPE: DNA
<213> ORGANISM: Artificial Sequence
<220> FEATURE:
<223> OTHER INFORMATION: Oligonucleotide

<400> SEQUENCE: 116

ctttccctca cggta                                                  15


<210> SEQ ID NO 117
<211> LENGTH: 19
<212> TYPE: DNA
<213> ORGANISM: Artificial Sequence
<220> FEATURE:
<223> OTHER INFORMATION: Oligonucleotide

<400> SEQUENCE: 117

ctattgccgt ctttacacc                                              19


<210> SEQ ID NO 118
<211> LENGTH: 21
<212> TYPE: DNA
<213> ORGANISM: Artificial Sequence
<220> FEATURE:
<223> OTHER INFORMATION: Oligonucleotide

<400> SEQUENCE: 118

gaatccgccc ccgactatct t                                           21


<210> SEQ ID NO 119
<211> LENGTH: 18
<212> TYPE: DNA
<213> ORGANISM: Artificial Sequence
<220> FEATURE:
<223> OTHER INFORMATION: Oligonucleotide

<400> SEQUENCE: 119

catggcttag tatcaatc                                               18


<210> SEQ ID NO 120
<211> LENGTH: 23
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: (3)...(3)
<223> OTHER INFORMATION: I
<220> FEATURE:
<221> NAME/KEY: modified_base
<222> LOCATION: (12)...(12)
<223> OTHER INFORMATION: I

<400> SEQUENCE: 120

acntacaacg gngacgaytt tga                                         23


<210> SEQ ID NO 121
<211> LENGTH: 21
```

-continued

```
<212> TYPE: DNA
<213> ORGANISM: Artificial Sequence
<220> FEATURE:
<223> OTHER INFORMATION: Oligonucleotide

<400> SEQUENCE: 121

caccccgaar tagttyttyt t                                  21


<210> SEQ ID NO 122
<211> LENGTH: 19
<212> TYPE: DNA
<213> ORGANISM: Artificial Sequence
<220> FEATURE:
<223> OTHER INFORMATION: Oligonucleotide

<400> SEQUENCE: 122

acacttcaac tatttcctg                                     19


<210> SEQ ID NO 123
<211> LENGTH: 19
<212> TYPE: DNA
<213> ORGANISM: Artificial Sequence
<220> FEATURE:
<223> OTHER INFORMATION: Oligonucleotide

<400> SEQUENCE: 123

acactttgac tatttcgtg                                     19
```